(12) United States Patent
Coleman et al.

(10) Patent No.: US 9,745,603 B2
(45) Date of Patent: Aug. 29, 2017

(54) BIOLOGICAL PRODUCTION OF MULTI-CARBON COMPOUNDS FROM METHANE

(71) Applicant: INTREXON CORPORATION, Blacksburg, VA (US)

(72) Inventors: William J. Coleman, Redwood City, CA (US); Genevieve M. Vidanes, San Francisco, CA (US); Guillaume Cottarel, Mountain View, CA (US); Sheela Muley, Fremont, CA (US); Roy Kamimura, Daly City, CA (US); Akbar F. Javan, Chapel Hill, NC (US); Jianping Sun, Belmont, CA (US); Eli S. Groban, San Francisco, CA (US)

(73) Assignee: Intrexon Corporation, Blacksburg, VA (US)

( * ) Notice: Subject to any disclaimer, the term of this patent is extended or adjusted under 35 U.S.C. 154(b) by 0 days.

(21) Appl. No.: 15/192,290

(22) Filed: Jun. 24, 2016

(65) Prior Publication Data
US 2017/0152529 A1    Jun. 1, 2017

Related U.S. Application Data

(62) Division of application No. 14/989,859, filed on Jan. 7, 2016, now Pat. No. 9,399,783, which is a division of application No. 14/206,835, filed on Mar. 12, 2014, now Pat. No. 9,267,158.

(60) Provisional application No. 61/782,830, filed on Mar. 14, 2013.

(51) Int. Cl.
| | |
|---|---|
| *C12P 7/16* | (2006.01) |
| *C12N 9/10* | (2006.01) |
| *C12N 9/88* | (2006.01) |
| *C12N 15/52* | (2006.01) |
| *C12N 9/04* | (2006.01) |

(52) U.S. Cl.
CPC .............. *C12P 7/16* (2013.01); *C12N 9/0006* (2013.01); *C12N 9/1022* (2013.01); *C12N 9/1025* (2013.01); *C12N 9/88* (2013.01); *C12N 15/52* (2013.01); *C12Y 101/01001* (2013.01); *C12Y 101/01004* (2013.01); *C12Y 202/01006* (2013.01); *C12Y 203/03006* (2013.01); *C12Y 401/01072* (2013.01); *C12Y 402/01033* (2013.01); *C12Y 403/01019* (2013.01)

(58) Field of Classification Search
None
See application file for complete search history.

(56) References Cited

U.S. PATENT DOCUMENTS

| | | | |
|---|---|---|---|
| 4,594,324 | A | 6/1986 | Dalton et al. |
| 4,982,023 | A | 1/1991 | Han et al. |
| 6,576,449 | B2 | 6/2003 | Clark et al. |
| 6,660,507 | B2 | 12/2003 | Cheng et al. |
| 6,767,744 | B2 | 7/2004 | Koffas et al. |
| 6,818,424 | B2 | 11/2004 | DiCosimo et al. |
| 6,969,595 | B2 | 11/2005 | Brzostowicz et al. |
| 7,026,464 | B2 | 4/2006 | DiCosimo et al. |
| 7,851,188 | B2 | 12/2010 | Donaldson et al. |
| 7,910,342 | B2 | 3/2011 | Liao et al. |
| 7,943,362 | B2 | 5/2011 | Frost |
| 7,977,084 | B2 | 7/2011 | Sun et al. |
| 7,993,889 | B1 | 8/2011 | Donaldson et al. |
| 8,017,375 | B2 | 9/2011 | Feldman et al. |
| 8,030,021 | B2 | 10/2011 | Criddle et al. |
| 8,101,808 | B2 | 1/2012 | Evanko et al. |
| 8,158,404 | B2 | 4/2012 | Lies et al. |
| 8,232,089 | B2 | 7/2012 | Urano et al. |
| 8,263,373 | B2 | 9/2012 | Herrema et al. |
| 8,268,599 | B2 | 9/2012 | Schirmer et al. |

(Continued)

FOREIGN PATENT DOCUMENTS

| | | |
|---|---|---|
| EP | 0306466 | 3/1989 |
| EP | 0418187 | 3/1991 |

(Continued)

OTHER PUBLICATIONS

Anthony, C. and Williams, P., "The structure and mechanism of methanol dehydrogenase," Biochimica et Biophysica Acta 1647:18-23, Elsevier Pub. Co., Netherlands (2003).

Atsumi, S., et al., "Engineering the isobutanol biosynthetic pathway in *Escherichia coli* by comparison of three aldehyde reductase/ alcohol dehydrogenase genes," Appl. Microbial Biotechnol 85:651-657, Springer-Verlag GmbH, Germany (2010).

Avalos, J.L., et at., "Compartmentalization of metabolic pathways in yeast mitochondria improves the production of branched-chain alcohols," Nature Biotechnology 31 (4):335-341, Nature Publishing Group, England (2013).

Bastian, S., et al., "Engineered ketol-acid reductoisomerase and alcohol dehydrogenase enable anaerobic 2-methylpropan-l-ol production at theoretical yield in *Escherichia coli*," Metabolic Engineering 13:345-352, Elsevier Inc., United States (201 I).

(Continued)

*Primary Examiner* — David J Steadman
*Assistant Examiner* — Jae W Lee
(74) *Attorney, Agent, or Firm* — Troutman Sanders LLP

(57) ABSTRACT

Multi-carbon compounds such as ethanol, n-butanol, sec-butanol, isobutanol, tert-butanol, fatty (or aliphatic long chain) alcohols, fatty acid methyl esters, 2,3-butanediol and the like, are important industrial commodity chemicals with a variety of applications. The present invention provides metabolically engineered host microorganisms which metabolize methane ($CH_4$) as their sole carbon source to produce multi-carbon compounds for use in fuels (e.g., bio-fuel, bio-diesel) and bio-based chemicals. Furthermore, use of the metabolically engineered host microorganisms of the invention (which utilize methane as the sole carbon source) mitigate current industry practices and methods of producing multi-carbon compounds from petroleum or petroleum-derived feedstocks, and ameliorate much of the ongoing depletion of arable food source "farmland" currently being diverted to grow bio-fuel feedstocks, and as such, improve the environmental footprint of future bio-fuel, bio-diesel and bio-based chemical compositions.

9 Claims, 9 Drawing Sheets

(56) References Cited

U.S. PATENT DOCUMENTS

| | | | |
|---|---|---|---|
| 8,283,143 | B2 | 10/2012 | Hu et al. |
| 8,349,587 | B2 | 1/2013 | Fischer et al. |
| 9,611,487 | B2 | 4/2017 | Blake et al. |
| 2006/0057726 | A1 | 3/2006 | Sharpe |
| 2007/0251141 | A1 | 11/2007 | Bist et al. |
| 2009/0263877 | A1 | 10/2009 | Eriksen et al. |
| 2010/0274033 | A1 | 10/2010 | Sanchez-Riera et al. |
| 2011/0301388 | A1 | 12/2011 | Donaldson et al. |
| 2012/0009640 | A1 | 1/2012 | Behrouzian et al. |
| 2013/0344553 | A1 | 12/2013 | Lee |
| 2014/0273128 | A1 | 9/2014 | Coleman et al. |

FOREIGN PATENT DOCUMENTS

| | | |
|---|---|---|
| WO | 0218617 | 3/2002 |
| WO | 03015534 | 2/2003 |
| WO | 03016460 | 2/2003 |
| WO | 2004104180 | 12/2004 |
| WO | 2005062867 | 7/2005 |
| WO | 2011019858 | 2/2011 |

OTHER PUBLICATIONS

Chistoserdova, L., et at., "A genomic view of methane oxidation by aerobic bacteria and anaerobic archaea," Genome Biology 6: 208. 1-208.6, BioMed Central Ltd., England (2005).

Chistoserdova, L., et at., "The Expanding World ofMethyltrophic Metabolism," Ann. Rev Microbiol 63:477-499, Annual Reviews, United States (2009).

Chistoserdov A, L., Modularity of methylotrophy, revisited, II Environmental Microbiology 13(10):2603-2622, Society for Applied Microbiology and Blackwell, Publishing Ltd., England (2011).

Culpepper, M.A. And Rosenzweig, A.C., "Architecture and active site of particulate methane monooxygenase," Crit Rev Mol Biol 47(6):483-492, CRC Press, England (2012).

Duan, Y., et al., "De novo Biosynthesis ofBiodiesel by *Escherichia coli* in Optimized Fed-Batch Cultivation," PLoS ONE 6(5): 1-7, Public Library of Science, U.S.A. (2011).

Dunfield, P.F., et al., "*Methylocella silvestris* sp. nov .. , a novel methanotroph isolated from an acidic cambisol," forest International Journal of Systemic and Evolutionary Microbiology 53: 1231-1239, IUMS, England (2003).

Energy Policy Act of2005, Pub. L. No. 109-58, 119 Stat. 594 (2005).

Gellissen, G., et al., "New yeast expression platforms based on methyltrophic Hansenufa polymorpha and Pichia pastoris and on dimorphic Arxula adeninivorans and Yarrowia lipo/ytica—A comparison," FEMS Yeast Research 5: 1 079•1 096, Elsevier Science B.V., Netherlands (2005).

Hakemian, A.S. and Rosenzweig, A.C., "The Biochemistry of Methane Oxidation," Annu Rev Biochem 76:223•241, Annual Reviews, United States (2007).

Hanson, R.S., and Hanson, T.E., "Methanottophic Bacteria," Microbiological Reviews 60(2):439-471, American for Society Microbiology, United States (1996).

Jaeger, W.K. and Egelkraut, T.M., "Biofuel Economics in a Setting of Multiple Objectives & Unintended Consequences," Renewable and Sustainable Energy Reviews 15(9):4320-4333, Elsevier Ltd., England (2011).

Jang, Y.-S. et at., "Enhanced Butanol Production Obtained by Reinforcing the Direct Butanl•Porming Route in Clostridium acetobutylicum," mBio 3(5):e00314-12, American Society for Microbiology, United States (2012).

Kidnay, AJ. and Parris, W.R., Fundamentals a/Natural Gas Processing, Faulkner, L.L., ed., Taylor and Francis Group, LLC, England (2006).

Kim, S., et al., "Cellulosic ethanol production using a yeast consortium displaying a minicellulosome and β-glucosidase," Microbial Cell Factories 12:14, BioMed Central Ltd., England (2013).

Klett, T. R. et al., "An Evaluation of the USGS World Petroleum Assessment 2000-Supporting Data," U.S. Geological Survey Open-File Report 2007-1021,9 p.

Murrell, J.C., et al., "Molecular biology and regulation of methane monooxygenase," Arch Microbiol173:325-332, Springer-Verlag GmbH, Germany (2000).

Patras, L.E. and Tang, A., "Bioconversion of methane to methanol by Methylobacterium organophilum," Unocal Science and Technology Division, Brea, California, pp. 462-468.

Phillips, R.B. et al., "Integration of pulp and paper technology with bioethanol production," Biotechnology for Biojitels 6: 13-25, BioMed Central Ltd., England (2013).

Rudolf, A. et al., "Ethanol Production from Traditional and Emerging Raw Materials," in Yeast Biotechnology: Diversity and Applications, Satyanarayana, T., ed., pp. 489-513, Springer-Verlag GmbH, Gennany (2009).

Saka, S., and Kusdiana, D., "Biodiesel fuel from rapeseed oil as prepared in supercritical methanol," Fuel 80:225-23 I, Elsevier Ltd., England (2001).

Schrader, J., et al., "Methanol-based industrial biotechnology: current status and future perspectives of methylotrophic bacteria," Trends in Biotechnology 27(2): 1 07-115, Elsevier Ltd., England (2009).

Semrau, J.D., et ai., "Facultative methanotrophy: false leads, true results, and suggestions for future research," FEMS Microbiol.Lett. 323:1-12, Blackwell Publishing Ltd., England (2011).

Stanley, S.H. and Dalton, I-I., "Role of Ribulose- I ,5-biphosphate Carboxylase/Oxygenase in Methylococcus capsulatus (Bath)," Journal of General Microbiology f 28:2927-2935, Society for General Microbiology, England (1982).

Tinberg, C.E. and Lippard, 5.1., "Dioxygen Activation in Soluble Methane Monooxygenase," Acc Chem Res 44 (4):280-288, American Chemical Society, United States (2011).

Trotsenko, Y.A. and Murrell, IC., "Metabolic Aspects of Aerobic obligate Methanotrophy," Advances in Applied Microbiology 63: 183-229, Elsevier Inc., United States (2008).

Veazey, M.V., "GTL Tech Converts Methane to Ethylene without Fischer Tropsch," Rigzone.com., accessed at http://rigzone.com/news/oil_gas/a/116784/GTL_Tech_Converts_Methane_to_Ethylene without Fischer Tropsch, made available on Apr. 10, 2012,2 pages.

Wright, C-K_ and Wimberly, M.e., "Recent land use change in the Western Corn Belt threatens grasslands and wetlands,".Proc Natl Acad Sci USA. J 10(10):4134-4139, National Academy of Sciences, United States (2012).

Yu, X et al., "In vitro reconstitution and steady-state analysis of the fatty acid synthase from *Escherichia coli*," Proc Natl Acad Sci US.A_ 108(46): 18643-18648, National Academy of Sciences, United States (2011).

Ala Yon, R.M.e., "Catalytic Conversion of Methane to Methanol Using Cu-Zeolites," Chimia 66(9):668-674, Schweizerische Chemische Gesellschaft, Switzerland (2012).

Arakawa, H., et al., "Catalysis Research of Relevance to Carbon Management: Progress, Challenges, and Opportunities," Chem. Rev. 101(4):953-996, American Chemical Society, United States (2001).

Yurimoto, R, et al., "Assimilation, Dissimilation, and Detoxification of Formaldehyde, a Central Metabolic Intermediate of Methylotrophic Metabolism," The Chemical Record 5:367-375, The Japan Chemical Journal Forum and Wiley Periodicals, Inc., Japan (2005).

Yurimoto, R, et al., "Genomic organization and biochemistry of the ribulose monophosphate pathway and its application in biotechnology," App/ Microbial Biotechnol 84:407-416, Springer-Verlag, Germany (2009).

BIOLOGICAL PRODUCTION OF MULTI-CARBON COMPOUNDS FROM METHANE

CROSS-REFERENCE TO RELATED APPLICATION

This application is a divisional of U.S. patent application Ser. No. 14/206,835, filed Mar. 12, 2014, which claims priority benefit of U.S. Provisional Application No. 61/782,830, filed Mar. 14, 2013, each of which is hereby incorporated by reference in its entirety.

REFERENCE TO SEQUENCE LISTING

This application includes a "Sequence Listing.ascii.txt," 331,571 bytes, created on Jan. 5, 2016, and submitted electronically via EFS-Web, which is hereby incorporated by reference in its entirety.

BACKGROUND OF THE INVENTION

Field of the Invention

The present invention is generally related to the fields of molecular biology and and methods of producing metabolically engineered microorganisms which utilize methane feedstocks for the biological production of bio-fuels and bio-chemicals such as 1-butanol, isobutanol, fatty alcohols, fatty acid esters, 2,3-butanediol and the like.

Background Art

Traditional fossil fuels (e.g., gasoline, diesel, kerosene and the like) and numerous chemicals (e.g., for use in pharmaceuticals, solvents, fertilizers, pesticides, plastics and the like) are derived (and refined from) non-renewable petroleum (oil) resources. Current estimates suggest that the world's supply of non-renewable petroleum will likely be exhausted somewhere between the years 2045 and 2065 (U.S. Department of the Interior, U.S. Geological Survey World Petroleum Assessment, 2000), with concomitant extensions or reductions of these estimates dependent on variables such as increased (or reduced) global demand, more efficient petroleum refining processes, more efficient use of energy and products derived from petroleum and the discovery of new petroleum sources/reserves.

Independent of any current or future methods contemplated to mitigate petroleum consumption, there is no debate that the world's supply of petroleum is a finite and a constantly diminishing (non-renewable) energy source. Thus, to meet the ever increasing global demands for energy consumption, renewable, biologically produced fuels (i.e., "bio-fuels" and "bio-diesel") have become an area of intense research, capital investment and government intervention.

For example, the U.S. "Energy Policy Act" of 2005 (42 USC, Title XV "Ethanol and Motor Fuels", §1501-§1533; enacted into law Aug. 8, 2005), sets forth parameters and definitions of "renewable fuels", and established the "minimum ethanol" volume to gasoline volume blending requirements (presently E10: 10% ethanol:90% gasoline), with E15 (15% ethanol:85% gasoline) enacted as law and being "phased-in" across the U.S. The Energy Policy Act defines "renewable fuel" as a "motor vehicle fuel produced from grain, starch, oil-seeds, vegetable, animal, or fish materials including fats, greases, and oils, sugarcane, sugar beets, sugar components, tobacco, potatoes, or other biomass; or a natural gas produced from a biogas source, including a landfill, sewage waste treatment plant, feedlot, or other place where decaying organic material is found; and is used to replace or reduce the quantity of fossil fuel present in a fuel mixture used to operate a motor vehicle. The term "renewable fuel" includes (a) cellulosic biomass ethanol and waste derived ethanol; and (b) biodiesel, and any blending components derived from renewable fuel".

In addition to the current E10 ethanol/gasoline blends and ongoing adoption of E15 ethanol/gasoline blends, ethanol volumes of up to E85 (i.e., 85% ethanol:15% gasoline) are also presently being utilized in "flex-fuel" vehicles (i.e., vehicles with engines and fuel systems capable of combusting and delivering, respectively, 85% ethanol blended gasoline) and it is estimated that the production of E85 fuel will only continue to increase as the supply (i.e., production) of "flex-fuel" vehicles increase. However, an inherent limitation of "ethanol" blended fuels (due to the decreased or lower "energy content" of ethanol relative to gasoline) is that increasing the percentage of ethanol blended into gasoline reduces the overall fuel economy of the vehicle (e.g., fuel economy of vehicles operating on E85 is about 25-30% less than vehicles operating on E10 gasoline blends). This limitation of ethanol's total energy content has further facilitated research and development of alternative bio-fuel blending additives (e.g., terpenoid hydrocarbons, n-butanol, isobutanol and the like) to replace bio-ethanol. Also predicated on the assumption of a finite, diminishing supply of non-renewable petroleum resources, research in the areas of biologically derived (hereinafter, "bio-based") chemicals (e.g., for use in pharmaceuticals, solvents, fertilizers, pesticides, plastics and the like) are being pursued, wherein these "bio-based" chemicals are contemplated as a means for reducing or eliminating their equivalents traditionally derived from petroleum feed stocks.

A considerable topic of ongoing debate is whether the ethanol fuel provisions of the Energy Policy Act of 2005 (and similar policies of other countries) have reduced (or will reduce) dependence on foreign oil/petroleum sources and/or have mitigated (or will mitigate) greenhouse gas emissions (two perceived benefits of the Act). For example, bio-fuels such as ethanol were initially seen as a solution to energy and environmental problems (i.e., considered carbon neutral) because the carbon dioxide emitted when ethanol is combusted is equivalent to the carbon dioxide absorbed from the atmosphere when the ethanol feed stock crop is grown (e.g., corn ethanol, sugarcane ethanol, cellulosic ethanol from switchgrass, etc.).

A recent study by economists at Oregon State University (Jaeger & Egelkraut, 2011) suggests however, that once additional factors/consequences are considered, such as (a) the use of fossil fuels to produce bio-fuel feedstocks and transport bio-fuels, (b) the use of nitrogen fertilizers to grow bio-fuel feedstocks and (c) that growing bio-fuel feedstock crops often pushes food production onto previously unfarmed land (which typically requires clearing tress and heavy tilling of the land), the perceived environmental benefits of ethanol derived bio-fuels may be lost. Likewise, another recent study on the environmental impact of bio-fuel production concludes that high corn and soybean prices, prompted largely by the demand for bio-fuel feedstocks (and partly by government incentives to use them as fuels instead of food), are driving one of the most important land cover/land use change events in recent U.S. history; the accelerated conversion of grassland to cropland in the U.S. Corn Belt (Wright and Wimberly, 2013).

The shift from petroleum based diesel fuel as a (transportation) energy source (e.g., used in automobiles, trucks and other heavy equipment) to renewable bio-diesel fuels is another source of scientific and policy disagreement similar to the arguments set forth above with regard to ethanol bio-fuels. Bio-diesel is generally made from plant oils or animal fats (triacylglycerides) by transesterification with methanol or ethanol, resulting in fatty acid methyl esters and fatty acid ethyl esters. However, the limited supply of bioresources to obtain triacylglycerides has become a major bottleneck for bio-diesel production, the primary reason being that vegetable oil feedstocks are also food sources and their planting is geographically limited.

There is therefore a pressing need in the art for novel methods of producing bio-fuel, bio-diesel and bio-based chemical compositions which reduce the world's dependence/utilization of petroleum products, ameliorate ongoing depletion of arable food source "farmland" currently being diverted to grow bio-fuel feedstocks and generally improve the environmental footprint of future bio-fuel, bio-diesel and bio-based chemical compositions.

As mentioned previously above, ethanol is currently the most abundant bio-fuel produced, but due to certain limitations (e.g., low energy content, high water solubility, incompatibility/corrosive with many fuel systems), ethanol based bio-fuels may not be the best option to meet future energy demands. Butanol, in comparison, has several advantages over ethanol as a bio-fuel, such as its high blending compatibility with gasoline, its low solubility in water allow it to be stored and distributed using the existing petrochemical infrastructure, it has a much higher energy content than ethanol (thereby improving fuel economy) and has a lower vapor pressure than ethanol blends, which is important in reducing evaporative hydrocarbon emissions. Isobutanol has the same advantages as butanol, with the additional advantage of having a higher octane number due to its branched carbon chain, and it is also useful as a commodity chemical.

Various methods for producing renewable bio-fuel, bio-diesel and other bio-based chemicals are known and described in the art. For example, traditional fermentation and distillation methods for producing and extracting bio-ethanol from starch or sugar rich biomass (e.g., corn) and the hydrolysis, fermentation and distillation methods of producing bio-ethanol from ligno-cellulosic biomass are well known in the art (Rudolph et al., 2009; Kim et al, 2013; Philips et al., 2013). The production of bio-diesel via extraction and esterification of vegetable oils, used cooking oils and animal fats using alcohols is also well known in the art (Saka & Kusdiana, 2001).

In more recent efforts, researchers have started to look at alternative methods for producing bio-fuels, bio-diesel and bio-based chemicals. For example, methods for producing bio-fuels such as butanol and isobutanol in various microorganisms such as *Escherichia coli* (Atsumi et al., 2010), *Clostridium acetobutylicum* (Jang et al., 2012) and *Saccharomyces cerevisiae* (Avalon et al., 2013) have been described in the art. Furthermore, the complete biosynthetic pathway for isobutanol production has been engineered in yeast (see, U.S. Pat. No. 8,232,089; U.S. Pat. No. 7,993,889) and bacteria (see, U.S. Patent Publication No. 2011/0301388). Similarly, de nova biosynthesis of bio-diesel using genetically engineered *E. coli* has been described in the art (Xingye et al., 2011; Yangkai et al., 2011).

However, each of the methods set forth above (i.e., traditional biomass fermentation methods and engineered biological/microorganism methods) for producing bio-fuel, bio-diesel, bio-based chemicals and the like, are limited by the choice of feedstock (or substrate) used to produce the end product (e.g., bio-ethanol, bio-butanol, bio-diesel, etc.). For example, the growth substrates utilized by each of the microorganisms set forth above (i.e., *E. coli, C. acetobutylicum* and *S. cerevisiae*) are dependent, in one way or another, on substrate feedstocks derived from crop-based food sources (e.g., glucose (growth) substrates fed to microorganisms are derived from plant sources).

Thus, as set forth previously, there is an ongoing need in the art for novel methods of producing bio-fuel, bio-diesel and bio-based chemical compositions, which not only reduce dependence/utilization of petroleum products, but also ameliorate the ongoing depletion of arable food source "farmland" currently being diverted to grow bio-fuel feedstocks and generally improve the environmental footprint of future bio-fuel, bio-diesel and bio-based chemical compositions.

Methane ($CH_4$) has great value as a chemical feedstock for the production of chemicals and food additives, due to its widespread availability, abundant supply and low price (Kidnay et al., 2011). Methane, in the form of natural gas, can be obtained from shale gas, oil drilling, municipal solid waste, biomass gasification/conversion, and methanogenic archaea. Wellhead natural gas varies in composition from about 40% to 95% methane, wherein the other components include ethane, propane, butane, pentane, and heavier hydrocarbons, along with hydrogen sulfide, carbon dioxide, helium and nitrogen. The proportion of methane in the gas feedstock can be increased by gas conditioning, which can produce natural gas consisting of 85-95% (v/v) methane (U.S. Pat. No. 4,982,023).

Current industrial methods for utilizing methane from natural gas include the Fischer-Tropsch process for converting methane into ethylene, steam-methane reforming from methane synthesis gas, as well as direct conversion from methane to methanol using inorganic catalysts (Veazey, 2012; Alayon et al., 2012; U.S. Pat. No. 4,982,023). Although the economics of syngas-to-liquids and methanol-to-gasoline from natural gas have become more favorable, these thermochemical methods for methane conversion still suffer from serious drawbacks (Arakawa et al., 2001). For example: (1) industrial plant construction requires high capital expenditure, (2) operating costs are high, (3) thermochemical conversion plants require elevated temperatures (150° C. to 300° C.) and high pressures (tens of atmospheres), which add to capital and operational costs, (4) the gas-to-liquids process is not always selective in producing liquid fuel and chemical products, further requiring expensive distillation costs and (5) the inorganic catalysts required for producing methanol and other products are susceptible to poisoning by contaminants in the process stream, and therefore the gas streams must be cleaned and the catalysts periodically replaced.

Certain embodiments of the present invention, as set forth below (see, "Detailed Description"), are directed to methods for biosynthetic production of multi-carbon compounds such as fuels (bio-fuels) and chemicals (bio-based) from methane. It is contemplated herein that the methods according to the present invention, using biological catalysts or biocatalysts (e.g., a genetically modified host microorganism) provide a number of economic advantages over current "industrial" methods for utilizing methane from natural gas. These advantages include (1) lower processing temperatures and pressures; (2) high selectivity for the reactions and (3) renewability, all of which lead to substantially lower capital and operational expenses.

A number of microorganisms, including bacteria and yeast, use single-carbon (C1) substrates as their sole source of carbon. These methylotrophs or C1-metabolizers can convert carbon compounds that do not contain carbon-carbon bonds, such as methane ($CH_4$) or methanol ($CH_3OH$)

into biomass (Gellissen et al., 2005; Trotsenko & Murrell, 2008; Chistoserdova et al., 2009; Schrader et al., 2009; Chistoserdova, 2011). With regard to methane utilization, one particularly important group of bacteria known as the methanotrophs, the "obligate" members of which convert methane into methanol ($CH_3OH$), formaldehyde ($H_2C=O$), formic acid (HCOOH) and ultimately $CO_2$ by sequential enzymatic oxidation (Hanson & Hanson, 1996; Trotsenko & Murrell, 2008; Rosenzweig & Ragsdale, 2011(a); Rosenzweig & Ragsdale 2011(b)). Certain "facultative" methanotrophs (e.g., from the genus *Methylocella*) can also be cultivated using methane, methanol or methylamines as growth substrates (Dunfield et al., 2003; Rosenzweig & Ragsdale, 2011(a); Rosenzweig & Ragsdale 2011(b); Semrau et al., 2011).

The initial step of methane oxidation to methanol in methanotrophs is carried out by the enzyme methane monooxygenase (MMO) (Hakemian & Rosenzweig, 2007; Rosenzweig & Ragsdale, 2011(b)). Methane monooxygenase (MMO) activity is expressed in two different forms: a particulate form (pMMO), which contains copper and is membrane-bound (Culpepper & Rosenzweig, 2012), and a soluble form (sMMO), which contains iron and is expressed when copper becomes limiting (Murrel et al., 2000; Hakemian & Rosenzweig, 2007; Tinberg & Lippard, 2007). The second step of converting methanol to formaldehyde is catalyzed by the enzyme methanol dehydrogenase (MDH), another membrane-bound enzyme (Anthony & Williams, 2003). From this point, the formaldehyde can be dissimilated into formate (by formaldehyde dehydrogenase) and carbon dioxide (by formate dehydrogenase). The dissimilation reactions generate reducing equivalents for the cell, but do not directly contribute to the production of biomass or other multi-carbon products, since the carbon is released as $CO_2$. In some methanotrophs, however, carbon dioxide can be fixed through the serine pathway and/or the Calvin-Benson-Bassham cycle (see below), both of which depend on methane consumption to support growth (Stanley & Dalton, 1982; Chistoserdova et al., 2005). Among the oxidized C1 products that can be generated in the above described reactions, formaldehyde is the most important product (or imtermediate), as it serves as a metabolite that can be "fixed" into multi-carbon compounds via its introduction (or assimilation) into a central metabolism pathway of the host microorganism.

For example, the assimilation of the carbon in the formaldehyde formed can occur via various metabolic routes (Hanson & Hanson, 1996; Yurimoto et al., 2005; Yurimoto et al., 2009; Trotsenko & Murrell, 2008; Rosenzweig & Ragsdale, 2011(a); Rosenzweig & Ragsdale, 2011(b)). For example, the Type I methanotrophs, which are members of the Gammaproteobacteria, use the ribulose monophosphate (RuMP) pathway (see, Hanson & Hanson, 1996). The Type II methanotrophs, which are members of the Alphaproteobacteria, utilize the serine pathway (Hanson & Hanson, 1996). The bacterium *Methylococcus capsulatus*, strain Bath, however, uses elements of both these pathways, and is sometimes referred to as a "Type X" methanotroph (Hanson & Hanson, 1996; Chistoserdova et al., 2005). *Methylococcus capsulatus* (Bath), also expresses the enzymes needed to fix carbon dioxide via the Calvin-Benson-Bassham cycle (Chistoserdova et al., 2005).

Turnover of these pathways (i.e., Type I, Type II or Type X) ultimately supplies multi-carbon intermediates for other pathways of central metabolism. For example, the 3-phospho-glyceraldehyde generated by the RuMP cycle can be converted into pyruvate, and the 2-phospho-glycerate generated by the serine cycle can eventually be converted into phosphoenolpyruvate, oxaloacetate and acetyl-CoA, among other intermediates.

Substantial efforts have been expended over the past 40 years to exploit methanotrophs for chemical production and transformations on an industrial scale. However, to date there are still significant deficiencies and unmet needs in the art for improved host microorganisms which can utilize "non-traditional" carbon sources such as oxidized single-carbon compounds (e.g., methane, methanol or formaldehyde) and produce industrial, commercially relevant, multi-carbon compounds such as ethanol, n-butanol, sec-butanol, isobutanol, tert-butanol, fatty alcohols, fatty acid methyl esters, 2,3-butanediol and the like.

The present invention fulfills a need in the art for improved host microorganisms (which can utilize methane as a sole-carbon source in the production of multi-carbon compounds) for use in the biological production of bio-fuels and bio-based chemical compositions. The metabolically engineered host microorganisms and methods of producing the same, as set forth in the present invention, further address a long felt need in the art to reduce dependence/consumption of petroleum products and mitigate the depletion of farmland currently being diverted to grow bio-fuel and bio-based chemical feedstocks.

SUMMARY OF THE INVENTION

The present invention provides metabolically engineered host microorganisms which metabolize methane ($CH_4$) as their sole carbon source to produce multi-carbon compounds for use in fuels (e.g., bio-fuel, bio-diesel) and bio-based chemicals. Furthermore, use of the metabolically engineered host microorganisms of the invention (which utilize methane as the sole carbon source) mitigate current industry practices and methods of producing multi-carbon compounds from petroleum or petroleum-derived feedstocks, and ameliorate much of the ongoing depletion of arable food source "farmland" currently being diverted to grow bio-fuel feedstocks, and as such, improve the environmental footprint of future bio-fuel, bio-diesel and bio-based chemical compositions.

Thus, in certain embodiments, the invention is directed to a method for producing isobutanol from a methane substrate comprising the steps of (a) providing a methanotrophic host microorganism that metabolizes methane ($CH_4$) to methanol ($CH_3OH$) and methanol to formaldehyde ($H_2C=O$); (b) introducing into the methanotroph host and expressing at least one polynucleotide open reading frame (ORF), under the control of suitable regulatory sequences, wherein the at least one polynucleotide ORF encodes a polypeptide that catalyzes a reaction in an isobutanol pathway; and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce isobutanol. In certain embodiments, the one or more polynucleotide ORFs introduced in step (b) encode an isobutanol pathway polypeptide selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In yet other embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol. In another embodiment, the ALS polypeptide comprises an amino acid sequence having at least 90% sequence homology to SEQ ID NO:2, the KARI polypeptide comprises an amino acid sequence having at least 90% sequence homology to SEQ ID NO:4, the DHAD polypeptide comprises an amino acid sequence having at least 90% sequence homology to SEQ ID NO:6, the KDC polypeptide comprises an amino acid sequence having at least 90% sequence homology to SEQ ID NO:8 and the ADH polypeptide comprises an amino acid sequence having at least 90% sequence homology to SEQ ID NO:10. In other embodiments, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In other embodiments a method for producing isobutanol from a methane substrate further comprises the step of recovering the isobutanol produced.

In another embodiment, the invention is directed to a method for producing isobutanol from a methane substrate comprising the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in an isobutanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce isobutanol. In certain embodiments, the one or more polynucleotide ORFs introduced in step (b) encode an isobutanol pathway polypeptide selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In yet other embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol. In certain other embodiments, the ALS polypeptide comprises an amino acid sequence having at least 90% sequence homology to SEQ ID NO:2, the KARI polypeptide comprises an amino acid sequence having at least 90% sequence homology to SEQ ID NO:4, the DHAD polypeptide comprises an amino acid sequence having at least 90% sequence homology to SEQ ID NO:6, the KDC polypeptide comprises an amino acid sequence having at least 90% sequence homology to SEQ ID NO:8 and the ADH polypeptide comprises an amino acid sequence having at least 90% sequence homology to SEQ ID NO:10. In another embodiment, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In other embodiments, the methane monooxygenase (MMO) is a soluble MMO of Enzyme Class EC 1.14.13.25 or a particulate MMO of Enzyme Class 1.14.18.3. In certain embodiments, the MMO comprises an amino acid sequence comprising at least 90% sequence homology to a particulate methane monooxygenase (pMMO) selected from the group consisting of SEQ ID NO:12, SEQ ID NO:14, SEQ ID NO: 16, SEQ ID NO:18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO:32 and SEQ ID NO:34. In other embodiments a method for producing isobutanol from a methane substrate further comprises the step of recovering the isobutanol produced.

In another embodiment, the invention is directed to a method for producing 1-butanol from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce 1-butanol. In certain embodiments, the one or more polynucleotide ORFs introduced in step (b) encode a 1-butanol pathway polypeptide selected from an Enzyme Class (EC) comprising EC 4.3.1.19, EC 2.3.3.6, EC 4.2.1.33, EC 4.1.1.72, and EC 1.1.1.1. In yet other embodiments, the one or more polynucleotide ORFs introduced in step (b) encode a 1-butanol pathway polypeptide selected from the group consisting of L-threonine ammonia lyase, 2-ethylmalate synthase, isopropylmalate isomerase, 3-isopropylmalate dehydratase, 3-isopropylmalate dehydrogenase, 2-ketoacid decarboxylase (KDC) and alcohol dehydrogenase (ADH). In another embodiment, the L-threonine ammonia lyase catalyzes the substrate to product conversion of L-threonine to 2-oxybutanoate and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butryaldehyde and the ADH catalyzes the substrate to product conversion of butyraldehyde to 1-butanol. In another embodiment, the L-threonine ammonia lyase comprises an amino acid sequence having at least 90% sequence homology to SEQ ID NO:56, the 2-ethylmalate synthase comprises an amino acid sequence having at least 90% sequence homology to SEQ ID NO:58, the isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In certain other embodiments, the one or more polynucleotide ORFs introduced in step (b) encode the complete 1-butanol pathway comprising L-threonine ammonia lyase, 2-ethylmalate synthase, isopropylmalate isomerase, 3-isopropylmalate dehydrogenase, 2-ketoacid decarboxylase (KDC) and alcohol dehydrogenase (ADH). In other embodiments a method for producing 1-butanol from a methane substrate further comprises the step of recovering the 1-butanol produced.

In another embodiment, the invention is directed to a method for producing 1-butanol from a methane substrate comprising the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce 1-butanol. In certain embodiments, the one or more polynucleotide ORFs introduced in step (b) encode an 1-butanol pathway polypeptide selected from an Enzyme Class (EC) comprising EC 4.3.1.19, EC 2.3.3.6, EC 4.2.1.33, EC 1.1.1.85, EC 4.1.1.72, and EC 1.1.1.1. In another embodiment, the one or more polynucleotide ORFs introduced in step (b) encode a 1-butanol pathway polypeptide selected from the group consisting of L-threonine ammonia lyase, 2-ethylmalate synthase, isopropylmalate isomerase, 3-isopropylmalate dehydrogenase, 2-ketoacid decarboxylase (KDC) and alcohol dehydrogenase (ADH). In yet other embodiments, the L-threonine ammonia lyase catalyzes the substrate to product conversion of L-threonine to 2-oxybutanoate and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butryaldehyde and the ADH catalyzes the substrate to product conversion of butyraldehyde to 1-butanol. In other embodiments, the L-threonine ammonia lyase comprises an amino acid sequence having at least 90% sequence homology to SEQ ID NO:56, the 2-ethylmalate synthase comprises an amino acid sequence having at least 90% sequence homology to SEQ ID NO:58, the isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In another embodiment, the methane monooxygenase (MMO) is a soluble MMO of Enzyme Class EC 1.14.13.25 or a particulate MMO of Enzyme Class 1.14.18.3. In certain other embodiments, the MMO comprises an amino acid sequence comprising at least 90% sequence homology to a particulate methane monooxygenase (pMMO) selected from the group consisting of SEQ ID NO:12, SEQ ID NO:14, SEQ ID NO: 16, SEQ ID NO:18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO:32 and SEQ ID NO:34. In other embodiments a method for producing 1-butanol from a methane substrate further comprises the step of recovering the 1-butanol produced.

In certain other embodiments, the invention is directed to a method for producing fatty alcohols from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a fatty-acyl-CoA reductase (FAR), and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol. In one embodiment, the FAR polypeptide is further defined as a polypeptide from Enzyme Class EC 1.2.1.50. In another embodiment, the FAR polypeptide catalyzes the substrate to product conversion of fatty acetyl-CoA to a fatty alcohol. In yet other embodiments, the FAR polypeptide comprises an amino acid sequence having at least 90% sequence homology to SEQ ID NO:66. In other embodiments a method for producing fatty alcohols from a methane substrate further comprises the step of recovering the fatty alcohol produced.

In certain other embodiments, the invention is directed to a method for producing a fatty alcohol from a methane substrate comprising the steps of (a) providing a non-methanotroph host microorganism which has been genetically engineered to express a methane monooxygenase (MMO), (b) introducing into the host microorganism and expressing a polynucleotide open reading frame (ORF), under the control of suitable regulatory sequences, wherein the polynucleotide ORF encodes a fatty-acyl-CoA reductase (FAR), and (c) feeding the host microorganism of step (b) a methane substrate under suitable growth conditions, wherein the host metabolizes methane to formaldehyde as set forth in step (a), wherein the formaldehyde is converted to acetyl-CoA by means of an endogenous RUMP or serine pathway and the host metabolizes acetyl-CoA to produce a fatty alcohol. In certain embodiments, the FAR polypeptide catalyzes the substrate to product conversion of fatty acetyl-CoA to a fatty alcohol. In certain other embodiments, the FAR polypeptide comprises an amino acid sequence comprising at least 90% sequence homology to SEQ ID NO:66. In another embodiment, the methane monooxygenase (MMO) is a soluble MMO of Enzyme Class EC 1.14.13.25 or a particulate MMO of Enzyme Class 1.14.18.3. In other embodiments, the MMO comprises an amino acid sequence having at least 90% sequence homology to a particulate methane monooxygenase (pMMO) selected from the group consisting of SEQ ID NO:12, SEQ ID NO:14, SEQ ID NO: 16, SEQ ID NO:18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO:32 and SEQ ID NO:34. In other embodiments a method for producing fatty alcohols from a methane substrate further comprises the step of recovering the fatty alcohol produced.

In another embodiment, the invention is directed to a method for producing a fatty acid ester from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a wax ester synthase (WES) and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes fatty acyl-CoA and alcohols to produce a fatty acid ester. In certain embodiments, the WES polypeptide is further defined as a polypeptide from Enzyme Class EC 2.3.1.75. In another embodiment, the WES polypeptide catalyzes the substrate to product conversion of fatty acyl-CoA and alcohols to fatty acid esters. In other embodiments, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78. In other embodiments a method for producing fatty acid esters from a methane substrate further comprises the step of recovering the fatty acid esters produced.

In another embodiment, the invention is directed to a method for producing a fatty acid ester from a methane substrate comprising the steps of (a) providing a non-methanotroph host microorganism which has been genetically engineered to express a methane monooxygenase (MMO), (b) introducing into the host microorganism and expressing at least one polynucleotide open reading frame (ORF), under the control of suitable regulatory sequences, wherein the at least one polynucleotide ORF encodes a wax ester synthase (WES) and (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to acetyl-CoA through an endogenous RuMP or serine pathway and the host metabolizes fatty acyl-CoA and alcohols to produce a fatty acid ester. In certain embodiments, the WES polypeptide catalyzes the substrate to product conversion of fatty acyl-CoA and alcohols to fatty acid esters. In certain embodiments, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78. In another embodiment, the methane monooxygenase (MMO) is a soluble MMO of Enzyme Class EC 1.14.13.25 or a particulate MMO of Enzyme Class 1.14.18.3. In other embodiments, the MMO comprises an amino acid sequence having at least 90% sequence homology to a particulate methane monooxygenase (pMMO) selected from the group consisting of SEQ ID NO:12, SEQ ID NO:14, SEQ ID NO: 16, SEQ ID NO:18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO:32 and SEQ ID NO:34. In other embodiments a method for producing fatty acid esters from a methane substrate further comprises the step of recovering the fatty acid esters produced.

In certain other embodiments, the invention is directed to a method for producing 2,3-butanediol from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the host and expressing a polynucleotide ORF, under the control of suitable regulatory sequences, wherein the ORF encodes a (2R,3R)-2,3-butanediol dehydrogenase (BDH1), and (c) feeding the host microorganism of step (b) a methane substrate under suitable growth conditions, wherein host metabolizes methane to formaldehyde as set forth in step (a), wherein the formaldehyde is converted to pyruvate by means of an endogenous type I RuMP pathway or a type II serine pathway and the host metabolizes pyruvate to produce (R)-acetoin and the BDH1 catalyzes the substrate to product conversion of (R)-acetoin to 2,3-butanediol. In certain embodiments, the (2R,3R)-2,3-butanediol dehydrogenase (BDH1) has at least 90% sequence homology to a BDH1 polypeptide of SEQ ID NO:157. In other embodiments, the polynucleotide ORF comprises a nucleotide sequence of SEQ ID NO:156. In other embodiments a method for producing 2,3-butanediol from a methane substrate further comprises the step of recovering the 2,3-butanediol produced.

In certain embodiments, a methanotroph host microorganism of the invention is selected from genus consisting of *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis,* and *Methyloacidophilum*. In other embodiments, the methanotroph host microorganism is selected from the phylum *Verrucomicrobia*. In another embodiment, the methanotroph host is *Methylococcus capsulatus*, strain Bath.

In certain other embodiments, a non-methanotroph host microorganism of the invention is a yeast microorganism or bacterial microorganism. In certain embodiments, the non-methanotroph yeast microorganism is selected from *Saccharomyces cerevisiae, Hansenuela polymorpha, Pichia pastoris* and *Kluyveromyces lactis*. In one particular embodiment, the yeast microorganism is *Pichia pastoris*.

In certain other embodiments, a non-methanotrophic bacterial microorganism of the invention is *Pseudomonas putida, Cupriavidus metallidurans* or *Rhodobacter sphaeroides*.

In other embodiments, recovering the isobutanol produced according to the methods of the invention is a process selected from distillation, liquid extraction, flash evaporation, membrane separation and phase separation.

In other embodiments, recovering the 1-butanol produced according to the methods of the invention is a process selected from distillation, liquid extraction, flash evaporation, membrane separation and phase separation.

In another embodiment, recovering the fatty alcohol produced according to the methods of the invention is a process selected from flash evaporation, membrane separation, centrifugation and phase separation.

In certain other embodiments, recovering the fatty acid ester produced according to the methods of the invention is a process selected from flash evaporation, membrane separation, centrifugation and phase separation.

In another embodiment, recovering the 2,3-butanediol produced according to the methods of the invention is a process selected from steam stripping, solvent extraction, aqueous two-phase extraction, reactive extraction and pervaporation.

In certain other embodiments, a methane substrate is provided as a dry natural gas, as a wet natural gas or as a biogas.

In other embodiments, the host microorganism is grown by a batch process, a fed-batch process or a continuous perfusion process.

In another embodiment, the fatty alcohol composition produced according to the methods of the invention comprises a carbon chain of about 5 to about 40 carbon atoms. In certain embodiments, the fatty alcohol comprises a carbon chain of 8 to 22 carbon atoms.

In another embodiment, the fatty acid ester composition produced according to the methods of the invention has a fatty acid moiety comprising a carbon chain of about 5 to about 40 carbon atoms. In one particular embodiment, the fatty acid moiety comprises a carbon chain of 8 to 22 carbon atoms.

In yet other embodiments, the fatty acid ester composition produced according to the methods of the invention has an alcohol moiety comprising a carbon chain of about 5 to about 40 carbon atoms. In one particular embodiment, the alcohol moiety comprises a chain of 8 to 22 carbon atoms.

In yet other embodiments, a non-methanotroph host microorganism of the invention is further engineered to express an exogenous methanol dehydrogenase (MDH). In certain embodiments, the MDH is a polypeptide from Enzyme Class 1.14.18.3. In other embodiments, the MDH comprises an amino acid sequence having at least 90% sequence homology to a MDH polypeptide selected from the group consisting of SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52 and SEQ ID NO:54.

In other embodiments, the invention is directed to a substantially purified isobutanol composition produced according to the methods of the invention.

In another embodiment, the invention is directed to a substantially purified 1-butanol composition produced according to the methods of the invention.

In other embodiments, the invention is directed to a substantially purified fatty alcohol composition produced according to the methods of the invention.

In another embodiment, the invention is directed to a substantially purified fatty acid ester composition produced according to the methods of the invention.

In other embodiments, the invention is directed to a substantially purified 2,3-butanediol composition produced according to the methods of the invention.

In yet other embodiments, the invention is directed to an isobutanol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in an isobutanol pathway, and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce isobutanol.

In another embodiment, the invention is directed to an isobutanol producing non-methanotroph host microorganism manufactured according to the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in an isobutanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce isobutanol.

In yet other embodiments, the invention is directed to a 1-butanol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce 1-butanol.

In other embodiments, the invention is directed to a 1-butanol producing non-methanotroph host microorganism manufactured according to the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce 1-butanol.

In another embodiment, the invention is directed to a fatty alcohol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a fatty-acyl-CoA reductase (FAR), and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol.

In other embodiments, the invention is directed to a fatty alcohol producing non-methanotroph host microorganism manufactured according to the steps of (a) providing a non-methanotroph host microorganism which has been genetically engineered to express a methane monooxygenase (MMO), (b) introducing into the host microorganism and expressing a polynucleotide open reading frame (ORF), under the control of suitable regulatory sequences, wherein the polynucleotide ORF encodes a fatty-acyl-CoA reductase (FAR), and (c) feeding the host microorganism of step (b) a methane substrate under suitable growth conditions, wherein the host metabolizes methane to formaldehyde as set forth in step (a), wherein the formaldehyde is converted to acetyl-CoA by means of an endogenous RuMP or serine pathway and the host metabolizes acetyl-CoA to produce a fatty alcohol.

In another embodiment, the invention is directed to a fatty acid ester producing methanotroph host microorganism manufactured according to the the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a wax ester synthase (WES) and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes fatty acyl-CoA and alcohols to produce a fatty acid ester.

In certain other embodiments, the invention is directed to a fatty acid ester producing non-methanotroph host microorganism manufactured according to the steps of (a) providing a non-methanotroph host microorganism which has been genetically engineered to express a methane monooxygenase (MMO), (b) introducing into the host microorganism and expressing at least one polynucleotide open reading frame (ORF), under the control of suitable regulatory sequences, wherein the at least one polynucleotide ORF encodes a wax ester synthase (WES) and (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to acetyl-CoA through an endogenous RuMP or serine pathway and the host metabolizes fatty acyl-CoA and alcohols to produce a fatty acid ester.

In certain other embodiments, the invention is directed to a 2,3-butanediol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the host and expressing a polynucleotide ORF, under the control of suitable regulatory sequences, wherein the ORF encodes a (2R,3R)-2,3-butanediol dehydrogenase (BDH1), and (c) feeding the host microorganism of step (b) a methane substrate under suitable growth conditions, wherein host metabolizes methane to formaldehyde as set forth in step (a), wherein the formaldehyde is converted to pyruvate by means of an endogenous type I RuMP pathway or a type II serine pathway and the host metabolizes pyruvate to produce (R)-acetoin and the BDH1 catalyzes the substrate to product conversion of (R)-acetoin to 2,3-butanediol.

BRIEF DESCRIPTION OF THE DRAWINGS

Certain embodiments of the invention are illustrated in the drawings, in which.

DETAILED DESCRIPTION OF THE INVENTION

Figure 1:
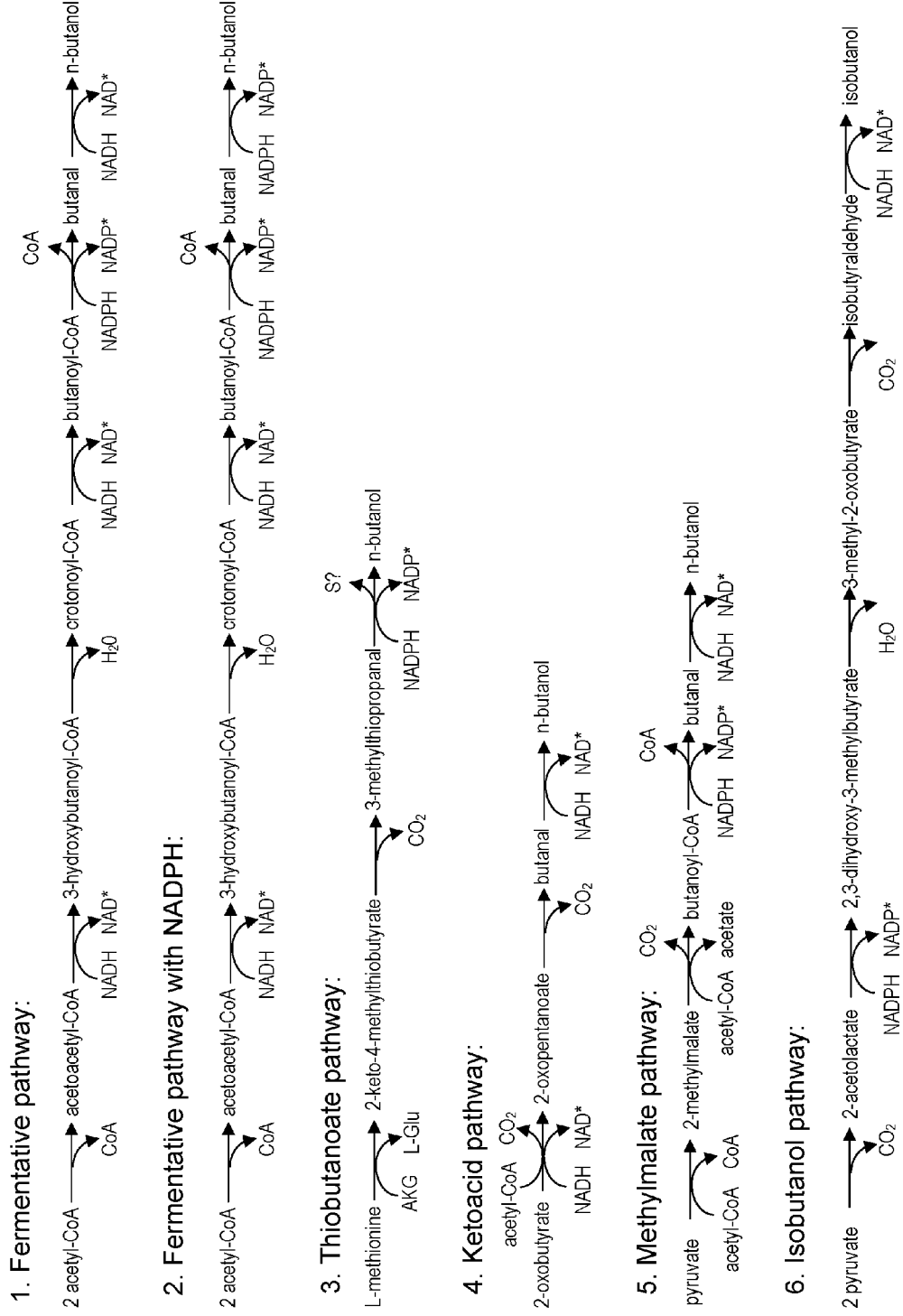
FIG. 1 depicts live pathways for the biosynthetic production of n-butanol (1-butanol) and one pathway for the biosynthetic production of isobutanol.

Unless defined otherwise, all technical and scientific terms used herein have the same meaning as commonly understood to one of ordinary skill in the art to which this disclosure pertains. Although methods and materials similar or equivalent to those described herein can be used in the practice of the disclosed methods and compositions, the exemplary methods, devices and materials are described herein.

In certain embodiments, the present invention is directed to host microorganisms metabolically engineered to produce multi-carbon compounds. Multi-carbon compounds such as ethanol, n-butanol, sec-butanol, isobutanol, tert-butanol, fatty (or aliphatic long chain) alcohols, fatty acid methyl esters, 2,3-butanediol and the like, are important industrial commodity chemicals with a variety of applications, including, but not limited to their use in fuels (e.g., bio-fuel, bio-diesel) and bio-based chemicals. The present invention addresses a number of commercial, industrial and environmental needs in the art related to the production of multi-carbon compounds.

As set forth herein, the metabolically engineered host microorganisms of the present invention utilize methane ($CH_4$) as their sole carbon source (i.e., the host microorganism does not require plant based feedstocks for growth and energy) and ameliorate much of the ongoing depletion of arable food source "farmland" currently being diverted to grow bio-fuel feedstocks, and as such, improve the environmental footprint of future bio-fuel, bio-diesel and bio-based chemical compositions. Furthermore, use of the metabolically engineered host microorganisms set forth in the present invention (which utilize methane as the sole carbon source) mitigate current industry practices and methods of producing multi-carbon compounds from petroleum or petroleum-derived feedstocks.

Thus, in certain embodiments of the invention, a host microorganism is genetically engineered to produce multi-carbon compounds. As is known in the art, methanotrophic organisms are able to metabolize methane as their primary source of carbon and energy, can grow aerobically or anaerobically, and require single-carbon compounds (e.g., methane, $CH_4$; methanol, $CH_3OH$ and/or formaldehyde, $H_2C=O$) to survive. In particular embodiments, a host microorganism of the invention is a methanotroph. As defined herein, a "methanotroph", a "methanotrophic" or a "methanophile" host microorganism of the invention is a "prokaryotic microorganism which can metabolize methane as its primary source of carbon and energy".

In other embodiments, the host microorganism of the invention is a non-methanotrophic microorganism genetically engineered to metabolize methane as its only source of carbon and energy. As defined herein, a "non-methanotroph" host microorganism of the invention is a host microorganism which "cannot metabolize (or utilize) methane as its sole carbon source", until the "non-methanotroph" host microorganism has been genetically modified or engineered according to the methods of the present invention. As further defined herein, a "non-methanotroph" host microorganism of the invention includes any prokaryotic and eukaryotic microbial species which comprise a complete or partial "endogenous ribulose monophosphate (RuMP) pathway, a serine pathway or a mixed RuMP/serine pathway" (e.g., see RuMP, serine and mixed (Type X) pathways described below). In certain embodiments, a "non-methanotroph" host microorganism of the invention includes prokaryotic and eukaryotic microbial species from the Domains Archaea, Bacteria and Eucarya, wherein the Domain Eucarya includes yeast, filamentous fungi, protozoa, algae or higher Protista. The terms "microbial" and "microbes" are used interchangeably with the term "microorganism".

As defined herein, the phrase "providing a methanotrophic host microorganism that metabolizes methane to methanol and metabolizes methanol to formaldehyde" refers to an "endogenous enzymatic activity encoded by one or more endogenous genes of the methanotroph host microorganism". For example, an endogenous enzyme (or polypeptide) encoded by one or more endogenous genes of a methanotroph host microorganism include a methane monooxygenase (MMO) enzyme (which metabolizes (or converts) methane to methanol) and a methanol dehydrogenase (MDH) enzyme (which metabolizes (or converts) methanol to formaldehyde). Stated another way, the phrase "providing a methanotrophic host microorganism that metabolizes methane to methanol and metabolizes methanol to formaldehyde" does not require the introduction of exogenous (or heterologous) genes encoding single-carbon (C1) oxidizing enzymes (or polypeptides), as such enzymes and the activity thereof are inherent (endogenous) attributes of a methanotrophic host microorganism of the invention.

Furthermore, as is known in the art, a "methanotrophic host microorganism" of the invention comprises endogenous genes encoding at least a Type I methanotroph RuMP pathway and/or a Type II methanotroph serine pathway. In general, Type I methanotrophs (e.g., *Methylomonas, Methylomicrobium, Methylobacter, Methylocaldum, Methylosphaera*) assimilate formaldehyde produced (i.e., from the oxidation of methane to methanol and methanol to formaldehyde), using the ribulose monophosphate pathway (RuMP), whereas Type II methanotrophs (e.g., *Methylocystis* and *Methylosinus*) assimilate formaldehyde produced (i.e., from the oxidation of methane to methanol and methanol to formaldehyde), using the serine pathway. Lastly, the genus *Methylococcus* are known to comprise a combination of characteristics of both Type I methanotroph (RuMP) pathway and Type II methanotroph (serine) pathway.

The ribulose monophosphate pathway (RuMP) was originally identified in methanotrophic bacteria, as described above. However, more recent genome sequence analysis of various microorganisms have revealed that the key enzymes of the RuMP pathway (e.g., 3-hexulose-6-phosphate (HPS), 6-phospho-3-hexuloisomerase (PHI)) are widely distributed (i.e., endogenous) among "non-methanotrophic" bacteria and archaeal genomes (Orita et al., 2006).

As defined herein, the phrases "recombinant host microorganism", "genetically engineered host microorganism", "engineered host microorganism" and "genetically modified host microorganism" may be used interchangeably and refer to host microorganisms that have been genetically modified to (a) express one or more exogenous polynucleotides, (b) over-express one or more endogenous and/or one or more exogenous polynucleotides, such as those included in a vector, or which have an alteration in expression of an endogenous gene or (c) knock-out or down-regulate an endogenous gene. In addition, certain genes may be physically removed from the genome (e.g., knock-outs) or they may be engineered to have reduced, altered or enhanced activity.

The terms "engineer", "genetically engineer" or "genetically modify" refer to any manipulation of a microorganism that results in a detectable change in the microorganism, wherein the manipulation includes, but is not limited to, introducing non-native metabolic functionality via heterologous (exogenous) polynucleotides or removing native-functionality via polynucleotide deletions, mutations or knock-outs. The term "metabolically engineered" generally involves rational pathway design and assembly of biosynthetic genes (or ORFs), genes associated with operons, and control elements of such polynucleotides, for the production of a desired metabolite. "Metabolically engineered" may further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

As defined herein, the term "introducing", as used in phrases such as "introducing into the methanotroph host" or "introducing into the non-methanotroph host" at least one polynucleotide open reading frame (ORF) or a gene thereof or a vector thereof includes methods known in the art for introducing polynucleotides into a cell, including, but not limited to transformation (e.g., calcium chloride, electroporation), transduction, transfection, conjugation and the like.

The phrases "metabolically engineered microorganism" and "modified microorganism" are used interchangeably herein, and refer not only to the particular subject host cell, but to the progeny or potential progeny of such a cell. Because certain modifications may occur in succeeding generations due to either mutation or environmental influences, such progeny may not, in fact, be identical to the parent cell, but are still included within the scope of the term as used herein.

The term "mutation" as used herein indicates any modification of a nucleic acid and/or polypeptide which results in an altered nucleic acid or polypeptide (i.e., relative to the wild-type nucleic acid or polypeptide sequence). Mutations include, for example, point mutations, substitutions, deletions, or insertions of single or multiple residues in a polynucleotide (or the encoded polypeptide), which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In certain embodiments, a portion of a genetically modified microorganism's genome may be replaced with one or more heterologous (exogenous) polynucleotides. In some embodiments, the mutations are naturally-occurring. In other embodiments, the mutations are the results of artificial selection pressure. In still other embodiments, the mutations in the microorganism genome are the result of genetic engineering.

The term "expression" or "expressed" with respect to a gene sequence, an ORF sequence or polynucleotide sequence, refers to transcription of the gene, ORF or polynucleotide and, as appropriate, translation of the resulting mRNA transcript to a protein. Thus, as will be clear from the context, expression of a protein results from transcription and translation of the open reading frame sequence. The level of expression of a desired product in a host microorganism may be determined on the basis of either the amount of corresponding mRNA that is present in the host, or the amount of the desired product encoded by the selected sequence. For example, mRNA transcribed from a selected sequence can be quantitated by PCR or by northern hybridization (see Sambrook et al., Molecular Cloning: A Laboratory Manual, Cold Spring Harbor Laboratory Press, 1989). Protein encoded by a selected sequence can be quantitated by various methods (e.g., by ELISA, by assaying for the biological activity of the protein, or by employing assays that are independent of such activity, such as western blotting or radioimmunoassay, using antibodies that are recognize and bind reacting the protein).

The term "endogenous", as used herein with reference to polynucleotides (and the polypeptides encoded therein), indicates polynucleotides and polypeptides that are expressed in the organism in which they originated (i.e., they are innate to the organism). In contrast, the terms "heterologous" and "exogenous" are used interchangeably, and as defined herein with reference to polynucleotides (and the polypeptides encoded therein), indicates polynucleotides and polypeptides that are expressed in an organism other than the organism from which they (i.e., the polynucleotide or polypeptide sequences) originated or where derived.

The term "feedstock" is defined as a raw material or mixture of raw materials supplied to a microorganism, or fermentation process, from which other products can be made. For example, as set forth in the present invention, a methane carbon source or a methanol carbon source or a formaldehyde carbon source, either alone or in combination, are feedstocks for a microorganism that produces a bio-fuel or bio-based chemical in a fermentation process. However, in addition to a feedstock (e.g., a methane substrate) of the invention, the fermentation media contains suitable minerals, salts, cofactors, buffers and other components, known to those skilled in the art, suitable for the growth of the cultures and promotion of the enzymatic pathways necessary for multi-carbon compound production.

The term "substrate" refers to any substance or compound that is converted, or meant to be converted, into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material (e.g., methane), but also intermediate and end product metabolites used in a pathway associated with a metabolically engineered microorganism as described herein.

The term "fermentation" or "fermentation process" is defined as a process in which a host microorganism is cultivated in a culture medium containing raw materials, such as feedstock and nutrients, wherein the microorganism converts raw materials, such as a feedstock, into products.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, including DNA, RNA, ORFs, analogs and fragments thereof.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) of more codons representing amino acids, and (iii) a termination codon, the ORF being read (or translated) in the 5' to 3' direction.

It is understood that the polynucleotides described herein include "genes" and that the nucleic acid molecules described herein include "vectors" or "plasmids". Accordingly, the term "gene", refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "promoter" refers to a nucleic acid sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "codon-optimized" as it refers to genes or coding regions of nucleic acid molecules (or ORFs) for transformation of various hosts, refers to the alteration of codons in the gene or coding regions of the nucleic acid molecules to reflect the typical codon usage of the host organism without altering the polypeptide encoded by the DNA.

The term "operon" refers to two or more genes which are transcribed as a single transcriptional unit from a common promoter. In certain embodiments, the genes, polynucleotides or ORFs comprising the operon are contiguous genes. It is understood that transcription of an entire operon can be modified (i.e., increased, decreased, or eliminated) by modifying the common promoter. Alternatively, any gene, polynucleotide or ORF, or any combination thereof in an operon can be modified to alter the function or activity of the encoded polypeptide. The modification can result in an increase or a decrease in the activity or function of the encoded polypeptide. Further, the modification can impart new activities on the encoded polypeptide.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes", that is, that replicate autonomously or can integrate into a chromosome of a host microorganism. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

The term "homolog", as used with respect to an original enzyme, polypeptide, gene or polynucleotide (or ORF encoding the same) of a first family or species, refers to distinct enzymes, genes or polynucleotides of a second family or species, which are determined by functional, structural or genomic analyses to be an enzyme, gene or polynucleotide of the second family or species, which corresponds to the original enzyme or gene of the first family or species. Most often, "homologs" will have functional, structural or genomic similarities. Techniques are known by which homologs of an enzyme, gene or polynucleotide can readily be cloned using genetic probes and PCR. Identity of cloned sequences as "homologs" can be confirmed using functional assays and/or by genomic mapping of the genes.

A polypeptide (or protein or enzyme) has "homology" or is "homologous" to a second polypeptide if the nucleic acid sequence that encodes the polypeptide has a similar sequence to the nucleic acid sequence that encodes the second polypeptide. Alternatively, a polypeptide has homology to a second polypeptide if the two proteins have "similar" amino acid sequences. Thus, the terms "homologous proteins" or "homologous polypeptides" is defined to mean that the two polypeptides have similar amino acid sequences. In certain embodiments of the invention, polynucleotides and polypeptides homologous to one or more polynucleotides and/or polypeptides set forth in Table 1 may be readily identified using methods known in the art for sequence analysis and comparison.

A homologous polynucleotide or polypeptide sequence of the invention may also be determined or identified by BLAST analysis (Basic Local Alignment Search Tool) or similar bioinformatic tools, which compare a query nucleotide or polypeptide sequence to a database of known sequences. For example, a search analysis may be done using BLAST to determine sequence identity or similarity to previously published sequences, and if the sequence has not yet been published, can give relevant insight into the function of the DNA or protein sequence.

Bioconversion of Methane to Multi-Carbon Compounds

In general, the conversion of methane ($CH_4$) to multi-carbon compounds such as isobutanol (($CH_3$)$_2$CHCH$_2$OH), 1-butanol or n-butanol ($CH_3CH_2CH_2CH_2OH$), ethanol ($CH_3CH_2OH$), fatty alcohols, fatty acid esters, 2,3-butanediol and the like, using a "methanotrophic host microorganism" requires at least the following three steps, all of which are innate (or endogenous) with respect to methanotrophic organisms: (1) a methane ($CH_4$) substrate is oxidized to methanol ($CH_3OH$) via a methane monooxygenase (MMO) (e.g., particulate methane monooxygenase (pMMO) or soluble methane monooxygenase (sMMO)), (2) the methanol ($CH_3OH$) is oxidized to formaldehyde ($H_2C=O$) via methanol dehydrogenase (MDH) and (3) the formaldehyde ($H_2C=O$) produced in step (2) above is assimilated into a central metabolism pathway (e.g., see type I (RuMP) and type II (serine) pathways described below).

In certain embodiments of the invention, a host microorganism is a methanotroph, which endogenously expresses a methane monooxygenase (MMO) enzyme and a methanol dehydrogenase (MDH) enzyme. In other embodiments of the invention, a host microorganism of the invention is a "non-methanotrophic" prokaryotic microorganism (e.g., a non-methanotrophic bacteria or archaea) or a eukaryotic microorganism (e.g., fungi and algae) engineered to utilize a methane substrate (as sole carbon source) for growth and energy. Thus, in certain embodiments of the invention, a "non-methanotrophic" microorganism is engineered to express (or over-express) an exogenous methane monooxygenase (MMO), an enzyme requisite to metabolize methane to methanol. The non-methanotroph host microorganisms of the invention comprise an endogenous dehydrogenase (MDH) enzyme, which converts methanol to formaldehyde. However, in certain embodiments, the "non-methanotroph" microorganism is further engineered to express an exogenous methanol dehydrogenase (MDH) enzyme, which converts methanol to formaldehyde. The expression of the exogenous MDH enzyme in a non-methanotroph host is not a strict requirement for the utilization of the methane substrate, but it is contemplated in certain embodiments, that the introduction and expression of an exogenous MDH in a non-methanotroph host thereof may facilitate, under certain growth conditions, the production of one or more multi-carbon compounds of the invention.

As mentioned briefly above with regard to methanotrophic host organisms, there are at least two known pathways (i.e., the ribulose monophosphate (RuMP) pathway and the serine pathway; Hanson & Hanson, 1996) for the assimilation of formaldehyde into central metabolism. In the Type I methanotroph RuMP pathway, formaldehyde combines with ribulose-5-phosphate to form hexulose-6-phosphate (catalyzed via hexulose-6-phosphate synthase), the hexulose-6-phosphate is then isomerized to fructose-6-phosphate (catalyzed via hexulose phosphate isomerase), which is an intermediate of a central metabolic pathway (i.e., glycolysis pathway). In the type II methanotroph serine pathway, formaldehyde reacts with terahydrofolate (THF) to form methylene-THF, the methylene-THF is then transferred to L-glycine to form L-serine, and finally the L-serine is transferred to glyoxylate to form hydroxypyruvate. The hydroxypyruvate formed is subsequently converted to 2-phosphoglycerate (catalyzed via hydroxypruvate reductase), which is an central metabolism intermediate of the glycolytic pathway.

Likewise, as mentioned briefly above, an endogenous pathway, which functions similarly (or analogous) to the ribulose monophosphate (RuMP) pathway in methanotrophs is also present in "non-methanotrophic" prokaryotes (Orita et al., 2006), wherein formaldehyde is fixed with ribulose 5-phosphate to form hexulose-6-phosphate (catalyzed via hexulose-6-phosphate synthase (HPS)) and then isomerized to fructose-6-phosphate (catalyzed via hexulose phosphate isomerase (PHI)), which is an intermediate of a central metabolic pathway. Thus, in certain preferred embodiments, a "non-methanotrophic" host microorganism of the invention comprises an endogenous RuMP pathway or an endogenous pathway analogous to the RuMP pathway. As defined herein, a pathway analogous to the RuMP pathway comprises at least a gene, polynucleotide or ORF encoding an enzyme having hexulose-6-phosphate synthase (HPS) activity from enzyme class EC 4.1.2.43 and at least a gene, polynucleotide or ORF encoding a an enzyme having hexulose phosphate isomerase (PHI) activity from enzyme class 5.3.1.27.

In other embodiments, wherein a "non-methanotrophic" host microorganism genome does not encode endogenous enzymes having HPS and PHI activity, the non-methanotroph host microorganism is genetically modified to express HPS and PHI enzymes. Thus, in certain embodiments, a gene, polynucleotide or ORF encoding a hexulose-6-phosphate synthase (HPS) is provided, wherein the gene, polynucleotide or ORF encodes a HPS polypeptide of enzyme class EC 4.1.2.43. In other embodiments, a gene, polynucleotide or ORF encoding a hexulose-6-phosphate synthase (HPS) is provided, wherein the gene, polynucleotide or ORF encodes a HPS polypeptide having at least 90% sequence homology to a *M. capsulatus* (Bath) HPS polypeptide of SEQ ID NO:173. In other embodiments, a gene, polynucleotide or ORF encoding a hexulose phosphate isomerase (PHI) is provided, wherein the gene, polynucleotide or ORF encodes a PHI polypeptide of enzyme class EC 5.3.1.27. In other embodiments, a gene, polynucleotide or ORF encoding a hexulose phosphate isomerase (PHI) is provided, wherein the gene, polynucleotide or ORF encodes a *M. capsulatus* (Bath) PHI polypeptide having at least 90% sequence homology to a PHI (also referred to as a sugar isomerase (SIS) domain) polypeptide of SEQ ID NO:175.

Once the formaldehyde has been assimilated into a central metabolic pathway of the methanotroph or non-methanotroph host organism (as described above), the fourth and final step for producing multi-carbon compounds from a methane substrate as described in steps (1)-(3) above, is the introduction of one or more nucleic acids into the host microorganism, wherein the one or more nucleic acids introduced encode one or more enzymes of a relevant multi-carbon compound pathway. Independent of the compound to be produced according to the present invention (e.g., isobutanol, 1-butanol, ethanol, fatty alcohols, fatty acid methyl esters, 2,3-butanediol and the like), any multi-carbon pathway introduced into a host microorganism must utilize a central metabolic molecule (e.g., pyruvate, acetyl-CoA, methionine and oxobutyrate) previously assimilated and introduced into the metabolic pathway through steps (1)-(3) described above. Stated another way, a salient feature of the present invention is the ability of the host microorganism to utilize methane (as a sole carbon source for growth and energy) and to produce multi-carbon compounds (via engineered metabolic pathways introduced therein), without the need for additional or supplemental carbon sources such as carbohydrates.

As defined herein, a relevant "multi-carbon compound pathway", includes, but is not limited to, a 1-butanol pathway (which includes, but is not limited to, a fermentative 1-butanol pathway, a thiobutanoate pathway, a ketoacid pathway and a methylmalate pathway), an isobutanol pathway, a fatty alcohol pathway, a fatty acid methyl ester pathway and a 2,3-butanediol pathway. A "multi-carbon compound pathway" as further defined herein, may include one specific enzyme from the pathway, multiple enzymes from the pathway or all of the enzymes of the pathway. It will be understood by a person of skill in the art, that the selection of one or more specific pathway enzymes (and nucleic acids encoding the same) may be dependent on the host microorganism (e.g., certain methanotroph hosts or "non-methanotroph" hosts may endogenously encode and express one or more enzymes of a given pathway).

For example, FIG. 1 depicts five representative 1-butanol (i.e., n-butanol) pathways (pathways 1-5), wherein one or more nucleic acids encoding one or more enzymes of any of these pathways may be introduced into a methanotroph (or non-methanotroph) host microorganism and be expressed (or over-expressed) therein to yield 1-butanol. Similarly, FIG. 1 depicts an isobutanol pathway (pathway 6), wherein one or more nucleic acids encoding one or more enzymes of the isobutanol pathway may be introduced into a methanotroph (or non-methanotroph) host microorganism and expressed (or over expressed) therein to yield isobutanol. Further contemplated herein, is the introduction into a methanotroph (or non-methanotroph) host microorganism a combination of nucleic acids encoding one or more enzymes from a 1-butanol pathway and one or more enzymes from an isobutanol pathway.

As depicted in FIG. 1, at least five pathways are known to exist for converting one or more of these metabolic precursors into n-butanol (i.e., 1-butanol). The first synthesis pathway is the classical fermentative n-butanol pathway. Beginning with acetyl-CoA, this six step pathway requires three NADH and one NADHPH, but loses no carbon atoms to by-products formed. The second n-butanol synthesis pathway is the fermentative pathway, but using NADPH instead of NADH as the electron donor for the final conversion of butanal to n-butanol. The third potential n-butanol pathway is the thiobutanoate pathway, which begins with L-methionine, which is subsequently deaminated and then converted to n-butanol in two additional steps that involve loss of carbon dioxide ($CO_2$) and a sulfur (S) atom by an unknown mechanism. The fourth n-butanol pathway is the ketoacid pathway, which starting from L-threonine, n-butanol is synthesized in four steps, involving both reduction of $NAD^+$ and oxidation of NADH, while losing two $CO_2$. The fifth n-butanol synthesis pathway is the methylmalate pathway, which begins by combining pyruvate with acetyl-CoA to form citramalate (methylmalate), a reaction known to be catalyzed by LeuA in many bacteria, followed by conversion to butanoyl-CoA, which is then converted to n-butanol using the final two reactions of the fermentative pathway. Likewise, as depicted in FIG. 1, at least one isobutanol pathway is known in the art for synthesizing isobutanol from pyruvate, wherein the five-step pathway loses two carbon atoms as $CO_2$ per molecule of isobutanol synthesized.

Thus, in certain embodiments, the present invention is directed to a method for producing isobutanol from a methane substrate comprising the steps of (a) providing a methanotrophic host microorganism that metabolizes methane ($CH_4$) to methanol ($CH_3OH$) and methanol to formaldehyde ($H_2C=O$); (b) introducing into the methanotroph host and expressing at least one polynucleotide open reading frame (ORF), under the control of suitable regulatory sequences, wherein the at least one polynucleotide ORF encodes a polypeptide that catalyzes a reaction in an isobutanol pathway; (c) feeding the methanotroph host of step (b) a methane substrate under suitable growth conditions, wherein the host metabolizes methane to formaldehyde as set forth in step (a), wherein the formaldehyde is converted to pyruvate by means of an endogenous RuMP pathway or a serine pathway and the host metabolizes pyruvate to produce isobutanol, and (d) optionally recovering the isobutanol produced.

In one particular embodiment, the one or more polynucleotide ORFs introduced in step (b) encode an isobutanol pathway polypeptide thereof selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In certain embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol. In other embodiments, the ALS polypeptide comprises an amino acid sequence comprising at least 90% sequence homology to SEQ ID NO:2, the KARI polypeptide comprises an amino acid sequence comprising at least 90% sequence homology to SEQ ID NO:4, the DHAD polypeptide comprises an amino acid sequence comprising at least 90% sequence homology to SEQ ID NO:6, the KDC polypeptide comprises an amino acid sequence comprising at least 90% sequence homology to SEQ ID NO:8 and the ADH polypeptide comprises an amino acid sequence comprising at least 90% sequence homology to SEQ ID NO:10. In yet other embodiments, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In certain embodiments, the ORFs encoding the complete isobutanol pathway are comprised in one operon, two operons or three operons, wherein each operon may comprise the same promoter or a different promoter, wherein the same or different promoters may be constitutive or inducible.

In certain embodiments, a methanotroph host microorganism is modified or genetically engineered to express one or more enzymes of a metabolic pathway capable of producing n-butanol, isobutanol, fatty (or aliphatic long chain) alcohols, fatty acid methyl esters and the like. In particular embodiments, a methanotroph of the invention is selected from genera consisting of *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis* and *Methyloacidophilum*. In other embodiments, the methanotroph is from the phylum *Verrucomicrobia*. Previously published work has shown that several species within these taxa can be genetically transformed by introducing DNA constructs on plasmid vectors (Stafford et al., 2003), or by integrating them into the bacterial chromosome (Welander & Summons, 2012). Thus, a vector construct of the invention will typically comprise the pathway genes or polynucleotide ORFs, which are initially constructed and cloned into E. coli to generate sufficient quantities of the vector, and then the vectors are subsequently transformed into the host microorganism for expression.

In other embodiments, the invention is directed to a method for producing isobutanol from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host and expressing at least one polynucleotide open reading frame (ORF), under the control of suitable regulatory sequences, wherein the at least one polynucleotide ORF encodes a polypeptide that catalyzes a reaction in an isobutanol pathway; (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to pyruvate through an endogenous RuMP or serine pathway and the host metabolizes pyruvate to produce isobutanol, and (d) optionally recovering the isobutanol produced. Methods for heterologous expression of pMMO genes have been described in Gou et al. (2006). Methods for heterologous expression of sMMO genes have been described in Lloyd et al. (1999). Suitable microbial hosts for heterologous expression include microorganisms that have the ability to process methanol and formaldehyde, that have multiple heterotrophic growth modes, and/or that can assemble complex membranes and metalloprotein complexes. Such organisms include methylotrophic yeasts (e.g., Pichia pastoris) as well as bacteria such as Pseudomonas putida, Cupriavidus metallidurans and Rhodobacter sphaeroides.

In certain embodiments, the one or more polynucleotide ORFs introduced in step (b) above, encode an isobutanol pathway polypeptide selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In yet other embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol.

In one particular embodiment, the ALS polypeptide comprises an amino acid sequence comprising at least 90% sequence homology to SEQ ID NO:2, the KARI polypeptide comprises an amino acid sequence comprising at least 90% sequence homology to SEQ ED NO:4, the DHAD polypeptide comprises an amino acid sequence comprising at least 90% sequence homology to SEQ ID NO:6, the KDC polypeptide comprises an amino acid sequence comprising at least 90% sequence homology to SEQ ID NO:8 and the ADH polypeptide comprises an amino acid sequence comprising at least 90% sequence homology to SEQ ID NO:10. In certain other embodiments, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In another embodiment, the methane monooxygenase (MMO) is a soluble MMO of Enzyme Class EC 1.14.13.25 or a particulate MMO of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO:20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO:34).

In certain embodiments where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxaI (SEQ ID NO:42), mxaR (SEQ ID NO:44), mxaA (SEQ ID NO:46), mxaC (SEQ ID NO:48), mxaK (SEQ ED NO:50), mxaL (SEQ ID NO:52) or mcaD (SEQ ID NO:54).

In other embodiments, the invention is directed to a method for producing 1-butanol from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in a 1-butanol pathway; (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce 1-butanol, and (d) optionally recovering the 1-butanol produced. In certain embodiments, the one or more polynucleotide ORFs introduced in step (b) encode a 1-butanol pathway polypeptide selected from an Enzyme Class (EC) comprising EC 4.3.1.19, EC 2.3.3.6, EC 4.2.1.33, EC 1.1.1.85, EC 4.1.1.72, and EC 1.1.1.1. In another embodiment, the one or more polynucleotide ORFs introduced in step (b) encode a 1-butanol pathway polypeptide selected from the group consisting of L-threonine ammonia-lyase, 2-ethylmalate synthase (or 2-isopropylmalate synthase), isopropylmalate isomerase (or 3-isopropylmalate dehydratase), 3-isopropylmalate dehydrogenase, 2-ketoacid decarboxylase (KDC) and alcohol dehydrogenase (ADH). In certain other embodiments, L-threonine ammonia-lyase catalyzes the substrate to product conversion of L-threonine to 2-oxybutanoate (2-ketobutyrate) and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylnalate to 2-ketovalerate, $CO_2$ and NADH; the KDC catalyzes the substrate to product conversion of 2-ketovalerate to butryaldehyde and the ADH catalyzes the substrate to product conversion of butyraldehyde to 1-butanol.

In certain embodiments, a L-threonine ammonia-lyase comprises an amino acid sequence having at least 90% sequence homology to SEQ ID NO:56, a 2-ethylmalate synthase comprises an amino acid sequence having at least 90% sequence homology to SEQ ID NO:58, a isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In one particular embodiment, the one or more polynucleotide ORFs introduced in step (b) encode the complete I-butanol pathway comprising an L-threonine ammonia-lyase, a 2-ethylrnalate synthase, an isopropylmalate isomerase, a 3-isopropylmalate dehydrogenase, a KDC and an ADH.

In other embodiments, the invention is directed to a method for producing 1-butanol from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host and expressing at least one polynucleotide open reading frame (ORF), under the control of suitable regulatory sequences, wherein the at least one polynucleotide ORF encodes a polypeptide that catalyzes a reaction in a 1-butanol pathway; (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to pyruvate through an endogenous RuMP or serine pathway and the host metabolizes pyruvate to produce 1-butanol, and (d) optionally recovering the 1-butanol produced.

In certain embodiments, the non-methanotroph host microorganism is genetically modified to express an exogenous methane monooxygenase (MMO). In one embodiment, the methane monooxygenase is a soluble MMO (sMMO) of Enzyme Class EC 1.14.13.25 or a particulate MMO (pMMO) of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO:20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO:34).

In certain embodiments where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxaI (SEQ ID NO:42), mxaR (SEQ ID NO:44), mxaA (SEQ ID NO:46), mxaC (SEQ ID NO:48), mxaK (SEQ ID NO:50), mxaL (SEQ ID NO:52) or mcaD (SEQ ID NO:54).

In one particular embodiment, the one or more polynucleotide ORFs introduced in step (b) encode a 1-butanol pathway polypeptide selected from an Enzyme Class (EC) comprising EC 4.3.1.19, EC 2.3.3.6, EC 4.2.1.33, EC 1.1.1.85, EC 4.1.1.72, and EC 1.1.1.1. In another embodiment, the one or more polynucleotide ORFs introduced in step (b) encode a 1-butanol pathway polypeptide selected from the group consisting of L-threonine ammonia-lyase, 2-ethylmalate synthase (or 2-isopropylmalate synthase), isopropylmalate isomerase (or 3-isopropylmalate dehydratase), 3-isopropylmalate dehydrogenase, 2-ketoacid decarboxylase (KDC) and alcohol dehydrogenase (ADH). In certain other embodiments, L-threonine ammonia-lyase catalyzes the substrate to product conversion of L-threonine to 2-oxybutanoate (2-ketobutyrate) and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butryaldehyde and the ADH catalyzes the substrate to product conversion of butyraldehyde to 1-butanol.

In certain embodiments, a L-threonine ammonia-lyase comprises an amino acid sequence having at least 90% sequence homology to SEQ ID NO:56, a 2-ethylmalate synthase comprises an amino acid sequence having at least 90% sequence homology to SEQ ID NO:58, a isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In one particular embodiment, the one or more polynucleotide ORFs introduced in step (b) encode the complete 1-butanol pathway comprising an L-threonine ammonia-lyase, a 2-ethylrnalate synthase, an isopropylmalate isomerase, a 3-isopropylmalate dehydrogenase, a KDC and an ADH.

In certain other embodiments, the invention is directed to a method for producing fatty alcohols from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a fatty-acyl-CoA reductase (FAR); (c) feeding the methanotroph host of step (b) a methane substrate under suitable growth conditions, wherein the host metabolizes methane to formaldehyde as set forth in step (a), wherein the formaldehyde is converted to acetyl- CoA by means of an endogenous type I RuMP pathway or a type II serine pathway and the host metabolizes acetyl-CoA to produce a fatty alcohol, and (d) recovering the fatty alcohol produced. In certain embodiments, the FAR polypeptide is further defined as a polypeptide from Enzyme Class EC 1.2.1.50. In yet other embodiments, the FAR polypeptide catalyzes the substrate to product conversion of fatty acetyl-CoA to a fatty alcohol. In another embodiment, a FAR polypeptide comprises an amino acid sequence having at least 90% sequence homology to SEQ ID NO:66.

In still other embodiments, the invention is directed to a method for producing a fatty alcohol from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host microorganism and expressing a polynucleotide open reading frame (ORF), under the control of suitable regulatory sequences, wherein the polynucleotide ORF encodes a fatty-acyl-CoA reductase (FAR), (c) feeding the host microorganism of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol, and (d) optionally recovering the fatty alcohol produced.

In certain embodiments, the non-methanotroph host microorganism is genetically modified to express an exogenous methane monooxygenase (MMO). In one embodiment, the methane monooxygenase is a soluble MMO (sMMO) of Enzyme Class EC 1.14.13.25 or a particulate MMO (pMMO) of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO:20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO:34).

In certain embodiments, where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxaI (SEQ ID NO:42), mxaR (SEQ ID NO:44), mxaA (SEQ ID NO:46), mxaC (SEQ ID NO:48), mxaK (SEQ ID NO:50), mxaL (SEQ ID NO:52) or mcaD (SEQ ID NO:54).

In another embodiment, the invention is directed to a method for producing a fatty acid ester from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a wax ester synthase (WES); (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes fatty-acyl-CoA and alcohols to produce a fatty acid ester, and (d) recovering the fatty acid ester produced. In one particular embodiment, the WES polypeptide is further defined as a polypeptide from Enzyme Class EC 2.3.1.75. In another embodiment, the WES polypeptide catalyzes the substrate to product conversion of a fatty acid to a fatty acid esters. In another embodiment, the WES polypeptide catalyzes the substrate to product conversion of fatty alcohol and acyl-CoA to fatty acid esters. In one particular embodiment, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78.

In another embodiment, the invention is directed to a method for producing a fatty acid ester from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host microorganism and expressing at least one polynucleotide open reading frame (ORF), under the control of suitable regulatory sequences, wherein the at least one polynucleotide ORF encodes a wax ester synthase; (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, wherein the formaldehyde is converted to acetyl-CoA by means of an endogenous RuMP or serine pathway and the host metabolizes fatty-acyl-CoA and alcohols to produce a fatty acid ester, and (d) recovering the fatty acid ester produced.

In one particular embodiment, the WES polypeptide is further defined as a polypeptide from Enzyme Class EC 2.3.1.75. In another embodiment, the WES polypeptide catalyzes the substrate to product conversion of a fatty acid to a fatty acid ester. In another embodiment, the WES polypeptide catalyzes the substrate to product conversion of fatty alcohol and acyl-CoA to fatty acid esters. In one particular embodiment, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78.

In certain embodiments, the non-methanotroph host microorganism is genetically modified to express an exogenous methane monooxygenase (MMO). In one embodiment, the methane monooxygenase is a soluble MMO (sMMO) of Enzyme Class EC 1.14.13.25 or a particulate MMO (pMMO) of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO:20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO:34).

In certain embodiments, where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxaI (SEQ ID NO:42), mxaR (SEQ ID NO:44), mxaA (SEQ ID NO:46), mxaC (SEQ ID NO:48), mxaK (SEQ ID NO:50), mxaL (SEQ ID NO:52) or mcaD (SEQ ID NO:54).

Figure 9:
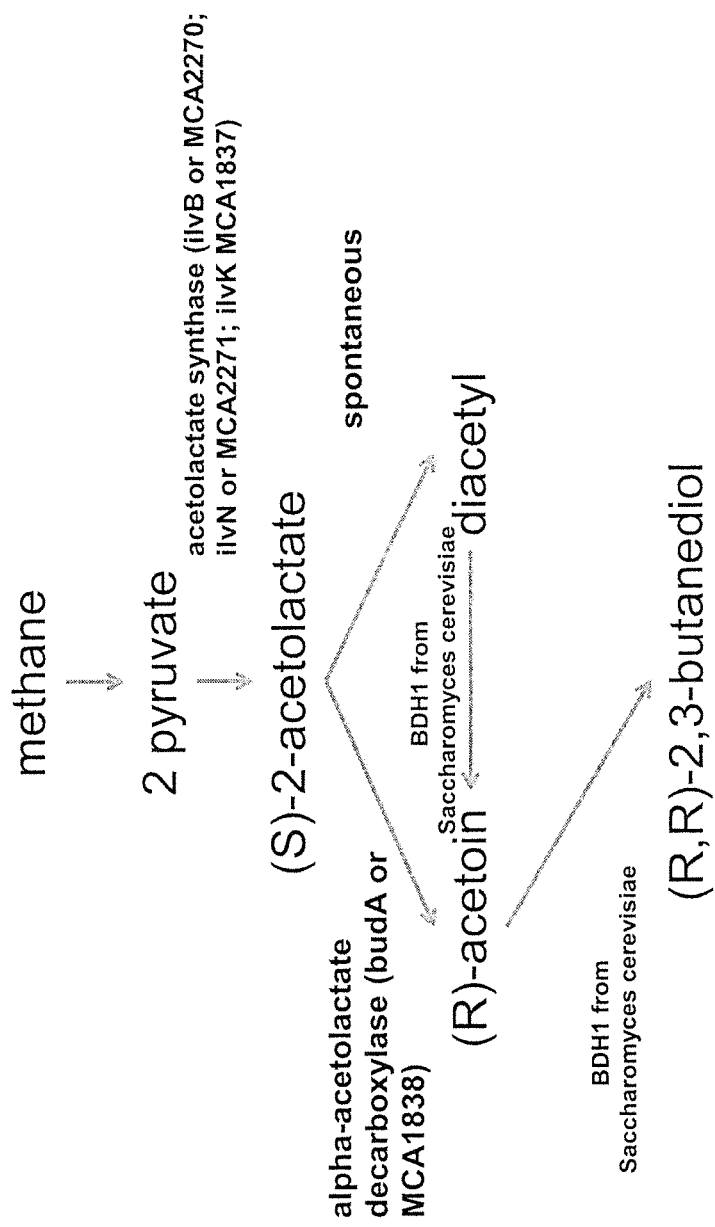
FIG. 9 shows an engineered pathway for 2,3-butanediol production from methane using a heterologously expressed BDH1 enzyme from *Saccharomyces cerevisiae*.

In certain other embodiments, the invention is directed to methods of producing 2,3-butanediol from a methane substrate. The compound 2,3-butanediol (a four-carbon diol) is an important intermediate for the chemical industry. At the commercial scale, 2,3-butanediol is mainly produced or generated from petroleum, where it serves as a precursor for the production of various commodity and specialty chemicals, such as the solvent methyl ethyl ketone (MEK), gamma-butyrolactone (GBL) and 1,3-butadiene. The biological production of 2,3-butanediol from methane requires engineering the native (or endogenous) metabolism of methanotrophs to take advantage of their endogenous production of (R)-acetoin (FIG. 9). The compound (R)-acetoin is produced in methanotrophs from two molecules of pyruvate, which are ultimately derived from methane. By introducing and expressing a single gene (SEQ ID NO:156) encoding a (2R,3R)-2,3-butanediol dehydrogenase (BDH1) from *Saccharomyces cerevisiae* in a suitable microbial expression host (such as *M. capsulalus* (Bath)), the (R)-acetoin is converted into 2,3-butanediol. Thus, in certain embodiments, a host microorganism of the invention is genetically modified to express an exogenous (2R,3R)-2,3-butanediol dehydrogenase (BDH1) having at least 90% sequence homology to a BDH1 polypeptide of SEQ ID NO:157.

General methods for gene synthesis and DNA cloning, as well as vector and plasmid construction, are well known in the art, and are described in a number of publications (Lipps, 2008; Peccoud, 2012; Ausubel et al., 2002). More specifically, techniques such as digestion and ligation-based cloning, as well as in vitro and in vivo recombination methods, can be used to assemble DNA fragments encoding a polypeptide that catalyzes a substrate to product conversion into a suitable vector. These methods include restriction digest cloning, sequence- and ligation-independent Cloning (SLIC) (Li & Elledge, 2012), Golden Gate cloning (Engler et al., 2009), Gibson assembly (Gibson et al., 2009), and the like (Merryman & Gibson, 2012; Wang et al., 2012). Some of these methods can be automated and miniaturized for high-throughput applications (Yehezkel et al., 2011; Ma et al., 2012).

In certain embodiments, the cloning procedures use in vitro homologous recombination, to insert DNA fragments into a vector (e.g., the In-Fusion kit from Clontech Laboratories, Inc. (Mountain View, Calif.)). For example, (1) the recipient vector is linearized by a restriction digest and purified: (2) PCR primers that are complementary to the fragment to be cloned and that are complementary (with 15-base pair extensions) to the ends of the linearized vector are used to amplify the insert, using high-fidelity polymerase; (3) the size of the PCR amplicon is verified by agarose gel electrophoresis; (4) the PCR product is purified by a spin-column; (5) the In-Fusion reaction is run according to the manufacturer's instructions; (6) competent *E. coli* cells are transformed with 2.5 µL of the reaction products; (7) positive transformants are selected from colonies grown on antibiotic selection medium and transferred to individual liquid cultures with the appropriate antibiotic; (8) the cells are harvested after overnight growth at 37° C. with 200 rpm shaking and (9) the plasmid DNA is extracted and analyzed for the correct insert.

The plasmid vector is chosen so that it will be capable of replicating in both an *E. coli* host (for cloning and amplification) and a methanotrophic or non-methanotrophic host microorganism (for metabolic pathway expression). The plasmid can be transferred from the *E. coli* donor cell to the recipient cell via bacterial conjugation. In addition, the vector contains a promoter sequence upstream of the one or more polynucleotide ORFs that are to be expressed. The promoter sequence can be included as part of the insert so that it can be adjusted and tested for each new construct. Broad-host-range (bhr) vectors for different gram-negative bacterial hosts have been described in the literature (Marx & Lidstrom, 2001). These vectors typically contain the following components: (1) an origin of replication that is functional in *E. coli* (colE1); (2) an oriV/IncP origin of replication for the non-*E. coli* host; (3) an oriT/IncP origin of transfer, which is needed for transferring a bacterial plasmid from a bacterial host such as *E. coli* to the recipient during bacterial conjugation; (4) a traJ' gene, which codes for a transcriptional activator that initiates production of the proteins needed for conjugative transfer; and (5) a trfA, the replication initiation protein gene of plasmid RK2 which binds to a activates oriV.

Figure 2:
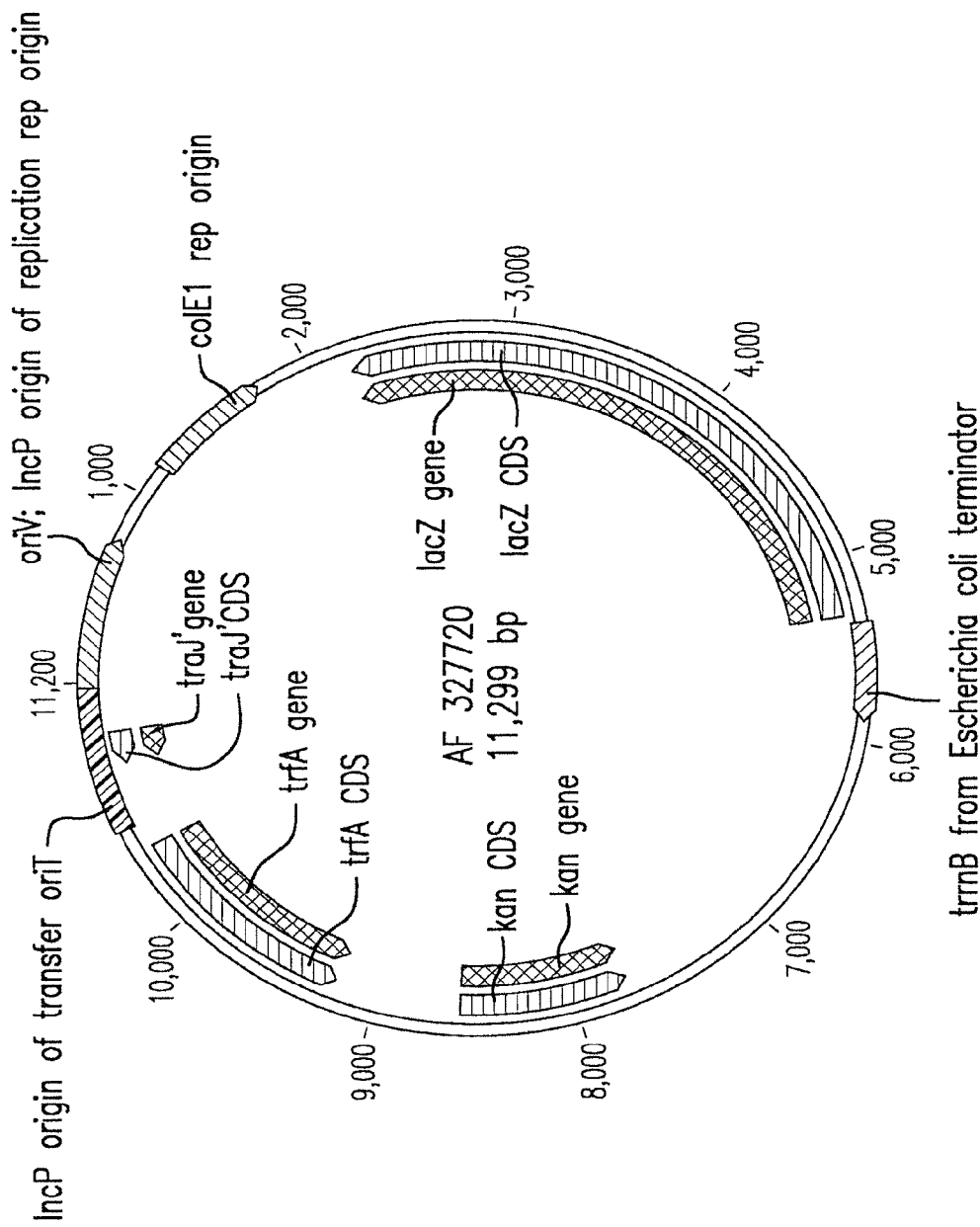
FIG. 2 depicts a vector map of the broad host range expression plasmid pCM 132. The vector map shows the following components: (1) an origin of replication that is functional in *E. coli* (colE1); (2) an criV/IncP origin of replication for the non-*E. coli* microbial host; (3) an oriT/IncP origin of transfer, which is needed for transferring a bacterial plasmid from a bacterial host such as *E. coli* to the recipient during bacterial conjugation; (4) a traJ gene, which codes for a transcriptional activator that initiates production of the proteins needed for conjugative transfer; (5) a trfA gene, the replication initiation protein gene of plasmid RK2 which binds to and activates oriV; (6) a lacZ (beta-galactosidase) gene for identifying plasmids with DNA inserts based on colony color using indolyl-galactoside-based substrates; and (7) a kanamycin resistance gene (kan). Genes of interest are inserted into the polylinker region that lies between the rrnB transcription terminator and the 5'-end of the lacZ gene.

In one embodiment, the conjugative bhr plasmid is based on pCM132 (GenBank Accession No. AF327720, SEQ ID NO:79) (Marx & Lidstrom, 2001), which has been engineered to contain a kanamycin resistance gene for plasmid selection and a lacZ (beta-galactosidase) gene for identifying plasmids with DNA inserts based on colony color using indolyl-galactoside-based substrates. Genes (or polynucleotide ORFs thereof) of interest can be inserted into the polylinker region that lies between the rrnB transcription terminator and the 5'-end of the lacZ gene (e.g., see, FIG. 2).

Figure 3:
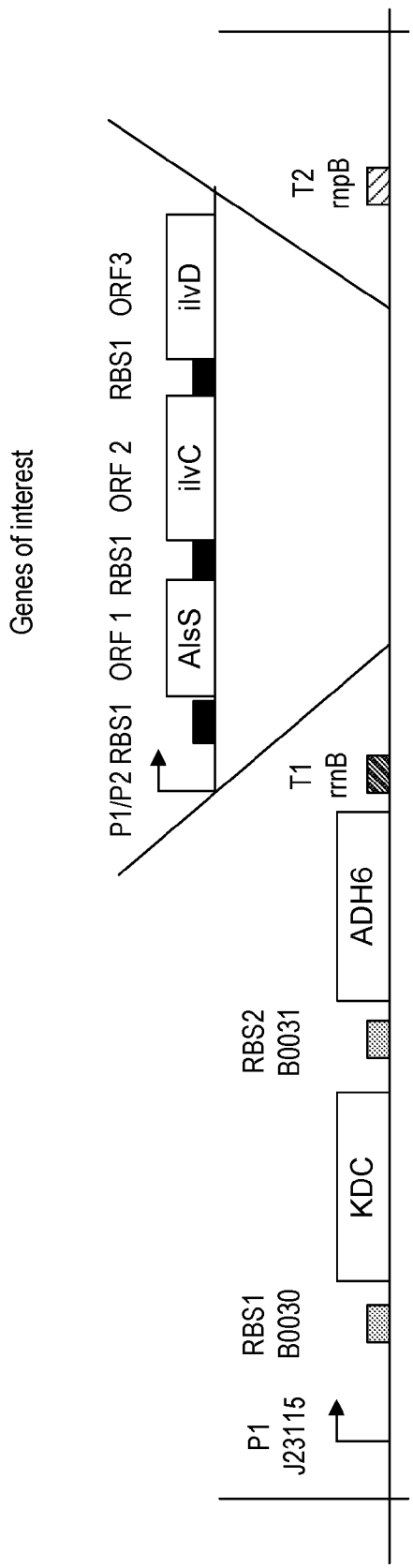
FIG. 3 shows a schematic diagram of component DNA arrangements for cloning into an expression vector.

Typical gene cassettes for expressing an engineered metabolic pathway in a host microorganism such as a methanotroph are shown in FIG. 3. The cassette comprises one or more open reading frames (ORFs) which encode the enzymes of the introduced pathway, a promoter for directing transcription of the downstream ORF(s) within the operon, ribosome binding sites for directing translation of the mRNAs encoded by the individual ORF(s), and a transcriptional terminator sequence. Due to the modular nature of the various components of the expression cassette, one can create combinatorial permutations of these arrangements by substituting different components at one or more of the positions. One can also reverse the orientation of one or more of the ORFs to determine whether any of these alternate orientations improve the product yield.

In one embodiment, the plasmids generated as part of the present invention are based on the broad-host-range expression vector pCM132 (Marx & Lidstrom, 2001). In this embodiment, the use of the Clontech (catalog no. 639647) InFusion HD Cloning System kit is one example of how to construct plasmids, but is not meant to limit or exclude other methods that are known in the art, including Gibson assembly, yeast in vivo recombination, PCR Splicing by Overlap Extension, or any combination of these with standard molecular biology techniques.

In certain embodiments of the invention, the plasmids of interest are generated in a modular fashion such that various modules, including suitable regulatory sequences, can be easily assembled or replaced as needed and are amenable to scaled-up, high-throughput assembly. The plasmids are designed to consist of multiple linear modules: a vector backbone and one or more vector inserts. The 5' and 3' ends of individual modules have overlapping sequence homology to the ends of adjacent modules within the designed plasmid. The overlapping homology between the modules allows them to be assembled into a circular plasmid using the Clontech InFusion HD Cloning System kit or other assembly method known in the art. Primers were designed to introduce homologous ends to the PCR-amplified products to facilitate assembly.

Vector backbones of the invention contain the components of the plasmid that will remain constant. In certain embodiments, the broad-host range vector pCM132 is modified to produce vector backbones for the plasmids (vectors) of the invention. The pCM132 vector, further described below in the Examples section, consists of the following components: trrnB terminator, kanamycin resistance gene, trfA, IncP oriT, IncP oriV, colE1 ori, and lacZ. This parental vector was modified to replace lacZ with a vector insert that contains promoter sequence(s) to produce plasmids pJSvec (SEQ ID NO: 80) and pMZT3 (SEQ ID NO: 81). In certain embodiments of the invention, vector backbones were PCR-amplified with the NEB Phusion master mix (M0531L) according to the manufacturer's instructions, unless specified otherwise.

The general rationale or procedure for selecting the appropriate ORFs for a given pathway was to examine a list of pathway-relevant genes as specified in the literature. Using this set of pathway-relevant genes as a target, BLAST searches were run, looking for genes in three groups: (1) similar genes found in microbial hosts that are phylogenetically close to the ones already listed in the literature, (2) similar genes found in microbes that are phylogenetically distant from the microbial host of the targeted gene, and (3) homologs that are similar to the target gene but that are found in the wild-type methanotroph or non-methanotroph organism that is to be used as the expression host. An example of the above strategy would be to target the kivD gene (encoding alpha-ketoisovalerate decarboxylase) from *Lactococcus lactis*: the first group would contain genes from species similar to *L. lactis*, including *Lactococcus* itself; the second group would be genes similar to kivD, but found in organisms phylogenetically distant from *L. lactis*; and finally the last group would include a kivD gene in a microbe of interest, specifically, *Methylococcus capsulatus* (Bath). Thus, in certain embodiments of the invention, the exemplary polynucleotide and polypeptide sequences set forth in Table 1 are used to identify similar or homologous polynucleotide, genes, ORFs and polypeptides found in microbial hosts that are (1) phylogenetically close to the ones already listed, (2) found in microbes that are phylogenetically distant from the microbial host of the targeted sequence, and (3) homologs that are similar to the target gene but that are found in the wild-type methanotroph or non-methanotroph organism that is to be used as the expression host.

For example, genes encoding similar proteins or polypeptides to those of the invention may isolated directly by using all or a portion of a nucleic acid (e.g., see Table 1, below) or a primer sequence (e.g., see Table 2, below) as DNA hybridization probes to screen libraries from any desired microorgansim using methodology well known to those skilled in the art. Specific oligonucleotide probes based upon these nucleic acid sequences can be designed and synthesized by methods known in the art (Sambrook et al., 1989; Ausubel et al., 1987). Moreover, the entire sequence can be used directly to synthesize DNA probes by methods known to the skilled artisan such as random primers, DNA labeling, nick translation, or end-labeling techniques, or RNA probes using available in vitro transcription systems. In addition, specific primers can be designed and used to amplify a part of or the full-length of the instant sequence. The resulting amplification products can be labeled directly during amplification reactions or labeled after amplification reactions, and used as probes to isolate full-length DNA fragments under conditions of appropriate stringency.

Alternatively a nucleic acid sequence of the invention may be employed as a hybridization reagent for the identification of homologs. The basic components of a nucleic acid hybridization test include a probe, a sample suspected of containing the gene or gene fragment of interest, and a specific hybridization method. Probes are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. base. Hybridization methods are well defined and know in the art.

An important component of these engineered operons is the promoter sequence. The promoter must be chosen based on its compatibility with the transcriptional machinery of the host organism, as well as its ability to tune the desired level of gene expression (e.g., high or low). For example, one may introduce the strong pmxaF or pmmoX promoters from a methanotroph to generate high expression levels in a methanotrophic or non-methanotroph host. Alternatively, one can introduce a promoter from the Anderson promoter collection, which is a library of constitutive sigma70 bacterial promoters (http://partsregistry.org/Promoters/Catalog/Andersow; Registry of Standard Biological Parts), such as J23100 (strong) or J23115 (weak), to modulate expression of different ORFs or combinations of ORB. Inducible promoters, whose activity is controlled by the addition of exogenous small molecule activators, such as IPTG, arabinose or salicylate, can also be used to provide temporal control of gene expression. However, regardless of the choice of promoter, its effect on host expression must be empirically tested in vivo to be certain of its effectiveness for achieving the desired level of expression.

These different combinatorial permutations of the cassette can be synthesized, cloned and expressed in the target host organism (via chemical transformation, electroporation, or conjugation of the DNA) so that the production of a multi-carbon product can be compared. The best candidate or candidates can then be further engineered to provide additional improvements in product yield by repeating the design-build-test cycle.

In one embodiment, the host microorganism for expressing the plasmid is a methanotroph, and plasmid vector(s) containing the metabolic pathway expression cassettes are readily mobilized into these organisms via conjugation. Various methods for bacterial conjugation are known in the art, and one of the most widely used methods takes advantage of a strain of *E. coli* S17-1, which has an RP4 plasmid (with the RK2 tra genes for transfer of genetic material) inserted into the chromosome for mobilizing oriT(RP4)-carrying plasmids (Simon et al. 1983; Simon, 1984).

The transfer of plasmid containing RP4-mob from *E. coli* to methanotrophs, as further described in the Examples section, was based on the conjugation methods described previously (Martin & Murrell, 1995; Ali, 2006). A 10 ml overnight *E. coli* S17-1 λ pir culture, containing RP4-mob plasmid, was collected on a 0.2 µm pore-size nitrocellulose filter (Millipore). The *E. coli* donor strain was washed twice with 50 ml NMS. A 50 ml methanotroph culture grown to mid exponential phase ($A_{540}$ of 0.2-0.5) was also collected on the same filter and washed again with 50 mL NMS medium. The filter was placed on an NMS agar plate containing 0.02% (w/v) proteose peptone and incubated for 24 hours at 30° C. with methane except for *M. capsulatus*, which was incubated at 37° C. for 24 hours.

Following incubation, the cells were washed with 10 ml NMS and collected by centrifugation (7,000×g for 10 min) before re-suspending the cells in 1 ml NMS. Aliquots (50-100 µl) of the cells were spread onto NMS plates containing selective antibiotics and incubated at the appropriate temperature. Colonies typically formed on the plates after 8-12 days. (Note: the *E. coli* S17-1 λ pir strain has chromosomally integrated conjugal transfer functions, thus allowing transfer of plasmid to occur by means of a bi-parental mating without a helper plasmid). Transconjugants can also be purified by serial cultivation in liquid medium containing the appropriate antibiotics for selection, followed by plating onto selective NMS agar plates to obtain single colonies.

In an alternative method for expressing metabolic pathway genes in a microbial host, the biosynthetic pathway genes are inserted directly into the chromosome. Methods for chromosomal modification include both non-targeted and targeted deletions and insertions. For example, non-targeted insertions can be achieved by using transposon mutagenesis to make insertion mutants or gene "knockouts" in vitro using the EZ-Tn5 <KAN-2> Insertion Kit (Epicentre). Briefly, the procedure is as follows, according to the manufacturer: Preparation: prepare 0.2 µg of recombinant DNA for the EZ-Tn5<KAN-2> insertion reaction. Day 1: perform the 2-hour in vitro EZ-Tn5<KAN-2> insertion reaction; transform competent recA-*E. coli* with 1 µl of the reaction mix and select for kanamycin-resistant transposon insertion clones on kanamycin plates overnight. Day 2: prepare DNA from kanamycin-resistant colonies, (and optionally map the EZ-Tn5 <KAN-2> Transposon insertion sites and optionally (DNA) sequence chosen clones bi-directionally using the unlabeled forward and reverse transposon-specific primers supplied in the kit.

For targeted modifications, various methods have been developed based on RecA-dependent homologous recombination (Hamilton et al., 1989; Link et al., 1997; Posfai et al., 1999). However, using antibiotic resistance markers for deletion/insertion is limited by the number of different antibiotics that can be used in a given target organism. For this reason, markerless insertion methods have been developed. For example, Yu et al. (2008) describe a deletion procedure in which expression of the λ-Red recombinase genes (gam, bet and exo) and the I-SceI endonuclease gene are controlled by tightly regulated promoters ParaB and PrhaB. Arabinose and rhamnose added to cultures to induce ParaB and PrhaB are used and depleted by the bacteria. Thus, by changing the carbon source in the medium from arabinose to rhamnose in bacteria that contain the pREDI plasmid, one can replace a targeted genomic region with a markerless deletion cassette and subsequently delete the selection markers that were introduced.

Sun et al. (2008) also describe methods for sequence-specific insertion or deletion of genes within a bacterial genome. This method permits multiple markerless insertions and scarless deletions in the targeted genome. In the Sun et al. method, a target gene can be deleted in two steps. In the first step, a linear DNA fragment is created that carries the cat (chloramphenicol resistance) gene and sacB (a levansucrase gene that confers sensitivity to sucrose). The fragment is flanked by long (500 bp) regions of DNA that are homologous to the regions that flank the targeted deletion site. The DNA fragment is electroporated into the host cell, which already contains plasmid pKD46, a vector containing the genes for λ Red recombination. Homologous recombination then directs the replacement of the targeted gene. Medium containing chloramphenicol is used to select for cells that contain the desired insertion or deletion. In the second step, a second DNA fragment that contains the desired deletion or insertion is electroporated into host cells that contain the pKD46 plasmid. By plating the resulting cells on medium containing sucrose, one can select for transformants in which the cat-sacB cassette has been replaced. These candidates are also screened for sensitivity to chloramphenicol, and the deletion can be confirmed by PCR and sequencing. By repeating the process, multiple deletions and/or insertions can be achieved. The pKD46 plasmid can then be removed by culturing the cells at 37 C. Thus, by using various genes encoding the isobutanol, butanol, fatty alcohol and fatty acid ester biosynthetic pathways, these pathways can be inserted into the genome of a methanotroph (or non-methanotroph), and unwanted genes (e.g., genes that encode for enzymes that produce competing products) can be removed.

U.S. Patent Publication No. 2006/0057726 describes using sacB gene and the pGP704 suicide vector to engineer markerless insertions into single carbon (C1) metabolizing bacteria. Yomantas et al. (2010) describes methods for markerless substitutions in the genome of the methylotrophic bacterium *Methylophilus methylotrophus*.

Several methanotroph strains were evaluated according to the present invention as potential hosts for pathway engineering. Of the well characterized methanotroph strains, *Methylosinus trichosporium* OB3b (NCIMB 11131) and *Methylococcus capsulatus* str. Bath (NCIMB 11853) were examined for their ease of transformability (via conjugation), growth rate, and suitability for industrial fermentation. Both strains can be cultivated in liquid or agar containing Nitrate Mineral Salts (NMS) medium (Whittenbury et al., 1970; Bowman, 2000). Although both strains were found to transform with approximately equal efficiency, *Methylococcus capsulatus* (Bath) has the advantage of growing about twice as fast as *M. trichosporium* (ca. 24-30 to reach saturation in shake flask growth). In addition, the ability of *M. capsulatus* (Bath) to grow more readily at 45° C. is an advantage in industrial cultivation, since this relatively high temperature will impede the growth of other potentially contaminating microorganisms. Furthermore, the complete genome sequence of *M. capsulatus* (Bath) has been published (Ward et al., 2004), and as such, manipulation of its genome via genetic engineering is readily available to one of skill in the art. Thus, in certain embodiments, *M. capsulatus* (Bath) is used as a model organism for further development of genetically modified host microorganisms.

Following conjugation, positive methanotroph trans-conjugants were purified on NMS agar containing the appropriate antibiotic selection (e.g., 15 µg/ml kanamycin for selecting the plasmid and counter-selecting the untransformed methanotroph host cells, and 10 µg/ml for counter-selecting the *E. coli* donor cells). Alternatively, transconjugants can be purified by serial cultivation in liquid medium containing the appropriate antibiotics for selection, followed by plating onto selective NMS agar plates to obtain single colonies. Colonies were used to inoculate small (5-10 ml) starter cultures in liquid NMS medium containing, for example, 15 µg/ml kanamycin in 125-ml flasks. The flasks were stoppered with tight-fitting Suba Seals to create a closed atmosphere inside the flasks. A volume of gas corresponding to 20% of the total volume of the flask and composed of 95% methane and 5% carbon dioxide was injected via a sterile syringe and 23-gauge needle into each flask. Flasks were shaken at 200 rpm and 45° C. When these cultures achieved an optical density of $A_{540}$>0.5 (after about 24 hours), a 1:100 dilution of these cells was used to inoculate 125 ml (or larger volume) cultures, and the same growth protocol was followed. Growth in shake flasks is most robust when the liquid volume is maintained at about 5-10% of the nominal volume of the flask so that good aeration of the liquid is achieved. These flasks were then used for the subsequent assays of product formation. In certain examples related to 2-KIV feeding experiments, only the ketoacid intermediate was added along with the methane and $CO_2$ at the zero time point.

After approximately 72 hours of growth, the cultures were harvested for analysis by gas chromatography. The sealed flasks were first chilled for at least 1 hour on ice, to concentrate any volatile organic compounds from the vapor phase into the liquid phase. After opening the flasks, an aliquot of the culture was diluted 1:2 with ethyl acetate in a clean 50 ml tube to extract and concentrate the isobutanol, butanol, fatty alcohols or fatty acid esters. After vortexing or shaking (and centrifugation to separate the phases), a small volume of the organic layer (approximately 1 ml) was filtered through a 0.2 µm PTFE filter, and 1 µl of the purified extract was then injected into an Agilent 7890A GC equipped with a Leap Technologies (Carrboro, N.C.) CombiPAL autosampler for analysis. Appropriate purified standards were included to generate a standard curve and determine the concentration of the targeted product. Each measurement included a positive control and a negative control (e.g., a wild-type sample or other appropriate background control) with each sample set. Additional details of the methods used for the specific products are given in the Examples section. Strains with the highest levels of production were designated for further scale-up in 1-10 liter fermentors.

During the analysis of the engineered host strains, unexpectedly high levels of isobutanol and butanol consumption (up to 30 mM after 72 hours of growth) was observed even in wild-type cultures of *M. capsulatus* (Bath), and therefore it was important to find mutant strains that can produce these products at a rate that is greater than their inherent rate of consumption. In certain embodiments of the invention, the competing alcohol dehydrogenase and alcohol oxidase activities are identified, and reduced or eliminated by gene knockouts, as described above.

For initial fermentation scale-up in the 1-10 liter range, methods similar to those described in Theisen et al. (2005) and U.S. Pat. No. 4,594,324 can be used, with specific modifications for *M. capsulatus* (Bath). A fermentation system such as the Sartorius-Stedim Biostat A plus system (Goettingen, Germany) can be used, or other equivalent fermentation systems and methods for methanotroph fermentation (e.g., see Jiang et al., 2010). An Applikon ADI 1030 Bio Controller and ADI 1035 BioConsole (Applikon Biotechnology Inc., Foster City, Calif.) can also be used for the 10 liter vessel.

The starting inoculum is created by inoculating a large colony of *M. capsulatus* (Bath) containing the desired plasmid from a plate culture into 10 ml of sterile NMS medium containing kanamycin, as described above. After 24 to 48 hours, when the optical density ($A_{540}$) of the culture is greater than 0.5, five starter flasks of NMS medium are inoculated at 1:100 dilution. The liquid volumes in these starter inocula can range in size from 20 ml each for a 1 liter fermentor to 200 ml each for a 10 liter fermentor (i.e., about a 10% inoculum).

After autoclaving the NMS medium in the fermentor vessel, the phosphate salts portion of the NMS medium and the kanamycin (both sterilized) are added to the vessel. The same inlet can be used to inject the starter cultures. Air is supplied as oil-free compressor air, and the methane carbon source is supplied from a pre-mixed tank (Airgas) containing 95% methane and 5% $CO_2$. The air and methane are mixed to 15-20% methane using equipment that is rated intrinsically safe or explosion proof to eliminate the possibility of sparking or static electricity, which could lead to an explosion. The gas flow rate depends on the fermentor size and culture density, but a value of 0.75 liters per minute for 10 liters is typical. The gas mixture is fed into the fermentor, and the entire culture is mixed with an impeller rotating at approximately 200 rpm for agitation, the rate of which may be increased during growth. For maintenance of the culture pH at 6.8, 0.1 M HCl or 1 M NaOH is added as needed. The temperature is maintained at 45° C. by a thermostatic jacket. The effluent gas is fed through a water-jacketed condenser to reduce liquid loss at 45° C., and vented to a fume hood.

The fermentation is monitored (via pH and dissolved oxygen probes) and controlled using Sartorius BioPAT MFCS bioprocess control software (Sartorius Corp, Bohemia, N.Y.). A dissolved oxygen concentration below 1% saturation with air (typically 0.2-0.3%) is desirable to avoid wasting methane. Periodically, small samples of the fermentation broth are removed by sterile transfer and used to measure the optical density of the culture. These samples can also be used to monitor product formation using the methods described above and in the Examples section. Purity of the culture can also be checked by plating a small sample onto R2A agar, which allows most organisms other than methanotrophs to grow. Cultures achieve an optical density ($A_{540}$) of greater than 9 after about 48 hours. For *M. capsulatus* (Bath), 1 ml of culture with $A_{540}$ equal to 1 corresponds to about 0.23-0.25 mg of dry weight of biomass. When the maximum cell density or product concentration is achieved, the culture can be harvested and analyzed.

For large-scale commercial fermentation, a system based on the fermentor design employed by Norfem (Norefem, A S; Stavanger, Norway) for production of single-cell protein can be used (Bothe et al., 2002; EP 1419234; U.S. Publication No. 2009/0263877). The largest system has a total volume of 300 $m^3$ (300,000 liters) and an annual production capacity of 10,000 tons of biomass (van Laere et al., 2005). Publications such as EP 1419234, U.S. Publication No. 2009/0263877 and Villadsen (2012), and references therein, describe a loop reactor and bioprocess methods for culturing methanotrophs at the commercial scale. The advantage of this design is that nutrient gases such as methane and oxygen are supplied to the system in such a way that exposure of the cells to nutrient-depleted culture medium or to unduly high concentrations of nutrient gases is minimized.

However, when using "wet" natural gas as a nutrient feedstock, the problem of acetate and propionate toxicity (resulting from the oxidation of ethane and propane, respectively) may need to be addressed (Bothe et al., 2002; Eiteman & Altman, 2006). A genetic approach is to eliminate (knock-out) or knock-down the ethanol and propanol dehydrogenases and acetaldehyde/propionaldehyde dehydrogenases that convert the ethanol and propanol to the corresponding acids. Another approach is to introduce the genes for acetate assimilation from an organism that can use it as a carbon source, such as E. coli (Wolfe, 2005). For example, AMP-ACS (acetate:CoA ligase [AMP forming]; EC 6.2.1.1) catalyzes the conversion of acetate and ATP to an enzyme-bound acetyladenylate (acetyl-AMP) and pyrophosphate. In a subsequent step, it reacts the acetyl-AMP with CoASH (CoenzymeA-SH) to acetyl-CoA and free AMP. Similarly, AMP-ACS can activate and assimilate propionate (Wolfe, 2005). In this way, the two potentially harmful organic acids are converted into the useful intermediate, acetyl-CoA. These genes can be cloned and expressed in a methanotroph host by the methods described above.

Another aspect of the commercial production of multi-carbon compounds from methane using the present invention involves recovering and purifying the desired product from the fermentation broth. The method to be used depends on the physico-chemical properties of the product and the nature and composition of the fermentation medium and cells. For example, U.S. Pat. No. 8,101,808 describes methods for recovering C3-C6 alcohols from fermentation broth using continuous flash evaporation and phase separation processing. Thus, the biologically produced multi-carbon compounds of the invention may be isolated from the fermentation medium using methods known in the art for Acetone-butanol-ethanol (ABE) fermentations For example, solids may be removed from the fermentation medium by centrifugation, filtration, decantation, wherein the multi-carbon compounds of the invention may be isolated from the fermentation medium using methods such as distillation, azeotropic distillation, liquid-liquid extraction, adsorption, gas stripping, membrane evaporation, or pervaporation.

In certain embodiments the invention, the fermentation process produces greater than about 7% (v/v) concentration of the desired multi-carbon product in the fermentation broth, and the product is separated from the rest of the medium using membrane separation technology to achieve about a 12% or greater concentration of the product, at which point relatively small molecules (such as isobutanol) can be further purified by phase separation in an integrated system (Hickey & Slater, 1990; Neel, 1995; Hägg, 1998; Liu et al., 2011). Continuous recovery of the product from the fermentation medium has the advantage of possibly reducing the toxicity effects of the multi-carbon products.

For longer-chain alcohols, such as fatty alcohols, U.S. Pat. No. 8,268,599 describes methods for separating these components from the aqueous phase of the fermentation by bi-phasic separation, whereby the immiscibility of the product compounds with the fermentation broth allows the organic phase to be collected and removed. This separation can also reduce the toxic effects of the product on the host microbial cells.

U.S. Publication No. 2007/0251141 describes methods for recovering fatty acid methyl esters (FAMEs) from a liquid suspension by adding urea and creating a phase separation whereby the saturated and unsaturated FAMEs can be recovered separately. Membrane separation methods can also be applied to purifying fatty acid ester products such as biodiesel (Saleh, 2011).

In certain embodiments, a methane substrate of the invention is provided or obtained from a natural gas source, wherein the natural gas is "wet" natural gas or "dry" natural gas. Natural gas is referred to as "dry" natural gas when it is almost pure methane, having had most of the other commonly associated hydrocarbons removed. When other hydrocarbons are present, the natural gas is referred to as "wet". Wet natural gas typically comprises about 70-90% methane, about 0-20% ethane, propane and butane (combined total), about 0-8% $CO_2$, about 0-5% $N_2$, about 0-5% $H_2S$ and trace amounts of oxygen, helium, argon, neon and xenon. In certain other embodiments, a methane substrate of the invention is provided or obtained from methane emissions, or methane off-gases, which are generated by a variety of natural and human-influenced processes, including anaerobic decomposition in solid waste landfills, enteric fermentation in ruminant animals, organic solids decomposition in digesters and wastewater treatment operations, and methane leakage in fossil fuel recovery, transport, and processing systems.

Table 1 below, provides exemplary polynucleotide and polypeptide sequences for implementing various embodiments of the present invention. These sequences are not meant to limit or exclude the use of other polynucleotide sequences encoding polypeptides or enzymes useful for producing multi-carbon compounds according to the present invention. For example, one of skill in the art can search gene sequence databases (or genome databases) and/or protein sequence databases (e.g., via BLAST or other sequence search algorithms) to identify homologous polynucleotides encoding one or more enzyme activities based on the reference sequences set forth in Table 1. Alternatively, a homologous polynucleotide may be isolated directly by using all or a portion of a nucleic acid sequence set forth in Table 1 (or a primer sequence set forth below in Table 2) as DNA hybridization probes to screen libraries from any desired microorgansim and/or PCR amplify a desired polynucleotide sequence using methodology well known to those skilled in the art.

TABLE 1

Exemplary Nucleic Acid and Polypeptide Sequences Described in the Invention

| Pathway or Reaction | Gene Name | Nucleic acid SEQ | Enzyme Name | Polypeptide SEQ ID | Organism |
|---|---|---|---|---|---|
| isobutanol | MCA1837 | SEQ ID NO: 1 | ALS | SEQ ID NO: 2 | M. capsulatus, Bath |
| isobutanol | MCA2272 | SEQ ID NO: 3 | KARI | SEQ ID NO: 4 | M. capsulatus, Bath |
| isobutanol | MCA2082 | SEQ ID NO: 5 | DHAD | SEQ ID NO: 6 | M. capsulatus, Bath |
| isobutanol | MCA0996 | SEQ ID NO: 7 | KDC | SEQ ID NO: 8 | M. capsulatus, Bath |
| isobutanol | YMR318C | SEQ ID NO: 9 | ADH | SEQ ID NO: 10 | S. cerevisiae |

TABLE 1-continued

Exemplary Nucleic Acid and Polypeptide Sequences Described in the Invention

| | | | | | |
|---|---|---|---|---|---|
| isobutanol | MtKDC | SEQ ID NO: 82 | KDC | SEQ ID NO: 162 | *M. trichosporium* |
| isobutanol | MtADH | SEQ ID NO: 83 | ADH | SEQ ID NO: 163 | *M. trichosporium* |
| isobutanol | McADH-2a | SEQ ID NO: 84 | ADH | SEQ ID NO: 164 | *M. capsulatus*, Bath |
| isobutanol | McADH-2b | SEQ ID NO: 85 | ADH | SEQ ID NO: 165 | *M. capsulatus*, Bath |
| Isobutanol | LlkivD | SEQ ID NO: 86 | KDC | SEQ ID NO: 166 | *L. lactis* |
| Isobutanol | ScPDC6 | SEQ ID NO: 87 | KDC | SEQ ID NO: 167 | *S. cerevisiae* |
| Isobutanol | ScARO10 | SEQ ID NO: 88 | KDC | SEQ ID NO: 168 | *S. cerevisiae* |
| Isobutanol | ScADH2 | SEQ ID NO: 89 | ADH | SEQ ID NO: 169 | *S. cerevisiae* |
| Isobutanol | ScPDC1 | SEQ ID NO: 90 | KDC | SEQ ID NO: 170 | *S. cerevisiae* |
| isobutanol | CaPDC | SEQ ID NO: 91 | KDC | SEQ ID NO: 171 | *C. acetobutylicum* |

| Pathway or Reaction | Gene Name | Nucleic acid SEQ ID | Enzyme Name | Polypeptide SEQ ID | Organism |
|---|---|---|---|---|---|
| $CH_4$ to $CH_3OH$ | MCA1798 | SEQ ID NO: 11 | pmoC subunit 1 | SEQ ID NO: 12 | *M. capsulatus*, Bath |
| $CH_4$ to $CH_3OH$ | MCA1797 | SEQ ID NO: 13 | pmoA subunit 1 | SEQ ID NO: 14 | *M. capsulatus*, Bath |
| $CH_4$ to $CH_3OH$ | MCA1796 | SEQ ID NO: 15 | pmoB subunit 1 | SEQ ID NO: 16 | *M. capsulatus*, Bath |
| $CH_4$ to $CH_3OH$ | MCA2855 | SEQ ID NO: 17 | pmoC subunit 2 | SEQ ID NO: 18 | *M. capsulatus*, Bath |
| $CH_4$ to $CH_3OH$ | MCA2854 | SEQ ID NO: 19 | pmoA subunit 2 | SEQ ID NO: 20 | *M. capsulatus*, Bath |
| $CH_4$ to $CH_3OH$ | MCA2853 | SEQ ID NO: 21 | pmoB subunit 2 | SEQ ID NO: 22 | *M. capsulatus*, Bath |
| $CH_4$ to $CH_3OH$ | MCA1194 | SEQ ID NO: 23 | mmoX | SEQ ID NO: 24 | *M. capsulatus*, Bath |
| $CH_4$ to $CH_3OH$ | MCA1195 | SEQ ID NO: 25 | mmoY | SEQ ID NO: 26 | *M. capsulatus*, Bath |
| $CH_4$ to $CH_3OH$ | MCA1196 | SEQ ID NO: 27 | mmoB | SEQ ID NO: 28 | *M. capsulatus*, Bath |
| $CH_4$ to $CH_3OH$ | MCA1198 | SEQ ID NO: 29 | mmoZ | SEQ ID NO: 30 | *M. capsulatus*, Bath |
| $CH_4$ to $CH_3OH$ | MCA1199 | SEQ ID NO: 31 | mmoD | SEQ ID NO: 32 | *M. capsulatus*, Bath |
| $CH_4$ to $CH_3OH$ | MCA1200 | SEQ ID NO: 33 | mmoC | SEQ ID NO: 34 | *M. capsulatus*, Bath |
| $CH_3OH$ to $H_2CO$ | MCA0779 | SEQ ID NO: 35 | mxaF | SEQ ID NO: 36 | *M. capsulatus*, Bath |
| $CH_3OH$ to $H_2CO$ | MCA0780 | SEQ ID NO: 37 | mxaJ | SEQ ID NO: 38 | *M. capsulatus*, Bath |
| $CH_3OH$ to $H_2CO$ | MCA0781 | SEQ ID NO: 39 | mxaG | SEQ ID NO: 40 | *M. capsulatus*, Bath |
| $CH_3OH$ to $H_2CO$ | MCA0782 | SEQ ID NO: 41 | mxaI | SEQ ID NO: 42 | *M. capsulatus*, Bath |
| $CH_3OH$ to $H_2CO$ | MCA0783 | SEQ ID NO: 43 | mxaR | SEQ ID NO: 44 | *M. capsulatus*, Bath |
| $CH_3OH$ to $H_2CO$ | MCA0785 | SEQ ID NO: 45 | mxaA | SEQ ID NO: 46 | *M. capsulatus*, Bath |
| $CH_3OH$ to $H_2CO$ | MCA0786 | SEQ ID NO: 47 | mxaC | SEQ ID NO: 48 | *M. capsulatus*, Bath |
| $CH_3OH$ to $H_2CO$ | MCA0787 | SEQ ID NO: 49 | mxaK | SEQ ID NO: 50 | *M. capsulatus*, Bath |
| $CH_3OH$ to $H_2CO$ | MCA0788 | SEQ ID NO: 51 | mxaL | SEQ ID NO: 52 | *M. capsulatus*, Bath |
| $CH_3OH$ to $H_2CO$ | MCA0789 | SEQ ID NO: 53 | mxaD | SEQ ID NO: 54 | *M. capsulatus*, Bath |
| 1-butanol | MCA0354 | SEQ ID NO: 55 | Threonine-ammonia-lyase | SEQ ID NO: 56 | *M. capsulatus*, Bath |
| 1-butanol | MCA2275 | SEQ ID NO: 57 | 2-ethylmalate synthase | SEQ ID NO: 58 | *M. capsulatus*, Bath |
| 1-butanol | MCA2065 | SEQ ID NO: 59 | Isopropyl malate dehydratase, large subunit | SEQ ID NO: 60 | *M. capsulatus*, Bath |
| 1-butanol | MCA2064 | SEQ ID NO: 61 | Isopropyl malate dehydratase, small subunit | SEQ ID NO: 62 | *M. capsulatus*, Bath |
| 1-butanol | VIMSS17191 | SEQ ID NO: 160 | tdcB | SEQ ID NO: 161 | *E. coli* |
| 1-butanol | MCA0996 | SEQ ID NO: 7 | KDC | SEQ ID NO: 8 | *M. capsulatus*, Bath |
| 1-butanol | YMR318C | SEQ ID NO: 9 | ADH | SEQ ID NO: 10 | *S. cerevisiae* |
| 1-butanol | MtKDC | SEQ ID NO: 82 | KDC | SEQ ID NO: 162 | *M. trichosporium* |
| 1-butanol | MtADH | SEQ ID NO: 83 | ADH | SEQ ID NO: 163 | *M. trichosporium* |
| 1-butanol | McADH-2a | SEQ ID NO: 84 | ADH | SEQ ID NO: 164 | *M. capsulatus*, Bath |
| 1-butanol | McADH-2b | SEQ ID NO: 85 | ADH | SEQ ID NO: 165 | *M. capsulatus*, Bath |
| 1-butanol | LlkivD | SEQ ID NO: 86 | KDC | SEQ ID NO: 166 | *L. lactis* |
| 1-butanol | ScPDC6 | SEQ ID NO: 87 | KDC | SEQ ID NO: 167 | *S. cerevisiae* |
| 1-butanol | ScARO10 | SEQ ID NO: 88 | KDC | SEQ ID NO: 168 | *S. cerevisiae* |
| 1-butanol | ScADH2 | SEQ ID NO: 89 | ADH | SEQ ID NO: 169 | *S. cerevisiae* |
| 1-butanol | ScPDC1 | SEQ ID NO: 90 | KDC | SEQ ID NO: 170 | *S. cerevisiae* |
| 1-butanol | CaPDC | SEQ ID NO: 91 | KDC | SEQ ID NO: 171 | *C. acetobutylicum* |
| Fatty alcohol | FAR | SEQ ID NO: 65 | FAR | SEQ ID NO: 66 | *M. algicola* |
| Fatty acid ester | Ab-wax-dgaT | SEQ ID NO: 67 | wax-dgaT | SEQ ID NO: 68 | *A. baylyi* |
| Fatty acid ester | Psyc_0223 | SEQ ID NO: 69 | PaWES | SEQ ID NO: 70 | *P. arcticus* |
| Fatty acid ester | ROP_02100 | SEQ ID NO: 71 | RoWES1 | SEQ ID NO: 72 | *R. opacus* |
| Fatty acid ester | ROP_13050 | SEQ ID NO: 73 | RoWES2 | SEQ ID NO: 74 | *R. opacus* |
| Fatty acid ester | ROP_54550 | SEQ ID NO: 75 | RoWES3 | SEQ ID NO: 76 | *R. opacus* |
| Fatty acid ester | ROP_26950 | SEQ ID NO: 77 | RoWES4 | SEQ ID NO: 78 | *R. opacus* |
| 2,3-butanediol | YAL060W | SEQ ID NO: 156 | Bdh1 | SEQ ID NO: 157 | *S. cerevisiae* |
| RuMP | MCA3049 | SEQ ID NO: 160 | HPS | SEQ ID NO: 161 | *M. capsulatus*, Bath |
| RuMP | MCA3050 | SEQ ID NO: 162 | HPS/PHI | SEQ ID NO: 163 | *M. capsulatus*, Bath |

TABLE 2

Plasmid, Primer, Promoter and Gene Fragment Sequences Described in the Invention

| Name | Nucleic acid SEQ ID |
| --- | --- |
| pCM132 | SEQ ID NO: 79 |
| pJSvec | SEQ ID NO: 80 |
| pMZT3 | SEQ ID NO: 81 |
| JPS00082 | SEQ ID NO: 92 |
| JPS00031 | SEQ ID NO: 93 |
| JPS00032 | SEQ ID NO: 94 |
| GMV257 | SEQ ID NO: 95 |
| JPS00118 | SEQ ID NO: 96 |
| JPS00119 | SEQ ID NO: 97 |
| ESG00087 | SEQ ID NO: 98 |
| GMV251 | SEQ ID NO: 99 |
| rnpB | SEQ ID NO: 100 |
| JPS00161 | SEQ ID NO: 101 |
| JPS00162 | SEQ ID NO: 102 |
| JPS00163 | SEQ ID NO: 103 |
| JPS00164 | SEQ ID NO: 104 |
| JPS00172 | SEQ ID NO: 105 |
| JPS00173 | SEQ ID NO: 106 |
| JPS00174 | SEQ ID NO: 107 |
| JPS00176 | SEQ ID NO: 108 |
| JPS00177 | SEQ ID NO: 109 |
| JPS00157 | SEQ ID NO: 110 |
| JPS00178 | SEQ ID NO: 111 |
| Me-AM1 PmxaF | SEQ ID NO: 112 |
| JPS00169 | SEQ ID NO: 113 |
| GMV00251 | SEQ ID NO: 114 |
| JPS00170 | SEQ ID NO: 115 |
| JPS00171 | SEQ ID NO: 116 |
| JPS00153 | SEQ ID NO: 117 |
| JPS00151 | SEQ ID NO: 118 |
| JPS00154 | SEQ ID NO: 119 |
| JPS00183 | SEQ ID NO: 120 |
| JPS00185 | SEQ ID NO: 121 |
| J23100 | SEQ ID NO: 122 |
| J23100 hybrid | SEQ ID NO: 123 |
| J23115 | SEQ ID NO: 124 |
| GMV00233 | SEQ ID NO: 125 |
| GMV00235 | SEQ ID NO: 126 |
| GMV00433 | SEQ ID NO: 127 |
| GMV00434 | SEQ ID NO: 128 |
| GMV00435 | SEQ ID NO: 129 |
| GMV00436 | SEQ ID NO: 130 |
| GMV00437 | SEQ ID NO: 131 |
| GMV00438 | SEQ ID NO: 132 |
| GMV00439 | SEQ ID NO: 133 |
| GMV00440 | SEQ ID NO: 134 |
| GMV00441 | SEQ ID NO: 135 |
| GMV00442 | SEQ ID NO: 136 |
| ESG00084 | SEQ ID NO: 137 |
| ESG00088 | SEQ ID NO: 138 |
| pMZT37 | SEQ ID NO: 139 |
| MaFAR-g1 | SEQ ID NO: 140 |
| MaFAR-g2 | SEQ ID NO: 141 |
| MaFAR-g3 | SEQ ID NO: 142 |
| MaFAR-g4 | SEQ ID NO: 143 |
| GMV410 | SEQ ID NO: 144 |
| GMV411 | SEQ ID NO: 145 |
| GMV412 | SEQ ID NO: 146 |
| GMV413 | SEQ ID NO: 147 |
| GMV414 | SEQ ID NO: 148 |
| GMV415 | SEQ ID NO: 149 |
| GMV416 | SEQ ID NO: 150 |
| GMV417 | SEQ ID NO: 151 |
| GMV418 | SEQ ID NO: 152 |
| GMV419 | SEQ ID NO: 153 |
| GMV420 | SEQ ID NO: 154 |
| GMV421 | SEQ ID NO: 155 |
| GMV422 | SEQ ID NO: 158 |
| GMV423 | SEQ ID NO: 159 |

EXAMPLES

The present invention is further defined in the following Examples. It should be understood that these examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Biosynthetic Production of Isobutanol from Methane

Initial experiments were performed to confirm and validate enzymatic activity of isobutanol pathway enzymes at the relatively high temperatures (i.e., 45° C.) requisite for growth of one preferred methanotroph host organism, *Methylococcus capsulatus* (Bath). Thus, in this example, the methanotroph *M. capsulatus* was engineered in the first series of experiments to overexpress two isobutanol pathway enzymes, ketoacid decarboxylase (KDC) and alcohol dehydrogenase (ADH), prior to introducing the full complement of five isobutanol pathway enzymes (Atsumi et al., 2010) into *M. capsulatus*. Following the functional validation of KDC and ADH activity in *M. capsulatus* (set forth below), the complete five-gene isobutanol pathway was introduced into *M. capsulatus*, the results of which are set forth below.

Gene Selection, Synthesis and Cloning

For the two-gene (isobutanol) pathway experiments (and for the downstream section of the five-gene isobutanol pathway set forth below), ketoacid decarboxylase (KDC) and alcohol dehydrogenase (ADH) genes were amplified by colony PCR from *Methylosinus trichosporium* (strain: OB3b, National Collection of Industrial, Food and Marine Bacteria (NCIMB) Accession No: 11131) and *Methylococcus capsulatus* (Bath). The *Methylosinus trichosporium* gene, MtKDC, encoding KDC is set forth in SEQ ID NO:82, *Methylosinus trichosporium* gene, MtADH, encoding ADH is set forth in SEQ ID NO:83. The *Methylococcus capsulatus* (Bath) gene, McKDC, encoding KDC is set forth in SEQ ID NO:7, the *Methylococcus capsulatus* (Bath) genes, McADH-2a and McADH-2b, encoding two ADH2 homologs, are set forth in SEQ ID NO:84 and SEQ ID NO:85, respectively.

Other KDC and ADH genes such as LIKIVD: *Lactococcus lactis* KDC (SEQ ID NO:86); ScPDC6: *Saccharomyces cerevisiae* PDC6 (SEQ ID NO:87); ScARO10: *S. cerevisiae* ARO10 (SEQ ID NO:88); ScADH2: *S. cerevisiae* ADH2 (SEQ ID NO:89); ScPDC1: *S. cerevisiae* PDC1 (SEQ ID NO:90); CaPDC: *Clostridium acetobutylicum* PDC (SEQ ID NO:91) were codon optimized for expression in *M. capsulatus* and de novo synthesized by GenScript (Piscataway, N.J.). Various KDC and ADH combinations were cloned with a constitutive promoter (J23115) or inducible (Ptrc) promoter into plasmid pCM132 (Accession No. AF327720; SEQ ID NO:79) with the Clontech In-Fusion kit (Mountain View, Calif.). A gene for the ds-Red protein was used as a control. Plasmids were transformed into *E. coli* S17-1 for conjugation.

Vector Inserts

Vector inserts contain the DNA fragments that are to be carried in the plasmid. The vector inserts were designed as exchangeable parts to the vector backbone described above. In one embodiment of the 2-gene pathway example, the plasmids were designed to contain two inserts made up of *Methylococcus capsulatus* KDC (MCA0996; SEQ ID NO:7) and *Saccharomyces cerevisiae* ADH6 (YMR318C; SEQ ID NO:9) genes. Both genes were amplified from genomic DNA of their respective hosts, with the primers described above in Tables 2 and below in Table 3.

TABLE 3

Plasmid insert modules, templates and primers

| Plasmid | PCR rxn: | Vector Backbone | Insert 1 | Insert 2 | Insert3 |
|---|---|---|---|---|---|
| pJS0025 | template | pJSvec | MCA0996 (*M. capsulatus* DNA) | YMR318C (*S. cerevisiae* DNA) | — |
| | primer 1 | JPS0082 | JPS0032 | JPS00118 | — |
| | primer 2 | JPS0031 | GMV00257 | JPS00119 | — |
| pGMV145 | template | pMZT3 | MCA0996 (*M. capsulatus* DNA) | YMR318C (*S. cerevisiae* DNA) | — |
| | primer 1 | JPS0082 | GMV00251 | JPS00118 | — |
| | primer 2 | ESG00087 | GMV00257 | JPS00119 | — |
| pJS034 | template | pGMV145 | IDT gBlock synthesized mpB DNA | — | — |
| | primer 1 | JPS00161 | JPS00163 | — | — |
| | primer 2 | JPS00162 | JPS00164 | — | — |
| pJS041 pJS041n | template | pJS034 | MCA1837 (*M. capsulatus* DNA) | MCA2272 (*M. capsulatus* DNA) | MCA2082 (*M. capsulatus* DNA) |
| | primer 1 | JPS00162 | JPS00173 | JPS00176 | JPS00157 |
| | primer 2 | JPS00172 | JPS00174 | JPS00177 | JPS00178 |
| pJS048 | template | pJS034 | IDT gBlock synthesized Me-AM1 PmxaF DNA | — | — |
| | primer 1 | JPS00169 | JPS00170 | — | — |
| | primer 2 | GMV251 | JPS00171 | — | — |
| pJS038 | template | pGMV145 | MCA1837 (*M. capsulatus* DNA) | — | — |
| | primer 1 | JPS00153 | JPS00151 | — | — |
| | primer 2 | GMV251 | JPS00154 | — | — |
| pJS042 pJS042n | template | pJS048 | pJS038 | — | — |
| | primer 1 | JPS00162 | JPS00173 | — | — |
| | primer 2 | JPS00172 | JPS00178 | — | — |
| pJS050 | template | pJS041n | pJS041n | — | — |
| | primer 1 | JPS00183 | JPS00174 | — | — |
| | primer 2 | JPS00176 | JPS00185 | — | — |

The modular parts i.e., vector backbone and vector inserts) were PCR amplified (as listed in Table 3) with NEB Phusion master mix (New England Biolabs: Ipswich, Mass.) according to the manufacturer's instructions and in vitro assembled with the Clontech InFusion HD Cloning System kit (Clontech; Mountain View, Calif.) according to the manufacturer's instructions to generate circular plasmid listed below.

The in vitro assembled plasmids (2 μl of the InFusion reaction) were transformed into chemically competent NEB Turbo *E. coli* cells, screened by colony PCR, purified, and subsequently sequence verified.

The plasmid pJSvec (SEQ ID NO:80) served as the template for the vector backbone with an inducible promoter and consisted of the pCM132 cloning vector (SEQ ID NO:79), lacIq, and the IPTG-inducible pTrc promoter.

The plasmid pMZT3 (SEQ ID NO:81) served as the template for the vector backbone with a constitutive promoter and consisted of the pCM132 (SEQ ID NO:79) cloning vector and *E. coli* J23115 promoter (SEQ ID NO:124).

The plasmid pJS0025 was designed to express *M. capsulatus* KDC (MCA0996; SEQ ID NO:7) and *S. cerevisiae* ADH6 (YMR 318C; SEQ ID NO:9) from the inducible promoter.

The plasmid pGMV145 was designed to express *M. capsulatus* KDC (MCA0996; SEQ ID NO:7) and *S. cerevisiae* ADH6 (YMR 318C; SEQ ID NO:9) from the constitutive promoter.

The plasmid pJS034 introduced a second terminator sequence into pGMV145. The pGMV145 vector backbone was PCR amplified with primers JPS00161 (SEQ ID NO:101)/JPS00162 (SEQ ID NO:102) and KOD mastermix. The insert contained DNA sequence for npB (SEQ ID NO:100) synthesized as a gBlock from Integrated DNA Technologies (Coralville, Iowa) and amplified with JPS00163 (SEQ ID NO:103)/JPS00164 (SEQ ID NO:104) primers.

Expression of the Full Five-Gene Pathway for Methane-to-Isobutanol Conversion

In order to synthesize isobutanol from methane (i.e., via pyruvate), without the need to exogenously supply a ketoacid intermediate, the pJSO4I and pJSO4In plasmids were designed to express all five isobutanol pathway genes: (1) *M. capsulatus* KDC (MCA0996; SEQ ID NO:7) and (2) *S. cerevisiae* ADH6 (YMR318C; SEQ ID NO:9) from the J23115 constitutive promoter (SEQ ID NO:124), and (3) *M. capsulatus* ilvK (MCA1837; SEQ ID NO:1), (4) *M. capsulatus* ilvC (MCA2272; SEQ ID NO:3), and (5) *M. capsulatus* ilvD (MCA2082; SEQ ID NO:5) from the J23100 constitutive promoter (see, FIG. 3). Plasmid pJS041n contains the canonical J23100 promoter sequence (5'-TTGACGGCTAGCTCAGTCCTAGGTACAGTGCTAGC-3'; SEQ ID NO:122), and plasmid pJS041 contains a modified J23100 promoter sequence (5'-TTGACGGCTAGCTCAGC-CCTTGGTACAATGCTAGC-3'; SEQ ID NO:123), which represents a hybrid fusion of the J23100 and J23115 (SEQ ID NO:124) promoters that arose during the process of cloning and generating the plasmid in *E. coli* (Table 3). This mutated construct was retained and tested to see whether the promoter mutations might impart improved production of isobutanol in the microbial expression host (e.g., *M. capsulatus* (Bath)).

TABLE 4

Sequence comparison between the "hybrid" promoters in plasmids pJS041 and pJS042 and the canonical promoters J23115 and J23100

| | |
|---|---|
| J23115 (SEQ ID NO: 124) | TTTATAGCTAGCTCAGCCCTTGGTACAATGCTAGC |
| pJS041-hybrid (SEQ ID NO: 123) | TTGACGGCTAGCTCAGCCCTTGGTACAATGCTAGC |
| J23100 (SEQ ID NO: 122) | TTGACGGCTAGCTCAGTCCTAGGTACAGTGCTAGC |

The pJS048 plasmid replaced the J23100 promoter with the MxaF promoter (SEQ ID NO:112) from *Methlyobacterium extorquens* AM-1 in pJS034.

The pJS050 plasmid was designed to express five genes: *M. capsulatus* KDC (MCA0996; SEQ ID NO:7) and *S. cerevisiae* ADH6 (YMR318C; SEQ ID NO:9) from the J23115 constitutive promoter and *M. capsulatus* ilvK (MCA1837; SEQ ID NO:1), *M. capsulatus* ilvC (MCA2272; SEQ ID NO:3), and *M. capsulatus* ilvD (MCA2082; SEQ ID NO:5) from the J23115 constitutive promoter.

Conjugations

The method for conjugal transfer of RP4-mob-containing plasmids into *M. trichasporium* and *M. capsulatus* (Bath) was based on the method described previously (Martin & Murrell, 1995; Stafford et. al., 2003). Briefly, 10 ml of a 16 hour culture of *E. coli* S17-1 carrying the plasmid was collected on a sterile 47 mm, 0.2 μm pore-size, nitrocellulose filter (Millipore). The cells were washed with 50 ml NMS medium without antibiotic. A fresh 50 ml culture of the *M. trichosporium* or *M. capsulatus* (Bath) recipient grown to an optical density ($A_{540}$) of 0.2-0.4 (mid-exponential phase of growth) was collected on the same filter as the *E. coli* S17-1 host cells. The cells were washed with 50 ml NMS and the filter was placed on an NMS agar plate supplemented with 0.02% (w/v) Proteose Peptone (Difco Laboratories, Detroit, Mich.) and incubated for 24 hours at 30° C. (for *M. trichosporium*) or 37° C. (*M. capsulatus* (Bath)) in the presence of 20-25% methane ($CH_4$) (v/v) in air. After incubation, the cells from the conjugation plate were washed from the filter with 10 ml of NMS, pelleted by centrifugation at 7,000×g, and re-suspended in 1 ml of NMS. 150 μl aliquots were spread onto selective NMS plates containing 10 μg/ml nalidixic acid to select against *E. coli* and 15 μg/ml kanamycin for plasmid selection and incubated at 30° C. or 45° C. for *M. trichosporium* or *M. capsulatus*, respectively. The remaining cells were grown in NMS liquid containing 10 mg/ml nalidixic acid and 15 μg/ml kanamycin (Sigma, St. Louis, Mo.) as a secondary selection process. Cells grown in liquid selection were serially passaged three times, before spreading onto selective NMS plates for clone isolation.

*M. capsulatus* Growth Conditions

From a saturated starter culture, *M. capsulatus* (Bath) cells were diluted 1:100 into 10 ml of fresh NMS containing 15 μg/ml kanamycin in a 125-ml shake flask. For ketoacid feeding experiments, cultures were treated with 1 g/L 2-ketovalerate (CAS#1821-02-9) or 8 g/L 2-ketoisovalerate (CAS#3715-19-5) with or without the inducer, 0.1 mM isopropylthiogalactoside (IPTG). The flasks were closed with Suba-seals, injected with 20-25% $CH_4$ (v/v) in air, and incubated at 45° C. for 0-120 hours.

Extraction of Alcohols from the Growth Medium

1. Isobutanol production: The shake-flask samples were prepared for extraction by cooling them on ice for 1 hour, which ensures that the volatile organic compounds (VOC's) in the vapor phase were not lost to the atmosphere after the Suba-seal is opened.

2. If extracting from a 9-10 ml culture, all of the culture was transferred to a 50 ml tube. For samples with high isobutanol productions (e.g., pGMV 145), 10 ml of ethyl acetate was added for extraction. For samples with low isobutanol production, only 3 ml of ethyl acetate was used. Once ethyl acetate was added to the cultures, they were subjected to either vortexing (1-2 minutes) or shaking at room temperature (for 1 hour) for efficient extraction.

3. The tubes were then centrifuged at 4000 rpm for 20 minutes in an Eppendorf 5810 centrifuge equipped with an A-4-81 rotor.

4. One (1) ml of the organic layer was then filtered (0.2 μm PTFE membrane) and transferred to 2 ml glass Agilent gas chromatography vials for analysis.

GC-FID Analysis for Isobutanol

The extracted alcohol compounds were quantified with the Agilent 7890A gas chromatograph (GC) with flame ionization detector and PAL auto-sampler. An HP InnoWax capillary column (30 m, 0.32-mm internal diameter, 0.25-mm film thickness; Agilent Technologies, Santa Clara, Calif.) was used to separate the alcohols. The GC oven temperature was initially set at 35° C. for 1 minute and ramped at rate of 10° C./minute until 85° C. was reached and held for 1 minute. A second temperature ramp of 80° C./minute up to 240° C. was performed and held for 2 minutes. Hydrogen gas was the carrier gas used with 9.3 psi constant inlet pressure. The inlet and detector were maintained at 240° C. A 1 μl sample was injected in split injection mode with a 25:1 split ratio.

Figure 4:
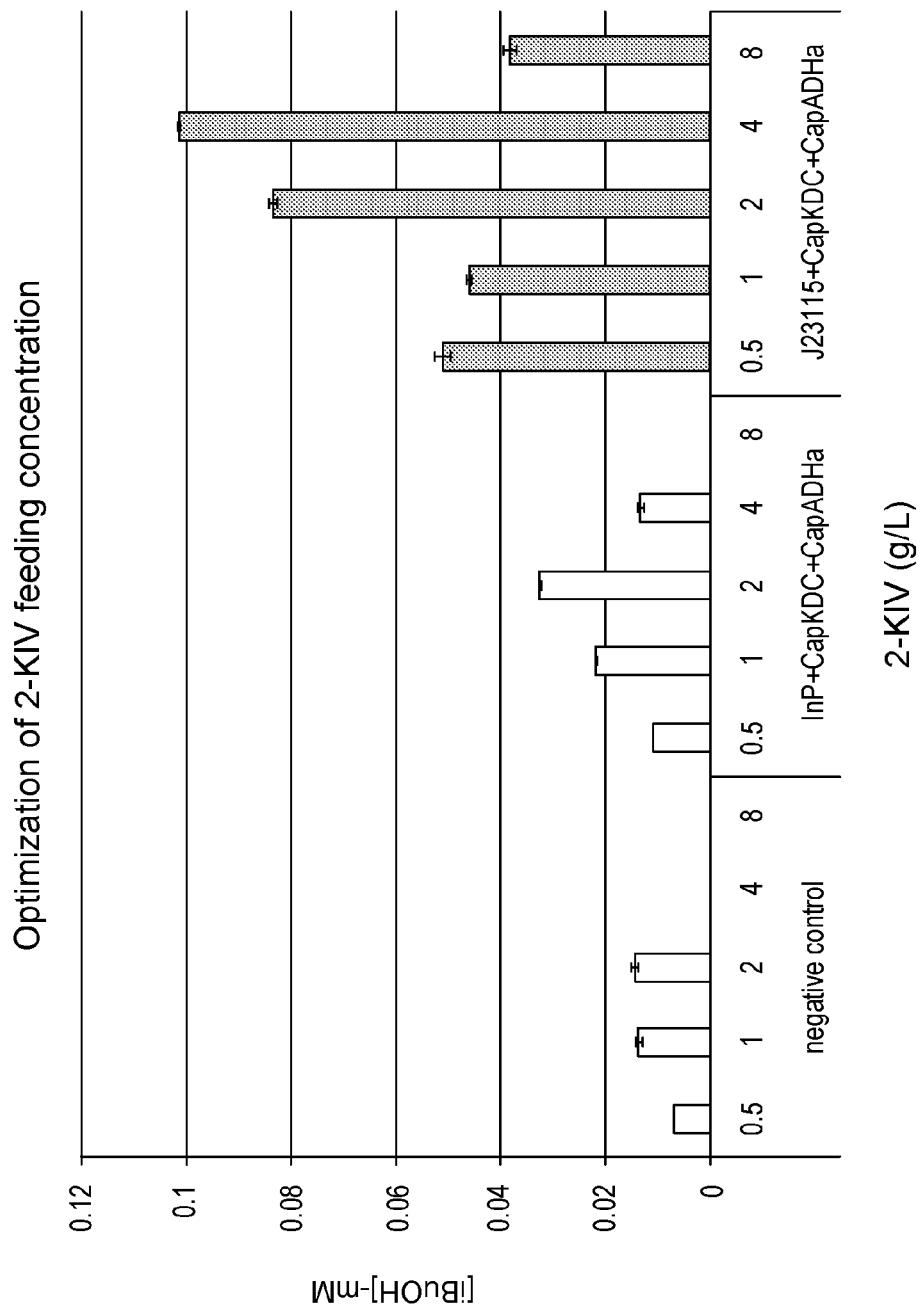
FIG. 4 shows the optimization of the 2-ketoisovalerate (2-KIV) concentration fed to various engineered host strains expressing the two-gene (isobutanol) pathway.
Figure 5:
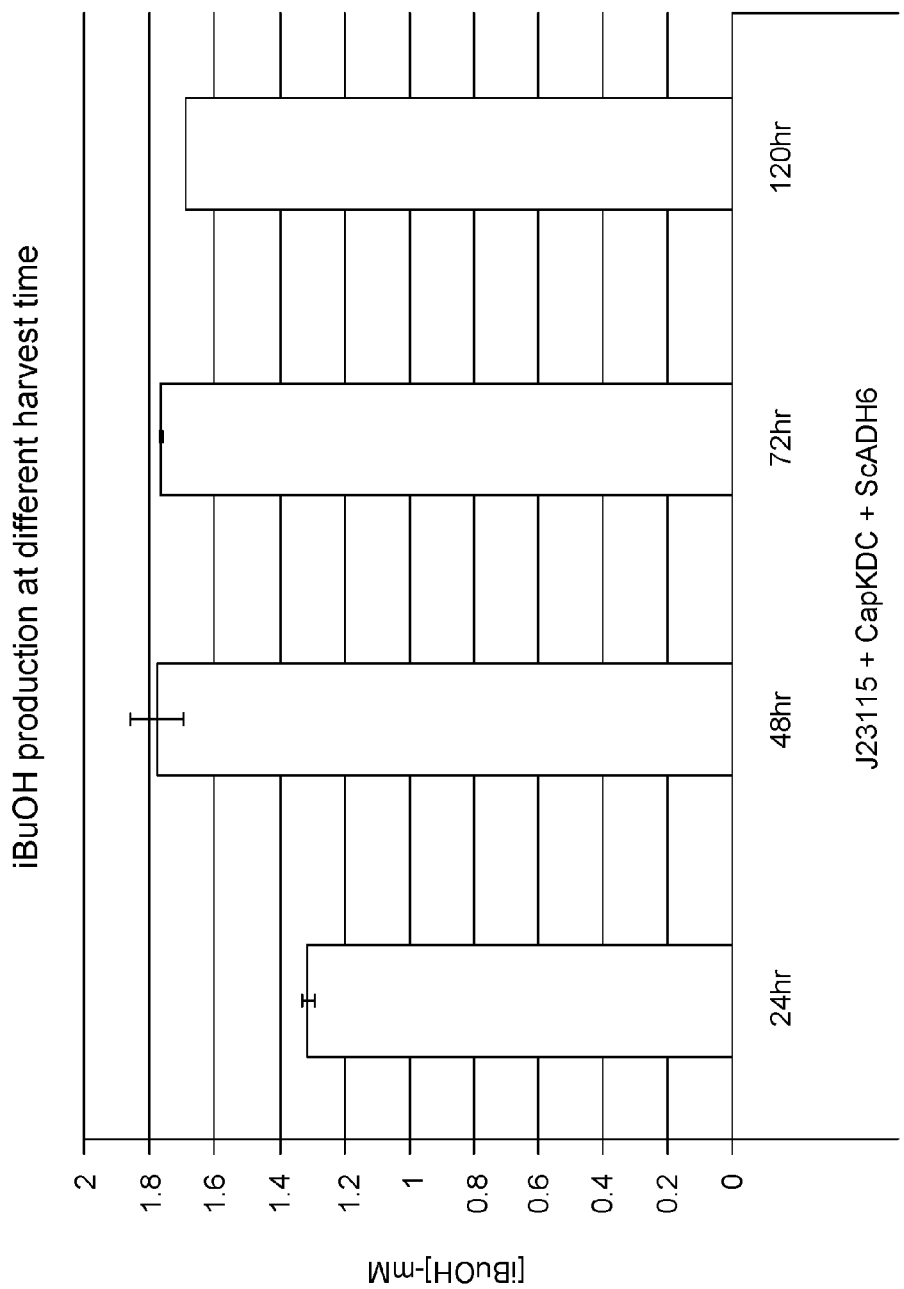
FIG. 5 shows the measured production of isobutanol in an *M. capsulatus* strain expressing plasmid pGMV145 (containing: promoter J23115, the gene for *M. capsulatus* (Bath) 2-ketoisovalerate decarboxylase (CapKDC) and the gene for *S. cerevisiae* alcohol dehydrogenase (ScADH6)), harvested at different time intervals after 2-KIV addition.
Figure 6:
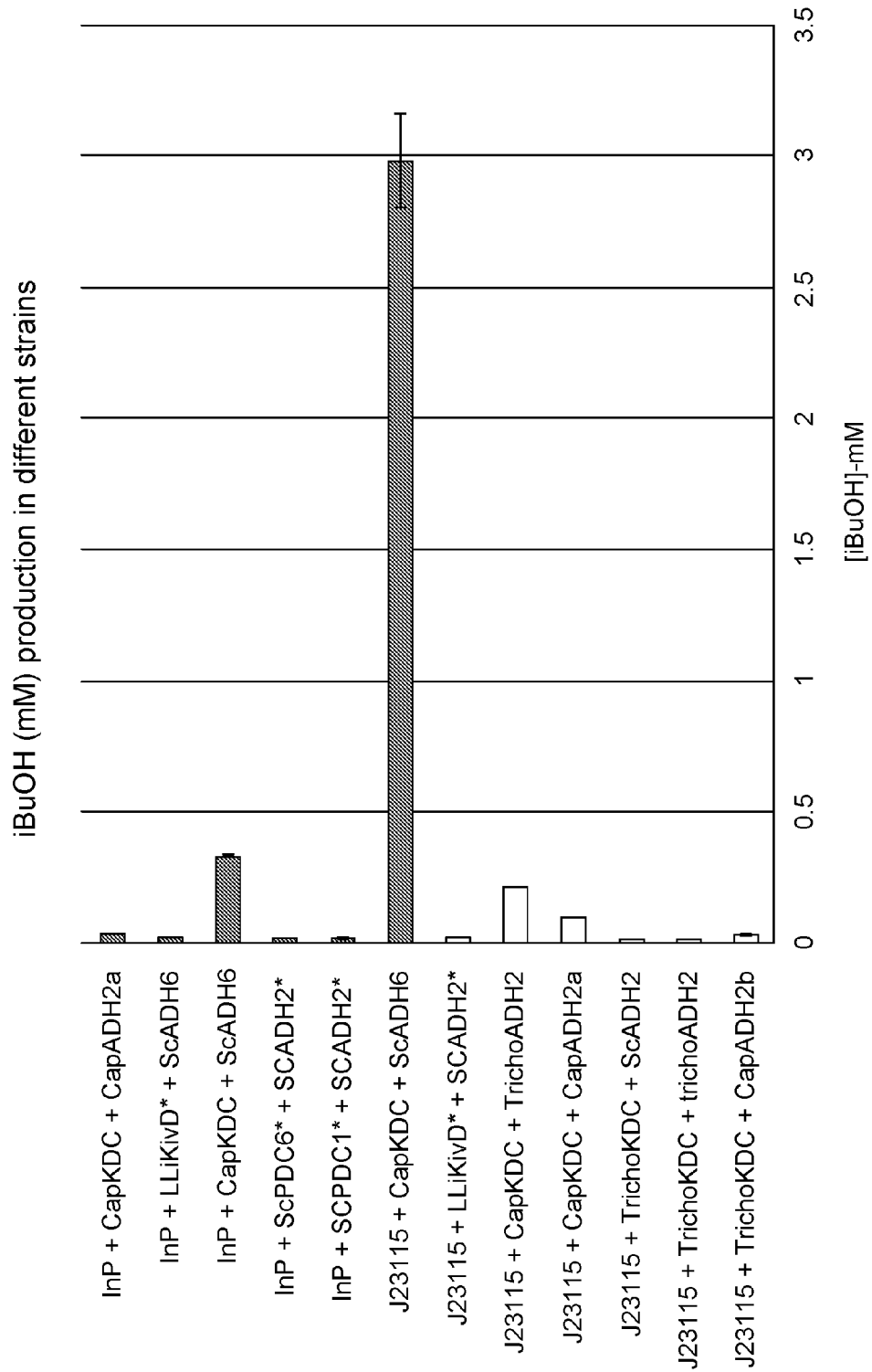
FIG. 6 is a comparison of isobutanol production after 2-KIV feeding in various engineered host strains expressing different combinations of two genes (i.e., isobutanol pathway genes) and with different promoters.

When the two-gene KDC/ADH pathway was expressed in *M. capsulatus* and the isobutanol production was measured (using exogenous 2-KIV feeding), the following results were observed. A concentration of 2-KIV greater than about 4 g/L had a toxic effect on growth, wherein a 2-KIV concentration of about 2 g/L yielded the best results (FIG. 4). Peak isobutanol production occurred about 48-72 hours after 2-KIV feeding (FIG. 5). *E. coli* promoters function in *M. capsulatus*, but not equally well. Constitutive promoters yielded better results than inducible promoters, but the optimal constitutive promoter will typically depend on the individual construct to be used. For example, J23115 was observed to work best for *M. capsulatus* KDC and *M. capsulatus* ADH (data not shown). Lastly, different host strains require slightly different concentrations of 2-KIV to maximize isobutanol production.

Figure 7:
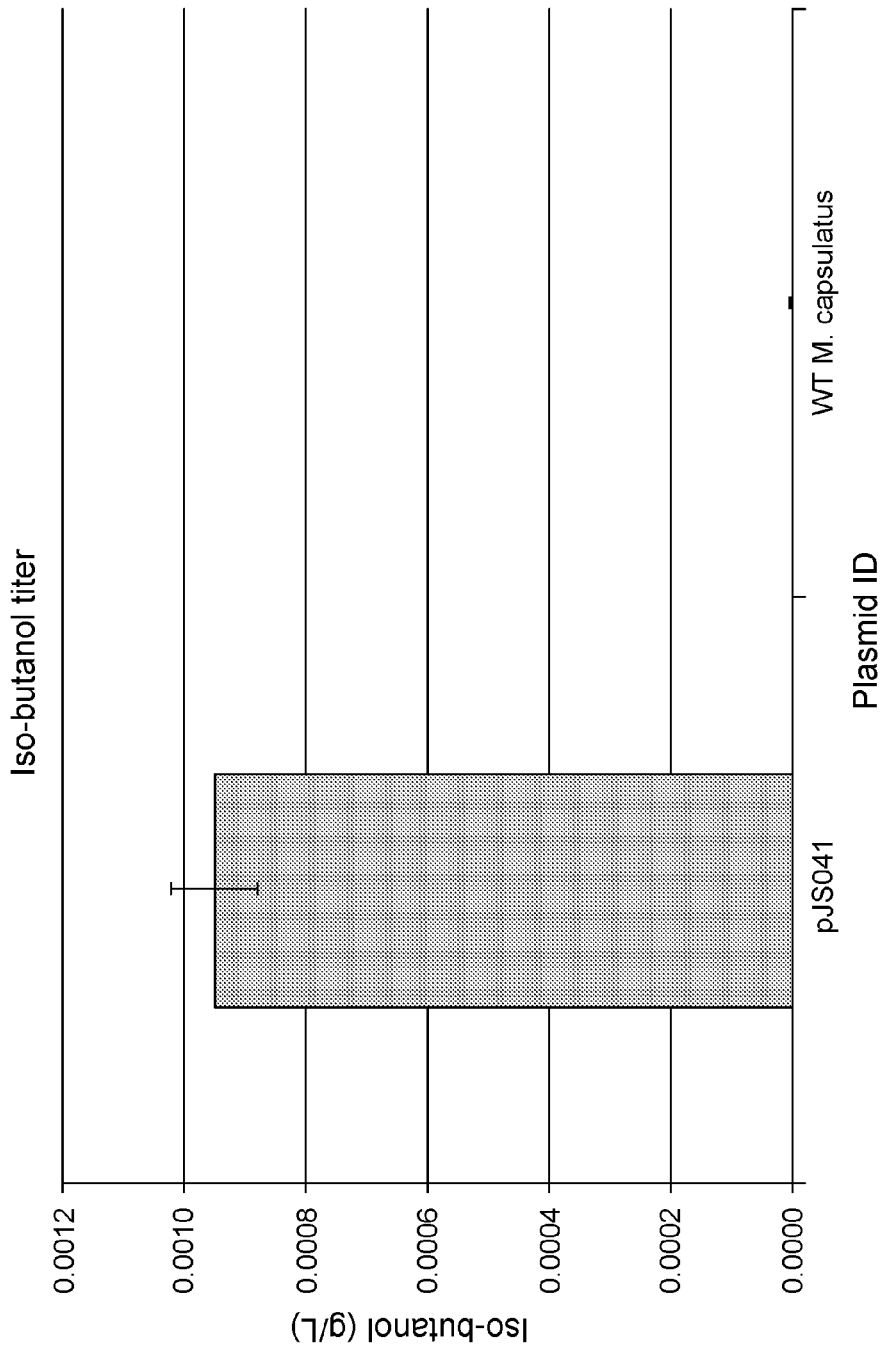
FIG. 7 compares production of isobutanol in the wild-type *M. capsulalus* str. Bath (no plasmid) and an engineered strain (pJS041) expressing the five-gene (isobutanol) pathway.

The best two-gene combination with a constitutive promoter (J23115; SEQ ID NO:124) was *M. capsulalus* KDC and *S. cerevisiae* ADH6 (plasmid pGMV145), wherein harvesting after 48-72 hours produced the most isobutanol (FIG. 7). The vector construct using pGMV145, having constitutive promoter J23115, a CapKDC gene (MCA0996; SEQ ID NO:7), and a ScADH6 gene (YMR318C; SEQ ID NO:9), produced the most isobutanol after 2-KIV feeding, which was about 3 mM (or about 0.22 g/L).

When the complete five-gene isobutanol pathway was introduced into a host strain, plasmid pJS041 yielded the highest levels of isobutanol production, with a measured titer of about 0.001 g/liter (FIG. 7), compared to no detectable production in the wild-type strain.

In certain embodiments, the production of isobutanol from methane substrate in a host strain (i.e., expressing the five-gene isobutanol pathway, e.g. via plasmid pJS041) is further optimized by genetic manipulations described above, as well as by cultivating the host strain in a fermentor culture with continuous $CH_4$ perfusion, instead of batch addition of $CH_4$ to the culture medium (as was done for the shake flasks experiments). In other embodiments, the production of increased isobutanol titers from methane in a host strain is further optimized via manipulations to the fermentation process (batch fed or perfusion), such as feeding additional media components as they are depleted (phosphate, nitrate, etc.) and maintaining the pH by continuously adding acid or base.

Example 2

Biosynthetic Production of 1-Butanol from Methane

A ketoacid pathway analogous to that described in Example 1, but designed to produce 1-butanol (n-butanol) is engineered in a single carbon (C1) metabolizing microbial host, such as *M. capsulatus* (Bath). In this example, L-threonine (which is ultimately generated from methane via phosphoenolpyruvate) is first de-aminated to 2-ketobutyrate (2-oxobutanoate) by the action of threonine dehydratase (also referred to in the art as threonine ammonia-lyase (EC 4.3.119) encoded by the genes ilvA or tdcB) (Shen & Liao, 2008). The tdcB gene product has the biotechnological advantage that the enzyme is a catabolic enzyme, and is not feedback inhibited by L-valine or L-isoleucine (Guillouet et al., 1999).

In the second reaction step, the reaction catalyzed by leuA (encoding isopropylmalate synthase/2-ethylmalate synthase (EC 2.3.3.6)) combines 2-ketobutyrate, acetyl-CoA, and $H_2O$ to create (R)-2-ethylmalate. In the third reaction step, the gene product of leuC and leuD (encoding the two subunits of isopropylmalate isomerase) converts 2-ethylmalate into 3-ethylmalate. In the fourth reaction step, the gene product of leuB (encoding the enzyme 3-isopropylmalate dehydrogenase) converts 3-ethylmalate into 2-ketovalerate). At this stage, the same two enzymes used in the previous example, KDC (acting as a 2-ketovalerate decarboxylase) and ADH2 (alcohol dehydrogenase), are used to convert 2-ketovalerate into 1-butanol.

An alternate pathway (the citramalate pathway) from phosphoenolpyruvate and pyruvate to 2-ketobutyrate has also been described for making 1-butanol (Atsumi & Liao, 2008).

As described, above, the plasmids generated in this study are based on the broad-host-range pCM132 (Accession No. AF327720, SEQ ID NO:79) cloning vector described by Marx & Lidstrom (2001). In this embodiment, the use of the Clontech (catalog no. 639647) InFusion HD Cloning System kit is one example of how to construct plasmids, but is not meant to limit or exclude other methods that are known in the art.

Vector Backbones

Vector backbones contain the components of the plasmid that will remain constant. The broad-host range pCM132 vector was modified to produce vector backbones for the plasmids in this study. The pCM132 vector consisted of the following components: trrnB terminator, kanamycin resistance gene, trfA, IncP oriT, IncP oriV, colE1 ori, and lacZ. This parental vector was modified to replace lacZ with a vector insert that contains promoter sequence to produce plasmids pMZT3 (SEQ ID NO:81) and pMZT37 (SEQ ID NO:139).

Vector Inserts

Vector inserts contain DNA to be added to a vector backbone. The inserts were designed as exchangeable (modular) parts to the vector and in this example consist of *Methylococcus capsulatus* KDC (MCA0996; SEQ ID NO:7), leuA (MCA2275; SEQ ID NO:57), leuCDB (MCA2063; SEQ ID NO:63, MCA2064; SEQ ID NO:61 and MCA2065; SEQ ID NO:59), *Saccharomyces cerevisiae* ADH6 (YMR318C; SEQ ID NO:9), and *M. capsulatus* ilvA (MCA0354; SEQ ID NO:55) or *E. coli* tdcB (SEQ ID NO:160) genes. The genes were amplified from genomic DNA of their respective hosts with the primers described in Table 5.

The modular parts (vector backbone and vector insert) were PCR amplified as listed in Table 4 with NEB Phusion master mix according to the manufacturer's instructions and in vitro assembled with the Clontech InFusion HD Cloning System kit according to the manufacturer's instructions to generate circular plasmid. The in vitro assembled plasmids (2 ul of the InFusion reaction) were transformed into chemically competent NEB Turbo *E. coli* cells, screened for by colony PCR, purified, and subsequently sequence verified.

The pGMV145 plasmid was designed to express *M. capsulatus* KDC (MCA0996; SEQ ID NO:7) and *S. cerevisiae* ADH6 (YMR318C; SEQ ID NO:9) from the constitutive promoter.

The pJS034 plasmid introduced a second terminator sequence into pGMV145. The pGMV145 vector backbone was PCR amplified with primers JPS00161 (SEQ ID NO:101)/JPS00162 (SEQ ID NO:102) and KOD mastermix. The insert was mpB DNA synthesized as a gBlock from IDT and amplified with JPS00163 (SEQ ID NO:103)/JPS00164 (SEQ ID NO:104) primers.

The pGMV165 plasmid was designed to express 3 genes: *M. capsulatus* ilvA (MCA0354; SEQ ID NO:55), *M. capsulatus* KDC (MCA0996; SEQ ID NO:7) and *S. cerevisiae* ADH6 (YMR318C; SEQ ID NO:9) from the J23115 (SEQ ID NO:124) constitutive promoter.

The pGMV166 plasmid was designed to express 3 genes: *E. coli* tdcB (SEQ ID NO:160), *M. capsulatus* KDC (MCA0996; SEQ ID NO:7) and *S. cerevisiae* ADH6 (YMR318C; SEQ ID NO:9) from the J23115 (SEQ ID NO:124) constitutive promoter.

The pGMV167 plasmid was designed to express 7 genes: *M. capsulatus* ilvA (MCA0354; SEQ ID NO:55), *M. capsulatus* KDC (MCA0996; SEQ ID NO:7) and *S. cerevisiae* ADH6 (YMR318C; SEQ ID NO:9) from the J23115 (SEQ ID NO:124) constitutive promoter and *M. capsulatus* leuCDB (MCA2063; SEQ ID NO:63, MCA2064; SEQ ID NO:61 and MCA2065; SEQ ID NO:59) and *M. capsulatus* leuA (MCA2275; SEQ ID NO:57) from second J23115 (SEQ ID NO:124) constitutive promoter.

The pGMV168 plasmid was designed to express 7 genes: *E. coli* tdcB (SEQ ID NO:160), *M. capsulatus* KDC (MCA0996; SEQ ID NO:7) and *S. cerevisiae* ADH6 (YMR318C; SEQ ID NO:9) from the J23115 constitutive promoter and *M. capsulatus* leuCDB (MCA2063; SEQ ID NO:63, MCA2064; SEQ ID NO:61 and MCA2065; SEQ ID NO:59) and leuA (MCA2275; SEQ ID NO:57) from a second J23115 constitutive promoter.

Host strains modified with these plasmids were grown on methane as described in the examples above, harvested, extracted, and analyzed for 1-butanol production.

TABLE 5

Insert Modules, Templates and Primers for 1-Butanol Production

| Plasmid | PCR rxn: | Vector backbone | Insert 1 | Insert 2 | Insert3 |
|---|---|---|---|---|---|
| pGMV145 | template | pMZT3 | MCA0996 (*M. capsulatus* DNA) | YMR318C (*S. cerevisiae* DNA) | — |
| | primer 1 | JPS0082 | GMV00251 | JPS00118 | — |
| | primer 2 | ESG00087 | GMV00257 | JPS00119 | — |
| pJS034 | template | pGMV145 | IDT gBlock synthesized mpB DNA | — | — |
| | primer 1 | JPS00161 | JPS00163 | — | — |
| | primer 2 | JPS00162 | JPS00164 | — | — |
| pGMV165 | template | pJS034 | pJS034 | MCA0354 (*M. capsulatus* DNA) | — |
| | primer 1 | GMV435 | GMV433 | GMV431 | — |
| | primer 2 | ESG000087 | GMV434 | GMV432 | — |
| pGMV166 | template | pJS034 | pJS034 | tdcB (*E. coli* DNA) | — |
| | primer 1 | GMV435 | GMV433 | GMV436 | — |
| | primer 2 | ESG000087 | GMV434 | GMV437 | — |
| pGMV167 | template | pGMV165 | pGMV165 | MCA2063-2065 (*M. capsulatus* DNA) | MCA2275 (*M. capsulatus* DNA) |
| | primer 1 | JPS163 | GMV235 | GMV439 | GMV441 |
| | primer 2 | GMV233 | GMV438 | GMV440 | GMV442 |
| pGMV168 | template | pGMV166 | pGMV166 | MCA2063-2065 (*M. capsulatus* DNA) | MCA2275 (*M. capsulatus* DNA) |
| | primer 1 | JPS163 | GMV235 | GMV439 | GMV441 |
| | primer 2 | GMV233 | GMV438 | GMV440 | GMV442 |

Example 3

Biosynthetic Production of Fatty Alcohols from Methane

Conversion of methane to diesel components requires engineering the native metabolism of methanotrophs. The two principal native pathways that can be engineered for increased production of diesel components are the fatty acid pathway and isoprenoid pathway. In the current example, the invention describes the use of the fatty acid pathway for synthesis of diesel (wax ester) components.

Fatty acids are an important source of energy and adenosine triphosphate (ATP) for many cellular organisms. Excess fatty acids, glucose, and other nutrients can be stored efficiently as fat. All cell membranes are built up of phospholipids, each of which contains fatty acids. Fatty acids are also used for protein modification. Fatty acid synthesis is the creation of fatty acids from acetyl-CoA and malonyl-CoA precursors through action of enzymes called fatty acid synthases. Fatty acid chain length and degree of saturation depends on the host microorganism. With regard to *M. capsulatus* (Bath), the primary fatty acids are C16 with saturated or mono unsaturated carbon chains.

The conversion of methane to diesel components requires the over-expression of specific heterologous (exogenous) enzymes within a methanotroph (or non-methanotroph) host microorganism, wherein the over-expression of specific heterologous (exogenous) enzymes can divert the flux from native fatty acid synthesis to compounds of interest. Key intermediates of the fatty acid pathway are the fatty acyl-ACP molecules. Thus, the over-expression of specific heterologous enzymes in a host microorganism divert the flux from acyl-ACP to diesel components such as fatty acids, fatty alcohols, fatty esters and derivatives thereof. Thus, in certain embodiments, a host microorganism has been engineered to over-express specific enzymes such as a fatty acyl ACP reductase (FAR), a fatty acyl CoA reductase (CAR) and wax ester synthases (WES) for diverting flux from native compounds to compounds of interest. Active expression of these enzymes results in the conversion of methane to diesel components via FARs, CARs and WES enzymes cloned and expressed in a host microorganism (e.g., *M. capsulatus* (Bath)).

A biosynthetic pathway analogous to that described in Example 1, but designed to produce fatty alcohols can be engineered in a (C1) metabolizing host microorganism, such as *M. capsulatus*. In this example, fatty acyl-CoA (which is ultimately generated from methane via pyruvate) is converted directly into fatty alcohols by the heterologous over-expression of a fatty-acyl-CoA reductase (FAR).

Construction of Methanotroph Plasmids for Fatty Alcohol Production

As described, above, the plasmids generated in this study are based on the broad-host-range pCM132 (Accession No. AF327720) cloning vector (SEQ ID NO:79) described by Marx & Lidstrom (2001). In this embodiment, the use of the Clontech (catalog no. 639647) InFusion HD Cloning System kit is one example of how to construct plasmids, but is not meant to limit or exclude other methods that are known in the art.

Vector Backbones

Vector backbones contain the components of the plasmid that will remain constant. The broad-host range pCM132 vector was modified to produce vector backbones for the plasmids in this study. The pCM132 vector consisted of the following components: trrnB terminator, kanamycin resistance gene, trfA, IncP oriT, IncP oriV, colE1 ori, and lacZ. This parental vector was modified to replace lacZ with a vector insert that contains promoter sequence to produce plasmids pMZT3 (SEQ ID NO:81) and pMZT37 (SEQ ID NO:139).

Vector Inserts

Vector inserts contain DNA to be added to the vector backbone. The inserts were designed as exchangeable (modular) parts to the vector and in this embodiment consist of the following components. In this example, the plasmids were designed to contain one insert: *Marinobacter algicola* fatty acid reductase (MaFAR; SEQ ID NO:65), also known as a fatty acyl-CoA reductase. The MaFAR gene was codon optimized and synthesized as a series of 4 gBlocks from Integrated DNA Technologies (Coralville, Iowa). The synthesized DNA was designed to include pivot regions to allow proper assembly by InFusion.

Assembly of the Constructs

The modular parts (vector backbone and vector insert) were PCR amplified as listed in Table 4 with NEB Phusion master mix according to the manufacturer's instructions and in vitro assembled with the Clontech InFusion HD Cloning System kit according to the manufacturer's instructions to generate circular plasmid. The in vitro assembled plasmids (2 μl of the InFusion reaction) were transformed into chemically competent NEB Turbo E. coli cells, screened for by colony PCR, purified, and subsequently sequence verified.

Plasmid pMZT3 (SEQ ID NO:81) served as the template for the vector backbone with a constitutive promoter and consisted of the pCM132 cloning vector, *E. coli* J23115 promoter. The vector backbone was PCR amplified from the pMZT3 template with primers ESG00084 (SEQ ID NO:137)/ESG00087 (SEQ ID NO:98).

Plasmid pMZT37 (SEQ ID NO:139) served as the template for the vector backbone with a constitutive promoter and consisted of the pCM132 cloning vector, *E. coli* J23100 promoter. The vector backbone was PCR amplified from the pMZT3 template with primers ESG00084 (SEQ ID NO:137)/ESG00088 (SEQ ID NO:138).

The pGMV147 plasmid was designed to express *M. algicola* FAR gene (SEQ ID NO:65) from the J23115 constitutive promoter (SEQ ID NO:124). The modules of this plasmid included the PCR amplified pMZT3 vector backbone and four synthesized DNA gene fragments from IDT (MaFAR-g1; SEQ ID NO:140, MaFAR-g2; SEQ ID NO:141, MaFAR-g3; SEQ ID NO:142 and MaFAR-g4; SEQ ID NO:143).

The pGMV148 plasmid was designed to express *M. algicola* FAR gene (SEQ ID NO:65) from the J23110 constitutive promoter (SEQ ID NO:122). The modules of this plasmid included the PCR amplified pMZT37 vector backbone and four synthesized DNA gene fragments from IDT (MaFAR-g1; SEQ ID NO:140, MaFAR-g2; SEQ ID NO:141, MaFAR-g3; SEQ ID NO:142 and MaFAR-g4; SEQ ID NO:143).

Figure 8:
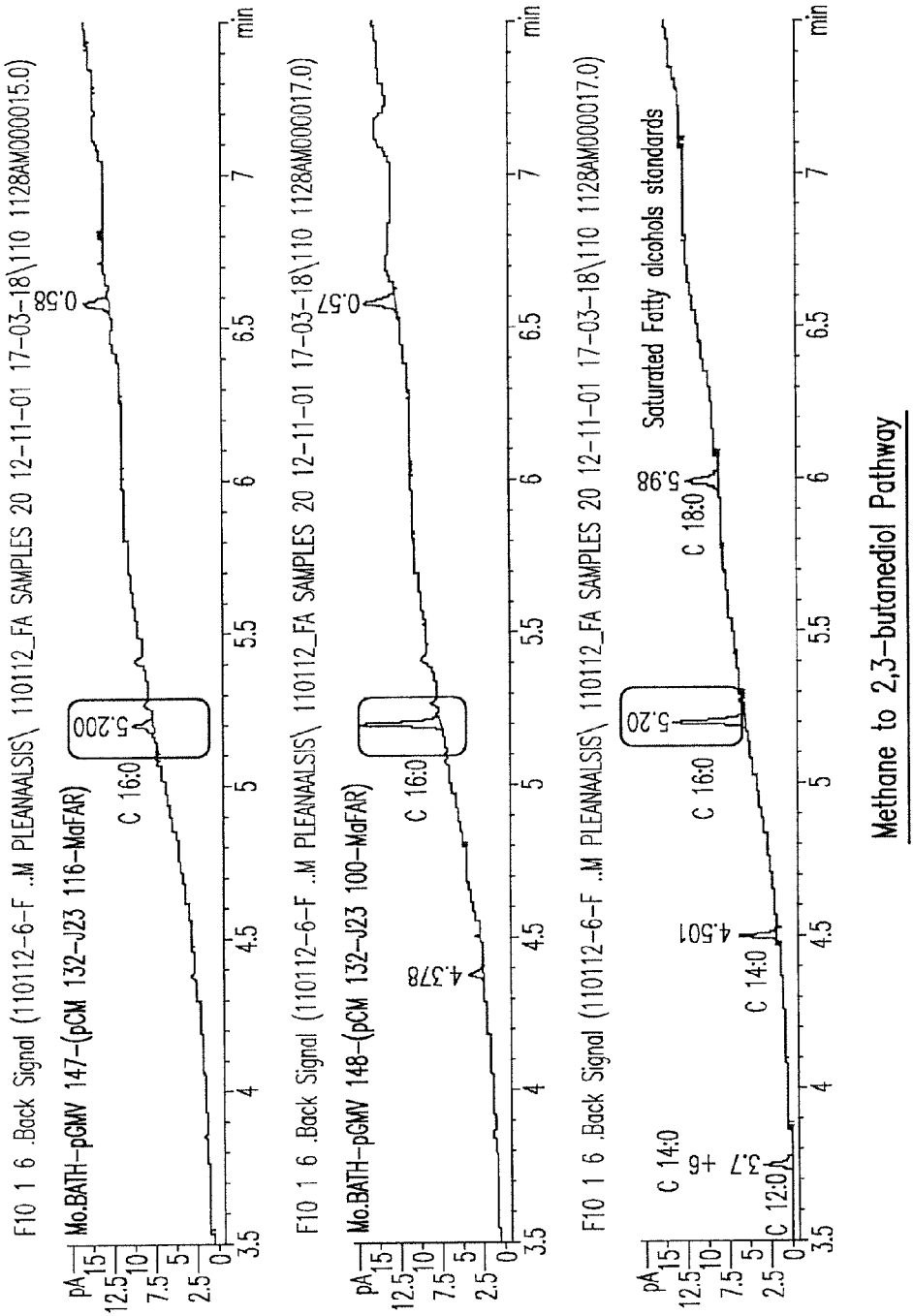
FIG. 8 is a gas chromatography (GC) analysis of fatty acid alcohol production by various engineered strains of *M. capsulatus* (Bath). The GC peak at about 5.2 minutes corresponds to a C16:0 fatty alcohol standard.

Gas chromatography results after various host strains were grown on methane in shake flasks, extracted, and analyzed as described above, are set forth in FIG. 8. The results indicate that the host strain containing plasmid pGMV148 produced C16:0 alcohol (a fatty alcohol) when grown on methane. The host strain containing plasmid pGMV147 produced only a trace amount of fatty alcohol.

TABLE 6

Insert Modules, Templates and Primers for Fatty Alcohol Production

| Plasmid | PCR rxn: | Vector backbone | Insert 1 | Insert 2 | Insert 3 | Insert 4 |
|---|---|---|---|---|---|---|
| pGMV147 | template | pMZT3 | MaFAR-g1 | MaFAR-g2 | MaFAR-g3 | MaFAR-g4 |
|  | primer 1 | ESG00084 | — | — | — | — |
|  | primer 2 | ESG00087 | — | — | — | — |
| pGMV148 | template | pMZT37 | MaFAR-g1 | MaFAR-g2 | MaFAR-g3 | MaFAR-g4 |
|  | primer 1 | ESG00084 | — | — | — | — |
|  | primer 2 | ESG00088 | — | — | — | — |

Example 4

Biosynthetic Production of Fatty Acid Methyl Esters from Methane

Construction of Methanotroph Plasmids for Fatty Acid Ester (Wax Ester) Production The plasmids generated in this example are based on the broad-host-range pCM132 (Accession no. AF327720, SEQ ID NO: 79) cloning vector described by Marx & Lidstrom (2001). In this embodiment, the use of the Clontech (catalogue no. 639647) InFusion HD Cloning System kit is one example of how to construct plasmids, but is not meant to limit or exclude other methods that are known in the art.

Vector Backbones

Vector backbones contain the components of the plasmid that will remain constant. The broad-host range pCM132 vector was modified to produce vector backbones for the plasmids in this study. The pCM132 vector consisted of the following components: trrnB terminator, kanamycin resistance gene, trfA, IncP oriT, IncP oriV, colE1 ori, and lacZ. This parental vector was modified to replace lacZ with a vector insert that contains promoter sequence to produce plasmids and pMZT3 and pMZT37.

Vector Inserts

Vector inserts contain DNA to be added to a vector backbone. The inserts were designed as exchangeable (modular) parts to the vector and in this embodiment consist of a wax ester synthase (WES) derived from *Acinetobacter* sp. ADP1 (SEQ ID NO:67), *Psychrobacter arcticum* 273-4 (SEQ ID NO:69) or *Rhodococcus opcaus* B4 (SEQ ID NO:71, SEQ ID NO:73, SEQ ID NO:75 or SEQ ID NO:77). The WES genes were codon-optimized and synthesized by GenScript.

Assembly of the Constructs

The modular parts (vector backbone and vector insert) were PCR amplified as listed in Table 7 with NEB Phusion master mix according to the manufacturer's instructions and in vitro assembled with the Clontech InFusion HD Cloning System kit according to the manufacturer's instructions to generate circular plasmid. The in vitro assembled plasmids (2 ul of the InFusion reaction) were transformed into chemically competent NEB Turbo *E. coli* cells, screened for by colony PCR, purified, and subsequently sequence verified.

Plasmid pMZT3 (SEQ ID NO:81) served as the template for the vector backbone with a constitutive promoter and consisted of the pCM132 cloning vector, *E. coli* J23115 promoter. The vector backbone was PCR amplified from the pMZT3 template with primers ESG00084 (SEQ ID NO:137)/ESG00087 (SEQ ID NO:98).

Plasmid pMZT37 (SEQ ID NO:139) served as the template for the vector backbone with a constitutive promoter and consisted of the pCM132 cloning vector, *E. coli* J23100 promoter. The vector backbone was PCR amplified from the pMZT3 template with primers ESG00084 (SEQ ID NO:137)/ESG00088 (SEQ ID NO:138).

The pGMV153 plasmid was designed to express *Acinetobacter* sp. ADP1 WES gene (wax-dgaT; SEQ ID NO:67) from the J23115 constitutive promoter. The modules of this plasmid included the PCR amplified pMZT3 vector backbone and the codon-optimized synthesized gene.

The pGMV154 plasmid was designed to express *Psychrobacter arcticum* 273-4 WES gene (Psyc_0223; SEQ ID NO:69) from the J23115 constitutive promoter. The modules of this plasmid included the PCR amplified pMZT3 vector backbone and the codon-optimized synthesized gene.

The pGMV155 plasmid was designed to express *Rhodococcus opcaus* B4 WES gene (ROP_02100; SEQ ID NO:71) from the J23115 constitutive promoter. The modules of this plasmid included the PCR amplified pMZT3 vector backbone and the codon-optimized synthesized gene.

The pGMV156 plasmid was designed to express *Rhodococcus opcaus* B4 WES gene (ROP_13050; SEQ ID NO:73) from the J23115 constitutive promoter. The modules of this plasmid included the PCR amplified pMZT3 vector backbone and the codon-optimized synthesized gene.

The pGMV157 plasmid was designed to express *Rhodococcus opcaus* B4 WS gene (ROP_26950; SEQ ID NO:77) from the J23115 constitutive promoter. The modules of this plasmid included the PCR amplified pMZT3 vector backbone and the codon-optimized synthesized gene.

The pGMV158 plasmid was designed to express *Rhodococcus opcaus* B4 WES gene (ROP_54550; SEQ ID NO:75) from the J23115 constitutive promoter. The modules of this plasmid included the PCR amplified pMZT3 vector backbone and the codon-optimized synthesized gene.

The pGMV159 plasmid was designed to express *Acinetobacter* sp. ADP1 WES gene (wax-dgaT; SEQ ID NO:67) from the J23100 constitutive promoter. The modules of this plasmid included the PCR amplified pMZT3 vector backbone and the codon-optimized synthesized gene.

The pGMV160 plasmid was designed to express *Psychrobacter arcticum* 273-4 WES gene (Psyc_0223; SEQ ID NO:69) from the J23100 constitutive promoter. The modules of this plasmid included the PCR amplified pMZT3 vector backbone and the codon-optimized synthesized gene.

The pGMV161 plasmid was designed to express *Rhodococcus opcaus* 134 WES gene (ROP_02100; SEQ ID NO:71) from the J23100 constitutive promoter. The modules of this plasmid included the PCR amplified pMZT3 vector backbone and the codon-optimized synthesized gene.

The pGMV162 plasmid was designed to express *Rhodococcus opcaus* B4 WES gene (ROP_13050; SEQ ID NO:73) from the J23100 constitutive promoter. The modules of this plasmid included the PCR amplified pMZT3 vector backbone and the codon-optimized synthesized gene.

The pGMV163 plasmid was designed to express *Rhodococcus opcaus* B4 WES gene (ROP_26950; SEQ ID NO:77) from the J23100 constitutive promoter. The modules of this plasmid included the PCR amplified pMZT3 vector backbone and the codon-optimized synthesized gene.

The pGMV164 plasmid was designed to express *Rhodococcus opcaus* B4 WES gene (ROP_54550; SEQ ID NO:75) from the J23100 constitutive promoter. The modules of this plasmid included the PCR amplified pMZT3 vector backbone and the codon-optimized synthesized gene.

Strains modified with these plasmids are grown on methane as described in the examples above, harvested, extracted, and analyzed for fatty acid ester production.

TABLE 7

Insert Modules, Templates and Primers for Fatty Acid Ester Production

| Plasmid | PCR rxn: | Vector backbone | Insert |
|---|---|---|---|
| pGMV153 | template | pMZT3 | pUC57-AbWS (WS-dgaT) |
| | primer 1 | ESG00084 | GMV410 |
| | primer 2 | ESG00087 | GMV416 |
| pGMV154 | template | pMZT3 | pUC57-PaWS (Psyc_0223) |
| | primer 1 | ESG00084 | GMV411 |
| | primer 2 | ESG00087 | GMV417 |
| pGMV155 | template | pMZT3 | pUC57-RoWS (ROP_02100) |
| | primer 1 | ESG00084 | GMV412 |
| | primer 2 | ESG00087 | GMV418 |
| pGMV156 | template | pMZT3 | pUC57-RoWS (ROP_13050) |
| | primer 1 | ESG00084 | GMV413 |
| | primer 2 | ESG00087 | GMV419 |
| pGMV157 | template | pMZT3 | pUC57-RoWS (ROP_26950) |
| | primer 1 | ESG00084 | GMV414 |
| | primer 2 | ESG00087 | GMV420 |
| pGMV158 | template | pMZT3 | pUC57-RoWS (ROP_54550) |
| | primer 1 | ESG00084 | GMV415 |
| | primer 2 | ESG00087 | GMV421 |
| pGMV159 | template | pMZT37 | pUC57-AbWS (WS-dgaT) |
| | primer 1 | ESG00084 | GMV410 |
| | primer 2 | ESG00088 | GMV416 |
| pGMV160 | template | pMZT37 | pUC57-PaWS (Psyc_0223) |
| | primer 1 | ESG00084 | GMV411 |
| | primer 2 | ESG00088 | GMV417 |
| pGMV161 | template | pMZT37 | pUC57-RoWS (ROP_02100) |
| | primer 1 | ESG00084 | GMV412 |
| | primer 2 | ESG00088 | GMV418 |
| pGMV162 | template | pMZT37 | pUC57-RoWS (ROP_13050) |
| | primer 1 | ESG00084 | GMV413 |
| | primer 2 | ESG00088 | GMV419 |
| pGMV163 | template | pMZT37 | pUC57-RoWS (ROP_26950) |
| | primer 1 | ESG00084 | GMV414 |
| | primer 2 | ESG00088 | GMV420 |
| pGMV164 | template | pMZT37 | pUC57-RoWS (ROP_54550) |
| | primer 1 | ESG00084 | GMV415 |
| | primer 2 | ESG00084 | GMV421 |

Example 5

Biosynthetic Production of 2,3-Butanediol from Methane

The four-carbon (C4) diol 2,3-butanediol is an important intermediate for the chemical industry. At the commercial scale, it is mostly generated from petroleum. It serves as a precursor for the production of various commodity and specialty chemicals, such as the solvent methyl ethyl ketone (MEK), gamma-butyrolactone (GBL), and 1,3-butadiene. The potential production of these downstream commercial products amounts to about 32 million tons per year, with a value of about $43 billion (Köpke et al., 2011).

Biological production of 2,3-butanediol from methane requires engineering the native (or endogenous) metabolism of methanotrophs to take advantage of their endogenous production of (R)-acetoin (FIG. 9). (R)-acetoin is produced in methanotrophs from two molecules of pyruvate, which are ultimately derived from methane. By introducing and expressing the gene (SEQ ID NO:156) encoding (2R,3R)-2,3-butanediol dehydrogenase (BDH1) from *Saccharomyces cerevisiae* in a suitable microbial expression host (such as *M. capsulatus* (Bath)), (R)-acetoin is converted into 2,3-butanediol.

Construction of Methanotroph Plasmids for 2,3-butanediol Production

As described, above, the plasmids generated in this study are based on the broad-host-range pCM132 (Accession no. AF327720, SEQ ID NO: 79) cloning vector described by Marx & Lidstrom (2001). In this embodiment, the use of the Clontech (catalogue 639647) InFusion HD Cloning System kit is one example of how to construct plasmids, but is not meant to limit or exclude other methods that are known in the art. Sequences for the ORF and PCR primers are presented below in Table 1.

Vector Backbones

Vector backbones contain the components of the plasmid that will remain constant. The broad-host range pCM132 vector was modified to produce vector backbones for the plasmids in this example. The pCM132 vector consists of the following components: trmB terminator, kanamycin resistance gene, trfA, IncP oriT, IncP oriV, colE1 ori, and lacZ. This parental vector has been modified to replace lacZ with a vector insert that contains promoter sequence to produce plasmid pMZT3, which was used for this example.

Vector Inserts

Vector inserts contain DNA to be added to the vector backbone. The inserts were designed as exchangeable (modular) parts to the vector, and in this embodiment consists of the components listed in Table 1 and Table 8. In this example, the plasmids were designed to contain one insert: *Saccharomyces cerevisiae* (R,R)-butanediol dehydrogenase (Standard name: Bdh1p (EC 1.1.1.4); SEQ ID NO:156; Systematic gene name: YAL060W).

The BDH1 gene (SEQ ID NO:156) was codon optimized and synthesized by Integrated DNA Technologies (Coralville, Iowa).

Assembly of the Constructs

The modular parts (vector backbone and vector insert) were PCR amplified as listed in Table 8 with NEB Phusion master mix according to the manufacturer's instructions and in vitro assembled with the Clontech InFusion HD Cloning System kit according to the manufacturer's instructions to generate circular plasmid. The in vitro assembled plasmids (2 μl of the InFusion reaction) were transformed into chemically competent NEB Turbo *E. coli* cells, screened for by colony PCR, purified, and subsequently sequence verified.

Plasmid pMZT3 served as the template for the vector backbone with a constitutive promoter and consisted of the pCM132 cloning vector, *E. coli* J23115 promoter. The vector backbone was PCR amplified from the pMZT3 template with primers ESG00084 (SEQ ID NO:137)/ESG00087 (SEQ ID NO:98).

The pGMV111 plasmid was designed to express the *S. cerevisiae* BDH1 gene (SEQ ID NO:156) from the J23115 constitutive promoter. The modules of this plasmid included the PCR amplified pMZT3 vector backbone and the ScBDH1 insert amplified from the shuttle vector pUC57-ScBDH1 template using primers GMV268 (SEQ ID NO:158)/GMV271 (SEQ ID NO:159). The plasmid was conjugated from *E. coli* donor strain S17-1 into the *M. capsulatus* (Bath) recipient as described above Example 1. The transconjugant strain was purified by repeated rounds of antibiotic selection using kanamycin and naladixic acid to remove the parent cells, as described in Example 1 above.

Cells expressing the pGMV111 plasmid were cultivated in liquid NMS medium in sealed shake flasks in the presence of 20% methane at 45° C. as described above in Example 1, for about 72 hours with 200 rpm shaking. For UPLC analysis, proteins and other debris were separated from the 2,3-butanediol in the growth medium using 2% (w/g/vol.) 5-sulfosalicylic acid and centrifugation as described in Köpke et al. (2011). Extracted samples can be analyzed using a BioRad (Hercules, Calif.) Fast Acid column on a Waters (Milford, Mass.) Acquity H-class UPLC equipped with a #2414 Refractive Index Detector. Other conditions are as follows: the mobile phase is 5 mM $H_2SO_4$, the flow rate is 0.4 ml/min, the column is maintained at 40 C, and the product is detected at 410 nm.

Methods for the processing of biologically produced 1,3-propanediol and 2,3-butanediol are further described by Xiu & Zeng, 2008.

For GC analysis, the 2,3-butanediol can be extracted from the culture medium with ethyl acetate, as described in Xiao et al., (2012). The extracted sample is analyzed on an Agilent (Santa Clara, Calif.) 7890A GC equipped with a Leap Technologies CombiPAL autosampler and a flame ionization detector. Either an Agilent HP-INNOWax or HP-SMS GC column can be used to separate the components according to the method of Xiao et al. (2012). Alternatively, the samples can be analyzed on a Waters Acquity H-Class UPLC equipped with a Waters 2414 Refractive Index detector using a method similar to that of Köpke et al. (2011). A BioRad (Hercules, Calif.) Fast Acid Column operated at 40° C. with a flow rate of 0.4 ml/minute and a 5 mM $H_2SO_4$ mobile phase can be used to perform the separation. Samples for either GC or UPLC can be quantitated against a series of known concentrations of purified (D-(−)-, L-(+)-, and mesa-) 2,3-butanediol standards (Sigma, St. Louis, Mo.).

At the industrial fermentation scale, the 2,3-butanediol product can be extracted from the fermentation medium using one of the following methods: steam stripping, solvent extraction, aqueous two-phase extraction, reactive extraction, and pervaporation. These methods are described in Xiu & Zeng (2008).

TABLE 8

| | | Modules | |
|---|---|---|---|
| Plasmid | PCR reaction: | Vector backbone | Insert |
| pGMV111 | template | pMZT3 | pUC57-ScBDH1 |
| | primer 1 | ESG00084 | GMV268 |
| | primer 2 | ESG00087 | GMV271 |

Following is a list of citations for application.
U.S. Pat. No. 4,594,324
U.S. Pat. No. 4,982,023

U.S. Pat. No. 6,576,449
U.S. Pat. No. 6,660,507
U.S. Pat. No. 6,767,744
U.S. Pat. No. 6,818,424
U.S. Pat. No. 6,969,595
U.S. Pat. No. 7,026,464
U.S. Pat. No. 7,851,188
U.S. Pat. No. 7,910,342
U.S. Pat. No. 7,943,362
U.S. Pat. No. 7,977,084
U.S. Pat. No. 7,993,889
U.S. Pat. No. 8,017,375
U.S. Pat. No. 8,030,021
U.S. Pat. No. 8,101,808
U.S. Pat. No. 8,158,404
U.S. Pat. No. 8,232,089
U.S. Pat. No. 8,263,373
U.S. Pat. No. 8,268,599
U.S. Pat. No. 8,283,143
U.S. Pat. No. 8,349,587
U.S. Publication No. 2006/0057726
U.S. Publication No. 2007/0251141
U.S. Publication No. 2009/0263877
U.S. Publication No. 2010/0274033
U.S. Publication No. 2011/0301388
U.S. Publication No. 2012/0009640
European Patent No. EP 1419234
European Patent No. EP 1328639
European Patent No. EP 1416808
European Patent No. EP 1625204
European Patent No. EP 1694854
European Patent No. EP 2464722
European Patent No. EP 306466
European Patent No. EP 418187
PCT Publication No. WO 2001/60974

Alayon et al., "Catalytic Conversion of Methane to Methanol Using Cu-Zeolites", *Chimia,* 66:668-674, 2012.

Ali, H., "Development of Genetic Tools in Methanotrophs and the Molecular Regulation of Methane Monooxygenase", Ph.D. Thesis, Univ. of Warwick, Coventry, U. K., 2006.

Anthony, C. and Williams, P., "The structure and mechanism of methanol dehydrogenase", *Biochim. Biophys. Acta.,* 1647:18-23, 2003.

Arakawa et al., "Catalysis research of relevance to carbon management: progress, challenges, and opportunities", *Chem. Rev.,* 101:953-996, 2001.

Atsumi, S. et al., "Engineering the isobutanol biosynthetic pathway in *Escherichia coli* by comparison of three aldehyde reductase/alcohol dehydrogenase genes", *Appl. Microbiol. Biotechnology,* 85:651-657, 2010.

Ausubel et al., "Current Protocols in Molecular Biology", pub. by Greene Publishing Assoc. and Wiley-Interscience, 1987.

Ausubel, F. M., Brent, R., Kingston, R. E., Moore, D. D., Seidman, J. G., Smith, J. A., and Struhl, K., eds., *Short Protocols in Molecular Biology, Fifth Edition.* Wiley, 2002.

Avalos et al., "Compartmentalization of Metabolic Pathways in Yeast Mitochondria Improves the Producrion of Branched-Chain Alcohols", *Nature Biotechnology,* Advanced Online Publication, Feb. 17, 2013, pages 1-7, doi:10.1038/nbt.2509.

Bothe et al., "Heterotrophic bacteria growing in association with *Methylococcus capsulatus* (Bath) in a single cell protein production process", *Appl. Microbiol. Biotechnol.,* 59:33-39, 2002.

Bothe, H., Jensen, K. M., Mergel, A., Larsen, J., Jorgensen, C., Bothe, H. and Jorgensen, L., "Heterotrophic bacteria growing in association with *Methylococcus capsulatus* (Bath) in a single cell protein production process", *Apple Microbiol. Biotechnol.* 59:33-39, 2002.

Bowman, J., "The methanotrophs—the families Methylococcaceae and Methylocystaceae", In: The Prokaryotes (Dworkin, M., ed.). Springer Verlag, New York, 2000 (http://link.springer-ny.com/link/service/books/10125).

Chistoserdova et al., "A genomic view of methane oxidation by aerobic bacteria and anaerobic archaea", *Genome Biol.,* 6:208, 2005.

Chistoserdova et al., "The Expanding World of Methylotrophic Metabolism", *Annu. Rev. Microbiol.,* 63:477-499, 2009.

Chistoserdova, L., "Modularity of methylotrophy, revisited", *Environ. Microbiol.,* 13:2603-2622, 2011.

Culpepper, M. A. and Rosenzweig, A. C., "Architecture and active site of particulate methane monooxygenase", *Crit. Rev. Biochem. Mol. Biol.,* 47:483-492, 2012.

Dunfield et al., "Methane oxidation by an extremely acidophilic bacterium of the phylum *Verrucomicrobia*", *Nature* 450:879-882, 2007, Dunfield et al., "*Methylocella silvestris* sp, nov., a novel methanotroph isolated from an acidic forest cambisol" *Int. J. Syst. Evol. Microbiol.,* 53:1231-1239, 2003.

Eiteman, M. A. and Altman, E., "Overcoming acetate in *Escherichia coli* recombinant protein fermentations", *Trends Biotechnol.* 24:53-536, 2006.

Engler et al., "Golden Gate Shuffling: A One-Pot DNA Shuffling Method Based on Type IIs Restriction Enzymes", *PLoS One* 4:e5553, 2009.

Gellissen et al., "New yeast expression platforms based on methylotrophic *Hansenula polymorpha* and *Pichia pastoris* and on dimorphic *Arxula adeninivorans* and *Yarrowia lipolytica*—a comparison", *FEMS Yeast Res.,* 5:1079-1096, 2005.

Gibson et al., "Enzymatic assembly of DNA molecules up to several hundred kilobases", *Nature Methods* 6: 343-345, 2009.

Gou et al., "Functional expression of the particulate methane mono-oxygenase gene in recombinant *Rhodococcus erythropolis*", *FEMS Microbiol. Lett.* 263:136-141, 2006.

Guillouet et al., "Expression of the *Escherichia coli* Catabolic Threonine Dehydratase in *Corynebacterium glutamicum* and Its Effect on Isoleucine Production", *Appl. Environ. Microbiol.* 65:3100-3107, 1999.

Hägg, M. B., "Membranes in Chemical Processing—A Review of Applications and Novel Developments, Separation and Purification Methods", *Separ. Purif. Meth.* 27:51-168, 1998.

Hakemian A S. and Rosenzweig, A. C, "The biochemistry of methane oxidation", *Annu. Rev. Biochem.* 76:223-241, 2007.

Hamilton, C. M., Aldea, M., Washburn, B. K., Rabitzke, P. & Kushner, S. R., "New method for generating deletions and gene replacements in *E. coli*", *J. Bacteriol.* 171:4617-4622, 1989.

Hanson, R. S. and Hanson, T. E., "Methanotrophic bacteria", *Microbiol. Rev.,* 60:439-471, 1996.

Hickey, P. J. and Slater, C. S., "The selective recovery of alcohols from fermentation broths by pervaporation', *Separ. Purif. Meth.* 19:93-115, 1990.

Jaeger, W. K. and Egelkraut, T. M., "Biofuel Economics in a Setting of Multiple Objectives and Unintended Consequences", *Renewable and Sustainable Energy Reviews,* 15(9):4320, 2011.

Jang, Y. S. et al., "Enhanced Butanol Production Obtained by Reinforcing the Direct Butanol-Forming Route in Clostridium acetobutylicum", mBio, 3(5):1-9, 2012.

Jiang, H., Chen, Y., Jiang, P., Zhang, C., Smith, T. J., Xing, X.-H. and Murrell, J. C., "Methanotrophs: Multifunctional bacteria with promising applications in environmental bioengineering", Biochem. Eng. J. 49:277-288, 2010.

Kidnay et al., "Fundamentals of Natural Gas Processing", Second Edition, 2011 (Dekker Mechanical Engineering). CRC Press, Boca Raton, Kim, S., Baek, S. H. and Hahn, J. S., "Cellulosic ethanol production using a yeast consortium displaying a minicellulosome and beta-glucosidase", Microb Cell Fact., 12(1): 14, 2013.

Kopke et. al., "2,3-Butanediol Production by Acetogenic Bacteria, an Alternative Route to Chemical Synthesis, Using Industrial Waste Gas", Appl. Environ. Microbiol., 77:5467-5475, 2011.

Li, M. Z. and Elledge, S. J., "SLIC: a method for sequence- and ligation-independent cloning", Methods Mol. Biol. 852:51-59, 2012.

Link, A. J., Phillips, D. and Church, G. M., "Methods for generating precise deletions and insertions in the genome wild-type Escherichia coli: applications to open reading frame characterization", J. Bacteriol. 179:6228-6237, 1997.

Lipps, G., ed. "Plasmids: Current Research and Future Trends", Caister Academic Press, Norfolk, England, U. K., 2008.

Liu, G., Hou D., Wei, W., Xiangli, F. and Jin, W., "Pervaporation separation of butanol-water mixtures using polydimethylsiloxane/ceramic composite membrane", Chin. J. Chem. Eng. 19:40-44, 2011.

Lloyd et al., "Heterologous expression of soluble methane monooxygenase genes in methanotrophs containing only particulate methane monooxygenase", Arch. Microbiol. 171: 364-370, 1999.

Ma et al., "DNA synthesis, assembly and applications in synthetic biology", Curr. Opin. Chem. Biol. 16:1-8, 2012.

Martin, H. and Murrell, J. C., "Methane monooxygenase mutants of Methylosinus trichosporium constructed by marker-exchange mutagenesis", FEMS Microbiol Lett. 127: 243-248, 1995.

Marx, C. J. & Lidstrom, M. E., "Development of improved versatile broad-host-range vectors for use in methylotrophs and other Gram-negative bacteria", Microbiology 147:2065-2075, 2001.

Merryman, C. and Gibson, D. G., "Methods and applications for assembling large DNA constructs", Metabol. Eng. 14: 196-204, 2012.

Murrel et al., "Molecular biology and regulation of methane monooxygenase", Arch. Microbiol., 173:325-332, 2000.

Neel, J., "Pervaporation" In: Membrane Science and Technology, 1995 (Noble, R. D. & Stern, S. A., eds.) Elsevier Science, Amsterdam, The Netherlands.

Orita et at, "The Ribulose Monophosphate Pathway Substitutes for the Missing Pentose Phosphate Pathway in the Archaeon Thermococcus kodakaraensis", J. Bacteriology, 188(13):4698-4704, 2006.

Peccoud, J., ed. "Gene Synthesis: Methods and Protocols" (Methods in Molecular Biology, Vol. 852). Humana Press, New York, 2012.

Phillips, R. B., Jameel, H, and Chang, H. M., "Integration of pulp and paper technology with bioethanol production", Biotechnol Biofuels, 6(1):13, 2013.

Posfai, G., Kolisnychenko, V., Bereczki, Z. and Blattner, F. R., "Markerless gene replacement in Escherichia coli stimulated by a double-strand break in the chromosome", Nucleic Acids Res. 27:4409-4415, 1999.

Rosenzweig, A. C. and Ragsdale, S. W. "Methods in Methane Metabolism", Part B: Methanotrophy. Methods Enzymol., 495:1-309, 2011(b).

Rosenzweig, A. C. and Ragsdale, S. W., "Methods in Methane Metabolism", Part A. Methods Enzymol., 494:1-373, 2011(a).

Rudolf, A., Karhumaa, K. and Hahn-Hagerdal, B., "Ethanol Production from Traditional and Emerging Raw Materials", Yeast Biotechnology: Diversity and Applications, Chapter 23, pages 489-513, 2009.

Saka, S. and Kusdiana, D., "Biodiesel fuel from rapeseed oil as prepared in supercritical methanol", Fuel, 80:225, 2001.

Saleh, J., "A Membrane Separation Process for Biodiesel Purification', Ph.D. Thesis, 2011, University of Ottawa, Canada.

Sambrook et al., Molecular Cloning: A Laboratory Manual, Cold Spring Harbor Laboratory Press, 1989.

Sambrook, J., Fritsch, E. F. and Maniatis, T., "Molecular Cloning: A Laboratory Manual"; Cold Spring Harbor Laboratory Press, Cold Spring Harbor, 1989.

Schrader et al., "Methanol-based industrial biotechnology: current status and future perspectives of methylotrophic bacteria", Trends Biotechnol., 27:107-115, 2009.

Semrau et al., "Facultative methanotrophy: false leads, true results, and suggestions for future research", FEMS Microbiol. Lett., 323:1-12, 2011.

Shen, C. R. and Liao, J. C., "Metabolic engineering of Echerichia coli for 1-butanol and 1-propanol production via the keto-acid pathways", Metab. Eng. 10:312-320, 2008.

Silhavy, et al., "Experiments with Gene Fusions", Cold Spring Harbor Laboratory, Cold. Spring Harbor, N.Y. 1984, Simon R. "High frequency mobilization of Gram-negative bacterial replicons by the in vitro constructed Tn5-mob transposons", Mol. Gen. Genet. 196:413-420, 1984.

Simon, R., Priefer, U. and Puhler, A. "A Broad Host Range Mobilization System for In Vivo Genetic Engineering: Transposon Mutagenesis in Gram Negative Bacteria", Nature Biotechnology 1:784-791, 1983.

Stafford et al., "rpoN, mmoR and mmoG, genes involved in regulating the expression of soluble methane monooxygenase in Methylosinus trichosporium OB3b", Microbiol. 149:1771-1784, 2003.

Stanley, S. H. and Dalton H., "Role of ribulose-1,5-biphosphate carboxylase/oxygenase in Methylococcus capsulatus", J. Gen. Microbiol, 128:2927-2935, 1982.

Sun, W., Wang, S. and Curtis III, R., "Highly efficient method for introducing successive multiple scarless gene deletions and markerless gene insertions into the Yersinia pestis chromosome", Appl. Environ. Microbiol. 74:4241-4245, 2008.

Theisen et al., "Regulation of methane oxidation in the facultative methanotroph Methylocella silvestris BL2", Mol. Microbiol. 58:682-692, 2005.

Tinberg, C. E. and Lippard, S. J., "Dioxygen activation in soluble methane monooxygenase", Acc. Chem. Res., 44:280-288, 2007.

Trotsenko, Y. A. and Murrell, J. C., "Metabolic Aspects of Aerobic Obligate Methanotrophy", Adv. Appl. Microbiol., 63:183-229, 2008.

U.S. Department of the Interior, U.S. Geological Survey World Petroleum Assessment, 2000, U.S. Geological Survey Digital Data Series-DDS-60 (URL: http://pubs.usgs.gov/dds/dds-060/)

van Laere, V., van Batenburg, O. & Huizing, N.J., "InnoFisk1: Feasibility study into a new concept for sustainable aquaculture on board of a ship", *Innovation Network Rural Areas and Agricultural Systems*, 2005.

Veazey, M. W., "*GTL Tech converts Methane to Ethylene without Fischer Tropsch*", Rigzone. Apr. 10, 2012 (http://www.rigzone.com/news/article.asp?a_id=116784)

Wang et al., "Available methods for assembling expression cassettes for synthetic biology", *Appl. Microbiol. Biotechnol.* 93:1853-1863, 2012.

Ward, N., Larsen, Ø., Sakwa, J., et al., *PLoS Biol.* 2:e303, 2004.

Welander, P. V. and Summons, R. E., "Discovery, taxonomic distribution, and phenotypic characterization of a gene required for 3-methylhopanoid production", *Proc. Natl, Acad. Sci.*, 109:12905-12910, 2012.

Whittenbury, R., Phillips, K. C. and Wilkinson, J. F., "Enrichment, isolation and some properties of methane-utilizing bacteria", *J. Gen. Microbiol.* 61:205-218, 1970.

Wolfe, A. J., "The acetate switch", *Microbiol. Mol. Biol. Rev.* 69:12-50, 2005.

Wright, C. K. and Wimberly, M. C., "Recent Land Use Change in the Western Corn Belt Threatens Grasslands and Wetlands", *Proceedings of the National Academy of Sciences—Early Edition*, February 19, pg. 1-6, 2013; DOI: 10.1073/pnas.1215404110.

Xiao et al., "Thermophilic fermentation of acetoin and 2,3-butanediol by a novel *Geobacillus* strain", *Biotechnol. for Biofuels* 5:88, 2012.

Xingye et al., "In vitro Reconstitution and Steady-State analysis of the Fatty Acid Synthase from *Escherichia coli*", *Proceedings of the National Academy of Sciences*, 10(8): 18643-18648, 2011.

Xiu, Z.-L. and Zeng, A.-P., "Present state and perspective of downstream processing of biologically produced 1,3-propanediol and 2,3-butanediol", *Appl. Microbiol. Biotechnol.* 78:917-926, 2008.

Yangkai a al., "De novo Biosynthesis of Biodiesel by *Escherichia coli* in Optimized Fed-Batch Cultivation", *PLoS ONE*, 6(5):1-7, 2011.

Yehezkel et al., "Computer-aided high-throughput cloning of bacteria in liquid medium", *Biotechniques* 50:124-127, 2011.

Yomantas, Y. A., Tokmakova, I. L., Gorshkova, N. V., Abalakina, E. G., Kazakova, S. M., Gak, E. R. and Mashko, S. V., "Aromatic amino acid auxotrophs constructed by recombinant marker exchange in *Methylophilus methylotrophus* AS1 cells expressing the aroP-encoded transporter of *Escherichia coli*", *Appl. Environ. Microbiol.* 76:75-83, 2010.

Yu, B. J., Kang, K. H., Lee, J. H., Sung, B. H., Kim, M. S. and Kim, S. C., "Rapid and efficient construction of markerless deletions in the *Escherichia coli* genome", *Nucleic Acids Res.* 36:e84, 2008.

Yurimoto, H., Katoh, N. and Sakai, Y., "Assimilation, dissimilation, and detoxification of formaldehyde, a central metabolic intermediate of methylotrophic metabolism", *Chem Rec.*, 5:367-375, 2005.

Yurimoto, H., Katoh, N. and Sakai, Y., "Genomic organization and biochemistry of the ribulose monophosphate pathway and its application in biotechnology", *Appl Microbiol Biotechnol.*, 84:407-416, 2009.

What is claimed is:

1. A genetically modified methanotroph that is capable of producing 2,3-butanediol from methane (CH$_4$), the genetically modified methanotroph comprising exogenous polynucleotides encoding acetolactate synthase and 2,3-butanediol dehydrogenase, wherein the acetolactate synthase has acetolactate synthase activity and comprises an amino acid sequence having at least 90% sequence homology to SEQ ID NO:2, and the 2,3-butanediol dehydrogenase has 2,3-butanediol dehydrogenase activity and comprises an amino acid sequence having at least 90% sequence homology to SEQ ID NO: 157, wherein said methanotroph is capable of converting methane to pyruvate through an endogenous type I RuMP pathway or a type II serine pathway.

2. The genetically modified methanotroph of claim 1, wherein said methanotroph is *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis,* or *Methyloacidophilum.*

3. The genetically modified microorganism of claim 2, wherein said methanotroph is *Methylococcus.*

4. The genetically modified microorganism of claim 3, wherein said *Methylococcus* is *Methylococcus capsulatus.*

5. A method of producing 2,3-butanediol from methane comprising:

(a) contacting a methanotroph with methane, (b) growing said methanotroph under suitable growth conditions to produce said 2,3-butanediol, wherein said methanotroph is capable of converting methane to pyruvate through an endogenous type I RuMP pathway or a type II serine pathway and comprises exogenous polynucleotides encoding acetolactate synthase and 2,3-butanediol dehydrogenase, wherein the acetolactate synthase has acetolactate synthase activity and comprises an amino acid sequence having at least 90% sequence homology to SEQ ID NO:2, and the 2,3-butanediol dehydrogenase has 2,3-butanediol dehydrogenase activity and comprises an amino acid sequence having at least 90% sequence homology to SEQ ID NO: 157.

6. The method of claim 5, wherein said methanotroph is *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis,* or *Methyloacidophilum.*

7. The method of claim 5, further comprising isolating and purifying said 2,3-butanediol.

8. The method of claim 6, wherein said methanotroph is *Methylococcus.*

9. The method of claim 8, wherein said *Methylococcus* is *Methylococcus capsulatus.*

* * * * *

SEQUENCE LISTING

<160> NUMBER OF SEQ ID NOS: 175

<210> SEQ ID NO 1
<211> LENGTH: 1662
<212> TYPE: DNA
<213> ORGANISM: Methylococcus capsulatus

<400> SEQUENCE: 1

```
atgcgtgaaa cgataccctcc ccgcaccggc gccgacctgc tggtcgactc cctccaggcg      60
ctgggcgtcg aatacgtctt cggcgtgccc ggcggcgcga tactcccgat cctgaacgtg     120
ctggccgacc gcggcccgcg cttcatcgtt tgccgggacg aaaccggcgc cgccttcatg     180
gcccagtcct ggggccggat caccggccgg cccggcgtgg tgctcaccac ctccggcccc     240
ggcctcatca acgccgtctg tggcgtcgct accgccacag aggaccgcga cccgctggtc     300
gtcatcaccg gccaggtgcc gcgggccgtg caattcaagc agagccacat gaacctggat     360
tcggtcggcc tgttcgcgcc gatcaccaaa tggagcgtcg aggtcgagga accgaatact     420
gtatcggaaa tcctggtcaa cgccttccgc accgcgcaga cgccgtgcgc cggagccgtc     480
cacgtctcgg taccgaacga catgctcacc gcgccggtca ccgcgcaggc cctggcgccg     540
gccgaacccg ccgtctgggg aacggcccg gccgccgtcg tcgaacgcgc ggcgtccctg      600
ctgaacgatg ccaaagcccc ggccatcctg ctcggattgc gggccagcac acctggagcg     660
gcggcggcgg tccggcgttt cctggagcgg catccgctgc cggtggcgat gaccttcgaa     720
gccgccggca ccctgtcccg cgatctggtc gatcagttcg tcggccgggt cggctacgtg     780
ctcaaccagc cgggcgacga ggtgctgcgc caagccgatc tggtactcac gatcggctac     840
gacccgatcg aatacgaacc ttccgcctgg atctcaccgc agtcgcaggc gatccacctg     900
```

-continued

```
gatgccctgc ccgccgccgt cgaccgggcc taccaccctg ccgccgaact ggtcggcgac      960
atcgccgcca acctggccgc gctcggcagc ctgctccgaa tcgaggatcg agccggacgc     1020
cccgccgtcg ccgcggcgcg gcggcgtctg ctggaggagc aagcccgcgg cgcagcactg     1080
accggtatgc cgatccaccc cttgcgcttc attcacgacc ttcgggccac gctggacgac     1140
gaggcgacgg tgacctgcga cgtcggcgcc cacgagatct ggatggcccg ctacttcttc     1200
tgctacgccc gcgtcacct gctgttcagc atgggccacc agaccatggg cgtcgccctg     1260
ccctgggcca tcggcgcggc cctggcccgg cccggcaaga aagtggtttc ggtatccggc     1320
gacggctcct tcctcatgac ctgcatggaa ctggaaaccg cggtgcgcct caaactgccg     1380
atcgtgcaca tcgtctggaa agacggcggc tacaacctga tccacagcct gcagatgcgc     1440
gactatgggc gcagcttcgg cgccgagttc ggccccaccg acttcgtcaa actggcggag     1500
gccttcggcg cgatcgggta ccggatcgag tccgcggacg ggatcgtccc tgtgctgaac     1560
cgggcgctcg cggccgacgc gccggtgctg atcgaagtgc ccatcgacta cagcgacaac     1620
gtccacctgg tcgaggcgat cgacgcctcg gcgcagcact ga                       1662
```

<210> SEQ ID NO 2
<211> LENGTH: 553
<212> TYPE: PRT
<213> ORGANISM: Methylococcus capsulatus

<400> SEQUENCE: 2

```
Met Arg Glu Thr Ile Pro Pro Arg Thr Gly Ala Asp Leu Leu Val Asp
1               5                   10                  15

Ser Leu Gln Ala Leu Gly Val Glu Tyr Val Phe Gly Val Pro Gly Gly
            20                  25                  30

Ala Ile Leu Pro Ile Leu Asn Val Leu Ala Asp Arg Gly Pro Arg Phe
        35                  40                  45

Ile Val Cys Arg Asp Glu Thr Gly Ala Ala Phe Met Ala Gln Ser Trp
    50                  55                  60

Gly Arg Ile Thr Gly Arg Pro Gly Val Val Leu Thr Thr Ser Gly Pro
65                  70                  75                  80

Gly Leu Ile Asn Ala Val Cys Gly Val Ala Thr Ala Thr Glu Asp Arg
                85                  90                  95

Asp Pro Leu Val Val Ile Thr Gly Gln Val Pro Arg Ala Val Gln Phe
            100                 105                 110

Lys Gln Ser His Met Asn Leu Asp Ser Val Gly Leu Phe Ala Pro Ile
        115                 120                 125

Thr Lys Trp Ser Val Glu Val Glu Pro Asn Thr Val Ser Glu Ile
    130                 135                 140

Leu Val Asn Ala Phe Arg Thr Ala Gln Thr Pro Cys Ala Gly Ala Val
145                 150                 155                 160

His Val Ser Val Pro Asn Asp Met Leu Thr Ala Pro Val Thr Ala Gln
                165                 170                 175

Ala Leu Ala Pro Ala Glu Pro Ala Val Trp Gly Thr Ala Pro Ala Ala
            180                 185                 190

Val Val Glu Arg Ala Ala Ser Leu Leu Asn Asp Ala Lys Ala Pro Ala
        195                 200                 205

Ile Leu Leu Gly Leu Arg Ala Ser Thr Pro Gly Ala Ala Ala Ala Val
    210                 215                 220

Arg Arg Phe Leu Glu Arg His Pro Leu Pro Val Ala Met Thr Phe Glu
225                 230                 235                 240
```

Ala Ala Gly Thr Leu Ser Arg Asp Leu Val Asp Gln Phe Val Gly Arg
            245                 250                 255

Val Gly Tyr Val Leu Asn Gln Pro Gly Asp Glu Val Leu Arg Gln Ala
        260                 265                 270

Asp Leu Val Leu Thr Ile Gly Tyr Asp Pro Ile Glu Tyr Glu Pro Ser
        275                 280                 285

Ala Trp Ile Ser Pro Gln Ser Gln Ala Ile His Leu Asp Ala Leu Pro
        290                 295                 300

Ala Ala Val Asp Arg Ala Tyr His Pro Ala Ala Glu Leu Val Gly Asp
305                 310                 315                 320

Ile Ala Ala Asn Leu Ala Ala Leu Gly Ser Leu Leu Arg Ile Glu Asp
                325                 330                 335

Arg Ala Gly Arg Pro Ala Val Ala Ala Ala Arg Arg Leu Leu Glu
                340                 345                 350

Glu Gln Ala Arg Gly Ala Ala Leu Thr Gly Met Pro Ile His Pro Leu
                355                 360                 365

Arg Phe Ile His Asp Leu Arg Ala Thr Leu Asp Asp Glu Ala Thr Val
        370                 375                 380

Thr Cys Asp Val Gly Ala His Glu Ile Trp Met Ala Arg Tyr Phe Phe
385                 390                 395                 400

Cys Tyr Ala Pro Arg His Leu Leu Phe Ser Met Gly His Gln Thr Met
                405                 410                 415

Gly Val Ala Leu Pro Trp Ala Ile Gly Ala Ala Leu Ala Arg Pro Gly
                420                 425                 430

Lys Lys Val Val Ser Val Ser Gly Asp Gly Ser Phe Leu Met Thr Cys
                435                 440                 445

Met Glu Leu Glu Thr Ala Val Arg Leu Lys Leu Pro Ile Val His Ile
        450                 455                 460

Val Trp Lys Asp Gly Gly Tyr Asn Leu Ile His Ser Leu Gln Met Arg
465                 470                 475                 480

Asp Tyr Gly Arg Ser Phe Gly Ala Glu Phe Gly Pro Thr Asp Phe Val
                485                 490                 495

Lys Leu Ala Glu Ala Phe Gly Ala Ile Gly Tyr Arg Ile Glu Ser Ala
                500                 505                 510

Asp Gly Ile Val Pro Val Leu Asn Arg Ala Leu Ala Ala Asp Ala Pro
                515                 520                 525

Val Leu Ile Glu Val Pro Ile Asp Tyr Ser Asp Asn Val His Leu Val
        530                 535                 540

Glu Ala Ile Asp Ala Ser Ala Gln His
545                 550

<210> SEQ ID NO 3
<211> LENGTH: 1017
<212> TYPE: DNA
<213> ORGANISM: Methylococcus capsulatus

<400> SEQUENCE: 3
atgcagattt actacgacaa agacgccgac ctttccatca tccagggaaa gaaggttgcc      60
atcatcggct acggctcgca gggccacgcc acgccaaca acctcaagga ttccggagtg     120
caggtcgtgg tgggctgcg tccgggttcg gcttccgcca agaaggccga gaacgccggc     180
ctcgcggtcg cctcggtcga ggatgcggtc aaacaggcgg acgtcatcat gatcctggcg     240
ccggacgagc atcaggcccg cctctacaat gaacagatcg cgccgaacat caagcagggc     300

```
gccgccctcg ccttcgccca cggcttcaac atccacttcg agcagatcac cccgcgcgcc      360
gacctcgacg tgatcatgat cgcgcccaag ggtcccggcc atctggtacg ttccacctac      420
acccagggcg gcggcgtgcc ctcgctgatc gccgtgtacc agaatgccag cgggcgcgcc      480
aaggaactcg cgctgtccta tgcttcggcc aatggcggcg gtcgggctgg tatcatcgag      540
accaccttcc gcgaagagac cgaaaccgat ctgttcggcg aacaggccgt cctgtgtggc      600
ggcgccaccg cactggtgca gcggggtttc gagacgctgg tcgaagccgg ttatgcgccc      660
gagatggcct atttcgagtg tctgcacgaa ctcaagctga tcgtcgacct gatgtacgaa      720
ggcggcatcg ccaacatgcg ttattcgatc tccaatacgg cagagtacgg cgacctgacc      780
cgtggtccgc gcatcgtcac cgagcagacc aagcaggaaa tgaagaaaat cctgcgcgag      840
atccagaccg gcgaattcgc ccgtgagttc attttggaaa accaggccgg agccgccacc      900
ctgaaagcga aacgccgtct cggccgagag catctcatcg agagcgtggg cgccaggctg      960
cgcgacatga tgccgtggat caaggccaac cgcattgtgg acacgagcaa gaactga       1017
```

<210> SEQ ID NO 4
<211> LENGTH: 338
<212> TYPE: PRT
<213> ORGANISM: Methylococcus capsulatus

<400> SEQUENCE: 4

```
Met Gln Ile Tyr Tyr Asp Lys Asp Ala Asp Leu Ser Ile Ile Gln Gly
1               5                   10                  15

Lys Lys Val Ala Ile Ile Gly Tyr Gly Ser Gln Gly His Ala His Ala
            20                  25                  30

Asn Asn Leu Lys Asp Ser Gly Val Gln Val Val Gly Leu Arg Pro
        35                  40                  45

Gly Ser Ala Ser Ala Lys Lys Ala Glu Asn Ala Gly Leu Ala Val Ala
    50                  55                  60

Ser Val Glu Asp Ala Val Lys Gln Ala Asp Val Ile Met Ile Leu Ala
65                  70                  75                  80

Pro Asp Glu His Gln Ala Arg Leu Tyr Asn Glu Gln Ile Ala Pro Asn
                85                  90                  95

Ile Lys Gln Gly Ala Ala Leu Ala Phe Ala His Gly Phe Asn Ile His
            100                 105                 110

Phe Glu Gln Ile Thr Pro Arg Ala Asp Leu Asp Val Ile Met Ile Ala
        115                 120                 125

Pro Lys Gly Pro Gly His Leu Val Arg Ser Thr Tyr Thr Gln Gly Gly
    130                 135                 140

Gly Val Pro Ser Leu Ile Ala Val Tyr Gln Asn Ala Ser Gly Arg Ala
145                 150                 155                 160

Lys Glu Leu Ala Leu Ser Tyr Ala Ser Ala Asn Gly Gly Gly Arg Ala
                165                 170                 175

Gly Ile Ile Glu Thr Thr Phe Arg Glu Glu Thr Glu Thr Asp Leu Phe
            180                 185                 190

Gly Glu Gln Ala Val Leu Cys Gly Gly Ala Thr Ala Leu Val Gln Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Arg Tyr Ser Ile Ser Asn Thr Ala Glu Tyr
                245                 250                 255
```

```
Gly Asp Leu Thr Arg Gly Pro Arg Ile Val Thr Glu Gln Thr Lys Gln
            260                 265                 270

Glu Met Lys Lys Ile Leu Arg Glu Ile Gln Thr Gly Glu Phe Ala Arg
        275                 280                 285

Glu Phe Ile Leu Glu Asn Gln Ala Gly Ala Thr Leu Lys Ala Lys
    290                 295                 300

Arg Arg Leu Gly Arg Glu His Leu Ile Glu Ser Val Gly Ala Arg Leu
305                 310                 315                 320

Arg Asp Met Met Pro Trp Ile Lys Ala Asn Arg Ile Val Asp Thr Ser
                325                 330                 335

Lys Asn

<210> SEQ ID NO 5
<211> LENGTH: 1689
<212> TYPE: DNA
<213> ORGANISM: Methylococcus capsulatus

<400> SEQUENCE: 5
atgaccgaca agcaccccg tccccattcg tcccaggtcg tcgacggcat ggagcgcgcc      60
ccgagccgcg cgatgctgca cgccgtcggc ttcgccgatg ccgacttcgc caaaccgcag     120
atcggcatcg cttccacctg ggcgatggtg acgccgtgca acatgcacat caacaagctc     180
gccgaggacg cagcacgcgg cgtcgacggc ggcggcggca aggcagtgat cttcaacacc     240
atcaccattt ccgacggcat ctcgatgggc accgaaggaa tgaaatactc cctcgtgtcg     300
cgggaagtca tcgccgactc gatcgaaacc gtggtggcct gtcagggtta tgacggcgtg     360
gtcgccatcg gcggctgcga caagaacatg cccggctgcc tgatcgccct cgcccgcctc     420
aaccgtccgg cggtgttcgt ctatggcggc accatcctgc cgggctgcca cgacggcaag     480
aagctggacg tggtgtcggt gttcgaagcg gtcggcgccc gcgccaacca ccgcatcgac     540
gatgccgaac tgcacgccat cgaatccaat gccatccccg tccgggctc ctgcggtggc     600
atgtataccg ccaacaccat ggcctccgcc atcgaggcat tagggatgag cctgccgggc     660
agttcggccc aggtggccat ttcccgcgcc aaggaactgg attgcgagcg ggccggcgcg     720
caggtcctca agctcctgga cctggggctc aaaccccgcg acatcatgac caagaaggcg     780
ttcgagaacg ccatcacggt ggtgatcgcc ctgggcggct ccaccaacgc cgtgctgcac     840
ctcctggcca tggccaacgc ctgcggcgtc gacctgaagc tcgacgattt cacccgcatc     900
gggcgcaaag tgccgatgct ggcggatctg aaaccagcg gcagatactc catggccgaa     960
ctggtggaaa tcggcggcat ccagccgctg atgaagacct tgctggacgc gggactcctg    1020
cacggcgact gcatgaccgt aaccggcaag accctggaag aaaacctggc cgacgcgccc    1080
gactacccgg ccggacaaga catgatccgg tcgctggaca accccatcaa aaaggacagc    1140
catctggtga tcctcaaggg caacctggcc cggaaggcg cggtcgccaa gatcaccggc    1200
aaggaaggac tgagcttcac cggcaccgcc cgcgtattcg actgcgagga agcggcgctc    1260
acggccatcc tcgacggcac gatcgtgaaa ggcgacgtca tcgtcatccg ctatgaaggc    1320
cccaagggcg ccccggcat gcgcgagatg ctctcgccga cctcggcggt catgggcaag    1380
ggattgggca aggaggtcgc cctcatcacc gacggccgct tttccggcgg cacccacggc    1440
ttcgtggtcg gccacatcac gccggaagcc tacaccggcg cccctggc gatcgtccgg    1500
gacggcgata ccatcaccat cgacgccgag acccgcgaat tgagcctgca cgtcaccgac    1560
gatgaaatcg ccggcgcct ggcgcagtgg actcaaccgg cgccgcgcta caccaagggc    1620
```

-continued

```
gtgctggcca aatacgccag gttggtgagc ccggcctcgg aaggcgccgt caccgacgac    1680
ggcctctga                                                            1689
```

<210> SEQ ID NO 6
<211> LENGTH: 562
<212> TYPE: PRT
<213> ORGANISM: Methylococcus capsulatus

<400> SEQUENCE: 6

```
Met Thr Asp Lys His Pro Arg Pro His Ser Gln Val Val Asp Gly
1               5                   10                  15

Met Glu Arg Ala Pro Ser Arg Ala Met Leu His Ala Val Gly Phe Ala
                20                  25                  30

Asp Ala Asp Phe Ala Lys Pro Gln Ile Gly Ile Ala Ser Thr Trp Ala
                35                  40                  45

Met Val Thr Pro Cys Asn Met His Ile Asn Lys Leu Ala Glu Asp Ala
            50                  55                  60

Ala Arg Gly Val Asp Gly Gly Gly Lys Ala Val Ile Phe Asn Thr
65                  70                  75                  80

Ile Thr Ile Ser Asp Gly Ile Ser Met Gly Thr Glu Gly Met Lys Tyr
                    85                  90                  95

Ser Leu Val Ser Arg Glu Val Ile Ala Asp Ser Ile Glu Thr Val Val
                100                 105                 110

Ala Cys Gln Gly Tyr Asp Gly Val Ala Ile Gly Gly Cys Asp Lys
            115                 120                 125

Asn Met Pro Gly Cys Leu Ile Ala Leu Ala Arg Leu Asn Arg Pro Ala
130                 135                 140

Val Phe Val Tyr Gly Gly Thr Ile Leu Pro Gly Cys His Asp Gly Lys
145                 150                 155                 160

Lys Leu Asp Val Val Ser Val Phe Glu Ala Val Gly Ala Arg Ala Asn
                165                 170                 175

His Arg Ile Asp Asp Ala Glu Leu His Ala Ile Glu Ser Asn Ala Ile
                180                 185                 190

Pro Gly Pro Gly Ser Cys Gly Gly Met Tyr Thr Ala Asn Thr Met Ala
            195                 200                 205

Ser Ala Ile Glu Ala Leu Gly Met Ser Leu Pro Gly Ser Ser Ala Gln
210                 215                 220

Val Ala Ile Ser Arg Ala Lys Glu Leu Asp Cys Glu Arg Ala Gly Ala
225                 230                 235                 240

Gln Val Leu Lys Leu Leu Asp Leu Gly Leu Lys Pro Arg Asp Ile Met
                245                 250                 255

Thr Lys Lys Ala Phe Glu Asn Ala Ile Thr Val Val Ile Ala Leu Gly
                260                 265                 270

Gly Ser Thr Asn Ala Val Leu His Leu Leu Ala Met Ala Asn Ala Cys
            275                 280                 285

Gly Val Asp Leu Lys Leu Asp Asp Phe Thr Arg Ile Gly Arg Lys Val
            290                 295                 300

Pro Met Leu Ala Asp Leu Lys Pro Ser Gly Arg Tyr Ser Met Ala Glu
305                 310                 315                 320

Leu Val Glu Ile Gly Gly Ile Gln Pro Leu Met Lys Thr Leu Leu Asp
                325                 330                 335

Ala Gly Leu Leu His Gly Asp Cys Met Thr Val Thr Gly Lys Thr Leu
            340                 345                 350
```

| | | | | | | | | | | | | |
|---|---|---|---|---|---|---|---|---|---|---|---|---|
|Glu|Glu|Asn|Leu|Ala|Asp|Ala|Pro|Asp|Tyr|Pro|Ala|Gly|Gln|Asp|Met|
| | |355| | | |360| | | |365| | |
|Ile|Arg|Ser|Leu|Asp|Asn|Pro|Ile|Lys|Lys|Asp|Ser|His|Leu|Val|Ile|
|370| | | | |375| | | | |380| | | | |
|Leu|Lys|Gly|Asn|Leu|Ala|Pro|Glu|Gly|Ala|Val|Ala|Lys|Ile|Thr|Gly|
|385| | | | |390| | | | |395| | | | |400|
|Lys|Glu|Gly|Leu|Ser|Phe|Thr|Gly|Thr|Ala|Arg|Val|Phe|Asp|Cys|Glu|
| | | | |405| | | | |410| | | | |415| |
|Glu|Ala|Ala|Leu|Thr|Ala|Ile|Leu|Asp|Gly|Thr|Ile|Val|Lys|Gly|Asp|
| | | |420| | | | |425| | | | |430| | |
|Val|Ile|Val|Ile|Arg|Tyr|Glu|Gly|Pro|Lys|Gly|Gly|Pro|Gly|Met|Arg|
| | |435| | | | |440| | | | |445| | | |
|Glu|Met|Leu|Ser|Pro|Thr|Ser|Ala|Val|Met|Gly|Lys|Gly|Leu|Gly|Lys|
| |450| | | | |455| | | | |460| | | | |
|Glu|Val|Ala|Leu|Ile|Thr|Asp|Gly|Arg|Phe|Ser|Gly|Thr|His|Gly|
|465| | | | |470| | | | |475| | | | |480|
|Phe|Val|Val|Gly|His|Ile|Thr|Pro|Glu|Ala|Tyr|Thr|Gly|Gly|Pro|Leu|
| | | | |485| | | | |490| | | | |495| |
|Ala|Ile|Val|Arg|Asp|Gly|Asp|Thr|Ile|Thr|Ile|Asp|Ala|Glu|Thr|Arg|
| | | |500| | | | |505| | | | |510| | |
|Glu|Leu|Ser|Leu|His|Val|Thr|Asp|Asp|Glu|Ile|Gly|Arg|Arg|Leu|Ala|
| | |515| | | | |520| | | | |525| | | |
|Gln|Trp|Thr|Gln|Pro|Ala|Pro|Arg|Tyr|Thr|Lys|Gly|Val|Leu|Ala|Lys|
| |530| | | | |535| | | | |540| | | | |
|Tyr|Ala|Arg|Leu|Val|Ser|Pro|Ala|Ser|Glu|Gly|Ala|Val|Thr|Asp|Asp|
|545| | | | |550| | | | |555| | | | |560|
|Gly|Leu| | | | | | | | | | | | | | |

<210> SEQ ID NO 7
<211> LENGTH: 1650
<212> TYPE: DNA
<213> ORGANISM: Methylococcus capsulatus

<400> SEQUENCE: 7

| | | |
|---|---|---|
|atgggcacgg ttgagcctgg cgctatcgga caacatctgc tcgcctgcct ttaccaggcg|60|
|ggcgtcgggc acatcttcgg cgttcccggc gattacgtgc tgggcttcta tgatctgatg|120|
|gccaaaggtc ccgtccggca tatcgggacc acgcgggagg acaccgccgc cttcgccgcc|180|
|gacggctatg cccgctgccg gggcatgggc gcgctggcgg tgacttacgg ggtcggtgcg|240|
|ctcaacaccg tcaacgccgt cgccggcgcc tatgcggaat cctcgccggt ggtggtcatc|300|
|agcggtgcgc ggggggtgcg cgagcaaagg gaagacccgt tgatccacca ccgcttcggg|360|
|ccgttccggt tccagcgcga gatattcgaa cggatcacct cgccgccgt ggtgctggac|420|
|gatccggtga tcgccttccg gcaggtggag cgtgcgctcg cggccgcccg tcagcactgc|480|
|aagccggtgt acatcgagat ccccgccgac cgggtgatgg cgccgggata tccgattcca|540|
|caggaaaccc cggaaacgcc ttccagcgac gattcggccc tggcggaggc ggtcgccgag|600|
|gccgcggagc tcctgggccg tgcggtgtcg ccggtgatcc ttgcaggcgt cgagttgcac|660|
|cggcgagggc tccaggacgc cctcgtcggc ctcgtcgagc aggcgcgcct gccggtggcg|720|
|gcgaccttga ccggcaagtc ggtgttcgcc gagcgccatc ccgcctatct gggggtgtac|780|
|gagggtgcga tgagcacgga aaacgcgcgc tacatggtcg agcagtccga cctcctgctg|840|
|atgctcgggg tcacgctgaa cgatgtcgac acgggcatct acacgcgcgc gtctcgatccg|900|

-continued

```
cagcgcatcg tccgcgcagc ccagaacgag gtcgtgattc gccatcaccg ctatccccgc    960
gtcctgctcg cggacttcgt cacggccctg gcgcggtccg tcaaggcccg gggcgaggcg   1020
tttccgatgc cggcggggcc ggaaccgtgg gactttcccg cgccggaccg gccgatgacg   1080
atcgcccggc tggtggagcg gctcgaccgc gcgctgacct ccgacatgat cgtagtgtgc   1140
gacgtcggcg actgcctgtt cgcagccacc gacctgcgcg tgcacgagcg cagcgaattc   1200
ctggcgtccg ccttctatac ctcgatgggg ttcgcggtgc ccgccgccct cggggcccag   1260
atcgcccgtc cggaccaccg ggcgctgatc ctggtcggcg acggtgcctt ccagatgacc   1320
ggaacggagc tgtcgaccca tgcccgtctc ggcctggcgc catcgtggt ggtgctcgac    1380
aatcgcggtt acagcaccga gcgcttcatc ctcgacggag ccttcaacga catcgccgac   1440
tggcgcttcc accggctggg cgaggtgttc ggccccctac agggctacga cgcgcccgac   1500
gaagcggcgt tcgaaaacgc gctcagcgaa gcgctggtca accgaaacat gccgagcctc   1560
atcaacgtcc gtctttcccc cggcgatgcc tcgatagcca tgaagcgtct cgccgggcat   1620
ctgcagtgcc gggtcaaggg cgagggctga                                   1650
```

<210> SEQ ID NO 8
<211> LENGTH: 549
<212> TYPE: PRT
<213> ORGANISM: Methylococcus capsulatus

<400> SEQUENCE: 8

```
Met Gly Thr Val Glu Pro Gly Ala Ile Gly Gln His Leu Leu Ala Cys
1               5                   10                  15

Leu Tyr Gln Ala Gly Val Gly His Ile Phe Gly Val Pro Gly Asp Tyr
            20                  25                  30

Val Leu Gly Phe Tyr Asp Leu Met Ala Lys Gly Pro Val Arg His Ile
        35                  40                  45

Gly Thr Thr Arg Glu Asp Thr Ala Ala Phe Ala Ala Asp Gly Tyr Ala
    50                  55                  60

Arg Cys Arg Gly Met Gly Ala Leu Ala Val Thr Tyr Gly Val Gly Ala
65                  70                  75                  80

Leu Asn Thr Val Asn Ala Val Ala Gly Ala Tyr Ala Glu Ser Ser Pro
                85                  90                  95

Val Val Val Ile Ser Gly Ala Pro Gly Val Arg Glu Gln Arg Glu Asp
            100                 105                 110

Pro Leu Ile His His Arg Phe Gly Pro Phe Arg Phe Gln Arg Glu Ile
        115                 120                 125

Phe Glu Arg Ile Thr Cys Ala Ala Val Val Leu Asp Asp Pro Val Ile
    130                 135                 140

Ala Phe Arg Gln Val Glu Arg Ala Leu Ala Ala Arg Gln His Cys
145                 150                 155                 160

Lys Pro Val Tyr Ile Glu Ile Pro Ala Asp Arg Val Met Ala Pro Gly
                165                 170                 175

Tyr Pro Ile Pro Gln Glu Thr Pro Glu Thr Pro Ser Ser Asp Asp Ser
            180                 185                 190

Ala Leu Ala Glu Ala Val Ala Glu Ala Ala Glu Leu Leu Gly Arg Ala
        195                 200                 205

Val Ser Pro Val Ile Leu Ala Gly Val Glu Leu His Arg Arg Gly Leu
    210                 215                 220

Gln Asp Ala Leu Val Gly Leu Val Glu Gln Ala Arg Leu Pro Val Ala
225                 230                 235                 240
```

```
Ala Thr Leu Thr Gly Lys Ser Val Phe Ala Glu Arg His Pro Ala Tyr
                245                 250                 255

Leu Gly Val Tyr Glu Gly Ala Met Ser Thr Glu Asn Ala Arg Tyr Met
            260                 265                 270

Val Glu Gln Ser Asp Leu Leu Met Leu Gly Val Thr Leu Asn Asp
        275                 280                 285

Val Asp Thr Gly Ile Tyr Thr Ala Arg Leu Asp Pro Gln Arg Ile Val
    290                 295                 300

Arg Ala Ala Gln Asn Glu Val Val Ile Arg His Arg Tyr Pro Arg
305                 310                 315                 320

Val Leu Leu Ala Asp Phe Val Thr Ala Leu Ala Arg Ser Val Lys Ala
                325                 330                 335

Arg Gly Glu Ala Phe Pro Met Pro Ala Gly Pro Glu Pro Trp Asp Phe
            340                 345                 350

Pro Ala Pro Asp Arg Pro Met Thr Ile Ala Arg Leu Val Glu Arg Leu
        355                 360                 365

Asp Arg Ala Leu Thr Ser Asp Met Ile Val Val Cys Asp Val Gly Asp
    370                 375                 380

Cys Leu Phe Ala Ala Thr Asp Leu Arg Val His Glu Arg Ser Glu Phe
385                 390                 395                 400

Leu Ala Ser Ala Phe Tyr Thr Ser Met Gly Phe Ala Val Pro Ala Ala
                405                 410                 415

Leu Gly Ala Gln Ile Ala Arg Pro Asp His Arg Ala Leu Ile Leu Val
            420                 425                 430

Gly Asp Gly Ala Phe Gln Met Thr Gly Thr Glu Leu Ser Thr His Ala
        435                 440                 445

Arg Leu Gly Leu Ala Pro Ile Val Val Leu Asp Asn Arg Gly Tyr
    450                 455                 460

Ser Thr Glu Arg Phe Ile Leu Asp Gly Ala Phe Asn Asp Ile Ala Asp
465                 470                 475                 480

Trp Arg Phe His Arg Leu Gly Glu Val Phe Gly Pro Leu Gln Gly Tyr
                485                 490                 495

Asp Ala Pro Asp Glu Ala Ala Phe Glu Asn Ala Leu Ser Glu Ala Leu
            500                 505                 510

Val Asn Arg Asn Met Pro Ser Leu Ile Asn Val Arg Leu Ser Pro Gly
        515                 520                 525

Asp Ala Ser Ile Ala Met Lys Arg Leu Ala Gly His Leu Gln Cys Arg
    530                 535                 540

Val Lys Gly Glu Gly
545

<210> SEQ ID NO 9
<211> LENGTH: 1083
<212> TYPE: DNA
<213> ORGANISM: Saccharomyces cerevisiae

<400> SEQUENCE: 9
atgtcttatc ctgagaaatt tgaaggtatc gctattcaat cacacgaaga ttggaaaaac     60
ccaaagaaga caaagtatga cccaaaacca ttttacgatc atgacattga cattaagatc    120
gaagcatgtg gtgtctgcgg tagtgatatt cattgtgcag ctggtcattg gggcaatatg    180
aagatgccgc tagtcgttgg tcatgaaatc gttggtaaag ttgtcaagct agggcccaag    240
tcaaacagtg ggttgaaagt cggtcaacgt gttggtgtag gtgctcaagt cttttcatgc    300
ttggaatgtg accgttgtaa gaatgataat gaaccatact gcaccaagtt tgttaccaca    360
```

```
tacagtcagc cttatgaaga cggctatgtg tcgcagggtg gctatgcaaa ctacgtcaga      420
gttcatgaac attttgtggt gcctatccca gagaatattc catcacattt ggctgctcca      480
ctattatgtg gtggtttgac tgtgtactct ccattggttc gtaacggttg cggtccaggt      540
aaaaaagttg gtatagttgg tcttggtggt atcggcagta tgggtacatt gatttccaaa      600
gccatggggg cagagacgta tgttatttct cgttcttcga gaaaagagaa agatgcaatg      660
aagatgggcg ccgatcacta cattgctaca ttagaagaag gtgattgggg tgaaaagtac      720
tttgacacct tcgacctgat tgtagtctgt gcttcctccc ttaccgacat tgacttcaac      780
attatgccaa aggctatgaa ggttggtggt agaattgtct caatctctat accagaacaa      840
cacgaaatgt tatcgctaaa gccatatggc ttaaggctgt ctccatttc ttacagtgct      900
ttaggttcca tcaaagaatt gaaccaactc ttgaaattag tctctgaaaa agatatcaaa      960
atttgggtgg aaacattacc tgttggtgaa gccggcgtcc atgaagcctt cgaaaggatg     1020
gaaaagggtg acgttagata tagatttacc ttagtcggct acgacaaaga attttcagac     1080
tag                                                                   1083

<210> SEQ ID NO 10
<211> LENGTH: 360
<212> TYPE: PRT
<213> ORGANISM: Saccharomyces cerevisiae

<400> SEQUENCE: 10

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240
```

```
Phe Asp Thr Phe Asp Leu Ile Val Val Cys Ala Ser Ser Leu Thr Asp
            245                 250                 255

Ile Asp Phe Asn Ile Met Pro Lys Ala Met Lys Val Gly Gly Arg Ile
        260                 265                 270

Val Ser Ile Ser Ile Pro Glu Gln His Glu Met Leu Ser Leu Lys Pro
    275                 280                 285

Tyr Gly Leu Lys Ala Val Ser Ile Ser Tyr Ser Ala Leu Gly Ser Ile
290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360

<210> SEQ ID NO 11
<211> LENGTH: 783
<212> TYPE: DNA
<213> ORGANISM: Methylococcus capsulatus

<400> SEQUENCE: 11
atggcagcaa caaccattgg tggtgcagct gcggcggaag cgccgctgct ggacaagaag      60
tggctcacgt tcgcactggc gatttacacc gtgttctacc tgtgggtgcg gtggtacgaa     120
ggtgtctatg gctggtccgc cggactggac tcgttcgcgc cggagttcga gacctactgg     180
atgaatttcc tgtacaccga gatcgtcctg gagatcgtga cggcttcgat cctgtggggc     240
tatctctgga gacccgcga ccgcaacctg gccgcgctga ccccgcgtga agagctgcgc     300
cgcaacttca cccacctggt gtggctggtg gcctacgcct gggccatcta ctggggcgca     360
tcctacttca ccgagcagga cggcacctgg catcagacga tcgtgcgcga caccgacttc     420
acgccgtcgc acatcatcga gttctatctg agctacccga tctacatcat caccggtttt     480
gcggcgttca tctacgccaa gacgcgtctg ccgttcttcg cgaagggcat ctcgctgccg     540
tacctggtgc tggtggtggg tccgttcatg attctgccga acgtgggtct gaacgaatgg     600
ggccacacct tctggttcat ggaagagctg ttcgtgcgc gctgcacta cggcttcgtg      660 atcttcggct ggctggcact ggccgtcatg gcaccctga cccagacctt ctacagcttc     720
gctcagggcg ggctggggca gtcgctctgt gaagccgtgg acgaaggctt gatcgcgaaa     780
taa                                                                  783

<210> SEQ ID NO 12
<211> LENGTH: 260
<212> TYPE: PRT
<213> ORGANISM: Methylococcus capsulatus

<400> SEQUENCE: 12

Met Ala Ala Thr Thr Ile Gly Gly Ala Ala Ala Glu Ala Pro Leu
1               5                   10                  15

Leu Asp Lys Lys Trp Leu Thr Phe Ala Leu Ala Ile Tyr Thr Val Phe
            20                  25                  30

Tyr Leu Trp Val Arg Trp Tyr Glu Gly Val Tyr Gly Trp Ser Ala Gly
        35                  40                  45

Leu Asp Ser Phe Ala Pro Glu Phe Glu Thr Tyr Trp Met Asn Phe Leu
```

```
            50                  55                  60
Tyr Thr Glu Ile Val Leu Glu Ile Val Thr Ala Ser Ile Leu Trp Gly
 65                  70                  75                  80

Tyr Leu Trp Lys Thr Arg Asp Arg Asn Leu Ala Ala Leu Thr Pro Arg
                 85                  90                  95

Glu Glu Leu Arg Arg Asn Phe Thr His Leu Val Trp Leu Val Ala Tyr
            100                 105                 110

Ala Trp Ala Ile Tyr Trp Gly Ala Ser Tyr Phe Thr Glu Gln Asp Gly
        115                 120                 125

Thr Trp His Gln Thr Ile Val Arg Asp Thr Asp Phe Thr Pro Ser His
    130                 135                 140

Ile Ile Glu Phe Tyr Leu Ser Tyr Pro Ile Tyr Ile Thr Gly Phe
145                 150                 155                 160

Ala Ala Phe Ile Tyr Ala Lys Thr Arg Leu Pro Phe Phe Ala Lys Gly
                165                 170                 175

Ile Ser Leu Pro Tyr Leu Val Leu Val Val Gly Pro Phe Met Ile Leu
            180                 185                 190

Pro Asn Val Gly Leu Asn Glu Trp Gly His Thr Phe Trp Phe Met Glu
        195                 200                 205

Glu Leu Phe Val Ala Pro Leu His Tyr Gly Phe Val Ile Phe Gly Trp
    210                 215                 220

Leu Ala Leu Ala Val Met Gly Thr Leu Thr Gln Thr Phe Tyr Ser Phe
225                 230                 235                 240

Ala Gln Gly Gly Leu Gly Gln Ser Leu Cys Glu Ala Val Asp Glu Gly
                245                 250                 255

Leu Ile Ala Lys
        260

<210> SEQ ID NO 13
<211> LENGTH: 744
<212> TYPE: DNA
<213> ORGANISM: Methylococcus capsulatus

<400> SEQUENCE: 13
atgagtgctg cgcaatctgc ggttcgttcg cacgccgaag cggtccaggt atcccggacc      60
atcgactgga tggcgttgtt cgtggtgttt ttcgtgatcg tgggctcgta ccacattcat     120
gccatgctca ccatgggtga ctgggacttc tggtcggact ggaaagaccg tcgactgtgg     180
gtcacggtga ccccgatcgt actggtcacc ttcccggcgg ccgtacaatc ctacctgtgg     240
gagcggtatc gtctgccctg gggagccacc gtgtgcgtcc tgggtctgct gctgggcgag     300
tggatcaacc gttatttcaa cttctggggc tggacctact cccgatcaa cttcgtgttc     360 cctgcctcgc tggtgccggg cgccatcatc ctggacaccg tgctgatgct gtcgggcagc     420
tacctgttca ccgcgatcgt cggtgcgatg ggctggggtc tgatcttcta cccgggcaac     480
tggccgatca tcgcgccgct gcacgtgccg gtgaataca acggcatgct gatgtcgatc     540
gccgacatcc agggttacaa ctatgtgcgt acgggtacgc tgagtacat ccgcatggta     600 gagaagggca ccctgcgtac cttcggtaag acgtggcgc cggtatcggc attcttctcc     660
gcgttcatgt cgatcctgat ctacttcatg tggcacttca tcggtcgctg gttctccaac     720
gaacggttcc tgcagagcac ctga                                            744

<210> SEQ ID NO 14
<211> LENGTH: 247
<212> TYPE: PRT
```

<213> ORGANISM: Methylococcus capsulatus

<400> SEQUENCE: 14

```
Met Ser Ala Ala Gln Ser Ala Val Arg Ser His Ala Glu Ala Val Gln
1               5                   10                  15

Val Ser Arg Thr Ile Asp Trp Met Ala Leu Phe Val Phe Phe Val
            20                  25                  30

Ile Val Gly Ser Tyr His Ile His Ala Met Leu Thr Met Gly Asp Trp
            35                  40                  45

Asp Phe Trp Ser Asp Trp Lys Asp Arg Arg Leu Trp Val Thr Val Thr
        50                  55                  60

Pro Ile Val Leu Val Thr Phe Pro Ala Ala Val Gln Ser Tyr Leu Trp
65                  70                  75                  80

Glu Arg Tyr Arg Leu Pro Trp Gly Ala Thr Val Cys Val Leu Gly Leu
                85                  90                  95

Leu Leu Gly Glu Trp Ile Asn Arg Tyr Phe Asn Phe Trp Gly Trp Thr
            100                 105                 110

Tyr Phe Pro Ile Asn Phe Val Phe Pro Ala Ser Leu Val Pro Gly Ala
            115                 120                 125

Ile Ile Leu Asp Thr Val Leu Met Leu Ser Gly Ser Tyr Leu Phe Thr
130                 135                 140

Ala Ile Val Gly Ala Met Gly Trp Gly Leu Ile Phe Tyr Pro Gly Asn
145                 150                 155                 160

Trp Pro Ile Ile Ala Pro Leu His Val Pro Val Glu Tyr Asn Gly Met
                165                 170                 175

Leu Met Ser Ile Ala Asp Ile Gln Gly Tyr Asn Tyr Val Arg Thr Gly
            180                 185                 190

Thr Pro Glu Tyr Ile Arg Met Val Glu Lys Gly Thr Leu Arg Thr Phe
            195                 200                 205

Gly Lys Asp Val Ala Pro Val Ser Ala Phe Phe Ser Ala Phe Met Ser
210                 215                 220

Ile Leu Ile Tyr Phe Met Trp His Phe Ile Gly Arg Trp Phe Ser Asn
225                 230                 235                 240

Glu Arg Phe Leu Gln Ser Thr
                245
```

<210> SEQ ID NO 15
<211> LENGTH: 1245
<212> TYPE: DNA
<213> ORGANISM: Methylococcus capsulatus

<400> SEQUENCE: 15

```
atgaaaacaa taaggaccg gattgcaaaa tggtctgcaa tcggactgct gtccgccgtg      60
gcagcgaccg ccttctatgc gccgagcgcc agcgcccacg gtgagaaatc gcaggccgcg    120
ttcatgcgta tgcgtaccat ccactggtac gacctgagct ggtcgaaaga gaaagtcaag    180
atcaacgaga ccgtggaaat caaaggcaag ttccacgtgt cgaaggctg gccggaaacg     240
gtcgacgaac cggatgtggc gttcctgaac gtcggcatgc cgggtccggt gttcatccgc    300
aaggaatcgt acatcggcgg tcagctggtg ccgcgttccg tacgtctgga atcggcaag    360
acctatgact tccgggttgt cctcaaagcc cgtcgtccgg gtgactggca cgttcacacc    420
atgatgaacg tccagggcgg tggaccgatc atcggtcccg gcaaatggat caccgtggaa    480
ggctccatga gtgaattccg caaccccgtc accaccctga ccggtcagac ggtggacctg    540
gagaactaca cgaaggcaa cacctatttc tggcacgcct tctggttcgc catcggagtt    600
```

```
gcctggatcg gctactggtc gcgtcgaccg atcttcatcc cccgtctgct gatggtggat      660
gccggtcgtg cggatgaact ggtgtccgcc accgaccgca aggtggcgat gggcttcctg      720
gccgccacca tcctgatcgt ggtcatggcc atgtccagcg ccaacagcaa gtacccgatc      780
accatcccgc tgcaggccgg caccatgcgt ggcatgaagc cgctggaact gccggcgccg      840
acggtatcgg tgaaagtgga agacgccacc taccgggtac cgggccgcgc catgcggatg      900
aagctgacca tcaccaacca cggcaacagc ccgatccggc tgggtgagtt ctacaccgcc      960
tcggtgcgtt tcctggattc cgacgtgtac aaggacacca ccggctatcc ggaagacctg     1020
ctggccgaag acggcctgag cgtcagcgac aacagcccgc tggctccggg tgagacgcgc     1080
acggtcgacg tgacggcgtc cgacgcggcg tgggaagtgt accgtctgtc cgacatcatc     1140
tacgatccgg acagccgttt cgccggtctg ctgttcttct tcgacgccac tggcaaccgc     1200
caggtcgtcc agatcgacgc accgctgatc ccgtcgttca tgtaa                     1245
```

<210> SEQ ID NO 16
<211> LENGTH: 414
<212> TYPE: PRT
<213> ORGANISM: Methylococcus capsulatus

<400> SEQUENCE: 16

```
Met Lys Thr Ile Lys Asp Arg Ile Ala Lys Trp Ser Ala Ile Gly Leu
1               5                   10                  15

Leu Ser Ala Val Ala Ala Thr Ala Phe Tyr Ala Pro Ser Ala Ser Ala
                20                  25                  30

His Gly Glu Lys Ser Gln Ala Ala Phe Met Arg Met Thr Ile His
            35                  40                  45

Trp Tyr Asp Leu Ser Trp Ser Lys Glu Lys Val Lys Ile Asn Glu Thr
        50                  55                  60

Val Glu Ile Lys Gly Lys Phe His Val Phe Glu Gly Trp Pro Glu Thr
65                  70                  75                  80

Val Asp Glu Pro Asp Val Ala Phe Leu Asn Val Gly Met Pro Gly Pro
                85                  90                  95

Val Phe Ile Arg Lys Glu Ser Tyr Ile Gly Gly Gln Leu Val Pro Arg
            100                 105                 110

Ser Val Arg Leu Glu Ile Gly Lys Thr Tyr Asp Phe Arg Val Val Leu
        115                 120                 125

Lys Ala Arg Arg Pro Gly Asp Trp His Val His Thr Met Met Asn Val
130                 135                 140

Gln Gly Gly Gly Pro Ile Ile Gly Pro Gly Lys Trp Ile Thr Val Glu
145                 150                 155                 160

Gly Ser Met Ser Glu Phe Arg Asn Pro Val Thr Thr Leu Thr Gly Gln
                165                 170                 175

Thr Val Asp Leu Glu Asn Tyr Asn Glu Gly Asn Thr Tyr Phe Trp His
            180                 185                 190

Ala Phe Trp Phe Ala Ile Gly Val Ala Trp Ile Gly Tyr Trp Ser Arg
        195                 200                 205

Arg Pro Ile Phe Ile Pro Arg Leu Leu Met Val Asp Ala Gly Arg Ala
    210                 215                 220

Asp Glu Leu Val Ser Ala Thr Asp Arg Lys Val Ala Met Gly Phe Leu
225                 230                 235                 240

Ala Ala Thr Ile Leu Ile Val Val Met Ala Met Ser Ser Ala Asn Ser
                245                 250                 255
```

Lys Tyr Pro Ile Thr Ile Pro Leu Gln Ala Gly Thr Met Arg Gly Met
                260                 265                 270

Lys Pro Leu Glu Leu Pro Ala Pro Thr Val Ser Val Lys Val Glu Asp
            275                 280                 285

Ala Thr Tyr Arg Val Pro Gly Arg Ala Met Arg Met Lys Leu Thr Ile
        290                 295                 300

Thr Asn His Gly Asn Ser Pro Ile Arg Leu Gly Glu Phe Tyr Thr Ala
305                 310                 315                 320

Ser Val Arg Phe Leu Asp Ser Asp Val Tyr Lys Asp Thr Thr Gly Tyr
                325                 330                 335

Pro Glu Asp Leu Leu Ala Glu Asp Gly Leu Ser Val Ser Asp Asn Ser
            340                 345                 350

Pro Leu Ala Pro Gly Glu Thr Arg Thr Val Asp Val Thr Ala Ser Asp
        355                 360                 365

Ala Ala Trp Glu Val Tyr Arg Leu Ser Asp Ile Ile Tyr Asp Pro Asp
    370                 375                 380

Ser Arg Phe Ala Gly Leu Leu Phe Phe Phe Asp Ala Thr Gly Asn Arg
385                 390                 395                 400

Gln Val Val Gln Ile Asp Ala Pro Leu Ile Pro Ser Phe Met
                405                 410

<210> SEQ ID NO 17
<211> LENGTH: 783
<212> TYPE: DNA
<213> ORGANISM: Methylococcus capsulatus

<400> SEQUENCE: 17
atggcagcaa caaccattgg tggtgcagct gcggcggaag cgccgctgct ggacaagaag      60
tggctcacgt tcgcactggc gatttacacc gtgttctacc tgtgggtgcg gtggtacgaa     120
ggtgtctatg ctggtccgc cggactggac tcgttcgcgc cggagttcga gacctactgg     180
atgaatttcc tgtacaccga gatcgtcctg gagatcgtga cggcttcgat cctgtggggc     240
tatctctgga gacccgcga ccgcaacctg gccgcgctga ccccgcgtga gagctgcgc      300
cgcaacttca cccacctggt gtggctggtg gcctacgcct gggccatcta ctggggcgca     360
tcctacttca ccgagcagga cggcacctgg catcagacga tcgtgcgcga caccgacttc     420
acgccgtcgc acatcatcga gttctatctg agctacccga tctacatcat caccggtttt     480
gcggcgttca tctacgccaa gacgcgtctg ccgttcttcg cgaagggcat ctcgctgccg     540
tacctggtgc tggtggtggg tccgttcatg attctgccga acgtgggtct gaacgaatgg     600
ggccacaccct tctggttcat ggaagagctg ttcgtggcgc cgctgcacta cggcttcgtg     660
atcttcggct ggctggcact ggccgtcatg ggcacccctga cccagacctt ctacagcttc     720
gctcagggcg ggctggggca gtcgctctgt gaagccgtgg acgaaggctt gatcgcgaaa     780
taa                                                                     783

<210> SEQ ID NO 18
<211> LENGTH: 260
<212> TYPE: PRT
<213> ORGANISM: Methylococcus capsulatus

<400> SEQUENCE: 18

Met Ala Ala Thr Thr Ile Gly Gly Ala Ala Ala Glu Ala Pro Leu
1               5                   10                  15

Leu Asp Lys Lys Trp Leu Thr Phe Ala Leu Ala Ile Tyr Thr Val Phe
            20                  25                  30

```
Tyr Leu Trp Val Arg Trp Tyr Glu Gly Val Tyr Gly Trp Ser Ala Gly
            35                  40                  45

Leu Asp Ser Phe Ala Pro Glu Phe Glu Thr Tyr Trp Met Asn Phe Leu
 50                  55                  60

Tyr Thr Glu Ile Val Leu Glu Ile Val Thr Ala Ser Ile Leu Trp Gly
 65                  70                  75                  80

Tyr Leu Trp Lys Thr Arg Asp Arg Asn Leu Ala Ala Leu Thr Pro Arg
                85                  90                  95

Glu Glu Leu Arg Arg Asn Phe Thr His Leu Val Trp Leu Val Ala Tyr
                100                 105                 110

Ala Trp Ala Ile Tyr Trp Gly Ala Ser Tyr Phe Thr Glu Gln Asp Gly
                115                 120                 125

Thr Trp His Gln Thr Ile Val Arg Asp Thr Asp Phe Thr Pro Ser His
                130                 135                 140

Ile Ile Glu Phe Tyr Leu Ser Tyr Pro Ile Tyr Ile Thr Gly Phe
145                 150                 155                 160

Ala Ala Phe Ile Tyr Ala Lys Thr Arg Leu Pro Phe Phe Ala Lys Gly
                165                 170                 175

Ile Ser Leu Pro Tyr Leu Val Leu Val Val Gly Pro Phe Met Ile Leu
                180                 185                 190

Pro Asn Val Gly Leu Asn Glu Trp Gly His Thr Phe Trp Phe Met Glu
                195                 200                 205

Glu Leu Phe Val Ala Pro Leu His Tyr Gly Phe Val Ile Phe Gly Trp
                210                 215                 220

Leu Ala Leu Ala Val Met Gly Thr Leu Thr Gln Thr Phe Tyr Ser Phe
225                 230                 235                 240

Ala Gln Gly Gly Leu Gly Gln Ser Leu Cys Glu Ala Val Asp Glu Gly
                245                 250                 255

Leu Ile Ala Lys
                260

<210> SEQ ID NO 19
<211> LENGTH: 744
<212> TYPE: DNA
<213> ORGANISM: Methylococcus capsulatus

<400> SEQUENCE: 19
atgagtgctg cgcaatctgc ggttcgttcg cacgccgaag cggtccaggt atcccggacc      60
atcgactgga tggcgttgtt cgtggtgttt ttcgtgatcg tgggctcgta ccacattcac     120
gccatgctca ccatgggtga ctgggacttc tggtcggact ggaaagaccg tcgactgtgg     180
gtcacggtga ccccgatcgt actggtcacc ttcccggcgg ccgtacaatc ctacctgtgg     240
gagcggtatc gtctgccctg gggagccacc gtgtgcgtcc tgggtctgct gctgggcgag     300
tggatcaacc gttatttcaa cttctggggc tggacctact tcccgatcaa cttcgtgttc     360
cctgcctcgc tggtgccggg cgccatcatc ctggacaccg tgctgatgct gtcgggcagc     420
tacctgttca ccgcgatcgt cggtgcgatg ggctggggtc tgatcttcta cccgggcaac     480
tggccgatca tcgcgccgct gcacgtgccg gtggaataca acggcatgct gatgtcgatc     540
gccgacatcc agggttacaa ctatgtgcgt acgggtacgc ctgagtacat ccgcatggta     600
gagaagggca ccctgcgtac cttcggtaag acgtggcgc cggtatcggc attcttctcc     660
gcgttcatgt cgatcctgat ctacttcatg tggcacttca tcggtcgctg gttctccaac     720
gaacggttcc tgcagagcac ctga                                            744
```

<210> SEQ ID NO 20
<211> LENGTH: 247
<212> TYPE: PRT
<213> ORGANISM: Methylococcus capsulatus

<400> SEQUENCE: 20

Met Ser Ala Ala Gln Ser Ala Val Arg Ser His Ala Glu Ala Val Gln
1               5                   10                  15

Val Ser Arg Thr Ile Asp Trp Met Ala Leu Phe Val Val Phe Phe Val
                20                  25                  30

Ile Val Gly Ser Tyr His Ile His Ala Met Leu Thr Met Gly Asp Trp
            35                  40                  45

Asp Phe Trp Ser Asp Trp Lys Asp Arg Arg Leu Trp Val Thr Val Thr
    50                  55                  60

Pro Ile Val Leu Val Thr Phe Pro Ala Ala Val Gln Ser Tyr Leu Trp
65                  70                  75                  80

Glu Arg Tyr Arg Leu Pro Trp Gly Ala Thr Val Cys Val Leu Gly Leu
                85                  90                  95

Leu Leu Gly Glu Trp Ile Asn Arg Tyr Phe Asn Phe Trp Gly Trp Thr
            100                 105                 110

Tyr Phe Pro Ile Asn Phe Val Phe Pro Ala Ser Leu Val Pro Gly Ala
        115                 120                 125

Ile Ile Leu Asp Thr Val Leu Met Leu Ser Gly Ser Tyr Leu Phe Thr
130                 135                 140

Ala Ile Val Gly Ala Met Gly Trp Gly Leu Ile Phe Tyr Pro Gly Asn
145                 150                 155                 160

Trp Pro Ile Ile Ala Pro Leu His Val Pro Val Glu Tyr Asn Gly Met
                165                 170                 175

Leu Met Ser Ile Ala Asp Ile Gln Gly Tyr Asn Tyr Val Arg Thr Gly
            180                 185                 190

Thr Pro Glu Tyr Ile Arg Met Val Glu Lys Gly Thr Leu Arg Thr Phe
        195                 200                 205

Gly Lys Asp Val Ala Pro Val Ser Ala Phe Ser Ala Phe Met Ser
210                 215                 220

Ile Leu Ile Tyr Phe Met Trp His Phe Ile Gly Arg Trp Phe Ser Asn
225                 230                 235                 240

Glu Arg Phe Leu Gln Ser Thr
                245

<210> SEQ ID NO 21
<211> LENGTH: 1245
<212> TYPE: DNA
<213> ORGANISM: Methylococcus capsulatus

<400> SEQUENCE: 21
atgaaaacaa taaggaccg gattgcaaaa tggtctgcaa tcggactgct gtccgccgtg      60
gcagcgaccg ccttctatgc gccgagcgcc agcgcccacg gtgagaaatc gcaggccgcg     120
ttcatgcgta tgcgtaccat ccactggtac gacctgagct ggtcgaaaga gaaagtcaag     180
atcaacgaga ccgtggaaat caaaggcaag ttccacgtgt cgaaggctg gccggaaacg      240 gtcgacgaac cggatgtggc gttcctgaac gtcggcatgc cgggtccggt gttcatccgc     300
aaggaatcgt acatcggcgg tcagctggtg ccgcgttccg tacgtctgga atcggcaag     360 acctatgact tccgggttgt cctcaaagcc cgtcgtccgg gtgactggca cgttcacacc     420

```
atgatgaacg tccagggcgg tggaccgatc atcggtcccg gcaaatggat caccgtggaa      480
ggctccatga gtgaattccg caaccccgtc accaccctga ccggtcagac ggtggacctg      540
gagaactaca acgaaggcaa cacctatttc tggcacgcct tctggttcgc catcggagtt      600
gcctggatcg gctactggtc gcgtcgaccg atcttcatcc cccgtctgct gatggtggat      660
gccggtcgtg cggacgaact ggtgtccgcc accgaccgca aggtggcgat gggcttcctg      720
gccgccacca tcctgatcgt ggtcatggcc atgtccagcg ccaacagcaa gtacccgatc      780
accatcccgc tgcaggccgg caccatgcgt ggcatgaagc cgctggaact gccggcgccg      840
acggtatcgg tgaaagtgga agacgccacc taccgggtac cgggccgcgc catgcggatg      900
aagctgacca tcaccaacca cggcaacagc ccgatccggc tgggtgagtt ctacaccgcc      960
tcggtgcgtt tcctggattc cgacgtgtac aaggacacca ccggctatcc ggaagacctg     1020
ctggccgaag acggcctgag cgtcagcgac aacagcccgc tggctccggg tgagacccgc     1080
acggtcgacg tgacggcgtc cgacgcggcg tgggaagtgt accgtctgtc cgacatcatc     1140
tacgatccgg acagccgttt cgccggtctg ctgttcttct tcgacgccac tggcaaccgc     1200
caggtcgtcc agatcgacgc accgctgatc ccgtcgttca tgtaa                     1245
```

<210> SEQ ID NO 22
<211> LENGTH: 414
<212> TYPE: PRT
<213> ORGANISM: Methylococcus capsulatus

<400> SEQUENCE: 22

```
Met Lys Thr Ile Lys Asp Arg Ile Ala Lys Trp Ser Ala Ile Gly Leu
1               5                   10                  15

Leu Ser Ala Val Ala Ala Thr Ala Phe Tyr Ala Pro Ser Ala Ser Ala
                20                  25                  30

His Gly Glu Lys Ser Gln Ala Ala Phe Met Arg Met Arg Thr Ile His
            35                  40                  45

Trp Tyr Asp Leu Ser Trp Ser Lys Glu Lys Val Lys Ile Asn Glu Thr
        50                  55                  60

Val Glu Ile Lys Gly Lys Phe His Val Phe Glu Gly Trp Pro Glu Thr
65                  70                  75                  80

Val Asp Glu Pro Asp Val Ala Phe Leu Asn Val Gly Met Pro Gly Pro
                85                  90                  95

Val Phe Ile Arg Lys Glu Ser Tyr Ile Gly Gly Gln Leu Val Pro Arg
            100                 105                 110

Ser Val Arg Leu Glu Ile Gly Lys Thr Tyr Asp Phe Arg Val Val Leu
        115                 120                 125

Lys Ala Arg Arg Pro Gly Asp Trp His Val His Thr Met Met Asn Val
    130                 135                 140

Gln Gly Gly Gly Pro Ile Ile Gly Pro Gly Lys Trp Ile Thr Val Glu
145                 150                 155                 160

Gly Ser Met Ser Glu Phe Arg Asn Pro Val Thr Thr Leu Thr Gly Gln
                165                 170                 175

Thr Val Asp Leu Glu Asn Tyr Asn Glu Gly Asn Thr Tyr Phe Trp His
            180                 185                 190

Ala Phe Trp Phe Ala Ile Gly Val Ala Trp Ile Gly Tyr Trp Ser Arg
        195                 200                 205

Arg Pro Ile Phe Ile Pro Arg Leu Leu Met Val Asp Ala Gly Arg Ala
    210                 215                 220

Asp Glu Leu Val Ser Ala Thr Asp Arg Lys Val Ala Met Gly Phe Leu
```

```
                225                 230                 235                 240
            Ala Ala Thr Ile Leu Ile Val Val Met Ala Met Ser Ser Ala Asn Ser
                            245                 250                 255

Lys Tyr Pro Ile Thr Ile Pro Leu Gln Ala Gly Thr Met Arg Gly Met
                            260                 265                 270

Lys Pro Leu Glu Leu Pro Ala Pro Thr Val Ser Val Lys Val Glu Asp
                            275                 280                 285

Ala Thr Tyr Arg Val Pro Gly Arg Ala Met Arg Met Lys Leu Thr Ile
                            290                 295                 300

Thr Asn His Gly Asn Ser Pro Ile Arg Leu Gly Glu Phe Tyr Thr Ala
            305                 310                 315                 320

Ser Val Arg Phe Leu Asp Ser Asp Val Tyr Lys Asp Thr Thr Gly Tyr
                            325                 330                 335

Pro Glu Asp Leu Leu Ala Glu Asp Gly Leu Ser Val Ser Asp Asn Ser
                            340                 345                 350

Pro Leu Ala Pro Gly Glu Thr Arg Thr Val Asp Val Thr Ala Ser Asp
                            355                 360                 365

Ala Ala Trp Glu Val Tyr Arg Leu Ser Asp Ile Ile Tyr Asp Pro Asp
                            370                 375                 380

Ser Arg Phe Ala Gly Leu Leu Phe Phe Phe Asp Ala Thr Gly Asn Arg
            385                 390                 395                 400

Gln Val Val Gln Ile Asp Ala Pro Leu Ile Pro Ser Phe Met
                            405                 410

<210> SEQ ID NO 23
<211> LENGTH: 1584
<212> TYPE: DNA
<213> ORGANISM: Methylococcus capsulatus

<400> SEQUENCE: 23
atggcactta gcaccgcaac caaggccgcg acggacgcgc tggctgccaa tcgggcaccc      60
accagcgtga atgcacagga agtgcaccgt tggctccaga gcttcaactg ggatttcaag     120
aacaaccgga ccaagtacgc caccaagtac aagatggcga acgagaccaa ggaacagttc     180
aagctgatcg ccaaggaata tgcgcgcatg gaggcagtca aggacgaaag gcagttcggt     240
agcctgcagg atgcgctgac ccgcctcaac gccggtgttc gcgttcatcc gaagtggaac     300
gagaccatga aagtggtttc gaacttcctg gaagtgggcg aatacaacgc catcgccgct     360
accgggatgc tgtgggattc cgcccaggcg gcggaacaga gaacggcta tctggcccag     420 gtgttggatg aaatccgcca cacccaccag tgtgcctacg tcaactacta cttcgcgaag     480
aacggccagg acccggccgg tcacaacgat gctcgccgca cccgtaccat cggtccgctg     540
tggaagggca tgaagcgcgt gttttccgac ggcttcattt ccggcgacgc cgtggaatgc     600
tccctcaacc tgcagctggt gggtgaggcc tgcttcacca atccgctgat cgtcgcagtg     660
accgaatggg ctgccgccaa cggcgatgaa atcaccccga cggtgttcct gtcgatcgag     720
accgacgaac tgcgccacat ggccaacggt taccagaccg tcgtttccat cgccaacgat     780
ccggcttccg ccaagtatct caacacggac ctgaacaacg ccttctggac ccagcagaag     840
tacttcacgc cggtgttggg catgctgttc gagtatggct ccaagttcaa ggtcgagccg     900
tgggtcaaga cgtggaaccg ctgggtgtac gaggactggg cggcatctg gatcggccgt     960 ctgggcaagt acggggtgga gtcgccgcgc agcctcaagg acgccaagca ggacgcttac    1020
tgggctcacc acgacctgta tctgctggct tatgcgctgt ggccgaccgg cttcttccgt    1080
```

-continued

```
ctggcgctgc cggatcagga agaaatggag tggttcgagg ccaactaccc cggctggtac    1140
gaccactacg gcaagatcta cgaggaatgg cgcgcccgcg gttgcgagga tccgtcctcg    1200
ggcttcatcc cgctgatgtg gttcatcgaa acaaccatc ccatctacat cgatcgcgtg     1260
tcgcaagtgc cgttctgccc gagcttggcc aagggcgcca gcaccctgcg cgtgcacgag    1320
tacaacggcc agatgcacac cttcagcgac cagtggggcg agcgcatgtg gctggccgag    1380
ccggagcgct acgagtgcca gaacatcttc gaacagtacg aaggacgcga actgtcggaa    1440
gtgatcgccg aactgcacgg gctgcgcagt gatggcaaga ccctgatcgc ccagccgcat    1500
gtccgtggcg acaagctgtg gacgttggac gatatcaaac gcctgaactg cgtcttcaag    1560
aacccggtga aggcattcaa ttga                                          1584
```

<210> SEQ ID NO 24
<211> LENGTH: 527
<212> TYPE: PRT
<213> ORGANISM: Methylococcus capsulatus

<400> SEQUENCE: 24

```
Met Ala Leu Ser Thr Ala Thr Lys Ala Ala Thr Asp Ala Leu Ala Ala
1               5                   10                  15

Asn Arg Ala Pro Thr Ser Val Asn Ala Gln Glu Val His Arg Trp Leu
            20                  25                  30

Gln Ser Phe Asn Trp Asp Phe Lys Asn Arg Thr Lys Tyr Ala Thr
        35                  40                  45

Lys Tyr Lys Met Ala Asn Glu Thr Lys Glu Gln Phe Lys Leu Ile Ala
50                  55                  60

Lys Glu Tyr Ala Arg Met Glu Ala Val Lys Asp Glu Arg Gln Phe Gly
65                  70                  75                  80

Ser Leu Gln Asp Ala Leu Thr Arg Leu Asn Ala Gly Val Arg Val His
                85                  90                  95

Pro Lys Trp Asn Glu Thr Met Lys Val Val Ser Asn Phe Leu Glu Val
            100                 105                 110

Gly Glu Tyr Asn Ala Ile Ala Ala Thr Gly Met Leu Trp Asp Ser Ala
        115                 120                 125

Gln Ala Ala Glu Gln Lys Asn Gly Tyr Leu Ala Gln Val Leu Asp Glu
    130                 135                 140

Ile Arg His Thr His Gln Cys Ala Tyr Val Asn Tyr Tyr Phe Ala Lys
145                 150                 155                 160

Asn Gly Gln Asp Pro Ala Gly His Asn Asp Ala Arg Arg Thr Arg Thr
                165                 170                 175

Ile Gly Pro Leu Trp Lys Gly Met Lys Arg Val Phe Ser Asp Gly Phe
            180                 185                 190

Ile Ser Gly Asp Ala Val Glu Cys Ser Leu Asn Leu Gln Leu Val Gly
        195                 200                 205

Glu Ala Cys Phe Thr Asn Pro Leu Ile Val Ala Val Thr Glu Trp Ala
    210                 215                 220

Ala Ala Asn Gly Asp Glu Ile Thr Pro Thr Val Phe Leu Ser Ile Glu
225                 230                 235                 240

Thr Asp Glu Leu Arg His Met Ala Asn Gly Tyr Gln Thr Val Val Ser
                245                 250                 255

Ile Ala Asn Asp Pro Ala Ser Ala Lys Tyr Leu Asn Thr Asp Leu Asn
            260                 265                 270

Asn Ala Phe Trp Thr Gln Gln Lys Tyr Phe Thr Pro Val Leu Gly Met
        275                 280                 285
```

Leu Phe Glu Tyr Gly Ser Lys Phe Lys Val Glu Pro Trp Lys Thr
            290                 295                 300

Trp Asn Arg Trp Val Tyr Glu Asp Trp Gly Ile Trp Ile Gly Arg
305                 310                 315                 320

Leu Gly Lys Tyr Gly Val Glu Ser Pro Arg Ser Leu Lys Asp Ala Lys
                325                 330                 335

Gln Asp Ala Tyr Trp Ala His His Asp Leu Tyr Leu Ala Tyr Ala
            340                 345                 350

Leu Trp Pro Thr Gly Phe Phe Arg Leu Ala Leu Pro Asp Gln Glu Glu
            355                 360                 365

Met Glu Trp Phe Glu Ala Asn Tyr Pro Gly Trp Tyr Asp His Tyr Gly
            370                 375                 380

Lys Ile Tyr Glu Glu Trp Arg Ala Arg Gly Cys Glu Asp Pro Ser Ser
385                 390                 395                 400

Gly Phe Ile Pro Leu Met Trp Phe Ile Glu Asn Asn His Pro Ile Tyr
                405                 410                 415

Ile Asp Arg Val Ser Gln Val Pro Phe Cys Pro Ser Leu Ala Lys Gly
            420                 425                 430

Ala Ser Thr Leu Arg Val His Glu Tyr Asn Gly Gln Met His Thr Phe
            435                 440                 445

Ser Asp Gln Trp Gly Glu Arg Met Trp Leu Ala Glu Pro Glu Arg Tyr
450                 455                 460

Glu Cys Gln Asn Ile Phe Glu Gln Tyr Glu Gly Arg Glu Leu Ser Glu
465                 470                 475                 480

Val Ile Ala Glu Leu His Gly Leu Arg Ser Asp Gly Lys Thr Leu Ile
                485                 490                 495

Ala Gln Pro His Val Arg Gly Asp Lys Leu Trp Thr Leu Asp Asp Ile
            500                 505                 510

Lys Arg Leu Asn Cys Val Phe Lys Asn Pro Val Lys Ala Phe Asn
            515                 520                 525

<210> SEQ ID NO 25
<211> LENGTH: 1170
<212> TYPE: DNA
<213> ORGANISM: Methylococcus capsulatus

<400> SEQUENCE: 25
atgagcatgt taggagaaag acgccgcggt ctgaccgatc cggaaatggc ggccgtcatt      60
ttgaaggcgc ttcctgaagc tccgctggac ggcaacaaca agatgggtta tttcgtcacc    120
ccccgctgga aacgcttgac ggaatatgaa gccctgaccg tttatgcgca gcccaacgcc    180
gactggatcg ccggcggcct ggactggggc gactggaccc agaaattcca cggcggccgc    240
ccttcctggg gcaacgagac cacggagctg cgcaccgtcg actggttcaa gcaccgtgac    300
ccgctccgcc gttggcatgc gccgtacgtc aaggacaagg ccgaggaatg cgcctacacc    360
gaccgcttcc tgcagggtta ctccgccgac ggtcagatcc gggcgatgaa cccgacctgg    420
cgggacgagt tcatcaaccg gtattggggc gccttcctgt caacgaata cggattgttc    480 aacgctcatt cgcagggcgc ccgggaggcg ctgtcggacg taacccgcgt cagcctggct    540
ttctggggct cgacaagat cgacatcgcc cagatgatcc aactcgaacg gggtttcctc    600
gccaagatcg tacccggttt cgacgagtcc acagcggtgc cgaaggccga atggacgaac    660
ggggaggtct acaagagcgc ccgtctggcc gtggaagggc tgtggcagga ggtgttcgac    720
tggaacgaga gcgctttctc ggtgcacgcc gtctatgacg cgctgttcgg tcagttcgtc    780

```
cgccgcgagt tctttcagcg gctggctccc cgcttcggcg acaatctgac gccattcttc    840
atcaaccagg cccagacata cttccagatc gccaagcagg gcgtacagga tctgtattac    900
aactgtctgg gtgacgatcc ggagttcagc gattacaacc gtaccgtgat cgcaactgg     960 accggcaagt ggctggagcc cacgatcgcc gctctgcgcg acttcatggg gctgtttgcg   1020
aagctgccgg cgggcaccac tgacaaggaa gaaatcaccg cgtccctgta ccgggtggtc   1080
gacgactgga tcgaggacta cgccagcagg atcgacttca aggcggaccg cgatcagatc   1140
gttaaagcgg ttctggcagg attgaaataa                                    1170
```

<210> SEQ ID NO 26
<211> LENGTH: 389
<212> TYPE: PRT
<213> ORGANISM: Methylococcus capsulatus

<400> SEQUENCE: 26

```
Met Ser Met Leu Gly Glu Arg Arg Gly Leu Thr Asp Pro Glu Met
1               5                   10                  15

Ala Ala Val Ile Leu Lys Ala Leu Pro Glu Ala Pro Leu Asp Gly Asn
                20                  25                  30

Asn Lys Met Gly Tyr Phe Val Thr Pro Arg Trp Lys Arg Leu Thr Glu
            35                  40                  45

Tyr Glu Ala Leu Thr Val Tyr Ala Gln Pro Asn Ala Asp Trp Ile Ala
        50                  55                  60

Gly Gly Leu Asp Trp Gly Asp Trp Thr Gln Lys Phe His Gly Arg
65                  70                  75                  80

Pro Ser Trp Gly Asn Glu Thr Thr Glu Leu Arg Thr Val Asp Trp Phe
                85                  90                  95

Lys His Arg Asp Pro Leu Arg Arg Trp His Ala Pro Tyr Val Lys Asp
            100                 105                 110

Lys Ala Glu Glu Trp Arg Tyr Thr Asp Arg Phe Leu Gln Gly Tyr Ser
        115                 120                 125

Ala Asp Gly Gln Ile Arg Ala Met Asn Pro Thr Trp Arg Asp Glu Phe
    130                 135                 140

Ile Asn Arg Tyr Trp Gly Ala Phe Leu Phe Asn Glu Tyr Gly Leu Phe
145                 150                 155                 160

Asn Ala His Ser Gln Gly Ala Arg Glu Ala Leu Ser Asp Val Thr Arg
                165                 170                 175

Val Ser Leu Ala Phe Trp Gly Phe Asp Lys Ile Asp Ile Ala Gln Met
            180                 185                 190

Ile Gln Leu Glu Arg Gly Phe Leu Ala Lys Ile Val Pro Gly Phe Asp
        195                 200                 205

Glu Ser Thr Ala Val Pro Lys Ala Glu Trp Thr Asn Gly Glu Val Tyr
    210                 215                 220

Lys Ser Ala Arg Leu Ala Val Glu Gly Leu Trp Gln Glu Val Phe Asp
225                 230                 235                 240

Trp Asn Glu Ser Ala Phe Ser Val His Ala Val Tyr Asp Ala Leu Phe
                245                 250                 255

Gly Gln Phe Val Arg Arg Glu Phe Phe Gln Arg Leu Ala Pro Arg Phe
            260                 265                 270

Gly Asp Asn Leu Thr Pro Phe Phe Ile Asn Gln Ala Gln Thr Tyr Phe
        275                 280                 285

Gln Ile Ala Lys Gln Gly Val Gln Asp Leu Tyr Tyr Asn Cys Leu Gly
    290                 295                 300
```

```
Asp Asp Pro Glu Phe Ser Asp Tyr Asn Arg Thr Val Met Arg Asn Trp
305                 310                 315                 320

Thr Gly Lys Trp Leu Glu Pro Thr Ile Ala Ala Leu Arg Asp Phe Met
            325                 330                 335

Gly Leu Phe Ala Lys Leu Pro Ala Gly Thr Thr Asp Lys Glu Glu Ile
        340                 345                 350

Thr Ala Ser Leu Tyr Arg Val Val Asp Asp Trp Ile Glu Asp Tyr Ala
            355                 360                 365

Ser Arg Ile Asp Phe Lys Ala Asp Arg Asp Gln Ile Val Lys Ala Val
        370                 375                 380

Leu Ala Gly Leu Lys
385

<210> SEQ ID NO 27
<211> LENGTH: 426
<212> TYPE: DNA
<213> ORGANISM: Methylococcus capsulatus

<400> SEQUENCE: 27
atgagcgtaa acagcaacgc atacgacgcc ggcatcatgg gcctgaaagg caaggacttc      60
gccgatcagt tctttgccga cgaaaaccaa gtggtccatg aaagcgacac ggtcgttctg     120
gtcctcaaga agtcggacga gatcaatacc tttatcgagg agatccttct gacggactac     180
aagaagaacg tcaatccgac ggtaaacgtg aagaccgcgc gggttactgt tggatcaag     240 gccaacggca gatcgaggt cgattgcgac gagatttccg agctgttggg cggcagttc     300 aacgtctacg acttcctcgt cgacgtttcc tccaccatcg gccgggccta ccctgggc      360 aacaagttca ccattaccag tgagctgatg ggcctggacc gcaagctcga agactatcac     420
gcttaa                                                                 426

<210> SEQ ID NO 28
<211> LENGTH: 138
<212> TYPE: PRT
<213> ORGANISM: Methylococcus capsulatus

<400> SEQUENCE: 28

Met Ser Val Asn Ser Asn Ala Tyr Asp Ala Gly Ile Met Gly Leu Lys
1               5                   10                  15

Gly Lys Asp Phe Ala Asp Gln Phe Phe Ala Asp Glu Asn Gln Val Val
            20                  25                  30

His Glu Ser Asp Thr Val Val Leu Val Leu Lys Lys Ser Asp Glu Ile
        35                  40                  45

Asn Thr Phe Ile Glu Glu Ile Leu Leu Thr Asp Tyr Lys Lys Asn Val
    50                  55                  60

Asn Pro Thr Val Asn Val Glu Asp Arg Ala Gly Tyr Trp Trp Ile Lys
65                  70                  75                  80

Ala Asn Gly Lys Ile Glu Val Asp Cys Asp Glu Ile Ser Glu Leu Leu
                85                  90                  95

Gly Arg Gln Phe Asn Val Tyr Asp Phe Leu Val Asp Val Ser Ser Thr
            100                 105                 110

Ile Gly Arg Ala Tyr Thr Leu Gly Asn Lys Phe Thr Ile Thr Ser Glu
        115                 120                 125

Leu Met Gly Leu Asp Arg Lys Leu Glu Asp
    130                 135
```

<210> SEQ ID NO 29
<211> LENGTH: 513
<212> TYPE: DNA
<213> ORGANISM: Methylococcus capsulatus

<400> SEQUENCE: 29

| | |
|---|---:|
| atggcgaaac tgggtataca cagcaacgac acccgcgacg cctgggtgaa caagatcgcg | 60 |
| cagctcaaca ccctggaaaa agcggccgag atgctgaagc agttccggat ggaccacacc | 120 |
| acgccgttcc gcaacagcta cgaactggac aacgactacc tctggatcga ggccaagctc | 180 |
| gaagagaagg tcgccgtcct caaggcacgc gccttcaacg aggtggactt ccgtcataag | 240 |
| accgctttcg gcgaggatgc caagtccgtt ctggacggca ccgtcgcgaa gatgaacgcg | 300 |
| gccaaggaca gtggggaggc ggagaagatc catatcggtt tccgccaggc ctacaagccg | 360 |
| ccgatcatgc cggtgaacta tttcctggac ggcgagcgtc agttggggac cggctgatg | 420 |
| gaactgcgca acctcaacta ctacgacacg ccgctggaag aactgcgcaa acagcgcggt | 480 |
| gtgcgggtgg tgcatctgca gtcgccgcac tga | 513 |

<210> SEQ ID NO 30
<211> LENGTH: 170
<212> TYPE: PRT
<213> ORGANISM: Methylococcus capsulatus

<400> SEQUENCE: 30

Met Ala Lys Leu Gly Ile His Ser Asn Asp Thr Arg Asp Ala Trp Val
1               5                   10                  15

Asn Lys Ile Ala Gln Leu Asn Thr Leu Glu Lys Ala Ala Glu Met Leu
            20                  25                  30

Lys Gln Phe Arg Met Asp His Thr Thr Pro Phe Arg Asn Ser Tyr Glu
        35                  40                  45

Leu Asp Asn Asp Tyr Leu Trp Ile Glu Ala Lys Leu Glu Glu Lys Val
    50                  55                  60

Ala Val Leu Lys Ala Arg Ala Phe Asn Glu Val Asp Phe Arg His Lys
65                  70                  75                  80

Thr Ala Phe Gly Glu Asp Ala Lys Ser Val Leu Asp Gly Thr Val Ala
                85                  90                  95

Lys Met Asn Ala Ala Lys Asp Lys Trp Glu Ala Glu Lys Ile His Ile
            100                 105                 110

Gly Phe Arg Gln Ala Tyr Lys Pro Pro Ile Met Pro Val Asn Tyr Phe
        115                 120                 125

Leu Asp Gly Glu Arg Gln Leu Gly Thr Arg Leu Met Glu Leu Arg Asn
    130                 135                 140

Leu Asn Tyr Tyr Asp Thr Pro Leu Glu Glu Leu Arg Lys Gln Arg Gly
145                 150                 155                 160

Val Arg Val Val His Leu Gln Ser Pro His
                165                 170

<210> SEQ ID NO 31
<211> LENGTH: 312
<212> TYPE: DNA
<213> ORGANISM: Methylococcus capsulatus

<400> SEQUENCE: 31

| | |
|---|---:|
| atggtcgaat cggcatttca gccattttcg ggcgacgcag acgaatggtt cgaggaacca | 60 |
| cggccccagg ccggtttctt ccccttccgcg gactggcatc tgctcaaacg ggacgagacc | 120 |
| tacgcagcct atgccaagga tctcgatttc atgtggcggt gggtcatcgt ccgggaagaa | 180 |

```
aggatcgtcc aggagggttg ctcgatcagc ctggagtcgt cgatccgcgc cgtgacgcac      240
gtactgaatt attttggtat gaccgaacaa cgcgccccgg cagaggaccg gaccggcgga      300
gttcaacatt ga                                                          312
```

```
<210> SEQ ID NO 32
<211> LENGTH: 103
<212> TYPE: PRT
<213> ORGANISM: Methylococcus capsulatus

<400> SEQUENCE: 32
```

```
Met Val Glu Ser Ala Phe Gln Pro Phe Ser Gly Asp Ala Asp Glu Trp
1               5                   10                  15

Phe Glu Glu Pro Arg Pro Gln Ala Gly Phe Phe Pro Ser Ala Asp Trp
            20                  25                  30

His Leu Leu Lys Arg Asp Glu Thr Tyr Ala Ala Tyr Ala Lys Asp Leu
        35                  40                  45

Asp Phe Met Trp Arg Trp Val Ile Val Arg Glu Arg Ile Val Gln
    50                  55                  60

Glu Gly Cys Ser Ile Ser Leu Glu Ser Ser Ile Arg Ala Val Thr His
65                  70                  75                  80

Val Leu Asn Tyr Phe Gly Met Thr Glu Gln Arg Ala Pro Ala Glu Asp
                85                  90                  95

Arg Thr Gly Gly Val Gln His
            100
```

```
<210> SEQ ID NO 33
<211> LENGTH: 1047
<212> TYPE: DNA
<213> ORGANISM: Methylococcus capsulatus

<400> SEQUENCE: 33
```

```
atgcagcgag ttcacactat cacggcggtg acggaggatg cgaatcgct ccgcttcgaa       60 tgccgttcgg acgaggacgt catcaccgcc gccctgcgcc agaacatctt tctgatgtcg      120
tcctgccggg agggcggctg tgcgacctgc aaggccttgt gcagcgaagg ggactacgac      180
ctcaagggct gcagcgttca ggcgctgccg ccggaagagg aggaggaagg gttggtgttg      240
ttgtgccgga cctacccgaa gaccgacctg gaaatcgaac tgccctatac ccattgccgc      300
atcagttttg gtgaggtcgg cagtttcgag gcggaggtcg tcggcctcaa ctgggtttcg      360
agcaacaccg tccagtttct tttgcagaag cggcccgacg agtgcggcaa ccgtggcgtg      420
aaattcgaac ccggtcagtt catggacctg accatccccg gcaccgatgt ctcccgctcc      480
tactcgccgg cgaaccttcc taatcccgaa ggccgcctgg agttcctgat ccgcgtgtta      540
ccggagggac ggttttcgga ctacctgcgc aatgacgcgc gtgtcggaca ggtcctctcg      600
gtcaaagggc cactgggcgt gttcggtctc aaggagcggg gcatggcgcc cgctatttc      660 gtggccggcg gcaccgggtt ggcgccgtg gtctcgatgg tgcggcagat gcaggagtgg      720
accgcgccga acgagacccg catctatttc ggtgtgaaca ccgagccgga attgttctac      780
atcgacgagc tcaaatccct ggaacgatcg atgcgcaatc tcaccgtgaa ggcctgtgtc      840
tggcacccga gcggggactg ggaaggcgag cagggctcgc ccatcgatgc gttgcgggaa      900
gacctggagt cctccgacgc caaccccgga catttatttgt gcggtccgcc gggcatgatc      960
gatgccgcct gcgagctggt acgcagccgc ggtatccccg cgaacaggt cttcttcgaa      1020 aaattcctgc cgtccggggc ggcctga                                         1047
```

<210> SEQ ID NO 34
<211> LENGTH: 348
<212> TYPE: PRT
<213> ORGANISM: Methylococcus capsulatus

<400> SEQUENCE: 34

| | | | | | | | | | | | | | | |
|---|---|---|---|---|---|---|---|---|---|---|---|---|---|---|
| Met | Gln | Arg | Val | His | Thr | Ile | Thr | Ala | Val | Thr | Glu | Asp | Gly | Glu | Ser |
| 1 | | | | 5 | | | | | 10 | | | | | 15 | |
| Leu | Arg | Phe | Glu | Cys | Arg | Ser | Asp | Glu | Asp | Val | Ile | Thr | Ala | Ala | Leu |
| | | | 20 | | | | | 25 | | | | | 30 | | |
| Arg | Gln | Asn | Ile | Phe | Leu | Met | Ser | Ser | Cys | Arg | Glu | Gly | Gly | Cys | Ala |
| | | | 35 | | | | 40 | | | | | 45 | | | |
| Thr | Cys | Lys | Ala | Leu | Cys | Ser | Glu | Gly | Asp | Tyr | Asp | Leu | Lys | Gly | Cys |
| | 50 | | | | | 55 | | | | | 60 | | | | |
| Ser | Val | Gln | Ala | Leu | Pro | Pro | Glu | Glu | Glu | Glu | Gly | Leu | Val | Leu |
| 65 | | | | | 70 | | | | | 75 | | | | | 80 |
| Leu | Cys | Arg | Thr | Tyr | Pro | Lys | Thr | Asp | Leu | Glu | Ile | Glu | Leu | Pro | Tyr |
| | | | | 85 | | | | | 90 | | | | | 95 | |
| Thr | His | Cys | Arg | Ile | Ser | Phe | Gly | Glu | Val | Gly | Ser | Phe | Glu | Ala | Glu |
| | | | 100 | | | | | 105 | | | | | 110 | | |
| Val | Val | Gly | Leu | Asn | Trp | Val | Ser | Ser | Asn | Thr | Val | Gln | Phe | Leu | Leu |
| | | | 115 | | | | | 120 | | | | | 125 | | |
| Gln | Lys | Arg | Pro | Asp | Glu | Cys | Gly | Asn | Arg | Gly | Val | Lys | Phe | Glu | Pro |
| 130 | | | | | 135 | | | | | 140 | | | | | |
| Gly | Gln | Phe | Met | Asp | Leu | Thr | Ile | Pro | Gly | Thr | Asp | Val | Ser | Arg | Ser |
| 145 | | | | | 150 | | | | | 155 | | | | | 160 |
| Tyr | Ser | Pro | Ala | Asn | Leu | Pro | Asn | Pro | Glu | Gly | Arg | Leu | Glu | Phe | Leu |
| | | | | 165 | | | | | 170 | | | | | 175 | |
| Ile | Arg | Val | Leu | Pro | Glu | Gly | Arg | Phe | Ser | Asp | Tyr | Leu | Arg | Asn | Asp |
| | | | 180 | | | | | 185 | | | | | 190 | | |
| Ala | Arg | Val | Gly | Gln | Val | Leu | Ser | Val | Lys | Gly | Pro | Leu | Gly | Val | Phe |
| | | | 195 | | | | | 200 | | | | | 205 | | |
| Gly | Leu | Lys | Glu | Arg | Gly | Met | Ala | Pro | Arg | Tyr | Phe | Val | Ala | Gly | Gly |
| | 210 | | | | | 215 | | | | | 220 | | | | |
| Thr | Gly | Leu | Ala | Pro | Val | Val | Ser | Met | Val | Arg | Gln | Met | Gln | Glu | Trp |
| 225 | | | | | 230 | | | | | 235 | | | | | 240 |
| Thr | Ala | Pro | Asn | Glu | Thr | Arg | Ile | Tyr | Phe | Gly | Val | Asn | Thr | Glu | Pro |
| | | | | 245 | | | | | 250 | | | | | 255 | |
| Glu | Leu | Phe | Tyr | Ile | Asp | Glu | Leu | Lys | Ser | Leu | Glu | Arg | Ser | Met | Arg |
| | | | 260 | | | | | 265 | | | | | 270 | | |
| Asn | Leu | Thr | Val | Lys | Ala | Cys | Val | Trp | His | Pro | Ser | Gly | Asp | Trp | Glu |
| | | | 275 | | | | | 280 | | | | | 285 | | |
| Gly | Glu | Gln | Gly | Ser | Pro | Ile | Asp | Ala | Leu | Arg | Glu | Asp | Leu | Glu | Ser |
| | 290 | | | | | 295 | | | | | 300 | | | | |
| Ser | Asp | Ala | Asn | Pro | Asp | Ile | Tyr | Leu | Cys | Gly | Pro | Pro | Gly | Met | Ile |
| 305 | | | | | 310 | | | | | 315 | | | | | 320 |
| Asp | Ala | Ala | Cys | Glu | Leu | Val | Arg | Ser | Arg | Gly | Ile | Pro | Gly | Glu | Gln |
| | | | | 325 | | | | | 330 | | | | | 335 | |
| Val | Phe | Phe | Glu | Lys | Phe | Leu | Pro | Ser | Gly | Ala | Ala |
| | | | 340 | | | | | 345 | | | |

<210> SEQ ID NO 35
<211> LENGTH: 1806
<212> TYPE: DNA

<213> ORGANISM: Methylococcus capsulatus

<400> SEQUENCE: 35

```
atgcaaattt gcaaactggc aagtggctgc ggcgggtcga tgctggcgat ggccgccgtg      60
ctagccgcgc aatccacgca cgccaattcg gagctggacc ggctgtcgaa ggacgaccgg     120
aactgggtca tgcagaccaa ggactacagc gccacccact tcagccggct gacggaaatc     180
aatagccaca cgtcaagaa cctgaaggtg gcctggaccc tgtccaccgg cacgttgcat      240
ggccacgaag gtgcgccgtt ggtggtggac ggcatcatgt acatccacac gccgttcccc     300
aacaacgtct atgcagtcga cctgaacgac acccgcaaga tgctgtggca gtacaagccc     360
aagcagaatc cggcggcccg cgcggtggct tgctgcgacg tggtcaaccg cggtctggcc     420
tacgtgccgg ccggcgagca cggtccggcg aagatcttcc tcaaccagct tgacggccac     480
atcgtcgcac tcaacgccaa gaccggcgaa gagatatgga gatggaaaaa ttccgacatc     540
gccatgggct ccacccctcac cggcgcgcct ttcgtggtga aggacaaggt actggtaggt     600
tcggccgggg ccgagctggg cgtgcgtggc tacgtcacgg cctataacat caaggacggc     660
aagcaggagt ggcgggccta tgccaccggt cccgacgaag acttgttgct ggacaaggac     720
ttcaacaagg acaacccgca ttacggtcag ttcggcctgg ggctctcaac ctgggagggt     780
gatgcctgga gatcggcgg cggcaccaat tggggctggt atgcctatga tcccaagttg     840
gacatgatct actacggttc cggcaatccg gcacccttgga acgagaccat gcggccggc      900
gacaacaaat ggaccatgac catctgggc gcgacgccg acaccggccg gccaagttc        960
ggctaccaga gacgccgca cgacgagtgg gattacgccg tgtcaacta catgggtctg      1020
tccgaacagg aagtggacgg caagctgacg ccgctgctga cccatcccga ccgcaacggt    1080
ctggtgtata cgctgaaccg ggaaaccggc gccctggtca atgccttcaa gatcgatgac    1140
accgtcaact gggtgaaaaa ggtcgatctg aagaccggcc tgccgatccg cgatccggag    1200
tacagcaccc gcatggacca caatgccaaa ggcatctgtc cctcggccat gggctatcac    1260
aaccagggca tcgagtccta cgatccggac aagaagctgt tcttcatggg cgtgaaccac    1320
atctgcatgg actgggagcc gttcatgctg ccctaccgcg ccggccagtt ctttgtgggg    1380
gcgaccctca acatgtatcc gggacccaag gggatgctgg gtcaggtcaa ggcgatgaac    1440
gcggtcaccg gcaagatgga atgggaagtg ccggagaagt ttgcggtctg ggtggcacc     1500
ttggcgaccg ccggcgacct cgtgttctac ggtaccctcg acggcttcat caaggcccgc    1560
gacacccgta ccggcgagct gaagtggcag ttccagttgc cctccggcgt gatcggccat    1620
cccatcacct atcagcacaa cggcaagcaa tacattgcca tctactccgg cgtcggcggc    1680
tggccaggag tagggctggt attcgacctg aaggacccga ccgcaggtct gggagctgtg    1740
ggtgcgttca gggaactggc gcattacacc cagatgggtg gatcggtgtt cgtgttctcg    1800
ctttga                                                               1806
```

<210> SEQ ID NO 36
<211> LENGTH: 601
<212> TYPE: PRT
<213> ORGANISM: Methylococcus capsulatus

<400> SEQUENCE: 36

```
Met Gln Ile Cys Lys Leu Ala Ser Gly Cys Gly Gly Ser Met Leu Ala
1               5                   10                  15
Met Ala Ala Val Leu Ala Ala Gln Ser Thr His Ala Asn Ser Glu Leu
            20                  25                  30
```

```
Asp Arg Leu Ser Lys Asp Asp Arg Asn Trp Val Met Gln Thr Lys Asp
         35                  40                  45

Tyr Ser Ala Thr His Phe Ser Arg Leu Thr Glu Ile Asn Ser His Asn
 50                  55                  60

Val Lys Asn Leu Lys Val Ala Trp Thr Leu Ser Thr Gly Thr Leu His
 65              70                  75                      80

Gly His Glu Gly Ala Pro Leu Val Val Asp Gly Ile Met Tyr Ile His
                 85                  90                  95

Thr Pro Phe Pro Asn Asn Val Tyr Ala Val Asp Leu Asn Asp Thr Arg
             100                 105                 110

Lys Met Leu Trp Gln Tyr Lys Pro Lys Gln Asn Pro Ala Ala Arg Ala
             115                 120                 125

Val Ala Cys Cys Asp Val Val Asn Arg Gly Leu Ala Tyr Val Pro Ala
             130                 135                 140

Gly Glu His Gly Pro Ala Lys Ile Phe Leu Asn Gln Leu Asp Gly His
145                 150                 155                 160

Ile Val Ala Leu Asn Ala Lys Thr Gly Glu Glu Ile Trp Lys Met Glu
                 165                 170                 175

Asn Ser Asp Ile Ala Met Gly Ser Thr Leu Thr Gly Ala Pro Phe Val
                 180                 185                 190

Val Lys Asp Lys Val Leu Val Gly Ser Ala Gly Ala Glu Leu Gly Val
             195                 200                 205

Arg Gly Tyr Val Thr Ala Tyr Asn Ile Lys Asp Gly Lys Gln Glu Trp
             210                 215                 220

Arg Ala Tyr Ala Thr Gly Pro Asp Glu Asp Leu Leu Leu Asp Lys Asp
225                 230                 235                 240

Phe Asn Lys Asp Asn Pro His Tyr Gly Gln Phe Gly Leu Gly Leu Ser
                 245                 250                 255

Thr Trp Glu Gly Asp Ala Trp Lys Ile Gly Gly Gly Thr Asn Trp Gly
             260                 265                 270

Trp Tyr Ala Tyr Asp Pro Lys Leu Asp Met Ile Tyr Tyr Gly Ser Gly
             275                 280                 285

Asn Pro Ala Pro Trp Asn Glu Thr Met Arg Pro Gly Asp Asn Lys Trp
             290                 295                 300

Thr Met Thr Ile Trp Gly Arg Asp Ala Asp Thr Gly Arg Ala Lys Phe
305                 310                 315                 320

Gly Tyr Gln Lys Thr Pro His Asp Glu Trp Asp Tyr Ala Gly Val Asn
                 325                 330                 335

Tyr Met Gly Leu Ser Glu Gln Glu Val Asp Gly Lys Leu Thr Pro Leu
                 340                 345                 350

Leu Thr His Pro Asp Arg Asn Gly Leu Val Tyr Thr Leu Asn Arg Glu
                 355                 360                 365

Thr Gly Ala Leu Val Asn Ala Phe Lys Ile Asp Asp Thr Val Asn Trp
         370                 375                 380

Val Lys Lys Val Asp Leu Lys Thr Gly Leu Pro Ile Arg Asp Pro Glu
385                 390                 395                 400

Tyr Ser Thr Arg Met Asp His Asn Ala Lys Gly Ile Cys Pro Ser Ala
                 405                 410                 415

Met Gly Tyr His Asn Gln Gly Ile Glu Ser Tyr Asp Pro Asp Lys Lys
             420                 425                 430

Leu Phe Phe Met Gly Val Asn His Ile Cys Met Asp Trp Glu Pro Phe
             435                 440                 445
```

```
Met Leu Pro Tyr Arg Ala Gly Gln Phe Phe Val Gly Ala Thr Leu Asn
            450                 455                 460

Met Tyr Pro Gly Pro Lys Gly Met Leu Gly Gln Val Lys Ala Met Asn
465                 470                 475                 480

Ala Val Thr Gly Lys Met Glu Trp Glu Val Pro Glu Lys Phe Ala Val
                485                 490                 495

Trp Gly Gly Thr Leu Ala Thr Ala Gly Asp Leu Val Phe Tyr Gly Thr
                500                 505                 510

Leu Asp Gly Phe Ile Lys Ala Arg Asp Thr Arg Thr Gly Glu Leu Lys
                515                 520                 525

Trp Gln Phe Gln Leu Pro Ser Gly Val Ile Gly His Pro Ile Thr Tyr
                530                 535                 540

Gln His Asn Gly Lys Gln Tyr Ile Ala Ile Tyr Ser Gly Val Gly Gly
545                 550                 555                 560

Trp Pro Gly Val Gly Leu Val Phe Asp Leu Lys Asp Pro Thr Ala Gly
                565                 570                 575

Leu Gly Ala Val Gly Ala Phe Arg Glu Leu Ala His Tyr Thr Gln Met
                580                 585                 590

Gly Gly Ser Val Phe Val Phe Ser Leu
                595                 600

<210> SEQ ID NO 37
<211> LENGTH: 573
<212> TYPE: DNA
<213> ORGANISM: Methylococcus capsulatus

<400> SEQUENCE: 37
atgctcacca gcagtcctta ttaccggtcc ggctacgtat tcgtctaccg caaggacacg    60
ggactgagca tccaagattg gaacagcgcg gcactgaaga ccgtgaagcg gatcgcattc   120
atgccggata ccccggctga cgatgatc cgcaccatcg ccgctacaa cgacatgttc      180 aactacatgc actctctggt cggttttcaag tcgcggcgta accagtacgt gcgctacgac  240
ccggccaagc tggtggcgga agtcgccgac ggcaacgcgg aagtcgcggt gttgtggggg   300
ccggcggcgg cgcgctatgt cagaggggcg gggctggcca tgaccgtcat ccccgacgac   360
aaccggcggt ccgacggcga gaaagtgccc caccactatt cgacttccgt cggcgtgcgc   420
aagggcgagg aggccctgct caagcagatc gaccaggttc tggcccgctt cggcaaggaa   480
gtgaatgcgg tgctggaggc ggaaggcatt ccgctgttgc ccatggatga aaaaccggcc   540
aggacggctt cccatgatcg aaggaaaggc tag                                573

<210> SEQ ID NO 38
<211> LENGTH: 190
<212> TYPE: PRT
<213> ORGANISM: Methylococcus capsulatus

<400> SEQUENCE: 38

Met Leu Thr Ser Ser Pro Tyr Tyr Arg Ser Gly Tyr Val Phe Val Tyr
1               5                   10                  15

Arg Lys Asp Thr Gly Leu Ser Ile Gln Asp Trp Asn Ser Ala Ala Leu
                20                  25                  30

Lys Thr Val Lys Arg Ile Ala Phe Met Pro Asp Thr Pro Ala Glu Thr
            35                  40                  45

Met Ile Arg Thr Ile Gly Arg Tyr Asn Asp Met Phe Asn Tyr Met His
        50                  55                  60

Ser Leu Val Gly Phe Lys Ser Arg Arg Asn Gln Tyr Val Arg Tyr Asp
```

```
                65                  70                  75                  80
Pro Ala Lys Leu Val Ala Glu Val Ala Asp Gly Asn Ala Glu Val Ala
                        85                  90                  95

Val Leu Trp Gly Pro Ala Ala Ala Arg Tyr Val Arg Gly Ala Gly Leu
                    100                 105                 110

Ala Met Thr Val Ile Pro Asp Asp Asn Arg Arg Ser Asp Gly Glu Lys
                115                 120                 125

Val Pro His His Tyr Ser Thr Ser Val Gly Val Arg Lys Gly Glu Glu
            130                 135                 140

Ala Leu Leu Lys Gln Ile Asp Gln Val Leu Ala Arg Phe Gly Lys Glu
145                 150                 155                 160

Val Asn Ala Val Leu Glu Ala Glu Gly Ile Pro Leu Leu Pro Met Asp
                    165                 170                 175

Glu Lys Pro Ala Arg Thr Ala Ser His Asp Arg Arg Lys Gly
                180                 185                 190

<210> SEQ ID NO 39
<211> LENGTH: 480
<212> TYPE: DNA
<213> ORGANISM: Methylococcus capsulatus

<400> SEQUENCE: 39
atgaagctga agaatgcgag gttcgacgtg gctggcatgt gtgtcgccgg gttgttggcg      60
ctgcccgcgc aggccgacat taccctgcgg catgccgtca ccggcgagac gctggagttg     120
tcctacgcca aggcgggcgg cgacacgcaa gccgtcaagc agttcctgca gaccggcaag     180
aacccttaca acggcaacaa ggaggtagtg gaacagggac atagtctgta tctgtcagcc     240
tgttccggct gccacggcca tgaggccgaa ggcaagctcg gtccgggatt ggcggacgac     300
tattggacct atccccgcgc ggccaccgac gtcggtttgt tcgaaatcct gttcggcggc     360
gcgcagggca tgatggggcc gcagtacgtc aacctcaaca tgacgaaat gctcaagatc      420 atggcctgga tccgcagcct ttaccggggc gatccagcca aggccgaatg gctgaaatga     480

<210> SEQ ID NO 40
<211> LENGTH: 159
<212> TYPE: PRT
<213> ORGANISM: Methylococcus capsulatus

<400> SEQUENCE: 40

Met Lys Leu Lys Asn Ala Arg Phe Asp Val Ala Gly Met Cys Val Ala
1               5                   10                  15

Gly Leu Leu Ala Leu Pro Ala Gln Ala Asp Ile Thr Leu Arg His Ala
                20                  25                  30

Val Thr Gly Glu Thr Leu Glu Leu Ser Tyr Ala Lys Ala Gly Gly Asp
            35                  40                  45

Thr Gln Ala Val Lys Gln Phe Leu Gln Thr Gly Lys Asn Pro Tyr Asn
        50                  55                  60

Gly Asn Lys Glu Val Val Glu Gln Gly His Ser Leu Tyr Leu Ser Ala
65                  70                  75                  80

Cys Ser Gly Cys His Gly His Glu Ala Glu Gly Lys Leu Gly Pro Gly
                85                  90                  95

Leu Ala Asp Asp Tyr Trp Thr Tyr Pro Arg Ala Ala Thr Asp Val Gly
                100                 105                 110

Leu Phe Glu Ile Leu Phe Gly Gly Ala Gln Gly Met Met Gly Pro Gln
            115                 120                 125
```

Tyr Val Asn Leu Asn Asn Asp Glu Met Leu Lys Ile Met Ala Trp Ile
    130                 135                 140

Arg Ser Leu Tyr Arg Gly Asp Pro Ala Lys Ala Glu Trp Leu Lys
145                 150                 155

<210> SEQ ID NO 41
<211> LENGTH: 285
<212> TYPE: DNA
<213> ORGANISM: Methylococcus capsulatus

<400> SEQUENCE: 41
atgatgcaga aaacgagttt cgtcgcggcc gccatggccg tttcgttcgc ggcgggtgtc    60
caggcctatg acggtaccca ctgcaaggcg cccggaaact gctgggagcc caagcccggt   120
tatccggaca aggtcgccgg cagcaagtac gaccccaagc atgacccgaa cgagctcaac   180
aagcaggcgg agtcgatcaa ggcgatggaa gcccgcaacc agaagcgcgt ggagaactac   240
gccaagaccg gcaagttcgt ctacaaggtc gaagacatca aatga                   285

<210> SEQ ID NO 42
<211> LENGTH: 94
<212> TYPE: PRT
<213> ORGANISM: Methylococcus capsulatus

<400> SEQUENCE: 42

Met Met Gln Lys Thr Ser Phe Val Ala Ala Met Ala Val Ser Phe
1               5                   10                  15

Ala Ala Gly Val Gln Ala Tyr Asp Gly Thr His Cys Lys Ala Pro Gly
                20                  25                  30

Asn Cys Trp Glu Pro Lys Pro Gly Tyr Pro Asp Lys Val Ala Gly Ser
            35                  40                  45

Lys Tyr Asp Pro Lys His Asp Pro Asn Glu Leu Asn Lys Gln Ala Glu
        50                  55                  60

Ser Ile Lys Ala Met Glu Ala Arg Asn Gln Lys Arg Val Glu Asn Tyr
65                  70                  75                  80

Ala Lys Thr Gly Lys Phe Val Tyr Lys Val Glu Asp Ile Lys
                85                  90

<210> SEQ ID NO 43
<211> LENGTH: 1020
<212> TYPE: DNA
<213> ORGANISM: Methylococcus capsulatus

<400> SEQUENCE: 43
atgaatctag acaccccct tgccgacggc ctggaacgcg ccaaacgctt cgaacagggg    60
ctgcagcaag tcgtgctcgg caggagcgcg ccgatccgcc tgctgaccct ggccgtgttc   120
gcccgcggtc atgcgctgct cgaaggcggc gtcggcgtcg gaagaccac cttgctccgt    180 gcggtggcgc gcggcatcgg cggcgattac gagcggatcg agggcaccat cgacctgatg   240
ccgaacgatc tggtctatta cacctacctg gacgagcaag gtaggccggg cgtcgcgccg   300
gggcctttgc tcaagcacgg ggagcagctt tccattttt tcttcaacga tcaaccgc     360 gcccggcccc aggtgcattc cctcctgcta cgggtcatgg ccgagcgcag cgtgtcggct   420
ttcaaccgcg agtaccggtt ccgtacctg caggtgttcg ccgaccgcaa ccgggtggaa    480
aaggaggaga ctttcgaatt gcccgcggcg gcgcgcgacc gcttcatgct cgaaatcgcc   540
atcgagccgc cggccgatcc tgcgcatatc gaccaaatcc tgttcgaccc gcgtttctac   600
gatcccgacc ggctggtcgc gtccgcgccg gccgatacgc tctcgttccg tgaactcaac   660

```
ggcattgccg aagccctgca aggcggcatc cacgtcagcg cccgtctcag atcctatgtc    720
caggatctgt ggcgcgcgac ccggcggccg gaggatttcg gcatcgctct ccacgaggcg    780
gattccggcg acatgatcga ggccggttcc agtccccgcg gcatgagcta cttggtccgg    840
ctggcgcggg tgcaggcgtg gctcagtggc cgggaccggg tcgagccgga ggacgttcaa    900
tacgtgttcg ctccggcggt cggccaccgc atcttcctca agccggtcta cgaataccgc    960
cgcgccgagc tgatcccgga gctggtcggc aagctgatcc gccggatcgc ggcgccatga   1020
```

<210> SEQ ID NO 44
<211> LENGTH: 339
<212> TYPE: PRT
<213> ORGANISM: Methylococcus capsulatus

<400> SEQUENCE: 44

```
Met Asn Leu Asp Thr Pro Leu Ala Asp Gly Leu Glu Arg Ala Lys Arg
1               5                   10                  15

Phe Glu Gln Gly Leu Gln Gln Val Val Leu Gly Gln Glu Arg Pro Ile
            20                  25                  30

Arg Leu Leu Thr Leu Ala Val Phe Ala Arg Gly His Ala Leu Leu Glu
        35                  40                  45

Gly Gly Val Gly Val Gly Lys Thr Thr Leu Leu Arg Ala Val Ala Arg
    50                  55                  60

Gly Ile Gly Gly Asp Tyr Glu Arg Ile Glu Gly Thr Ile Asp Leu Met
65                  70                  75                  80

Pro Asn Asp Leu Val Tyr Tyr Thr Tyr Leu Asp Glu Gln Gly Arg Pro
                85                  90                  95

Gly Val Ala Pro Gly Pro Leu Leu Lys His Gly Glu Gln Leu Ser Ile
            100                 105                 110

Phe Phe Phe Asn Glu Ile Asn Arg Ala Arg Pro Gln Val His Ser Leu
        115                 120                 125

Leu Leu Arg Val Met Ala Glu Arg Ser Val Ser Ala Phe Asn Arg Glu
    130                 135                 140

Tyr Arg Phe Pro Tyr Leu Gln Val Phe Ala Asp Arg Asn Arg Val Glu
145                 150                 155                 160

Lys Glu Glu Thr Phe Glu Leu Pro Ala Ala Ala Arg Asp Arg Phe Met
                165                 170                 175

Leu Glu Ile Ala Ile Glu Pro Pro Ala Asp Pro Ala His Ile Asp Gln
            180                 185                 190

Ile Leu Phe Asp Pro Arg Phe Tyr Asp Pro Asp Arg Leu Val Ala Ser
        195                 200                 205

Ala Pro Ala Asp Thr Leu Ser Phe Arg Glu Leu Asn Gly Ile Ala Glu
    210                 215                 220

Ala Leu Gln Gly Gly Ile His Val Ser Ala Arg Leu Arg Ser Tyr Val
225                 230                 235                 240

Gln Asp Leu Trp Arg Ala Thr Arg Arg Pro Glu Asp Phe Gly Ile Ala
                245                 250                 255

Leu His Glu Ala Asp Ser Gly Asp Met Ile Glu Ala Gly Ser Ser Pro
            260                 265                 270

Arg Gly Met Ser Tyr Leu Val Arg Leu Ala Arg Val Gln Ala Trp Leu
        275                 280                 285

Ser Gly Arg Asp Arg Val Glu Pro Glu Asp Val Gln Tyr Val Phe Ala
    290                 295                 300

Pro Ala Val Gly His Arg Ile Phe Leu Lys Pro Val Tyr Glu Tyr Arg
```

```
            305                 310                 315                 320
Arg Ala Glu Leu Ile Pro Glu Leu Val Gly Lys Leu Ile Arg Arg Ile
                325                 330                 335

Ala Ala Pro

<210> SEQ ID NO 45
<211> LENGTH: 873
<212> TYPE: DNA
<213> ORGANISM: Methylococcus capsulatus

<400> SEQUENCE: 45
gtggtttggt ctctcctgcc ggtcgcggcc ttggtatcgg ttccacttca tggcgccact    60
tcgctctcgt tcgacacgcc ccgcgccttc ggctacgtca tcggtgatct catccgccac   120
gaggttcggg tcgaaaccga tgcggggcag ggaatagagg ctgcgtccct gcccaaggaa   180
ggctggatca accgctggct gctgctgcgg cgggtcgaag tccgccgcga gggcaggcac   240
cggatactga cgctggaata ccagactttc tacgccccgt tggaagtgaa gaacctcacg   300
attccgggct tcgagctgca actggccggt tcgggcgaac ggttggcggt cccggactgg   360
actttcacca ccgcgccgat ccgggagctg tcggtgctgc gcgccgaagg cccgtcgatg   420
cgtccggacg ccgcaccggc gccgctgccg actctcggcc ccgccgccgc gagcgtcggt   480
tccggcctcg cagccacggg cgcgctggcc tggtgggcct atctgagcgc ctggctgccg   540
ttcgtgtcgc gcggccgtca tttcgccgag gcccgccggg tgctgcggga tctgcgcggc   600
ctggagacag ccggggaggc attgcgcaga ggttttttcct gtctgcacca ggctttcaat   660
cggacttcgg gtgagccgct gttcatcgaa gggctggacg agttcttccg gagccatccg   720
gcctacgatc tcttgcggga cgagatccag gacttcttcc tggcctcgta tgaagtcttt   780
ttcggagagg gcgcaccggc gccgtcgttc gacctggcgc gcatggaggc gttggcccgt   840
tcgtgccagc ttgccgaaag gaggcggcca tga                              873

<210> SEQ ID NO 46
<211> LENGTH: 290
<212> TYPE: PRT
<213> ORGANISM: Methylococcus capsulatus

<400> SEQUENCE: 46

Val Val Trp Ser Leu Leu Pro Val Ala Ala Leu Val Ser Val Pro Leu
1               5                   10                  15

His Gly Ala Thr Ser Leu Ser Phe Asp Thr Pro Arg Ala Phe Gly Tyr
                20                  25                  30

Val Ile Gly Asp Leu Ile Arg His Glu Val Arg Val Glu Thr Asp Ala
            35                  40                  45

Gly Gln Gly Ile Glu Ala Ala Ser Leu Pro Lys Glu Gly Trp Ile Asn
        50                  55                  60

Arg Trp Leu Leu Leu Arg Arg Val Glu Val Arg Glu Gly Arg His
65                  70                  75                  80

Arg Ile Leu Thr Leu Glu Tyr Gln Thr Phe Tyr Ala Pro Leu Glu Val
                85                  90                  95

Lys Asn Leu Thr Ile Pro Gly Phe Glu Leu Gln Leu Ala Gly Ser Gly
            100                 105                 110

Glu Arg Leu Ala Val Pro Asp Trp Thr Phe Thr Thr Ala Pro Ile Arg
        115                 120                 125

Glu Leu Ser Val Leu Arg Ala Glu Gly Pro Ser Met Arg Pro Asp Ala
    130                 135                 140
```

-continued

```
Ala Pro Ala Pro Leu Pro Thr Leu Gly Pro Ala Ala Ser Val Gly
145                 150                 155                 160

Ser Gly Leu Ala Ala Thr Gly Ala Leu Ala Trp Trp Ala Tyr Leu Ser
                165                 170                 175

Ala Trp Leu Pro Phe Val Ser Arg Gly Arg His Phe Ala Glu Ala Arg
            180                 185                 190

Arg Val Leu Arg Asp Leu Arg Gly Leu Gly Asp Ser Arg Glu Ala Leu
        195                 200                 205

Arg Arg Gly Phe Ser Cys Leu His Gln Ala Phe Asn Arg Thr Ser Gly
    210                 215                 220

Glu Pro Leu Phe Ile Glu Gly Leu Asp Glu Phe Arg Ser His Pro
225                 230                 235                 240

Ala Tyr Asp Leu Leu Arg Asp Glu Ile Gln Asp Phe Leu Ala Ser
                245                 250                 255

Tyr Glu Val Phe Phe Gly Glu Gly Ala Pro Ala Pro Ser Phe Asp Leu
            260                 265                 270

Ala Arg Met Glu Ala Leu Ala Arg Ser Cys Gln Leu Ala Glu Arg Arg
        275                 280                 285

Arg Pro
    290
```

<210> SEQ ID NO 47
<211> LENGTH: 984
<212> TYPE: DNA
<213> ORGANISM: Methylococcus capsulatus

<400> SEQUENCE: 47

```
atgaccgatt gggcgctgga cacgccgtac ttgctgtggg cctgccgct ggcgctgctt      60
ccgttgtggc ggttgccgct gcgccctgcc ccgtgttcct ggcatgcatt gttgcccgcc    120
gatactgcgt cgcgggccgt cgacctgagt ctgcgcctcg ccggtgccgg cgccatcctg    180
gcgctgctgc tgggcagtgc cggtctgcat cggcgcgagt acaccgtcga acgcaccggc    240
tacggcgccc acatggtgct gctgctggac cgcagccgca gcatggatga cagcttcgca    300
gggcgtactc ccacgggcgg cgaggaatcc aagtccgccg cggcggagcg cctcctgagc    360
ggtttcgtct cgagcggacg caacgatctg gtcggggtcg ccgccttcag cacctccccg    420
ttgttcgtgc tgccgctgac cgacaacaag gctgcggtgc tggcggcggt ccacgccatg    480
aagctgccgg gtctggcgca gacgcatgtg agcaaggggc tggcgatggc gctttcgtat    540
ttcggcgacg attcgaccgc gggttcgcgt atcgtcctgc tggtgtccga cggtgccgcc    600
gaggtggacc cggacagcga gctgaagctg cgccgctggt tcaaggagaa gggcgtacgg    660
ctgtactgga tattcctgcg caccgcgggc agccacggta tcttcgaaac tccggacaac    720
ccggaggaag acaacgccca ggcgcggccc gagcgctatc tgcatctgtt tttcaacagt    780
ctgggcatcc cctaccgcgc ctacgaggcg aagacgccg acgccctcaa gcgcgccatc    840
gccgacgtcg accgcgagga gcagcggccg ctgcgctatg ccgagcgggt gccgcggcgg    900
gatctgcaag cctttttgtta tctggcggcg gcgctggctc tggcctggct ggtcgccgcg    960
aagggcatgg aggtggcgcg atga                                            984
```

<210> SEQ ID NO 48
<211> LENGTH: 327
<212> TYPE: PRT
<213> ORGANISM: Methylococcus capsulatus

<400> SEQUENCE: 48

Met Thr Asp Trp Ala Leu Asp Thr Pro Tyr Leu Leu Trp Gly Leu Pro
1               5                   10                  15

Leu Ala Leu Leu Pro Leu Trp Arg Leu Pro Leu Arg Pro Ala Pro Cys
            20                  25                  30

Ser Trp His Ala Leu Leu Pro Ala Asp Thr Ala Ser Arg Ala Val Asp
        35                  40                  45

Leu Ser Leu Arg Leu Ala Gly Ala Gly Ala Ile Leu Ala Leu Leu Leu
    50                  55                  60

Gly Ser Ala Gly Leu His Arg Arg Glu Tyr Thr Val Glu Arg Thr Gly
65                  70                  75                  80

Tyr Gly Ala His Met Val Leu Leu Leu Asp Arg Ser Arg Ser Met Asp
                85                  90                  95

Asp Ser Phe Ala Gly Arg Thr Pro Thr Gly Gly Glu Glu Ser Lys Ser
            100                 105                 110

Ala Ala Ala Glu Arg Leu Leu Ser Gly Phe Val Ser Ser Gly Arg Asn
        115                 120                 125

Asp Leu Val Gly Val Ala Ala Phe Ser Thr Ser Pro Leu Phe Val Leu
    130                 135                 140

Pro Leu Thr Asp Asn Lys Ala Ala Val Leu Ala Ala Val His Ala Met
145                 150                 155                 160

Lys Leu Pro Gly Leu Ala Gln Thr His Val Ser Lys Gly Leu Ala Met
                165                 170                 175

Ala Leu Ser Tyr Phe Gly Asp Asp Ser Thr Ala Gly Ser Arg Ile Val
            180                 185                 190

Leu Leu Val Ser Asp Gly Ala Ala Glu Val Asp Pro Asp Ser Glu Leu
        195                 200                 205

Lys Leu Arg Arg Trp Phe Lys Glu Lys Gly Val Arg Leu Tyr Trp Ile
    210                 215                 220

Phe Leu Arg Thr Ala Gly Ser His Gly Ile Phe Glu Thr Pro Asp Asn
225                 230                 235                 240

Pro Glu Glu Asp Asn Ala Gln Ala Arg Pro Glu Arg Tyr Leu His Leu
                245                 250                 255

Phe Phe Asn Ser Leu Gly Ile Pro Tyr Arg Ala Tyr Glu Ala Glu Asp
            260                 265                 270

Ala Asp Ala Leu Lys Arg Ala Ile Ala Asp Val Asp Arg Glu Glu Gln
        275                 280                 285

Arg Pro Leu Arg Tyr Ala Glu Arg Val Pro Arg Arg Asp Leu Gln Ala
    290                 295                 300

Phe Cys Tyr Leu Ala Ala Leu Ala Leu Ala Trp Leu Val Ala Ala
305                 310                 315                 320

Lys Gly Met Glu Val Ala Arg
            325

<210> SEQ ID NO 49
<211> LENGTH: 519
<212> TYPE: DNA
<213> ORGANISM: Methylococcus capsulatus

<400> SEQUENCE: 49
atgctggcct tgtcggcgtt gctggagctc aggcaatggc ggaaggccgc ggcggccaat    60
gccgatatcg ccgagctgct gggggggcac gacatcgccc cggaacggct ggcggcggca   120
tcgccccaag tcctgttggc gcgggccgtg tatttcgtgc ggcacgagcg ctacggcgac   180

```
gcgctggagc tgctgaacct gctggagacc cggggcgatg gcgccttccg cgccgacgtg      240
tattacaacc agggcaatct gcagcttgcc caggctctgg accgcgtcga aaaatcggaa      300
atggaccagg cccgggtctt cgccgaactg gccaaggaag cctaccggcg tgccttgtcg      360
ctggcacccg ccactgggga cgccaaatac aacctggaag tggccatgcg cctcatgccc      420
gaaatggacc gggtcagccc tgccgatgac gaggcgcccg cggctgaatc caaacggctg      480
tggacaggtt tgcccggact cccgcgaggc ctgccttga                             519
```

<210> SEQ ID NO 50
<211> LENGTH: 172
<212> TYPE: PRT
<213> ORGANISM: Methylococcus capsulatus

<400> SEQUENCE: 50

```
Met Leu Ala Leu Ser Ala Leu Leu Glu Leu Arg Gln Trp Arg Lys Ala
1               5                   10                  15

Ala Ala Ala Asn Ala Asp Ile Ala Glu Leu Leu Gly Gly His Asp Ile
            20                  25                  30

Ala Pro Glu Arg Leu Ala Ala Ala Ser Pro Gln Val Leu Leu Ala Arg
        35                  40                  45

Ala Val Tyr Phe Val Arg His Glu Arg Tyr Gly Asp Ala Leu Glu Leu
    50                  55                  60

Leu Asn Leu Leu Glu Thr Arg Gly Asp Gly Ala Phe Arg Ala Asp Val
65                  70                  75                  80

Tyr Tyr Asn Gln Gly Asn Leu Gln Leu Ala Gln Ala Leu Asp Arg Val
                85                  90                  95

Glu Lys Ser Glu Met Asp Gln Ala Arg Val Phe Ala Glu Leu Ala Lys
            100                 105                 110

Glu Ala Tyr Arg Arg Ala Leu Ser Leu Ala Pro Gly His Trp Asp Ala
        115                 120                 125

Lys Tyr Asn Leu Glu Val Ala Met Arg Leu Met Pro Glu Met Asp Arg
    130                 135                 140

Val Ser Pro Ala Asp Asp Glu Ala Pro Ala Ala Glu Ser Lys Arg Leu
145                 150                 155                 160

Trp Thr Gly Leu Pro Gly Leu Pro Arg Gly Leu Pro
                165                 170
```

<210> SEQ ID NO 51
<211> LENGTH: 972
<212> TYPE: DNA
<213> ORGANISM: Methylococcus capsulatus

<400> SEQUENCE: 51

```
ttgagcatct ggcggcagcg cgttgccgat ccggtttttg ccggcctgat tgtagccctc      60
cttctggcgg tagccgcctg tttcccgctc cggctggtgc tggagcggct ggtgttcagc      120
cacatcgtcg tcgtcgacat caccgcagc atgaacgtcg aggactaccg gcgaggcgcg       180
cgcgccgtgt cgcggctgga attcgtcagg cagagcctga tcggcgccgt ggccgacctg      240
ccctgcggct ccgctgtggg ggtgggcgtt tcaccgaac gcgagccggc gctactgttc        300
gagccgatcg aaacctgcgc cggctttttcc gccatcagcg ccgccatcga acagctcgac     360
tggcgcatgg cctgggctgc cgacagtctg atcgccgcag gtctgcacaa caccctggat     420
ttgctggggc gcggcgatgc ggacgtgatt ttcgtcaccg acggccatga ggcgccgcca      480
ctcaatcccc gctactgccc ggacttcagc gacctcagag gcaaggtccg ggggctgatc      540
```

-continued

```
gtcggagtgg gaggactgag cctctcgccc atccccaagt acgacgagtc ggggcggcgt    600
tcgggcgttt atggcgagga cgaagtcccg cagcgctcga gcttcggcct gtcggagctg    660
ccgcccgagc agatcgaggg ctaccacgcc cgcaacgctc ccttcggcag cgagagagcc    720
gggggcacgg aacatctgtc ccagctcaag gaaggatatt tgcgccagct cgccgaagcc    780
gccggcctgg gctaccaccg cctggaatcg cccgaaggac tgggccgcgc tctcacggca    840
ccggccttgg cgcggcgcca gcggatcgcc acagacgtcc gctggattcc cgccgccctg    900
gcgctcgccg tactgatggc ggtgtatctg cgggtgctgc tgccgcgtcc tggattttca    960
acctcaaact ga                                                        972
```

<210> SEQ ID NO 52
<211> LENGTH: 323
<212> TYPE: PRT
<213> ORGANISM: Methylococcus capsulatus

<400> SEQUENCE: 52

```
Leu Ser Ile Trp Arg Gln Arg Val Ala Asp Pro Val Phe Ala Gly Leu
1               5                   10                  15

Ile Val Ala Leu Leu Ala Val Ala Ala Cys Phe Pro Leu Arg Leu
            20                  25                  30

Val Leu Glu Arg Leu Val Phe Ser His Ile Val Val Asp Ile Thr
        35                  40                  45

Arg Ser Met Asn Val Glu Asp Tyr Arg Arg Gly Ala Arg Ala Val Ser
    50                  55                  60

Arg Leu Glu Phe Val Arg Gln Ser Leu Ile Gly Ala Val Ala Asp Leu
65                  70                  75                  80

Pro Cys Gly Ser Ala Val Gly Val Gly Val Phe Thr Glu Arg Glu Pro
                85                  90                  95

Ala Leu Leu Phe Glu Pro Ile Glu Thr Cys Ala Gly Phe Ser Ala Ile
            100                 105                 110

Ser Ala Ala Ile Glu Gln Leu Asp Trp Arg Met Ala Trp Ala Ala Asp
        115                 120                 125

Ser Leu Ile Ala Ala Gly Leu His Asn Thr Leu Asp Leu Leu Gly Arg
    130                 135                 140

Gly Asp Ala Asp Val Ile Phe Val Thr Asp Gly His Glu Ala Pro Pro
145                 150                 155                 160

Leu Asn Pro Arg Tyr Cys Pro Asp Phe Ser Asp Leu Arg Gly Lys Val
                165                 170                 175

Arg Gly Leu Ile Val Gly Val Gly Gly Leu Ser Leu Ser Pro Ile Pro
            180                 185                 190

Lys Tyr Asp Glu Ser Gly Arg Arg Ser Gly Val Tyr Gly Glu Asp Glu
        195                 200                 205

Val Pro Gln Arg Ser Ser Phe Gly Leu Ser Glu Leu Pro Pro Glu Gln
    210                 215                 220

Ile Glu Gly Tyr His Ala Arg Asn Ala Pro Phe Gly Ser Glu Arg Ala
225                 230                 235                 240

Gly Gly Thr Glu His Leu Ser Gln Leu Lys Glu Gly Tyr Leu Arg Gln
                245                 250                 255

Leu Ala Glu Ala Ala Gly Leu Gly Tyr His Arg Leu Glu Ser Pro Glu
            260                 265                 270

Gly Leu Gly Arg Ala Leu Thr Ala Pro Ala Leu Ala Arg Arg Gln Arg
        275                 280                 285

Ile Ala Thr Asp Val Arg Trp Ile Pro Ala Ala Leu Ala Leu Ala Val
```

```
          290                 295                 300
Leu Met Ala Val Tyr Leu Arg Val Leu Leu Pro Arg Pro Gly Phe Ser
305                 310                 315                 320

Thr Ser Asn
```

<210> SEQ ID NO 53
<211> LENGTH: 525
<212> TYPE: DNA
<213> ORGANISM: Methylococcus capsulatus

<400> SEQUENCE: 53

```
atgaaaccga tgctcatcct gaccgcgttg ctgttcgcct ccgtttcgtt ggcgcacgga     60
cccaccccc aaaaggtcgt cgagaccgtg gagatcgcgg ctcccgtgga ccgggtctgg    120
aacgccgtga aggatttcgg tgccatcgcg cagtggaatc ccgctctggc caagagcgaa    180
agcaccggcg gcaacaccac cggcgagaag cgcatcctcc attttcccaa cggcgagcag    240
ctcaccgagg aactcgatgc ctacgacccg gcagcccacg aatacaccta ccggctgggc    300
aaggacaacg tcaaggcgct gccggccagt tcctactccg ccgtgctcaa ggtcaaggcc    360
accgagacgg gcagccagat cgaatggaag agtcggctct atcgcggcga taccggaaac    420
ttcccgccgg acgagctgaa cgacgaggcc gccgttgcgg cgatgcagag gttttccgc    480
gccgggctgg acaatctcaa gaaaagtctt gggcccctcg aatga                    525
```

<210> SEQ ID NO 54
<211> LENGTH: 174
<212> TYPE: PRT
<213> ORGANISM: Methylococcus capsulatus

<400> SEQUENCE: 54

```
Met Lys Pro Met Leu Ile Leu Thr Ala Leu Leu Phe Ala Ser Val Ser
1               5                   10                  15

Leu Ala His Gly Pro Thr Pro Gln Lys Val Val Glu Thr Val Glu Ile
            20                  25                  30

Ala Ala Pro Val Asp Arg Val Trp Asn Ala Val Lys Asp Phe Gly Ala
        35                  40                  45

Ile Ala Gln Trp Asn Pro Ala Leu Ala Lys Ser Glu Ser Thr Gly Gly
    50                  55                  60

Asn Thr Thr Gly Glu Lys Arg Ile Leu His Phe Pro Asn Gly Glu Gln
65                  70                  75                  80

Leu Thr Glu Glu Leu Asp Ala Tyr Asp Pro Ala Ala His Glu Tyr Thr
                85                  90                  95

Tyr Arg Leu Gly Lys Asp Asn Val Lys Ala Leu Pro Ala Ser Ser Tyr
            100                 105                 110

Ser Ala Val Leu Lys Val Lys Ala Thr Glu Thr Gly Ser Gln Ile Glu
        115                 120                 125

Trp Lys Ser Arg Leu Tyr Arg Gly Asp Thr Gly Asn Phe Pro Pro Asp
    130                 135                 140

Glu Leu Asn Asp Glu Ala Ala Val Ala Ala Met Gln Arg Phe Phe Arg
145                 150                 155                 160

Ala Gly Leu Asp Asn Leu Lys Lys Ser Leu Gly Pro Leu Glu
                165                 170
```

<210> SEQ ID NO 55
<211> LENGTH: 1530
<212> TYPE: DNA
<213> ORGANISM: Methylococcus capsulatus

<400> SEQUENCE: 55

```
atgctgcaaa aatacataga gaagattctg cgcgcccgtg tctacgacgt tgcccaggag      60
accccgctgg acccggcgcc cggcctgtcg cggcggctgg acaacacggt gctgatcaag     120
cgcgaggacc tgcagccggt gttctcgttc aagctgcgcg gcgcctacaa caagatcgcc     180
tcgctcacac ccgaggcgcg cgcggccggc gtgatcgcgg cctccgccgg caaccacgcc     240
cagggcgtgg cactggcggc gcagcggctg ggcatccgcg ccgtgatcgt gatgccttgc     300
accaccccgc atatcaaggt cgatgcggtg cgcaaccgag gcggtgaggt cgtactgcat     360
ggcgacgcct atgacgaagc ctacgaacat gcgctggaac tggcccgcga ccagtgcctg     420
accttcgtcc accctacga cgatccggaa gtcatcgccg gcaaggcac catcggcatg       480
gaaatcctgc ccagcacca ggacgccatc acgccatct tcgtgcctgt gggcggcggc       540
ggattgatcg ccggcatcgc cgcctacgtc aagttcgtgc gcccggacat ccgcgtcatc     600
ggcgtggaac cagtggactc cgactgcctg caccgggcgc tgaaagccaa gcggcgggtg     660
atcctgaagc aggtgggcct gttcgccgac ggcgtcgcgg tgaagcaggt cggcaaggaa     720
ccgttccatc tcgcccacca gtgggtggac gaggtcgtga ccgtcgacac cgacgaaatc     780
tgcgccgcca tcaaggacat cttcgacgac acccgctcca tcgccgagcc ggcgggcgcg     840
ctgggcatcg ccgggctcaa gaaatacgtg gccgaaacag gaatcaagaa cgcgtgcctg     900
gtggcgatcg aaagcggcgc caacatcaac ttcgaccggc tgcgccacgt cgctgagcgc     960
gccgagatcg cgaaaagcg cgaactgctg ctggcagtga cgatcccga gcggcccggc      1020
agcttcctcg aattctgccg ggtgctgggc cgccgcaaca tcaccgaatt caactaccgc    1080
ttcttcgacg aaaaggccgc ccaggtgttc gtcggcctcc cggtggcgag cggcgcgatc    1140
gaccgcgaaa gcctggtccg cgaattcgaa cgccagggtt tcggcgtgct cgacctgacc    1200
ggcaacgaac tcgccatcga acacatccgc tacatggtcg gcggccacgc gccgaaactg    1260
ctggacgaac aggtctacag cttcgaattc cccgagcgac ccggcgcgct gctgcgcttc    1320
ctgtccatca tgggcgggcg ctggaacatc agcctgttcc attaccgcaa ccacggcgcc    1380
gccttcggcc gggtactgat gggcatccag gtgccgaaac cggaacgcaa ggccttccgg    1440
gaattcctcg aagccatcgg ctacgccttc aaggaggaaa cccaaaatcc cgcctaccgg    1500
ctgttcgcgg gggcagcga gcgggggtga                                       1530
```

<210> SEQ ID NO 56
<211> LENGTH: 509
<212> TYPE: PRT
<213> ORGANISM: Methylococcus capsulatus

<400> SEQUENCE: 56

```
Met Leu Gln Lys Tyr Ile Glu Lys Ile Leu Arg Ala Arg Val Tyr Asp
1               5                   10                  15

Val Ala Gln Glu Thr Pro Leu Asp Pro Ala Pro Gly Leu Ser Arg Arg
            20                  25                  30

Leu Asp Asn Thr Val Leu Ile Lys Arg Glu Asp Leu Gln Pro Val Phe
        35                  40                  45

Ser Phe Lys Leu Arg Gly Ala Tyr Asn Lys Ile Ala Ser Leu Thr Pro
    50                  55                  60

Glu Ala Arg Ala Ala Gly Val Ile Ala Ala Ser Ala Gly Asn His Ala
65                  70                  75                  80

Gln Gly Val Ala Leu Ala Ala Gln Arg Leu Gly Ile Arg Ala Val Ile
```

```
                     85                  90                  95
Val Met Pro Cys Thr Thr Pro His Ile Lys Val Asp Ala Val Arg Asn
                100                 105                 110

Arg Gly Gly Glu Val Val Leu His Gly Asp Ala Tyr Asp Glu Ala Tyr
                115                 120                 125

Glu His Ala Leu Glu Leu Ala Arg Asp Gln Cys Leu Thr Phe Val His
                130                 135                 140

Pro Tyr Asp Asp Pro Glu Val Ile Ala Gly Gln Gly Thr Ile Gly Met
145                 150                 155                 160

Glu Ile Leu Arg Gln His Gln Asp Ala Ile His Ala Ile Phe Val Pro
                165                 170                 175

Val Gly Gly Gly Gly Leu Ile Ala Gly Ile Ala Ala Tyr Val Lys Phe
                180                 185                 190

Val Arg Pro Asp Ile Arg Val Ile Gly Val Glu Pro Val Asp Ser Asp
                195                 200                 205

Cys Leu His Arg Ala Leu Lys Ala Lys Arg Arg Val Ile Leu Lys Gln
                210                 215                 220

Val Gly Leu Phe Ala Asp Gly Val Ala Val Lys Gln Val Gly Lys Glu
225                 230                 235                 240

Pro Phe His Leu Ala His Gln Trp Val Asp Glu Val Val Thr Val Asp
                245                 250                 255

Thr Asp Glu Ile Cys Ala Ala Ile Lys Asp Ile Phe Asp Asp Thr Arg
                260                 265                 270

Ser Ile Ala Glu Pro Ala Gly Ala Leu Gly Ile Ala Gly Leu Lys Lys
                275                 280                 285

Tyr Val Ala Glu Thr Gly Ile Lys Asn Ala Cys Leu Val Ala Ile Glu
                290                 295                 300

Ser Gly Ala Asn Ile Asn Phe Asp Arg Leu Arg His Val Ala Glu Arg
305                 310                 315                 320

Ala Glu Ile Gly Glu Lys Arg Glu Leu Leu Ala Val Thr Ile Pro
                325                 330                 335

Glu Arg Pro Gly Ser Phe Leu Glu Phe Cys Arg Val Leu Gly Arg Arg
                340                 345                 350

Asn Ile Thr Glu Phe Asn Tyr Arg Phe Phe Asp Glu Lys Ala Ala Gln
                355                 360                 365

Val Phe Val Gly Leu Pro Val Ala Ser Gly Ala Ile Asp Arg Glu Ser
                370                 375                 380

Leu Val Arg Glu Phe Glu Arg Gln Gly Phe Gly Val Leu Asp Leu Thr
385                 390                 395                 400

Gly Asn Glu Leu Ala Ile Glu His Ile Arg Tyr Met Val Gly Gly His
                405                 410                 415

Ala Pro Lys Leu Leu Asp Glu Gln Val Tyr Ser Phe Glu Phe Pro Glu
                420                 425                 430

Arg Pro Gly Ala Leu Leu Arg Phe Leu Ser Ile Met Gly Gly Arg Trp
                435                 440                 445

Asn Ile Ser Leu Phe His Tyr Arg Asn His Gly Ala Ala Phe Gly Arg
                450                 455                 460

Val Leu Met Gly Ile Gln Val Pro Lys Pro Glu Arg Lys Ala Phe Arg
465                 470                 475                 480

Glu Phe Leu Glu Ala Ile Gly Tyr Ala Phe Lys Glu Glu Thr Gln Asn
                485                 490                 495

Pro Ala Tyr Arg Leu Phe Ala Gly Gly Ser Glu Arg Gly
                500                 505
```

<210> SEQ ID NO 57
<211> LENGTH: 1545
<212> TYPE: DNA
<213> ORGANISM: Methylococcus capsulatus

<400> SEQUENCE: 57

```
atgcacgaca gactgatcat tttcgacacg accttgcgcg acggagagca gagccccggc      60
gcgtccatga cccgcgatga aaaggtccgc atcgcccggg cgctggagcg tctgaaggtc     120
gacgtcatcg aggcgggctt tcccgccgcc agccccggcg atttcgaggc cgtccaggcc     180
gtggcccgga ccatcaagga cagcagggtc tgcggcctgg cccgcgccct cgaccgcgac     240
atcgaccgcg ccggcgaagc cctcaaggac gcccagcgcg cccgcatcca caccttcatc     300
gccacctcgc ccatccacat gcggcacaag ctgcagatgt cgcccgacca ggtggtggaa     360
tacgcggtca aggccgtcaa gcgggcccgc cagtacaccg acgacgtgga attctcgccc     420
gaggacgccg acgctccga ggaggatttc ctctgccgca tcctggaagc cgtgatcgat     480
gcggggggcga ccacgctgaa catccccgac accgtcggct acgccttccc ggaacagttc     540
gggcacatga tcggccggct gatcgagcgg attccgaact ccgacaaggc cgtgttctcg     600
gttcactgcc acaacgacct gggactggcg gtcgccaatt cgctggccgc cgtgctgcac     660
ggcgcgcgcc aggtggaatg caccatcaac gggctgggcg agcgggccgg caacgccgcg     720
ctggaagaga tcgtcatggc ggtgcgcacc cgtaaagaca tcttcccctg ccacaccgac     780
atcgagacac gggaaatcgt ggcctgctcc aaactggtct ccagcatcac cggtttcccg     840
atccagccca caaggccat cgtcggcgcc aacgccttcg cccacgagtc gggcatccac     900
caggacggtg tgctcaagag ccgggaaacc tacgagatca tgagcgccga ggacgtgggg     960
tggagcacca accgcatggt gctgggcaaa cattccggcc gcaacgcgtt ccgtacccgg    1020
atgcaggaac tcggcatcga gttcgcctcg gaagaggaac tgaactcggt gttccagcgc    1080
ttcaaggtgc tggccgacaa gaagcacgag atcttcgacg aggacctcca ggccctcatc    1140
accgaagccg cgcagaaagc cgaagacgaa cgggtcaagc tggtcgcgct gcgggtctgc    1200
tcggaaacgg gcgagattcc ccacgcccag gtcaccatca aggtggacaa cgaggaacgc    1260
accggcacat cgagcggcgg cggcgccgtg gacgccagcc tcaaggccat cgaatcgctg    1320
ctgcacacga caccgcgct gacgctgtac tcggtcaaca acatcaccag cggcaccgac    1380
gcccagggcg aggtcaccgt gcggctcgag aaaggcgggc gcatcgtcaa cggccagggc    1440
gccgataccg acatcgtgat cgcctcggcc aaggcctacg tcaacgccgt gaacaagctg    1500
ctggcgccca tccagcgcac ccacccgcaa gtcgggatg tgtga                    1545
```

<210> SEQ ID NO 58
<211> LENGTH: 514
<212> TYPE: PRT
<213> ORGANISM: Methylococcus capsulatus

<400> SEQUENCE: 58

```
Met His Asp Arg Leu Ile Ile Phe Asp Thr Thr Leu Arg Asp Gly Glu
1               5                   10                  15

Gln Ser Pro Gly Ala Ser Met Thr Arg Asp Glu Lys Val Arg Ile Ala
            20                  25                  30

Arg Ala Leu Glu Arg Leu Lys Val Asp Val Ile Glu Ala Gly Phe Pro
        35                  40                  45

Ala Ala Ser Pro Gly Asp Phe Glu Ala Val Gln Ala Val Ala Arg Thr
```

-continued

```
                50                  55                  60
Ile Lys Asp Ser Arg Val Cys Gly Leu Ala Arg Ala Leu Asp Arg Asp
 65                  70                  75                  80

Ile Asp Arg Ala Gly Glu Ala Leu Lys Asp Ala Gln Arg Ala Arg Ile
                 85                  90                  95

His Thr Phe Ile Ala Thr Ser Pro Ile His Met Arg His Lys Leu Gln
                100                 105                 110

Met Ser Pro Asp Gln Val Val Glu Tyr Ala Val Lys Ala Val Lys Arg
                115                 120                 125

Ala Arg Gln Tyr Thr Asp Asp Val Glu Phe Ser Pro Glu Asp Ala Gly
                130                 135                 140

Arg Ser Glu Glu Asp Phe Leu Cys Arg Ile Leu Glu Ala Val Ile Asp
145                 150                 155                 160

Ala Gly Ala Thr Thr Leu Asn Ile Pro Asp Thr Val Gly Tyr Ala Phe
                165                 170                 175

Pro Glu Gln Phe Gly His Met Ile Gly Arg Leu Ile Glu Arg Ile Pro
                180                 185                 190

Asn Ser Asp Lys Ala Val Phe Ser Val His Cys His Asn Asp Leu Gly
                195                 200                 205

Leu Ala Val Ala Asn Ser Leu Ala Ala Val His Gly Ala Arg Gln
210                 215                 220

Val Glu Cys Thr Ile Asn Gly Leu Gly Glu Arg Ala Gly Asn Ala Ala
225                 230                 235                 240

Leu Glu Glu Ile Val Met Ala Val Arg Thr Arg Lys Asp Ile Phe Pro
                245                 250                 255

Cys His Thr Asp Ile Glu Thr Arg Glu Ile Val Ala Cys Ser Lys Leu
                260                 265                 270

Val Ser Ser Ile Thr Gly Phe Pro Ile Gln Pro Asn Lys Ala Ile Val
                275                 280                 285

Gly Ala Asn Ala Phe Ala His Glu Ser Gly Ile His Gln Asp Gly Val
290                 295                 300

Leu Lys Ser Arg Glu Thr Tyr Glu Ile Met Ser Ala Glu Asp Val Gly
305                 310                 315                 320

Trp Ser Thr Asn Arg Met Val Leu Gly Lys His Ser Gly Arg Asn Ala
                325                 330                 335

Phe Arg Thr Arg Met Gln Glu Leu Gly Ile Glu Phe Ala Ser Glu Glu
                340                 345                 350

Glu Leu Asn Ser Val Phe Gln Arg Phe Lys Val Leu Ala Asp Lys Lys
                355                 360                 365

His Glu Ile Phe Asp Glu Asp Leu Gln Ala Leu Ile Thr Glu Ala Gly
                370                 375                 380

Ala Glu Ala Glu Asp Glu Arg Val Lys Leu Val Ala Leu Arg Val Cys
385                 390                 395                 400

Ser Glu Thr Gly Glu Ile Pro His Ala Gln Val Thr Ile Lys Val Asp
                405                 410                 415

Asn Glu Glu Arg Thr Gly Thr Ser Ser Gly Gly Ala Val Asp Ala
                420                 425                 430

Ser Leu Lys Ala Ile Glu Ser Leu Leu His Thr Asp Thr Ala Leu Thr
                435                 440                 445

Leu Tyr Ser Val Asn Asn Ile Thr Ser Gly Thr Asp Ala Gln Gly Glu
                450                 455                 460

Val Thr Val Arg Leu Glu Lys Gly Gly Arg Ile Val Asn Gly Gln Gly
465                 470                 475                 480
```

Ala Asp Thr Asp Ile Val Ile Ala Ser Ala Lys Ala Tyr Val Asn Ala
            485                 490                 495

Val Asn Lys Leu Leu Ala Pro Ile Gln Arg Thr His Pro Gln Val Gly
        500                 505                 510

Asp Val

<210> SEQ ID NO 59
<211> LENGTH: 1413
<212> TYPE: DNA
<213> ORGANISM: Methylococcus capsulatus

<400> SEQUENCE: 59

| | | | | |
|---|---|---|---|---|
| atgagcggaa | aaacccttta | cgacaagctg | tgggacgacc acgtcgtgca tgtcgatgcg | 60 |
| gacggatcgt | gcctgatcta | catcgatcgt | catctaatcc acgaggtgac ctcgcctcag | 120 |
| gcattcgaag | gctgcggat | ggcggggcgt | gtaccctggc gggtggatgc caatcttgcg | 180 |
| gtggccgacc | acaacgtccc | caccgccgac | cgcgacaggg gtatcgccga tccggtgtcg | 240 |
| cgcctgcagg | tggaaaccct | ggacaagaac | tgcgccgatt tcggcatcac cgaattcgcg | 300 |
| atggacgacg | tgcgccaggg | tatcgtgcat | gtgatcgggc cgagcagggg cgcgacccctg | 360 |
| ccgggcatga | ccatcgtttg | cggcgattcg | catacttcga ctcacggtgc tttcggggcg | 420 |
| ctcgccttcg | ggatcggcac | ttccgaggtc | gagcacgtac tggccacgca atgcctggtg | 480 |
| cagcgcaagg | cgaagaacat | gctggtccgc | gtccagggca gctggcgcc gggcgtgacg | 540 |
| gcgaaagatc | tggtactggc | ggtcatcggc | cgtatcggaa ccgccggcgg caccggctac | 600 |
| accatcgaat | cgctggcga | agccattcgc | ggcctgtcga tggaaggccg gatgacggtc | 660 |
| tgcaacatgg | cgatcgaggc | gggcgcacgt | gccggcctgg tggcggtgga cgaagtcacg | 720 |
| ctcgactatc | tcgagggccg | cccgttcgct | ccggcggggcg cgttgtggga gcgggcggtc | 780 |
| gaggcatgga | agacctgca | cagcgatccg | gatgcggtat tcgacaaggt cgtcgagatc | 840 |
| gatgccgcca | gcatcaagcc | gcaggtgacc | tggggaactt cgccggaaca ggtcgtgccg | 900 |
| gtggatgccg | aggtgcccga | cccggccacg | gaagccgatc ccgtgcggcg ggaaagcatg | 960 |
| gagcgggcgc | tgcagtacat | ggatctcctg | ccgggcacgc caatcggcgc gatccgggtc | 1020 |
| gatcgggtgt | catcggctc | ctgcaccaat | gccaggatcg aggatctgcg cgccgcggcg | 1080 |
| gaagtcgtcc | gggggcacaa | gcgcgctgcc | agcgtgaagc aggcactggt ggtgcccggc | 1140 |
| tcgggtttgg | tcaagcggca | ggcggagcag | gaggggctgg acaaggtgtt cctcgaggcc | 1200 |
| ggtttcgaat | ggcgcgaccc | gggttgttcc | atgtgtctgg cgatgaacgc cgaccgcctg | 1260 |
| gaacccggcg | agcgttgcgc | ctcgacctcc | aaccggaatt ttgagggggcg ccagggctat | 1320 |
| ggcgggcgta | cccatctggt | gagtccggcc | atggcggctg cggcggccat tcacgggcat | 1380 |
| ttcgtcgaca | tcaccgaagg | agggcgcgca | tga | 1413 |

<210> SEQ ID NO 60
<211> LENGTH: 470
<212> TYPE: PRT
<213> ORGANISM: Methylococcus capsulatus

<400> SEQUENCE: 60

Met Ser Gly Lys Thr Leu Tyr Asp Lys Leu Trp Asp Asp His Val Val
1               5                   10                  15

His Val Asp Ala Asp Gly Ser Cys Leu Ile Tyr Ile Asp Arg His Leu
            20                  25                  30

-continued

```
Ile His Glu Val Thr Ser Pro Gln Ala Phe Glu Gly Leu Arg Met Ala
         35                  40                  45

Gly Arg Val Pro Trp Arg Val Asp Ala Asn Leu Ala Val Ala Asp His
 50                  55                  60

Asn Val Pro Thr Ala Asp Arg Asp Arg Gly Ile Ala Asp Pro Val Ser
 65                  70                  75                  80

Arg Leu Gln Val Glu Thr Leu Asp Lys Asn Cys Ala Asp Phe Gly Ile
                 85                  90                  95

Thr Glu Phe Ala Met Asp Asp Val Arg Gln Gly Ile Val His Val Ile
            100                 105                 110

Gly Pro Glu Gln Gly Ala Thr Leu Pro Gly Met Thr Ile Val Cys Gly
        115                 120                 125

Asp Ser His Thr Ser Thr His Gly Ala Phe Gly Ala Leu Ala Phe Gly
130                 135                 140

Ile Gly Thr Ser Glu Val Glu His Val Leu Ala Thr Gln Cys Leu Val
145                 150                 155                 160

Gln Arg Lys Ala Lys Asn Met Leu Val Arg Val Gln Gly Lys Leu Ala
                165                 170                 175

Pro Gly Val Thr Ala Lys Asp Leu Val Leu Ala Val Ile Gly Arg Ile
            180                 185                 190

Gly Thr Ala Gly Gly Thr Gly Tyr Thr Ile Glu Phe Ala Gly Glu Ala
        195                 200                 205

Ile Arg Gly Leu Ser Met Glu Gly Arg Met Thr Val Cys Asn Met Ala
210                 215                 220

Ile Glu Ala Gly Ala Arg Ala Gly Leu Val Ala Val Asp Glu Val Thr
225                 230                 235                 240

Leu Asp Tyr Leu Glu Gly Arg Pro Phe Ala Pro Ala Gly Ala Leu Trp
                245                 250                 255

Glu Arg Ala Val Glu Ala Trp Lys Asp Leu His Ser Asp Pro Asp Ala
            260                 265                 270

Val Phe Asp Lys Val Val Glu Ile Asp Ala Ala Ser Ile Lys Pro Gln
        275                 280                 285

Val Thr Trp Gly Thr Ser Pro Glu Gln Val Val Pro Val Asp Ala Glu
290                 295                 300

Val Pro Asp Pro Ala Thr Glu Ala Asp Pro Val Arg Arg Glu Ser Met
305                 310                 315                 320

Glu Arg Ala Leu Gln Tyr Met Asp Leu Leu Pro Gly Thr Pro Ile Gly
                325                 330                 335

Ala Ile Arg Val Asp Arg Val Phe Ile Gly Ser Cys Thr Asn Ala Arg
            340                 345                 350

Ile Glu Asp Leu Arg Ala Ala Ala Glu Val Val Arg Gly His Lys Arg
        355                 360                 365

Ala Ala Ser Val Lys Gln Ala Leu Val Val Pro Gly Ser Gly Leu Val
370                 375                 380

Lys Arg Gln Ala Glu Gln Glu Gly Leu Asp Lys Val Phe Leu Glu Ala
385                 390                 395                 400

Gly Phe Glu Trp Arg Asp Pro Gly Cys Ser Met Cys Leu Ala Met Asn
                405                 410                 415

Ala Asp Arg Leu Glu Pro Gly Glu Arg Cys Ala Ser Thr Ser Asn Arg
            420                 425                 430

Asn Phe Glu Gly Arg Gln Gly Tyr Gly Gly Arg Thr His Leu Val Ser
        435                 440                 445

Pro Ala Met Ala Ala Ala Ala Ile His Gly His Phe Val Asp Ile
```

Thr Glu Gly Gly Arg Ala
465             470

<210> SEQ ID NO 61
<211> LENGTH: 639
<212> TYPE: DNA
<213> ORGANISM: Methylococcus capsulatus

<400> SEQUENCE: 61

```
atgaagcctt tcaagaaatt cacttcgcga gtcgtgccgt tggaccgcgc caatgtcgac     60
accgacgcca tcattcccaa gcagttcctg aagtccatcc gccgcagcgg gttcggtccc    120
tatctgttcg acgagtggcg ttacctggac cgtggcgagc ccgacatgga ttgcagccac    180
cgtccgctca acccggagtt cgtgctcaac ctgccctgtt acgccggcgc caggatattg    240
ctggcccgca agaacttcgg ctgtggctcc tcgcgcgagc atgcgccctg gcgctggag     300
gattacggct tccgcgccat catcgcgccg agtttcgccg atatcttcta caacaactgc    360
ttcaagaacg gcatcctgcc catcgtgctc gacgaggcca cggtcgaccg gctgtttagc    420
gaggccgggc ccggcttcga gctcaccgtc gacctggagt cgcagaccgt ggcgacgccg    480
ttcggcgaga ccttccattt cgacgtggat gcctcccgca agcatcgtct gctgaacggc    540
ctggacgaca tcggtctgac ccttcagcat gccgatgcca tccgcgccta cgaagccgcc    600
cgcaggaagt ccgcaccctg gctgtttgcc gtcccttga                           639
```

<210> SEQ ID NO 62
<211> LENGTH: 212
<212> TYPE: PRT
<213> ORGANISM: Methylococcus capsulatus

<400> SEQUENCE: 62

Met Lys Pro Phe Lys Lys Phe Thr Ser Arg Val Val Pro Leu Asp Arg
1               5                   10                  15

Ala Asn Val Asp Thr Asp Ala Ile Ile Pro Lys Gln Phe Leu Lys Ser
            20                  25                  30

Ile Arg Arg Ser Gly Phe Gly Pro Tyr Leu Phe Asp Glu Trp Arg Tyr
        35                  40                  45

Leu Asp Arg Gly Glu Pro Asp Met Asp Cys Ser His Arg Pro Leu Asn
    50                  55                  60

Pro Glu Phe Val Leu Asn Leu Pro Cys Tyr Ala Gly Ala Arg Ile Leu
65                  70                  75                  80

Leu Ala Arg Lys Asn Phe Gly Cys Gly Ser Ser Arg Glu His Ala Pro
                85                  90                  95

Trp Ala Leu Glu Asp Tyr Gly Phe Arg Ala Ile Ile Ala Pro Ser Phe
            100                 105                 110

Ala Asp Ile Phe Tyr Asn Asn Cys Phe Lys Asn Gly Ile Leu Pro Ile
        115                 120                 125

Val Leu Asp Glu Ala Thr Val Asp Arg Leu Phe Ser Glu Ala Gly Pro
    130                 135                 140

Gly Phe Glu Leu Thr Val Asp Leu Glu Ser Gln Thr Val Ala Thr Pro
145                 150                 155                 160

Phe Gly Glu Thr Phe His Phe Asp Val Asp Ala Ser Arg Lys His Arg
                165                 170                 175

Leu Leu Asn Gly Leu Asp Asp Ile Gly Leu Thr Leu Gln His Ala Asp
            180                 185                 190

Ala Ile Arg Ala Tyr Glu Ala Ala Arg Arg Lys Ser Ala Pro Trp Leu
        195                 200                 205

Phe Ala Val Pro
    210

<210> SEQ ID NO 63
<211> LENGTH: 1083
<212> TYPE: DNA
<213> ORGANISM: Methylococcus capsulatus

<400> SEQUENCE: 63

```
atgactatca aaatcgctgt cttgcccggt gacggcatcg gtcccgaaat cgtcgccgag      60
gccctgaagg ttctggactg cctgcggtcc gacttcggcc tcgcggtcga aaccgaacac    120
gccctgatcg gcggcgcagc ctatgatgcg cacggcacgc cgttccccaa ggaaaccctg    180
gagctgtgcc gggctgccga ttcgatcctg cttggagcgg tcggcggtcc caaatgggag    240
ccgttggatt attcgctgcg gcccgagcgg gggctcctgg gcttgcgttc ggagctggaa    300
ctgtttttcca acctgcgccc ggcggtgctc taccctcagc tggtgtcggc ttcgaccctc    360
aagcccgagg tggtcgccgg cctcgacatc atgatcgtgc gggagctgac cggcggcata    420
tatttcggca agccgcgcgg tcgtcgcatc aacgaggacg gagagcggga gggctacaac    480
accctggtat acagcgaatc ggaaatccgc cgcatagccc atagcgcgtt ccagatcgcc    540
cggaagcgta caggcgcct gtgcagcatc gacaaggcca atgtgctgga atgcacggaa    600
ctgtggcgcg aggtggtgat cgaggtcggc aaggactatc ccgacgtggc gctgagccac    660
atgtacgtgg acaacgccgc gatgcagctg gtccgtaacc cgaagcagtt cgacgtgatg    720
ctgaccgaca acatgttcgg cgacatcctg tccgactgtg ccgccatgct gaccggctcg    780
atcggcatgc tgccttcggc ttccctcgcc gagagcggca aggggatgta cgagcccatc    840
cacggttcgg ccccggatat cgccggccgc ggcatcgcca accgatcgc caccatcctg    900
tcgctggcca tgatgttgcg ctacagcttc gatgacgcgg tctcggcaga gcggatcggg    960
aaggcggtgc agacggcgct ggatcagggt ttccgcacgg cggacatcgc ctcggaaggc   1020
accgtcgagg tcggtaccgc tgcgatgggc gatgccatcg tcgccgcctt gcgcgccgtc   1080
tga                                                                 1083
```

<210> SEQ ID NO 64
<211> LENGTH: 360
<212> TYPE: PRT
<213> ORGANISM: Methylococcus capsulatus

<400> SEQUENCE: 64

Met Thr Ile Lys Ile Ala Val Leu Pro Gly Asp Gly Ile Gly Pro Glu
1               5                   10                  15

Ile Val Ala Glu Ala Leu Lys Val Leu Asp Cys Leu Arg Ser Asp Phe
            20                  25                  30

Gly Leu Ala Val Glu Thr Glu His Ala Leu Ile Gly Gly Ala Ala Tyr
        35                  40                  45

Asp Ala His Gly Thr Pro Phe Pro Lys Glu Thr Leu Glu Leu Cys Arg
    50                  55                  60

Ala Ala Asp Ser Ile Leu Leu Gly Ala Val Gly Pro Lys Trp Glu
65                  70                  75                  80

Pro Leu Asp Tyr Ser Leu Arg Pro Glu Arg Gly Leu Leu Gly Leu Arg
                85                  90                  95

Ser Glu Leu Glu Leu Phe Ser Asn Leu Arg Pro Ala Val Leu Tyr Pro

|     |     |     | 100 |     |     |     | 105 |     |     |     | 110 |     |     |
|-----|-----|-----|-----|-----|-----|-----|-----|-----|-----|-----|-----|-----|-----|

Gln Leu Val Ser Ala Ser Thr Leu Lys Pro Glu Val Ala Gly Leu
    115        120        125

Asp Ile Met Ile Val Arg Glu Leu Thr Gly Gly Ile Tyr Phe Gly Lys
 130        135        140

Pro Arg Gly Arg Arg Ile Asn Glu Asp Gly Glu Arg Glu Gly Tyr Asn
145        150        155        160

Thr Leu Val Tyr Ser Glu Ser Glu Ile Arg Arg Ile Ala His Ser Ala
    165        170        175

Phe Gln Ile Ala Arg Lys Arg Asn Arg Arg Leu Cys Ser Ile Asp Lys
    180        185        190

Ala Asn Val Leu Glu Cys Thr Glu Leu Trp Arg Glu Val Val Ile Glu
    195        200        205

Val Gly Lys Asp Tyr Pro Asp Val Ala Leu Ser His Met Tyr Val Asp
    210        215        220

Asn Ala Ala Met Gln Leu Val Arg Asn Pro Lys Gln Phe Asp Val Met
225        230        235        240

Leu Thr Asp Asn Met Phe Gly Asp Ile Leu Ser Asp Cys Ala Ala Met
    245        250        255

Leu Thr Gly Ser Ile Gly Met Leu Pro Ser Ala Ser Leu Ala Glu Ser
    260        265        270

Gly Lys Gly Met Tyr Glu Pro Ile His Gly Ser Ala Pro Asp Ile Ala
    275        280        285

Gly Arg Gly Ile Ala Asn Pro Ile Ala Thr Ile Leu Ser Leu Ala Met
    290        295        300

Met Leu Arg Tyr Ser Phe Asp Asp Ala Val Ser Ala Glu Arg Ile Gly
305        310        315        320

Lys Ala Val Gln Thr Ala Leu Asp Gln Gly Phe Arg Thr Ala Asp Ile
    325        330        335

Ala Ser Glu Gly Thr Val Glu Val Gly Thr Ala Ala Met Gly Asp Ala
    340        345        350

Ile Val Ala Ala Leu Arg Ala Val
    355        360

<210> SEQ ID NO 65
<211> LENGTH: 1477
<212> TYPE: DNA
<213> ORGANISM: Marinobacter algicola

<400> SEQUENCE: 65

| | | | | | |
|---|---|---|---|---|---|
| atggcgaccc | agcagcagca | gaacggcgcc | tcggcgagcg | gcgtcctgga | acagttgcgc | 60 |
| gggaagcatg | tcctgataac | cggtaccacc | ggtttccttg | gcaaggtagt | cctggaaaag | 120 |
| ctgatccgca | cagtcccgga | catcggcggc | atccacctcc | tgatccgggg | caacaagagg | 180 |
| catccggccg | cccgtgaacg | gttcttgaac | gagatcgcca | gcagttcggt | cttcgagcgt | 240 |
| ctgcgccacg | acgacaacga | ggccttcgaa | accttcctgg | aagaaagggt | gcactgtata | 300 |
| accggagagg | tcaccgagag | tcgtttcggc | cttaccccgg | agcgcttccg | cgcgctggcg | 360 |
| ggtcaggtgg | acgccttcat | caattcggcc | gcctccgtca | acttccgcga | ggaactggac | 420 |
| aaggcgctga | agatcaatac | gctgtgcctg | agaatgtcg | cggcccttgc | tgaactcaac | 480 |
| agtgcgatgg | cggtcatcca | ggtttcgacc | tgctacgtta | acggcaagaa | tagcgggcag | 540 |
| atcaccgaat | cggtcatcaa | gcccgcgggg | gagtccatcc | cgcgtagcac | cgatgggtac | 600 |
| tatgaaatcg | aagaattggt | gcacctgctg | caggacaaaa | tcagcgatgt | gaaggcccga | 660 |

```
tactccggga aggttctgga aaaaaaattg gtggacctag gcatccggga agccaataac    720
tacgggtgga gcgatacata taccttcacc aagtggctgg gcgaacagct cctcatgaag    780
gccctgagcg gcagatcgct gaccatcgtg cggccgtcga tcatcgagtc ggcattggaa    840
gagcccagcc cggggtggat tgaaggcgtc aaggtcgccg atgccatcat actggcctac    900
gcgagggaga aggtatcgct ctttcctggc aagcggagcg gcatcatcga cgtcatccca    960
gtggatctgg tggccaattc gatcattctg tccctggcgg aggcgctctc cggttcgggc   1020
cagcggcgta tctatcagtg ctgcagcggc ggctcgaacc ccatctccct cgggaagttc   1080
atcgactatc tgatggcgga ggcgaagacc aactacgcgg cctacgatca gctgttctac   1140
cgccgcccca ccaagccgtt cgtggccgtc aaccgcaaac tcttcgacgt cgtcgtgggc   1200
ggcatgcggg tcccgctctc gatcgcgggc aaagccatgc gcctggcggg acaaaaccgc   1260
gaactgaagg tcctgaagaa tctggatacg acccggtccc tggccaccat tttcggggttc   1320 tacaccgctc cggactacat cttttcgcaat gacagcctga tggccctggc ctcgcgcatg   1380
ggcgagctgg accgcgtgtt gttccccgtt gacgcccgtc agatcgactg gcagctgtat   1440
ctgtgcaaaa tccacctcgg cgggctgaat cggtacg                             1477
```

<210> SEQ ID NO 66
<211> LENGTH: 511
<212> TYPE: PRT
<213> ORGANISM: Marinobacter algicola

<400> SEQUENCE: 66

```
Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Asn Phe Arg Glu Glu Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220
```

```
Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
            245                 250                 255

Leu Leu Met Lys Ala Leu Ser Gly Arg Ser Leu Thr Ile Val Arg Pro
        260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
            355                 360                 365

Lys Thr Asn Tyr Ala Ala Tyr Asp Gln Leu Phe Tyr Arg Arg Pro Thr
370                 375                 380

Lys Pro Phe Val Ala Val Asn Arg Lys Leu Phe Asp Val Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
            435                 440                 445

Arg Asn Asp Ser Leu Met Ala Leu Ala Ser Arg Met Gly Glu Leu Asp
450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala
            500                 505                 510

<210> SEQ ID NO 67
<211> LENGTH: 1377
<212> TYPE: DNA
<213> ORGANISM: Acinetobacter baylyi

<400> SEQUENCE: 67
atgcgccccc tgcacccat cgacttcatc ttcctgagcc tggaaaagcg gcagcagccc        60
atgcacgtcg gcggcctgtt cctgttccag atcccggaca cgcccccga caccttcatc       120 caggacctgg tcaacgacat ccgcatctcc aagagcatcc cggtgccgcc cttcaacaac       180
aagctgaacg gcctgttctg ggacgaagac gaggagttcg acctggacca ccatttccgg       240
cacatcgccc tgccgcatcc cggccgcatc cgggaactgc tgatctacat ctcccaggag       300
cacagcaccc tgctggaccg cgcgaagccg ctgtggacct gcaacatcat cgaaggcatc       360
gagggcaacc ggttcgccat gtatttcaag atccaccatg cgatggtcga cggcgtggcc       420
ggcatgcgcc tgatcgaaaa gtcgctgtcc catgacgtca ccgagaagag catcgtcccg       480
ccctggtgcg tggaaggcaa gcgggcgaag cgcctgcggg agccgaagac cggcaagatc       540
```

```
aagaagatca tgtcgggcat caagtcccag ctgcaggcca cccccaccgt catccaggaa    600
ctgtcgcaga ccgtgttcaa ggacatcggc cgcaacccgg accacgtcag ctcgttccag    660 gcccctgct ccatcctgaa ccagcgggtg tccagctcgc gccggttcgc cgcgcagtcg    720
ttcgacctgg accgcttccg gaacatcgcg aagtccctga acgtcaccat caacgacgtc    780
gtgctggccg tgtgcagcgg cgccctgcgc gcgtacctga tgagccacaa ctcgctgccg    840
tccaagcccc tgatcgcgat ggtcccggcg tcgatccgca acgacgacag cgacgtgtcg    900
aaccggatca ccatgatcct ggccaacctg gcgacccata aggacgaccc gctgcagcgc    960
ctggagatca tccgccggag cgtccagaac tcgaagcagc gcttcaagcg gatgaccgcc   1020
gaccagatcc tgaactacag cgcggtcgtg tatggcccgg ccggcctgaa catcatcagc   1080
ggcatgatgc ccaagcgcca ggccttcaac ctggtcatct cgaacgtgcc gggcccgcgc   1140
gagccgctgt actggaacgg cgccaagctg gacgcgctgt atcccgcctc catcgtcctg   1200
gacggccagg ccctgaacat caccatgacc agctacctgg acaagctgga ggtcggcctg   1260
atcgcgtgcc gcaacgccct gccgcggatg cagaacctgc tgacccatct ggaggaagag   1320
atccagctgt cgaaggcgt gatcgcgaag caggaggaca tcaagaccgc caactga      1377
```

<210> SEQ ID NO 68
<211> LENGTH: 458
<212> TYPE: PRT
<213> ORGANISM: Acinetobacter baylyi

<400> SEQUENCE: 68

```
Met Arg Pro Leu His Pro Ile Asp Phe Ile Phe Leu Ser Leu Glu Lys
1               5                  10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220
```

Ile Leu Asn Gln Arg Val Ser Ser Arg Arg Phe Ala Ala Gln Ser
225                 230                 235                 240

Phe Asp Leu Asp Arg Phe Arg Asn Ile Ala Lys Ser Leu Asn Val Thr
            245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
        275                 280                 285

Pro Ala Ser Ile Arg Asn Asp Asp Ser Asp Val Ser Asn Arg Ile Thr
290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
            325                 330                 335

Arg Met Thr Ser Asp Gln Ile Leu Asn Tyr Ser Ala Val Val Tyr Gly
            340                 345                 350

Pro Ala Gly Leu Asn Ile Ile Ser Gly Met Met Pro Lys Arg Gln Ala
        355                 360                 365

Phe Asn Leu Val Ile Ser Asn Val Pro Gly Pro Arg Glu Pro Leu Tyr
370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
            405                 410                 415

Glu Val Gly Leu Ile Ala Cys Arg Asn Ala Leu Pro Arg Met Gln Asn
            420                 425                 430

Leu Leu Thr His Leu Glu Glu Glu Ile Gln Leu Phe Glu Gly Val Ile
        435                 440                 445

Ala Lys Gln Glu Asp Ile Lys Thr Ala Asn
450                 455

<210> SEQ ID NO 69
<211> LENGTH: 1428
<212> TYPE: DNA
<213> ORGANISM: Psychrobacter articus

<400> SEQUENCE: 69

```
atgcgcctgc tgaccgccgt cgaccagctg ttcctgctgc tggagtcccg caagcacccg      60
atgcacgtgg cggcctgtt cctgttcgaa ctgccggaga cgccgacat ctcgttcgtc     120
caccagctgg tgaagcagat gcaggactcc gacgtcccgc ccaccttccc cttcaaccag     180
gtgctggaac acatgatgtt ctggaaggag gacaagaact cgacgtcga caccatctg     240
caccatgtgg ccctgccgaa gcccgcgcgc gtccgggagc tgctgatgta cgtgtcccgc     300
gaacacggcc ggctgctgga ccgcgcgatg ccgctgtggg aatgccatgt catcgagggc     360
atccagccga aaaccgaggg cagccccgag cggttcgccc tgtatttcaa gatccaccat     420
tcgctggtcg acggcatcgc cgcgatgcgc ctggtgaaga gagcctgtc gcagtcgccg     480
aacgaacccg tgaccctgcc gatctggagc ctgatggccc accatcggaa ccagatcgac     540
gcgatcttcc ccaaggagcg gagcgccctg cgcatcctga ggaacaggt ctcgaccatc     600
aagccggtgt tcaccgagct gctgaacaac ttcaagaact acaacgacga ctcgtatgtc     660
tccaccttcg acgcgccccg cagcatcctg aaccgccgga tcagcgcctc cgcgccggatc     720
gccgcgcagt cgtacgacat caagcggttc aacgacatcg ccgaacgcat caacatctcc     780
```

-continued

| | |
|---|---|
| aagaacgacg tcgtgctggc cgtgtgcagc ggcgcgatcc gccgctacct gatcagcatg | 840 |
| gacgcgctgc cgagcaagcc cctgatcgcc ttcgtcccga tgtcgctgcg caccgacgac | 900 |
| tccatcgcgg gcaaccagct gtcgttcgtg ctggccaacc tgggcaccca cctggacgac | 960 |
| cccctgtccc ggatcaagct gatccatcgc tccatgaaca acagcaagcg ccggttccgc | 1020 |
| cggatgaacc aggcccaggt catcaactac agcatcgtgt cgtatgcctg ggagggcatc | 1080 |
| aacctggcga ccgacctgtt cccgaagaag caggccttca acctgatcat ctcgaacgtg | 1140 |
| ccgggcagcg agaagcccct gtactggaac ggcgcgcgcc tggaaagcct gtatccggcc | 1200 |
| tcgatcgtgt tcaacggcca ggccatgaac atcaccctgg cgtcctacct ggacaagatg | 1260 |
| gagttcggca tcaccgcctg cagcaaggcg ctgccgcacg tccaggacat gctgatgctg | 1320 |
| atcgaggaag agctgcagct gctggagtcc gtcagcaagg aactggagtt caacggcatc | 1380 |
| accgtgaagg acaagtcgga aaagaagctg aagaagctgg ccccgtga | 1428 |

<210> SEQ ID NO 70
<211> LENGTH: 475
<212> TYPE: PRT
<213> ORGANISM: Psychrobacter articus

<400> SEQUENCE: 70

Met Arg Leu Leu Thr Ala Val Asp Gln Leu Phe Leu Leu Glu Ser
1               5                   10                  15

Arg Lys His Pro Met His Val Gly Gly Leu Phe Leu Phe Glu Leu Pro
            20                  25                  30

Glu Asn Ala Asp Ile Ser Phe Val His Gln Leu Val Lys Gln Met Gln
        35                  40                  45

Asp Ser Asp Val Pro Pro Thr Phe Pro Phe Asn Gln Val Leu Glu His
    50                  55                  60

Met Met Phe Trp Lys Glu Asp Lys Asn Phe Asp Val Glu His His Leu
65                  70                  75                  80

His His Val Ala Leu Pro Lys Pro Ala Arg Val Arg Glu Leu Leu Met
                85                  90                  95

Tyr Val Ser Arg Glu His Gly Arg Leu Leu Asp Arg Ala Met Pro Leu
            100                 105                 110

Trp Glu Cys His Val Ile Glu Gly Ile Gln Pro Glu Thr Glu Gly Ser
        115                 120                 125

Pro Glu Arg Phe Ala Leu Tyr Phe Lys Ile His His Ser Leu Val Asp
    130                 135                 140

Gly Ile Ala Ala Met Arg Leu Val Lys Lys Ser Leu Ser Gln Ser Pro
145                 150                 155                 160

Asn Glu Pro Val Thr Leu Pro Ile Trp Ser Leu Met Ala His Arg
                165                 170                 175

Asn Gln Ile Asp Ala Ile Phe Pro Lys Glu Arg Ser Ala Leu Arg Ile
            180                 185                 190

Leu Lys Glu Gln Val Ser Thr Ile Lys Pro Val Phe Thr Glu Leu Leu
        195                 200                 205

Asn Asn Phe Lys Asn Tyr Asn Asp Asp Ser Tyr Val Ser Thr Phe Asp
    210                 215                 220

Ala Pro Arg Ser Ile Leu Asn Arg Arg Ile Ala Ser Arg Arg Ile
225                 230                 235                 240

Ala Ala Gln Ser Tyr Asp Ile Lys Arg Phe Asn Asp Ile Ala Glu Arg
                245                 250                 255

Ile Asn Ile Ser Lys Asn Asp Val Val Leu Ala Val Cys Ser Gly Ala

```
                260                 265                 270
Ile Arg Arg Tyr Leu Ile Ser Met Asp Ala Leu Pro Ser Lys Pro Leu
            275                 280                 285

Ile Ala Phe Val Pro Met Ser Leu Arg Thr Asp Asp Ser Ile Ala Gly
            290                 295                 300

Asn Gln Leu Ser Phe Val Leu Ala Asn Leu Gly Thr His Leu Asp Asp
305                 310                 315                 320

Pro Leu Ser Arg Ile Lys Leu Ile His Arg Ser Met Asn Asn Ser Lys
            325                 330                 335

Arg Arg Phe Arg Arg Met Asn Gln Ala Gln Val Ile Asn Tyr Ser Ile
            340                 345                 350

Val Ser Tyr Ala Trp Glu Gly Ile Asn Leu Ala Thr Asp Leu Phe Pro
            355                 360                 365

Lys Lys Gln Ala Phe Asn Leu Ile Ile Ser Asn Val Pro Gly Ser Glu
            370                 375                 380

Lys Pro Leu Tyr Trp Asn Gly Ala Arg Leu Glu Ser Leu Tyr Pro Ala
385                 390                 395                 400

Ser Ile Val Phe Asn Gly Gln Ala Met Asn Ile Thr Leu Ala Ser Tyr
            405                 410                 415

Leu Asp Lys Met Glu Phe Gly Ile Thr Ala Cys Ser Lys Ala Leu Pro
            420                 425                 430

His Val Gln Asp Met Leu Met Leu Ile Glu Glu Leu Gln Leu Leu
            435                 440                 445

Glu Ser Val Ser Lys Glu Leu Glu Phe Asn Gly Ile Thr Val Lys Asp
450                 455                 460

Lys Ser Glu Lys Lys Leu Lys Lys Leu Ala Pro
465                 470                 475

<210> SEQ ID NO 71
<211> LENGTH: 1386
<212> TYPE: DNA
<213> ORGANISM: Rhodococcus opacus

<400> SEQUENCE: 71
atgtccgtga tgtccccgac cgaggcgatg ttcgtcctgt tcgagacccc gagccacccg      60
atgcacatgg gcgcgctgga gctgttcgag ccgccgcgcg agtcgggccc ggaccacgcc     120
cgcctgatgt tcgaggcgct gatctcccag gaaggcgcca cgacaccttc cgccggcgc     180 gccgtccggc cgctgcgcgg cgcgtcgtac ccctggtggt ccgtcgacga ccgggtggac     240
ctgggctatc acgtccgcca taccgccgtg ccgggccggg ccgcatgga ggacctgctg     300 tcgctggtgt cccagatgca cggcatgccc ctggacccgc agcaccccat gtgggagatc     360
catgtcatcg aaggcctggc cgacggccgc accgcgtgt tcagcaagat ccatctgtcg     420
ctgatggacg gccggccgg cctgcggctg ctgcaccatg cgctgagcac cgacccggac     480
gcccgcgact gccccgcgcc gtggaccccc ggcgtcagcg gcacctcgcg cgcgaatcg     540 gccctgccgg tcgccgcggt gcgggcgggc gtgcgcgccg cgacctccat cgtcggcgtg     600
ctgcccgccc tggcgaaggt cgcctacgac ggcgtgcggg accagcacct gaccctgccg     660
ctgcagagcc cgcccaccat gctgaacgtc ccgtgggcc gggccgcaa gctggccgcg     720 cggagctggc cgatccggcg cctggtctcg gtggccgcgg ccgcgcgcac caccatcaac     780
gccgtcgtgc tggcgatgtg ctcgggcgcc ctgcgccact acctggtcga gcagtatgcc     840
ctgccggaag cgccctgac cgccatgctg cccgtgccgc tggacctggg cggcaccatg     900
```

-continued

```
atcggcccgc gtggccgcga ccacggcgtc ggcgcgatgg tcgtgggcct ggcgaccgac    960
gaggccgacc ccgccgcgcg gctggccgcg atcagcgagt cggtcgaaca caccaaccgc   1020
gtgttcggcg cgctgtccca tacccagttc caggtcatgt ccgccctggc gatcagcccg   1080
atcctgctgg aacccgtccg cgcttcgtg gacgacaccc cgcccccgtt caacgtgatg    1140
atctcgtaca tgccgggtcc gtcccggccg cgctattgga acggcgcgcg gctggacgcc   1200
gtctaccccg cgccgaccgt gctgggcggc caggccctga gcatcaccct gacctcccgc   1260
agcggccagc tggacgtcgg cgtcgtgggc gaccggcagg ccgtgccgca cctgcagcgc   1320
atcatcaccc atctggagac ctccctgacc gacctggaaa acgccgtggc cgcgagcggc   1380
acctga                                                              1386
```

<210> SEQ ID NO 72
<211> LENGTH: 461
<212> TYPE: PRT
<213> ORGANISM: Rhodococcus opacus

<400> SEQUENCE: 72

```
Met Ser Val Met Ser Pro Thr Glu Ala Met Phe Val Leu Phe Glu Thr
1               5                   10                  15

Pro Ser His Pro Met His Met Gly Ala Leu Glu Leu Phe Glu Pro Pro
            20                  25                  30

Arg Glu Ser Gly Pro Asp His Ala Arg Leu Met Phe Glu Ala Leu Ile
        35                  40                  45

Ser Gln Glu Gly Ala Ser Asp Thr Phe Arg Arg Arg Ala Val Arg Pro
    50                  55                  60

Leu Arg Gly Ala Ser Tyr Pro Trp Trp Ser Val Asp Asp Arg Val Asp
65                  70                  75                  80

Leu Gly Tyr His Val Arg His Thr Ala Val Pro Gly Arg Gly Arg Met
                85                  90                  95

Glu Asp Leu Leu Ser Leu Val Ser Gln Met His Gly Met Pro Leu Asp
            100                 105                 110

Pro Gln His Pro Met Trp Glu Ile His Val Ile Glu Gly Leu Ala Asp
        115                 120                 125

Gly Arg Thr Ala Val Phe Ser Lys Ile His Leu Ser Leu Met Asp Gly
    130                 135                 140

Pro Ala Gly Leu Arg Leu Leu His His Ala Leu Ser Thr Asp Pro Asp
145                 150                 155                 160

Ala Arg Asp Cys Pro Ala Pro Trp Thr Pro Gly Val Ser Gly Thr Ser
                165                 170                 175

Arg Arg Glu Ser Ala Leu Pro Val Ala Ala Val Arg Ala Gly Val Arg
            180                 185                 190

Ala Ala Thr Ser Ile Val Gly Val Leu Pro Ala Leu Ala Lys Val Ala
        195                 200                 205

Tyr Asp Gly Val Arg Asp Gln His Leu Thr Leu Pro Leu Gln Ser Pro
    210                 215                 220

Pro Thr Met Leu Asn Val Pro Val Gly Arg Ala Arg Lys Leu Ala Ala
225                 230                 235                 240

Arg Ser Trp Pro Ile Arg Arg Leu Val Ser Val Ala Ala Ala Ala Arg
                245                 250                 255

Thr Thr Ile Asn Ala Val Val Leu Ala Met Cys Ser Gly Ala Leu Arg
            260                 265                 270

His Tyr Leu Val Glu Gln Tyr Ala Leu Pro Glu Ala Pro Leu Thr Ala
        275                 280                 285
```

```
Met Leu Pro Val Pro Leu Asp Leu Gly Gly Thr Met Ile Gly Pro Arg
    290                 295                 300

Gly Arg Asp His Gly Val Gly Ala Met Val Val Gly Leu Ala Thr Asp
305                 310                 315                 320

Glu Ala Asp Pro Ala Ala Arg Leu Ala Arg Ile Ser Glu Ser Val Glu
                325                 330                 335

His Thr Asn Arg Val Phe Gly Ala Leu Ser His Thr Gln Phe Gln Val
                340                 345                 350

Met Ser Ala Leu Ala Ile Ser Pro Ile Leu Leu Glu Pro Val Arg Arg
            355                 360                 365

Phe Val Asp Asp Thr Pro Pro Pro Phe Asn Val Met Ile Ser Tyr Met
    370                 375                 380

Pro Gly Pro Ser Arg Pro Arg Tyr Trp Asn Gly Ala Arg Leu Asp Ala
385                 390                 395                 400

Val Tyr Pro Ala Pro Thr Val Leu Gly Gly Gln Ala Leu Ser Ile Thr
                405                 410                 415

Leu Thr Ser Arg Ser Gly Gln Leu Asp Val Gly Val Val Gly Asp Arg
                420                 425                 430

Gln Ala Val Pro His Leu Gln Arg Ile Ile Thr His Leu Glu Thr Ser
            435                 440                 445

Leu Thr Asp Leu Glu Asn Ala Val Ala Ala Ser Gly Thr
    450                 455                 460

<210> SEQ ID NO 73
<211> LENGTH: 1356
<212> TYPE: DNA
<213> ORGANISM: Rhodococcus opacus

<400> SEQUENCE: 73
atgccggtca ccgactccat cttcctgctg ggcgaaagcc gcgagcaccc gatgcacgtg      60
ggctccctgg aactgttcac ccccccggac gacgccggcc cggactacgt caagtcgatg     120
cacgagaccc tgctgaagca taccgacgtg accccacct tccgcaagaa gccggcgggc      180
cccgtcggct cgctgggcaa cgtgtggtgg ccgacgagt ccgacgtcga cctggaatac      240
cacgtgcgcc atagcgcgct gccggccccc tatcgcgtcc gggaactgct gaccctgacc     300
tcgcggctgc acggcaccct gctggaccgc atcggccgc tgtgggagat gtacctgatc      360
gaaggcctga gcgacggccg cttcgccatc tataccaagc tgcaccatag cctgatggac     420
ggcgtctcgg gcctgcgcct gctgatgcgg accctgtcga ccgacccgga cgtgcgcgac     480
gccccgcccc gtggaaccct gccgcggccc gccgcggcca acggcgcggc cccggacctg     540
tggtcggtcg tgaacggcgt ccgccggacc gtcggcgacg tggccggcct ggcgcccgcc     600
tccctgcgca tcgcgcggac cgcgatgggc cagcacgaca tgcgcttccc gtacgaggcg     660
ccccggacca tgctgaacgt gccgatcggc ggcgcccgcc ggttcgcggc ccagtcctgg     720 ccctggaac gcgtccatgc cgtgcggaag gcggccggcc tcagcgtgaa cgacgtcgtg     780
atggccatgt gcgcgggcgc cctgcgcggc tatctggagg aacagaacgc gctgccggac     840
gagcccctga tcgcgatggt cccggtgtcc ctgcgggacg aacagcaggc ggacgccggc     900
ggcaacgccg tcggcgtgac cctgtgcaac ctggcgaccg acgtcgacga ccccgccgag     960
cgcctgaccg cgatcagcgc ctcgatgtcc cagggcaagg aactgttcgg cagcctgacc    1020
tcgatgcagg cgctggcctg gtcggcggtg aacatgtccc cgatcgccct gaccccggtc    1080
cccggcttcg tgcggttcac cccccgccc ttcaacgtca tcatcagcaa cgtgccgggc    1140
```

```
cccccgcaaga ccatgtactg gaacggctcc cggctggacg gcatctatcc gaccagcgtc   1200
gtgctggacg gccaggccct gaacatcacc ctgaccacca acggcggcaa cctggacttc   1260
ggcgtcatcg gctgccgccg gtccgtgccg agcctgcagc gcatcctgtt ctacctggaa   1320
gcggccctgg gcgagctgga agcggccctg ctgtga                             1356
```

<210> SEQ ID NO 74
<211> LENGTH: 451
<212> TYPE: PRT
<213> ORGANISM: Rhodococcus opacus

<400> SEQUENCE: 74

```
Met Pro Val Thr Asp Ser Ile Phe Leu Leu Gly Glu Ser Arg Glu His
1               5                   10                  15

Pro Met His Val Gly Ser Leu Glu Leu Phe Thr Pro Pro Asp Asp Ala
            20                  25                  30

Gly Pro Asp Tyr Val Lys Ser Met His Glu Thr Leu Leu Lys His Thr
        35                  40                  45

Asp Val Asp Pro Thr Phe Arg Lys Lys Pro Ala Gly Pro Val Gly Ser
    50                  55                  60

Leu Gly Asn Val Trp Trp Ala Asp Glu Ser Asp Val Asp Leu Glu Tyr
65                  70                  75                  80

His Val Arg His Ser Ala Leu Pro Ala Pro Tyr Arg Val Arg Glu Leu
                85                  90                  95

Leu Thr Leu Thr Ser Arg Leu His Gly Thr Leu Leu Asp Arg His Arg
            100                 105                 110

Pro Leu Trp Glu Met Tyr Leu Ile Glu Gly Leu Ser Asp Gly Arg Phe
        115                 120                 125

Ala Ile Tyr Thr Lys Leu His His Ser Leu Met Asp Gly Val Ser Gly
    130                 135                 140

Leu Arg Leu Leu Met Arg Thr Leu Ser Thr Asp Pro Asp Val Arg Asp
145                 150                 155                 160

Ala Pro Pro Pro Trp Asn Leu Pro Arg Pro Ala Ala Ala Asn Gly Ala
                165                 170                 175

Ala Pro Asp Leu Trp Ser Val Val Asn Gly Val Arg Arg Thr Val Gly
            180                 185                 190

Asp Val Ala Gly Leu Ala Pro Ala Ser Leu Arg Ile Ala Arg Thr Ala
        195                 200                 205

Met Gly Gln His Asp Met Arg Phe Pro Tyr Glu Ala Pro Arg Thr Met
    210                 215                 220

Leu Asn Val Pro Ile Gly Gly Ala Arg Arg Phe Ala Ala Gln Ser Trp
225                 230                 235                 240

Pro Leu Glu Arg Val His Ala Val Arg Lys Ala Ala Gly Val Ser Val
                245                 250                 255

Asn Asp Val Val Met Ala Met Cys Ala Gly Ala Leu Arg Gly Tyr Leu
            260                 265                 270

Glu Glu Gln Asn Ala Leu Pro Asp Glu Pro Leu Ile Ala Met Val Pro
        275                 280                 285

Val Ser Leu Arg Asp Glu Gln Gln Ala Asp Ala Gly Gly Asn Ala Val
    290                 295                 300

Gly Val Thr Leu Cys Asn Leu Ala Thr Asp Val Asp Asp Pro Ala Glu
305                 310                 315                 320

Arg Leu Thr Ala Ile Ser Ala Ser Met Ser Gln Gly Lys Glu Leu Phe
                325                 330                 335
```

```
Gly Ser Leu Thr Ser Met Gln Ala Leu Ala Trp Ser Ala Val Asn Met
            340                 345                 350

Ser Pro Ile Ala Leu Thr Pro Val Pro Gly Phe Val Arg Phe Thr Pro
        355                 360                 365

Pro Pro Phe Asn Val Ile Ile Ser Asn Val Pro Gly Pro Arg Lys Thr
370                 375                 380

Met Tyr Trp Asn Gly Ser Arg Leu Asp Gly Ile Tyr Pro Thr Ser Val
385                 390                 395                 400

Val Leu Asp Gly Gln Ala Leu Asn Ile Thr Leu Thr Asn Gly Gly
            405                 410                 415

Asn Leu Asp Phe Gly Val Ile Gly Cys Arg Arg Ser Val Pro Ser Leu
            420                 425                 430

Gln Arg Ile Leu Phe Tyr Leu Glu Ala Ala Leu Gly Glu Leu Glu Ala
            435                 440                 445

Ala Leu Leu
    450

<210> SEQ ID NO 75
<211> LENGTH: 1395
<212> TYPE: DNA
<213> ORGANISM: Rhodococcus opacus

<400> SEQUENCE: 75
atgcccctgc cgatgtcccc cctggactcc atgttcctgc tgggcgaaag ccgcgagcac      60
ccgatgcacg tgggcggcgt cgaaatcttc cagctgcccg agggcgccga cacctacgac     120
atgcgggcga tgctggaccg cgccctggcg acggcgacg gcatcgtcac cccgcggctg      180
gccaagcgcg cgcgccggtc gttcagctcg ctgggccagt ggtcctggga accgtggac      240 gacatcgacc tgggccacca tatccggcac gacgccctgc cggcccctgg cggcgaggcc     300
gaactgatgg cgctgtgctc gcgcctgcac ggctccctgc tggaccgcag ccggccgctg     360
tgggagatgc atctgatcga aggcctgagc gacgcccgct cgccgtctca taccaagatc     420
caccatgccg tcgcgacgg cgtgaccgcc atgaagatgc tgcggaacgc gctgagcgag      480
aactcggacg accgcgacgt gccggccccc tggcagccgc gtggcccgcg gccccagcgc     540 acccctcca gcaagggctt ctccctgagc ggcctggccg gctcgaccct gcggaccgcg      600
cgcgagaccg tcggcgaagt ggccggcctg gtcccggccc tggcgggcac cgtgagccgg     660
gccttccgcg accagggcgg cccgctggcc ctgtcggcgc cgaagacccc cttcaacgtc     720
cccatcaccg gcgcccgcca gttcgccgcg cagtcgtggc cgctggaacg cctgcggctg     780
gtggccaagc tgtcggactc caccatcaac gacgtcgtgc tggccatgtc gtccggcgcg     840
ctgcggtcct acctggagga ccagaacgcc ctgccggcgg accccctgat cgcgatggtc     900
ccggtgtccc tgaagagcca gcgcgaagcc gcgaccggca caacatcgg cgtcctgatg      960 tgcaacctgg caccccacct gcgggagccg ccgaccgcc tggaaaccat ccggaccagc     1020
atgcgcgagg gcaaggaagc ctatggctcg atgaccgcga cccagatcct ggccatgtcc    1080
gcgctgggcg ccgcgccgat cggcgccagc atgctgttcg ccataactc gcgcgtccgg     1140 ccgcccttca acctgatcat ctccaacgtg ccgggcccca gctcgccgct gtactggaac    1200
ggcgcccgcc tggacgcgat ctatccgctg agcgtccccg tggacggcca gggcctgaac    1260
atcacctgca cctcgaacga cgacatcatc tccttcggcg tcaccggctg ccggtccgcc    1320
gtgccggacc tgaagagcat ccccgcgcgc ctgggccatg agctgcgggc cctggaacgc    1380
```

-continued

```
gcggtgggca tctga                                                      1395
```

<210> SEQ ID NO 76
<211> LENGTH: 464
<212> TYPE: PRT
<213> ORGANISM: Rhodococcus opacus

<400> SEQUENCE: 76

| Met | Pro | Leu | Pro | Met | Ser | Pro | Leu | Asp | Ser | Met | Phe | Leu | Leu | Gly | Glu |
|---|---|---|---|---|---|---|---|---|---|---|---|---|---|---|---|
| 1 | | | | 5 | | | | | 10 | | | | | 15 | |

| Ser | Arg | Glu | His | Pro | Met | His | Val | Gly | Val | Glu | Ile | Phe | Gln | Leu |
|---|---|---|---|---|---|---|---|---|---|---|---|---|---|---|
| | | | 20 | | | | 25 | | | | 30 | | | |

| Pro | Glu | Gly | Ala | Asp | Thr | Tyr | Asp | Met | Arg | Ala | Met | Leu | Asp | Arg | Ala |
|---|---|---|---|---|---|---|---|---|---|---|---|---|---|---|---|
| | | 35 | | | | | 40 | | | | | 45 | | | |

| Leu | Ala | Asp | Gly | Asp | Gly | Ile | Val | Thr | Pro | Arg | Leu | Ala | Lys | Arg | Ala |
|---|---|---|---|---|---|---|---|---|---|---|---|---|---|---|---|
| | 50 | | | | | 55 | | | | | 60 | | | | |

| Arg | Arg | Ser | Phe | Ser | Ser | Leu | Gly | Gln | Trp | Ser | Trp | Glu | Thr | Val | Asp |
|---|---|---|---|---|---|---|---|---|---|---|---|---|---|---|---|
| 65 | | | | | 70 | | | | | 75 | | | | | 80 |

| Asp | Ile | Asp | Leu | Gly | His | His | Ile | Arg | His | Asp | Ala | Leu | Pro | Ala | Pro |
|---|---|---|---|---|---|---|---|---|---|---|---|---|---|---|---|
| | | | | 85 | | | | | 90 | | | | | 95 | |

| Gly | Gly | Glu | Ala | Glu | Leu | Met | Ala | Leu | Cys | Ser | Arg | Leu | His | Gly | Ser |
|---|---|---|---|---|---|---|---|---|---|---|---|---|---|---|---|
| | | | 100 | | | | | 105 | | | | | 110 | | |

| Leu | Leu | Asp | Arg | Ser | Arg | Pro | Leu | Trp | Glu | Met | His | Leu | Ile | Glu | Gly |
|---|---|---|---|---|---|---|---|---|---|---|---|---|---|---|---|
| | | 115 | | | | | 120 | | | | | 125 | | | |

| Leu | Ser | Asp | Gly | Arg | Phe | Ala | Val | Tyr | Thr | Lys | Ile | His | His | Ala | Val |
|---|---|---|---|---|---|---|---|---|---|---|---|---|---|---|---|
| | 130 | | | | | 135 | | | | | 140 | | | | |

| Ala | Asp | Gly | Val | Thr | Ala | Met | Lys | Met | Leu | Arg | Asn | Ala | Leu | Ser | Glu |
|---|---|---|---|---|---|---|---|---|---|---|---|---|---|---|---|
| 145 | | | | | 150 | | | | | 155 | | | | | 160 |

| Asn | Ser | Asp | Asp | Arg | Asp | Val | Pro | Ala | Pro | Trp | Gln | Pro | Arg | Gly | Pro |
|---|---|---|---|---|---|---|---|---|---|---|---|---|---|---|---|
| | | | | 165 | | | | | 170 | | | | | 175 | |

| Arg | Pro | Gln | Arg | Thr | Pro | Ser | Ser | Lys | Gly | Phe | Ser | Leu | Ser | Gly | Leu |
|---|---|---|---|---|---|---|---|---|---|---|---|---|---|---|---|
| | | | 180 | | | | | 185 | | | | | 190 | | |

| Ala | Gly | Ser | Thr | Leu | Arg | Thr | Ala | Arg | Glu | Thr | Val | Gly | Glu | Val | Ala |
|---|---|---|---|---|---|---|---|---|---|---|---|---|---|---|---|
| | | 195 | | | | | 200 | | | | | 205 | | | |

| Gly | Leu | Val | Pro | Ala | Leu | Ala | Gly | Thr | Val | Ser | Arg | Ala | Phe | Arg | Asp |
|---|---|---|---|---|---|---|---|---|---|---|---|---|---|---|---|
| | 210 | | | | | 215 | | | | | 220 | | | | |

| Gln | Gly | Gly | Pro | Leu | Ala | Leu | Ser | Ala | Pro | Lys | Thr | Pro | Phe | Asn | Val |
|---|---|---|---|---|---|---|---|---|---|---|---|---|---|---|---|
| 225 | | | | | 230 | | | | | 235 | | | | | 240 |

| Pro | Ile | Thr | Gly | Ala | Arg | Gln | Phe | Ala | Ala | Gln | Ser | Trp | Pro | Leu | Glu |
|---|---|---|---|---|---|---|---|---|---|---|---|---|---|---|---|
| | | | | 245 | | | | | 250 | | | | | 255 | |

| Arg | Leu | Arg | Leu | Val | Ala | Lys | Leu | Ser | Asp | Ser | Thr | Ile | Asn | Asp | Val |
|---|---|---|---|---|---|---|---|---|---|---|---|---|---|---|---|
| | | | 260 | | | | | 265 | | | | | 270 | | |

| Val | Leu | Ala | Met | Ser | Ser | Gly | Ala | Leu | Arg | Ser | Tyr | Leu | Glu | Asp | Gln |
|---|---|---|---|---|---|---|---|---|---|---|---|---|---|---|---|
| | | 275 | | | | | 280 | | | | | 285 | | | |

| Asn | Ala | Leu | Pro | Ala | Asp | Pro | Leu | Ile | Ala | Met | Val | Pro | Val | Ser | Leu |
|---|---|---|---|---|---|---|---|---|---|---|---|---|---|---|---|
| | 290 | | | | | 295 | | | | | 300 | | | | |

| Lys | Ser | Gln | Arg | Glu | Ala | Ala | Thr | Gly | Asn | Asn | Ile | Gly | Val | Leu | Met |
|---|---|---|---|---|---|---|---|---|---|---|---|---|---|---|---|
| 305 | | | | | 310 | | | | | 315 | | | | | 320 |

| Cys | Asn | Leu | Gly | Thr | His | Leu | Arg | Glu | Pro | Ala | Asp | Arg | Leu | Glu | Thr |
|---|---|---|---|---|---|---|---|---|---|---|---|---|---|---|---|
| | | | | 325 | | | | | 330 | | | | | 335 | |

| Ile | Arg | Thr | Ser | Met | Arg | Glu | Gly | Lys | Glu | Ala | Tyr | Gly | Ser | Met | Thr |
|---|---|---|---|---|---|---|---|---|---|---|---|---|---|---|---|
| | | | 340 | | | | | 345 | | | | | 350 | | |

| Ala | Thr | Gln | Ile | Leu | Ala | Met | Ser | Ala | Leu | Gly | Ala | Ala | Pro | Ile | Gly |
|---|---|---|---|---|---|---|---|---|---|---|---|---|---|---|---|
| | | 355 | | | | | 360 | | | | | 365 | | | |

```
Ala Ser Met Leu Phe Gly His Asn Ser Arg Val Arg Pro Pro Phe Asn
        370                 375                 380
Leu Ile Ile Ser Asn Val Pro Gly Pro Ser Ser Pro Leu Tyr Trp Asn
    385                 390                 395                 400
Gly Ala Arg Leu Asp Ala Ile Tyr Pro Leu Ser Val Pro Val Asp Gly
                405                 410                 415
Gln Gly Leu Asn Ile Thr Cys Thr Ser Asn Asp Asp Ile Ile Ser Phe
            420                 425                 430
Gly Val Thr Gly Cys Arg Ser Ala Val Pro Asp Leu Lys Ser Ile Pro
            435                 440                 445
Ala Arg Leu Gly His Glu Leu Arg Ala Leu Glu Arg Ala Val Gly Ile
    450                 455                 460
```

<210> SEQ ID NO 77
<211> LENGTH: 1407
<212> TYPE: DNA
<213> ORGANISM: Rhodococcus opacus

<400> SEQUENCE: 77

| | | | | | | |
|---|---|---|---|---|---|---|
| atggccccga | ccgactccct | gttcctgctg | ggcgaatccc | gcgagcaccc | gatgcacgtg | 60 |
| ggcggcctgg | cggtcttcac | cccggcgagg | ggcagctcgg | ccgcgacgt | ccgcgccatg | 120 |
| ttcgacgccg | cgctggtcgg | cgaccgggtg | gccgcgccgt | tccgcaagcg | ggcccgccgg | 180 |
| agcgtgacct | cgctgggcca | gtggggctgg | gacaccctgc | gcgacgacga | ggtcgacctg | 240 |
| gaacaccatg | tgcgccggga | cgccctgccg | cagccgggtg | gcatggcgga | actgatgacc | 300 |
| ctggtctccc | gcctgcatgg | caccctgctg | accgcagcc | ggccgctgtg | ggagatgcac | 360 |
| ctgatcgaag | gcctggccga | cggccggtac | gcggtgtata | ccaagatcca | ccatgccctg | 420 |
| gcggacggcg | ccagcgcgat | cgccctgctg | cgggactcga | tgtccgagga | cccgcatcgc | 480 |
| cggaacatgc | cgacccctg | gcagccgcgc | aacccctgt | cggccgtccc | ggacgccggc | 540 |
| gtcgcggtga | ccccggccc | cggcagcgcc | ctgcccgcga | tggcctggga | cgccgcgcgc | 600 |
| tccgccgcgg | gcgaagtcgc | cggcctgctg | ccggccgcgc | tgggcaccgt | ggaccgggcc | 660 |
| ctgcacggca | agggcggcgc | cctgtccctg | accgcgccgc | ataccctgtt | caacgtcccc | 720 |
| atcagcggcg | cccgccacgt | ggccgcgcgg | tcgttcccga | tcgagcgcat | ccggctgctg | 780 |
| gccaagcatg | ccgacgcgac | catcaacgac | atcgtgctga | ccatgtgcgc | cggcaccctg | 840 |
| cgcgcgtacc | tgcacacccg | cgacgccctg | ccggacaacc | cctgatcgc | gatggtcccg | 900 |
| gtgagcctgc | gcgccccga | aaccggcacc | ggcgaccgcg | ccctggcgg | caaccgggtc | 960 |
| ggcgtgctga | tgtgcaacct | ggccacccac | ctgccggacc | ccgcgcatcg | cctggagacc | 1020 |
| gtccggaact | gcatgaacga | aggcaaggcc | gcgctgcagg | ccatgtcgcc | ggcgcaggtc | 1080 |
| ctggccatgt | ccgcgctggg | cgccgcgccg | ctgggcgtgg | agatgttcct | gggccgccgg | 1140 |
| ggccccctgc | gcccgccctt | caacgtcgtg | atctcgaacg | tggcgggccc | cgcgcacccc | 1200 |
| ctgtactgga | acgcgcccg | gctggaatcc | ctgtatccgc | tgagcatccc | caccaccggc | 1260 |
| caggccctga | acatcacctg | cacctccagc | gacgaccaga | tcgtcttcgg | cctgaccggc | 1320 |
| tgccgccgga | ccgtgccgga | cctgcacccc | atgctggacc | agctggacgc | ggagctggac | 1380 |
| ctgctggaaa | ccgcggtcgg | cctgtga | | | | 1407 |

<210> SEQ ID NO 78
<211> LENGTH: 468
<212> TYPE: PRT
<213> ORGANISM: Rhodococcus opacus -continued

```
<400> SEQUENCE: 78

Met Ala Pro Thr Asp Ser Leu Phe Leu Leu Gly Glu Ser Arg Glu His
1               5                   10                  15

Pro Met His Val Gly Gly Leu Ala Val Phe Thr Pro Ala Glu Gly Ser
            20                  25                  30

Ser Ala Ala Asp Val Arg Ala Met Phe Asp Ala Ala Leu Val Gly Asp
        35                  40                  45

Arg Val Ala Ala Pro Phe Arg Lys Arg Ala Arg Ser Val Thr Ser
    50                  55                  60

Leu Gly Gln Trp Gly Trp Asp Thr Leu Arg Asp Asp Glu Val Asp Leu
65                  70                  75                  80

Glu His His Val Arg Arg Asp Ala Leu Pro Gln Pro Gly Gly Met Ala
                85                  90                  95

Glu Leu Met Thr Leu Val Ser Arg Leu His Gly Thr Leu Leu Asp Arg
            100                 105                 110

Ser Arg Pro Leu Trp Glu Met His Leu Ile Glu Gly Leu Ala Asp Gly
        115                 120                 125

Arg Tyr Ala Val Tyr Thr Lys Ile His His Ala Leu Ala Asp Gly Ala
    130                 135                 140

Ser Ala Met Arg Leu Leu Arg Asp Ser Met Ser Glu Asp Pro His Arg
145                 150                 155                 160

Arg Asn Met Pro Thr Pro Trp Gln Pro Arg Asn Pro Leu Ser Ala Val
                165                 170                 175

Pro Asp Ala Gly Val Ala Val Thr Pro Gly Pro Gly Ser Ala Leu Pro
            180                 185                 190

Ala Met Ala Trp Asp Ala Ala Arg Ser Ala Ala Gly Glu Val Ala Gly
        195                 200                 205

Leu Leu Pro Ala Ala Leu Gly Thr Val Asp Arg Ala Leu His Gly Lys
210                 215                 220

Gly Gly Ala Leu Ser Leu Thr Ala Pro His Thr Leu Phe Asn Val Pro
225                 230                 235                 240

Ile Ser Gly Ala Arg His Val Ala Ala Arg Ser Phe Pro Ile Glu Arg
                245                 250                 255

Ile Arg Leu Leu Ala Lys His Ala Asp Ala Thr Ile Asn Asp Ile Val
            260                 265                 270

Leu Thr Met Cys Ala Gly Thr Leu Arg Ala Tyr Leu His Thr Arg Asp
        275                 280                 285

Ala Leu Pro Asp Asn Pro Leu Ile Ala Met Val Pro Val Ser Leu Arg
    290                 295                 300

Ala Pro Glu Thr Gly Thr Gly Asp Arg Ala Pro Gly Gly Asn Arg Val
305                 310                 315                 320

Gly Val Leu Met Cys Asn Leu Ala Thr His Leu Pro Asp Pro Ala His
                325                 330                 335

Arg Leu Glu Thr Val Arg Asn Cys Met Asn Glu Gly Lys Ala Ala Leu
            340                 345                 350

Gln Ala Met Ser Pro Ala Gln Val Leu Ala Met Ser Ala Leu Gly Ala
        355                 360                 365

Ala Pro Leu Gly Val Glu Met Phe Leu Gly Arg Arg Gly Pro Leu Arg
    370                 375                 380

Pro Pro Phe Asn Val Val Ile Ser Asn Val Ala Gly Pro Arg Thr Pro
385                 390                 395                 400

Leu Tyr Trp Asn Gly Ala Arg Leu Glu Ser Leu Tyr Pro Leu Ser Ile
```

```
              405                 410                 415
Pro Thr Thr Gly Gln Ala Leu Asn Ile Thr Cys Thr Ser Ser Asp Asp
            420                 425                 430

Gln Ile Val Phe Gly Leu Thr Gly Cys Arg Arg Thr Val Pro Asp Leu
            435                 440                 445

His Pro Met Leu Asp Gln Leu Asp Ala Glu Leu Asp Leu Leu Glu Thr
    450                 455                 460

Ala Val Gly Leu
465

<210> SEQ ID NO 79
<211> LENGTH: 11299
<212> TYPE: DNA
<213> ORGANISM: Artificial Sequence
<220> FEATURE:
<223> OTHER INFORMATION: pCM132

<400> SEQUENCE: 79 gacccttcc   gacgctcacc  gggctggttg  ccctcgccgc  tgggctggcg  gccgtctatg     60
gccctgcaaa  cgcgccagaa  acgccgtcga  agccgtgtgc  gagacaccgc  ggccgccggc    120
gttgtggata  cctcgcggaa  aacttggccc  tcactgacag  atgaggggcg  gacgttgaca    180
cttgaggggc  cgactcaccc  ggcgcggcgt  tgacagatga  ggggcaggct  cgatttcggc    240
cggcgacgtg  gagctggcca  gcctcgcaaa  tcggcgaaaa  cgcctgattt  tacgcgagtt    300
tcccacagat  gatgtggaca  agcctgggga  taagtgccct  gcggtattga  cacttgaggg    360
gcgcgactac  tgacagatga  ggggcgcgat  ccttgacact  tgaggggcag  agtgctgaca    420
gatgaggggc  gcacctattg  acatttgagg  ggctgtccac  aggcagaaaa  tccagcattt    480
gcaagggttt  ccgcccgttt  ttcggccacc  gctaacctgt  cttttaacct  gcttttaaac    540
caatatttat  aaaccttgtt  tttaaccagg  gctgcgccct  gtgcgcgtga  ccgcgcacgc    600
cgaagggggg  tgcccccct   tctcgaaccc  tcccggcccg  ctaacgcggg  cctcccatcc    660
ccccagggcc  tgcgcccctc  ggccgcgaac  ggcctcaccc  caaaaatggc  agccaagctg    720
accacttctg  cgctcggccc  ttccggctgg  ctggtttatt  gctgataaat  ctggagccgg    780
tgagcgtggg  tctcgcggta  tcattgcagc  actggggcca  gatggtaagc  cctcccgtat    840
cgtagttatc  tacacgacgg  ggagtcaggc  aactatggat  gaacgaaata  gacagatcgc    900
tgagataggt  gcctcactga  ttaagcattg  gtaactgtca  gaccaagttt  actcatatat    960
actttagatt  gatttaaaac  ttcattttta  atttaaaagg  atctaggtga  agatcctttt   1020
tgataatctc  atgaccaaaa  tcccttaacg  tgagttttcg  ttccactgag  cgtcagaccc   1080
cgtagaaaag  atcaaaggat  cttcttgaga  tccttttttt  ctgcgcgtaa  tctgctgctt   1140
gcaaacaaaa  aaaccaccgc  taccagcggt  ggtttgtttg  ccggatcaag  agctaccaac   1200 tcttttccg   aaggtaactg  gcttcagcag  agcgcagata  ccaaatactg  tccttctagt   1260
gtagccgtag  ttaggccacc  acttcaagaa  ctctgtagca  ccgcctacat  acctcgctct   1320
gctaatcctg  ttaccagtgg  ctgctgccag  tggcgataag  tcgtgtctta  ccgggttgga   1380
ctcaagacga  tagttaccgg  ataaggcgca  gcggtcgggc  tgaacggggg  gttcgtgcac   1440
acagcccagc  ttggagcgaa  cgacctacac  cgaactgaga  tacctacagc  gtgagctatg   1500
agaaagcgcc  acgcttcccg  aagggagaaa  ggcggacagg  tatccggtaa  gcggcagggt   1560
cggaacagga  gagcgcacga  gggagcttcc  agggggaaac  gcctggtatc  tttatagtcc   1620
tgtcgggttt  cgccacctct  gacttgagcg  tcgatttttg  tgatgctcgt  caggggggcg   1680
```

```
gagcctatgg aaaaacgcca gcaacgcggc cttttttacgg ttcctggcct tttgctggcc   1740
ttttgctcac atgttctttc ctgcgttatc ccctgattct gtggataacc gtattaccgc   1800
ctttgagtga gctgataccg ctcgccgcag ccgaacgacc gagcgcagcg agtcagtgag   1860
cgaggaagcg gaagagcgcc caatacgcaa accgcctctc cccgcgcgtt ggccgattca   1920
ttaatgcagc tggcacgaca ggtttcccga ctggaaagcg ggcagtgagc gcaacgcaat   1980
taatgtgagt tagctcactc attaggcacc ccaggcttta cactttatgc ttccggctcg   2040
tatgttgtgt ggaattgtga gcggataaca atttcacaca ggaaacagct atgaccatga   2100
ttacgccaag cttgcatgcc tgcaggtcga ctctagagga tcaattcggc ttccaccgga   2160
attagcttga aatagtacat aatggatttc cttacgcgaa atacgggcag acatggcctg   2220
cccggttatt attatttttg acaccagacc aactggtaat ggtagcgacc ggcgctcagc   2280
tgtaattccg ccgatactga cgggctccag gagtcgtcgc caccaatccc catatggaaa   2340
ccgtcgatat tcagccatgt gccttcttcc gcgtgcagca gatggcgatg gctggtttcc   2400
atcagttgct gttgactgta gcggctgatg ttgaactgga agtcgccgcg ccactggtgt   2460
gggccataat tcaattcgcg cgtcccgcag cgcagaccgt tttcgctcgg gaagacgtac   2520
ggggtataca tgtctgacaa tggcagatcc cagcggtcaa acaggcggc agtaaggcgg   2580
tcggatagt tttcttgcgg ccctaatccg agccagttta cccgctctgc tacctgcgcc   2640
agctggcagt tcaggccaat ccgcgccgga tgcggtgtat cgctcgccac ttcaacatca   2700
acggtaatcg ccatttgacc actaccatca atccggtagg ttttccggct gataaataag   2760
gttttcccct gatgctgcca cgcgtgagcg gtcgtaatca gcaccgcatc agcaagtgta   2820
tctgccgtgc actgcaacaa cgctgcttcg gcctggtaat ggcccgccgc cttccagcgt   2880
tcgacccagg cgttagggtc aatgcgggtc gcttcactta cgccaatgtc gttatccagc   2940
ggtgcacggg tgaactgatc gcgcagcggc gtcagcagtt gttttttatc gccaatccac   3000
atctgtgaaa gaaagcctga ctggcggtta aattgccaac gcttattacc cagctcgatg   3060
caaaaatcca tttcgctggt ggtcagatgc gggatggcgt gggacgcggc ggggagcgtc   3120
acactgaggt tttccgccag acgccactgc tgccaggcgc tgatgtgccc ggcttctgac   3180
catgcggtcg cgttcggttg cactacgcgt actgtgagcc agagttgccc ggcgctctcc   3240
ggctgcggta gttcaggcag ttcaatcaac tgtttacctt gtggagcgac atccagaggc   3300
acttcaccgc ttgccagcgg cttaccatcc agcgccacca tccagtgcag gagctcgtta   3360
tcgctatgac ggaacaggta ttcgctggtc acttcgatgg tttgcccgga taaacggaac   3420
tggaaaaact gctgctggtg ttttgcttcc gtcagcgctg gatgcggcgt gcggtcggca   3480
aagaccagac cgttcataca gaactggcga tcgttcggcg tatcgccaaa atcaccgccg   3540
taagccgacc acgggttgcc gttttcatca tatttaatca gcgactgatc cacccagtcc   3600
cagacgaagc cgccctgtaa acggggatac tgacgaaacg cctgccagta tttagcgaaa   3660
ccgccaagac tgttacccat cgcgtgggcg tattcgcaaa ggatcagcgg gcgcgtctct   3720
ccaggtagcg aaagccattt tttgatggac catttcggca cagccgggaa gggctggtct   3780
tcatccacgc gcgcgtacat cggcaaaata atatcggtgg ccgtggtgtc ggctccgccg   3840
ccttcatact gcaccgggcg ggaaggatcg acagatttga tccagcgata cagcgcgtcg   3900
tgattagcgc cgtggcctga ttcattcccc agcgaccaga tgatcacact cgggtgatta   3960
cgatcgcgct gcaccattcg cgttacgcgt tcgctcatcg ccggtagcca gcgcggatca   4020
```

-continued

```
tcggtcagac gattcattgg caccatgccg tgggtttcaa tattggcttc atccaccaca    4080
tacaggccgt agcggtcgca cagcgtgtac cacagcggat ggttcggata atgcgaacag    4140
cgcacggcgt taaagttgtt ctgcttcatc agcaggatat cctgcaccat cgtctgctca    4200
tccatgacct gaccatgcag aggatgatgc tcgtgacggt taacgcctcg aatcagcaac    4260
ggcttgccgt tcagcagcag cagaccattt tcaatccgca cctcgcggaa accgacatcg    4320
caggcttctg cttcaatcag cgtgccgtcg cggtgtgca gttcaaccac cgcacgatag     4380
agattcggga tttcggcgct ccacagtttc gggttttcga cgttcagacg tagtgtgacg    4440
cgatcggcat aaccaccacg ctcatcgata atttcaccgc cgaaaggcgc ggtgccgctg    4500
gcgacctgcg tttcacccctg ccataaagaa actgttaccc gtaggtagtc acgcaactcg   4560
ccgcacatct gaacttcagc ctccagtaca gcgcggctga aatcatcatt aaagcgagtg    4620
gcaacatgga aatcgctgat ttgtgtagtc ggtttatgca gcaacgagac gtcacggaaa   4680
atgccgctca tccgccacat atcctgatct tccagataac tgccgtcact ccaacgcagc   4740
accatcaccg cgaggcggtt ttctccggcg cgtaaaaatg cgctcaggtc aaattcagac    4800
ggcaaacgac tgtcctggcc gtaaccgacc cagcgcccgt tgcaccacag atgaaacgcc    4860
gagttaacgc catcaaaaat aattcgcgtc tggccttcct gtagccagct ttcatcaaca    4920
ttaaatgtga gcgagtaaca acccgtcgga ttctccgtgg gaacaaacgg cggattgacc    4980
gtaatgggat aggttacgtt ggtgtagatg ggcgcatcgt aaccgtgcat ctgccagttt    5040
gaggggacga cgacagtatc ggcctcagga agatcgcact ccagccagct ttccggcacc   5100
gcttctggtg ccgaaaacca ggcaaagcgc cattcgccat tcaggctgcg caactgttgg   5160
gaagggcgat cggtgcgggc ctcttcgcta ttacgccagc tggcgaaagg gggatgtgct    5220
gcaaggcgat taagttgggt aacgccaggg ttttcccggt cgacccgtaa tcttacgtca    5280
gtaacttcca cagtagttca ccacctttttc cctatagatc ttccgtgcag tttaagccga   5340
attgatcccc gggtaccgag ctcgaatcta gaattccctg cttttcctgat gcaaaaacga   5400 ggctagttta ccgtatctgt gggggggatgg cttgtagata tgacgacagg aagagtttgt   5460
agaaacgcaa aaaggccatc cgtcaggatg gccttctgct taatttgatg cctggcagtt    5520
tatggcgggc gtcctgcccg ccaccctccg ggccgttgct tcgcaacgtt caaatccgct    5580
cccggcggat ttgtcctact caggagagcg ttcaccgaca aacaacagat aaaacgaaag    5640
gcccagtctt tcgactgagc ctttcgtttt atttgatgcc tggcagttcc ctactctcgc    5700
atggggagac cccacactac catcggcgct acggcgtttc acttctgagt tcggcatggg   5760
gtcaggtggg accaccgcgc tactgccgcc aggcaaattc tgttttatca gaccgcttct    5820
gcgttctgat ttaatctgta tcaggctgaa aaattcactg gccgtcgttt tacaacgtcg    5880
tgactgggaa aaccctggcg ttacccaact taatcgcctt gcagcacatc cccctttcgc    5940
cagctggcgt aatagcgaag aggcccgcac cgatcgccct tcccaacagt tgcgcagcct    6000
gaatggcgaa tggcgcctga tgcggtattt tctccttacg catctgtgcg gtatttcaca    6060
ccgcatatgg tgcactctca gtacaatctg ctctgatgcc gcatagttaa gccagccccg    6120
acacccgcca cacccgctg acgcgccctg acgggcttgt ctgctcccgg catccgctta    6180
cagacaagct gtgaccgtct ccgggagctg catgtgtcag aggttttcac cgtcatcacc    6240
gaaacgcgcg agacgaaagg gcctcgtgat acgcctattt ttataggtta atgtcatgat    6300
aataatggtt tcttagcacc cttttctcgg ccttcaacgt tcctgacaac gagcctcctt    6360
ttcgccaatc catcgacaat caccgcgagt ccctgctcga acgctgcgtc cggaccggct    6420
```

-continued

```
tcgtcgaagg cgtctatcgc ggcccgcaac agcggcgaga gcggagcctg ttcaacggtg    6480
ccgccgcgct cgccggcatc gctgtcgccg gcctgctcct caagcacggc cccaacagtg    6540
aagtagctga ttgtcatcag cgcattgacg gcgtccccgg ccgaaaaacc cgcctcgcag    6600
aggaagcgaa gctgcgcgtc ggccgtttcc atctgcggtg cgcccggtcg cgtgccggca    6660
tggatgcgcg cgccatcgcg gtaggcgagc agcgcctgcc tgaagctgcg ggcattcccg    6720
atcagaaatg agcgccagtc gtcgtcggct ctcggcaccg aatgcgtatg attctccgcc    6780
agcatggctt cggccagtgc gtcgagcagc gcccgcttgt tcctgaagtg ccagtaaagc    6840
gccggctgct gaaccccaa ccgttccgcc agtttgcgtg tcgtcagacc gtctacgccg     6900
acctcgttca acaggtccag ggcggcacgg atcactgtat tcggctgcaa ctttgtcatg    6960
attgacactt tatcactgat aaacataata tgtccaccaa cttatcagtg ataaagaatc    7020
cgcgcgttca atcggaccag cggaggctgg tccggaggcc agacgtgaaa cccaacatac    7080
ccctgatcgt aattctgagc actgtcgcgc tcgacgctgt cggcatcggc ctgattatgc    7140
cggtgctgcc gggcctcctg cgcgatctgg ttcactcgaa cgacgtcacc gcccactatg    7200
gcattctgct ggcgctgtat gcgttggtgc aatttgcctg cgcacctgtg ctgggcgcgc    7260
tgtcggatcg tttcgggcgg cggccaatct tgctcgtctc gctggccggc gccactgtcg    7320
actacgccat catggcgaca gcgccttttcc tttgggttct ctatatcggg cggatcgtgg    7380
ccggcatcac cggggcgact ggggcggtag ccggcgctta tattgccgat gacctgcagg    7440
gggggggggg cgctgaggtc tgcctcgtga agaaggtgtt gctgactcat accaggcctg    7500
aatcgcccca tcatccagcc agaaagtgag ggagccacgg ttgatgagag ctttgttgta    7560
ggtggaccag ttggtgattt tgaacttttg ctttgccacg gaacggtctg cgttgtcggg    7620
aagatgcgtg atctgatcct tcaactcagc aaaagttcga tttattcaac aaagccgccg    7680
tcccgtcaag tcagcgtaat gctctgccag tgttacaacc aattaaccaa ttctgattag    7740
aaaaactcat cgagcatcaa atgaaactgc aatttattca tatcaggatt atcaatacca    7800
tatttttgaa aaagccgttt ctgtaatgaa ggagaaaact caccgaggca gttccatagg    7860
atggcaagat cctggtatcg gtctgcgatt ccgactcgtc caacatcaat acaacctatt    7920
aatttcccct cgtcaaaaat aaggttatca agtgagaaat caccatgagt gacgactgaa    7980
tccggtgaga atggcaaaag cttatgcatt tctttccaga cttgttcaac aggccagcca    8040
ttacgctcgt catcaaaatc actcgcatca accaaaccgt tattcattcg tgattgcgcc    8100
tgagcgagac gaaatacgcg atcgctgtta aaaggacaat tacaaacagg aatcgaatgc    8160
aaccggcgca ggaacactgc cagcgcatca acaatatttt cacctgaatc aggatattct    8220
tctaatacct ggaatgctgt tttcccgggg atcgcagtgg tgagtaacca tgcatcatca    8280
ggagtacgga taaaatgctt gatggtcgga agaggcataa attccgtcag ccagtttagt    8340
ctgaccatct catctgtaac atcattggca acgctacctt tgccatgttt cagaaacaac    8400
tctggcgcat cgggcttccc atacaatcga tagattgtcg cacctgattg cccgacatta    8460
tcgcgagccc atttataccc atataaatca gcatccatgt tggaatttaa tcgcggcctc    8520
gagcaagacg tttcccgttg aatatggctc ataacacccc ttgtattact gtttatgtaa    8580
gcagacagtt ttattgttca tgatgatata tttttatctt gtgcaatgta acatcagaga    8640
ttttgagaca caacgtggct ttccccccccc ccctgcagg tccgacacgg ggatggatgg    8700
cgttcccgat catggtcctg cttgcttcgg gtggcatcgg aatgccggcg ctgcaagcaa    8760
```

```
tgttgtccag gcaggtggat gaggaacgtc aggggcagct gcaaggctca ctggcggcgc    8820
tcaccagcct gacctcgatc gtcggacccc tcctcttcac ggcgatctat gcggcttcta    8880
taacaacgtg gaacgggtgg gcatggattg caggcgctgc cctctacttg ctctgcctgc    8940
cggcgctgcg tcgcgggctt tggagcggcg cagggcaacg agccgatcgc tgatcgtgga    9000
aacgataggc ctatgccatg cgggtcaagg cgacttccgg caagctatac gcgccctaga    9060
attgtcaatt ttaatcctct gtttatcggc agttcgtaga gcgcgccgtg cgtcccgagc    9120
gatactgagc gaagcaagtg cgtcgagcag tgcccgcttg ttcctgaaat gccagtaaag    9180
cgctggctgc tgaaccccca gccggaactg accccacaag gccctagcgt ttgcaatgca    9240
ccaggtcatc attgacccag gcgtgttcca ccaggccgct gcctcgcaac tcttcgcagg    9300
cttcgccgac ctgctcgcgc cacttcttca cgcgggtgga atccgatccg cacatgaggc    9360
ggaaggtttc cagcttgagc gggtacggct cccggtgcga gctgaaatag tcgaacatcc    9420
gtcgggccgt cggcgacagc ttgcggtact tctcccatat gaatttcgtg tagtggtcgc    9480
cagcaaacag cacgacgatt tcctcgtcga tcaggacctg gcaacgggac gttttcttgc    9540
cacggtccag gacgcggaag cggtgcagca gcgacaccga ttccaggtgc ccaacgcggt    9600
cggacgtgaa gcccatcgcc gtcgcctgta ggcgcgacag gcattcctcg gccttcgtgt    9660
aataccggcc attgatcgac cagcccaggt cctggcaaag ctcgtagaac gtgaaggtga    9720
tcggctcgcc gataggggtg cgcttcgcgt actccaacac ctgctgccac accagttcgt    9780
catcgtcggc ccgcagctcg acgccggtgt aggtgatctt cacgtccttg ttgacgtgga    9840
aaatgacctt gttttgcagc gcctcgcgcg ggattttctt gttgcgcgtg gtgaacaggg    9900
cagagcgggc cgtgtcgttt ggcatcgctc gcatcgtgtc cggccacggc gcaatatcga    9960
acaaggaaag ctgcatttcc ttgatctgct gcttcgtgtg tttcagcaac gcggcctgct    10020
tggcctcgct gacctgtttt gccaggtcct cgccggcggt ttttcgcttc ttggtcgtca    10080
tagttcctcg cgtgtcgatg gtcatcgact tcgccaaacc tgccgcctcc tgttcgagac    10140
gacgcgaacg ctccacggcg gccgatggcg cgggcagggc aggggagcc agttgcacgc    10200 tgtcgcgctc gatcttggcc gtagcttgct ggaccatcga gccgacggac tggaaggttt    10260
cgcggggcgc acgcatgacg gtgcggcttg cgatggtttc ggcatcctcg gcggaaaacc    10320
ccgcgtcgat cagttcttgc ctgtatgcct tccggtcaaa cgtccgattc attcaccctc    10380
cttgcgggat tgccccgact cacgccgggg caatgtgccc ttattcctga tttgacccgc    10440
ctggtgcctt ggtgtccaga taatccacct tatcggcaat gaagtcggtc ccgtagaccg    10500
tctggccgtc cttctcgtac ttggtattcc gaatcttgcc ctgcacgaat accagctccg    10560
cgaagtcgct cttcttgatg gagcgcatgg ggacgtgctt ggcaatcacg cgcacccccc    10620
ggccgtttta gcggctaaaa aagtcatggc tctgccctcg ggcggaccac gcccatcatg    10680
accttgccaa gctcgtcctg cttctcttcg atcttcgcca gcagggcgag gatcgtggca    10740
tcaccgaacc gcgcgtgcg cgggtcgtcg gtgagccaga gtttcagcag gccgcccagg    10800
cggcccaggt cgccattgat gcgggccagc tcgcggacgt gctcatagtc cacgacgccc    10860
gtgattttgt agccctggcc gacggccagc aggtaggcct acaggctcat gccggccgcc    10920
gccgcctttt cctcaatcgc tcttcgttcg tctggaaggc agtacacctt gataggtggg    10980
ctgcccttcc tggttggctt ggtttcatca gccatccgct tgccctcatc tgttacgccg    11040
gcggtagccg gccagcctcg cagagcagga ttccgttga gcaccgccag gtgcgaataa    11100
gggacagtga agaaggaaca cccgctcgcg ggtgggccta cttcacctat cctgcccggc    11160
```

| | |
|---|---:|
| tgacgccgtt ggatacacca aggaaagtct cacgaaccc tttggcaaaa tcctgtatat | 11220 |
| cgtgcgaaaa aggatggata taccgaaaaa atcgctataa tgaccccgaa gcagggttat | 11280 |
| gcagcggaaa agatccgtc | 11299 |

<210> SEQ ID NO 80
<211> LENGTH: 7341
<212> TYPE: DNA
<213> ORGANISM: Artificial Sequence
<220> FEATURE:
<223> OTHER INFORMATION: pJSvec

<400> SEQUENCE: 80

| | |
|---|---:|
| gacccttttcc gacgctcacc gggctggttg ccctcgccgc tgggctggcg gccgtctatg | 60 |
| gccctgcaaa cgcgccagaa acgccgtcga agccgtgtgc gagacaccgc ggccgccggc | 120 |
| gttgtggata cctcgcggaa aacttggccc tcactgacag atgaggggcg gacgttgaca | 180 |
| cttgaggggc cgactcaccc ggcgcggcgt tgacagatga ggggcaggct cgatttcggc | 240 |
| cggcgacgtg gagctggcca gcctcgcaaa tcggcgaaaa cgcctgattt tacgcgagtt | 300 |
| tcccacagat gatgtggaca gcctggggga taagtgccct gcggtattga cacttgaggg | 360 |
| gcgcgactac tgacagatga ggggcgcgat ccttgacact tgaggggcag agtgctgaca | 420 |
| gatgaggggc gcacctattg acatttgagg ggctgtccac aggcagaaaa tccagcattt | 480 |
| gcaagggttt ccgcccgttt tcggccacc gctaacctgt cttttaacct gcttttaaac | 540 |
| caatatttat aaaccttgtt tttaaccagg gctgcgccct gtgcgcgtga ccgcgcacgc | 600 |
| cgaagggggg tgccccccct tctcgaaccc tcccggcccg ctaacgcggg cctcccatcc | 660 |
| ccccagggc tgcgcccctc ggccgcgaac ggcctcaccc caaaaatggc agccaagctg | 720 |
| accacttctg cgctcggccc ttccggctgg ctggtttatt gctgataaat ctggagccgg | 780 |
| tgagcgtggg tctcgcggta tcattgcagc actgggggcca gatggtaagc cctcccgtat | 840 |
| cgtagttatc tacacgacgg ggagtcaggc aactatggat gaacgaaata gacagatcgc | 900 |
| tgagataggt gcctcactga ttaagcattg gtaactgtca gaccaagttt actcatatat | 960 |
| actttagatt gatttaaaac ttcatttttta atttaaaagg atctaggtga agatcctttt | 1020 |
| tgataatctc atgaccaaaa tcccttaacg tgagtttttcg ttccactgag cgtcagaccc | 1080 |
| cgtagaaaag atcaaaggat cttcttgaga tcctttttttt ctgcgcgtaa tctgctgctt | 1140 |
| gcaaacaaaa aaaccaccgc taccagcggt ggtttgtttg ccggatcaag agctaccaac | 1200 |
| tcttttttccg aaggtaactg gcttcagcag agcgcagata ccaaatactg tccttctagt | 1260 |
| gtagccgtag ttaggccacc acttcaagaa ctctgtagca ccgcctacat acctcgctct | 1320 |
| gctaatcctg ttaccagtgg ctgctgccag tggcgataag tcgtgtctta ccgggttgga | 1380 |
| ctcaagacga tagttaccgg ataaggcgca gcggtcgggc tgaacggggg gttcgtgcac | 1440 |
| acagcccagc ttggagcgaa cgacctacac cgaactgaga tacctacagc gtgagctatg | 1500 |
| agaaagcgcc acgcttcccg aagggagaaa ggcggacagg tatccggtaa gcggcagggt | 1560 |
| cggaacagga gagcgcacga gggagcttcc agggggaaac gcctggtatc tttatagtcc | 1620 |
| tgtcgggttt cgccacctct gacttgagcg tcgatttttg tgatgctcgt caggggggcg | 1680 |
| gagcctatgg aaaaacgcca gcaacgcggc cttttttacgg ttcctggcct tttgctggcc | 1740 |
| ttttgctcac atgttctttc ctgcgttatc ccctgattct gtggataacc gtattaccgc | 1800 |
| ctttgagtga gctgataccg ctcgccgcag ccgaacgacc gagcgcagcg agtcagtgag | 1860 |

```
cgaggaagcg gaagagcgcc caatacgcaa accgcctctc cccgcgcgtt ggccgattca    1920
ttaatgcagc tggcaggaag cggcgatggc ggagctgaat tacattccca accgcgtggc    1980
acaacaactg gcgggcaaac agtcgttgct gattggcgtt gccacctcca gtctggccct    2040
gcacgcgccg tcgcaaattg tcgcggcgat taaatctcgc gccgatcaac tgggtgccag    2100
cgtggtggtg tcgatggtag aacgaagcgg cgtcgaagcc tgtaaagcgg cggtgcacaa    2160
tcttctcgcg caacgcgtca gtgggctgat cattaactat ccgctggatg accaggatgc    2220
cattgctgtg gaagctgcct gcactaatgt tccggcgtta tttcttgatg tctctgacca    2280
gacacccatc aacagtatta ttttctccca tgaagacggt acgcgactgg gcgtggagca    2340
tctggtcgca ttgggtcacc agcaaatcgc gctgttagcg ggcccattaa gttctgtctc    2400
ggcgcgtctg cgtctggctg gctggcataa atatctcact cgcaatcaaa ttcagccgat    2460
agcggaacgg gaaggcgact ggagtgccat gtccggtttt caacaaacca tgcaaatgct    2520
gaatgagggc atcgttccca ctgcgatgct ggttgccaac gatcagatgg cgctgggcgc    2580
aatgcgcgcc attaccgagt ccgggctgcg cgttggtgcg gatatctcgg tagtgggata    2640
cgacgatacc gaagacagct catgttatat cccgccgtca accaccatca aacaggattt    2700
tcgcctgctg gggcaaacca gcgtggaccg cttgctgcaa ctctctcagg ccaggcggt    2760
gaagggcaat cagctgttgc ccgtctcact ggtgaaaaga aaaccaccc tggcgcccaa    2820
tacgcaaacc gcctctcccc gcgcgttggc cgattcatta atgcagctgg cacgacaggt    2880
ttcccgactg gaaagcgggc agtgagcgca acgcaattaa tgtgagttag cgcgaattga    2940
tctggtttga cagcttatca tcgactgcac ggtgcaccaa tgcttctggc gtcaggcagc    3000
catcggaagc tgtggtatgg ctgtgcaggt cgtaaatcac tgcataattc gtgtcgctca    3060
aggcgcactc ccgttctgga taatgttttt tgcgccgaca tcataacggt tctggcaaat    3120
attctgaaat gagctgttga caattaatca tccggctcgt ataatgtgtg gaattgtgag    3180
cggataacaa tttcacacag gaaacagcgc cgctgagaaa aagcgaagcg gcactgctct    3240
ttaacaattt atcagacaat ctgtgtgggc actcgaccgg aattatcgat taactttatt    3300
attaaaaatt aaagaggtat atattaatgt atcgattaaa taaggaggaa taaacccaga    3360
acgcagaagc ggtctgataa aacagaattt gcctggcggc agtagcgcgg tggtcccacc    3420
tgacccccatg ccgaactcag aagtgaaacg ccgtagcgcc gatggtagtg tggggtctcc    3480
ccatgcgaga gtagggaact gccaggcatc aaataaaacg aaaggctcag tcgaaagact    3540
gggcctttcg ttttatctgt tgtttgtcgg tgaacgctct cctgagtagg acaaatcttg    3600
taggtggacc agttggtgat tttgaacttt tgctttgcca cggaacggtc tgcgttgtcg    3660
ggaagatgcg tgatctgatc cttcaactca gcaaaagttc gatttattca acaaagccgc    3720
cgtcccgtca agtcagcgta atgctctgcc agtgttacaa ccaattaacc aattctgatt    3780
agaaaaactc atcgagcatc aaatgaaact gcaatttatt catatcagga ttatcaatac    3840
catatttttg aaaaagccgt ttctgtaatg aaggagaaaa ctcaccgagg cagttccata    3900
ggatggcaag atcctggtat cggtctgcga ttccgactcg tccaacatca atacaaccta    3960
ttaatttccc ctcgtcaaaa ataaggttat caagtgagaa atcaccatga gtgacgactg    4020
aatccggtga gaatggcaaa agcttatgca tttctttcca gacttgttca acaggccagc    4080
cattacgctc gtcatcaaaa tcactcgcat caaccaaacc gttattcatt cgtgattgcg    4140
cctgagcgag acgaaatacg cgatcgctgt taaaaggaca attacaaaca ggaatcgaat    4200
gcaaccggcg caggaacact gccagcgcat caacaatatt ttcacctgaa tcaggatatt    4260
```

```
cttctaatac ctggaatgct gttttcccgg ggatcgcagt ggtgagtaac catgcatcat      4320
caggagtacg gataaaatgc ttgatggtcg gaagaggcat aaattccgtc agccagttta      4380
gtctgaccat ctcatctgta acatcattgg caacgctacc tttgccatgt ttcagaaaca      4440
actctggcgc atcgggcttc ccatacaatc gatagattgt cgcacctgat tgcccgacat      4500
tatcgcgagc ccatttatac ccatataaat cagcatccat gttggaattt aatcgcggcc      4560
tcgagcaaga cgtttcccgt tgaatatggc tcataacacc ccttgtatta ctgtttatgt      4620
aagcagacag ttttattgtt catgatgata tatttttatc ttgtgcaatg taacatcaga      4680
gattttgaga cacaacgtgg ctttccccccc cccccctgca ggtccgacac ggggatggat      4740
ggcgttcccg atcatggtcc tgcttgcttc gggtggcatc ggaatgccgg cgctgcaagc      4800
aatgttgtcc aggcaggtgg atgaggaacg tcaggggcag ctgcaaggct cactggcggc      4860
gctcaccagc ctgacctcga tcgtcggacc cctcctcttc acggcgatct atgcggcttc      4920
tataacaacg tggaacgggt gggcatggat tgcaggcgct gccctctact tgctctgcct      4980
gccggcgctg cgtcgcgggc tttggagcgg cgcagggcaa cgagccgatc gctgatcgtg      5040
gaaacgatag gcctatgcca tgcgggtcaa ggcgacttcc ggcaagctat acgcccctca      5100
gaattgtcaa ttttaatcct ctgtttatcg gcagttcgta gagcgcgccg tgcgtcccga      5160
gcgatactga gcgaagcaag tgcgtcgagc agtgcccgct tgttcctgaa atgccagtaa      5220
agcgctggct gctgaacccc cagccggaac tgaccccaca aggccctagc gtttgcaatg      5280
caccaggtca tcattgaccc aggcgtgttc caccaggccg ctgcctcgca actcttcgca      5340
ggcttcgccg acctgctcgc gccacttctt cacgcgggtg gaatccgatc cgcacatgag      5400
gcggaaggtt tccagcttga gcgggtacgg ctcccggtgc gagctgaaat agtcgaacat      5460
ccgtcgggcc gtcggcgaca gcttgcggta cttctcccat atgaatttcg tgtagtggtc      5520
gccagcaaac agcacgacga tttcctcgtc gatcaggacc tggcaacggg acgttttctt      5580
gccacggtcc aggacgcgga agcggtgcag cagcgacacc gattccaggt gcccaacgcg      5640
gtcggacgtg aagcccatcg ccgtcgcctg taggcgcgac aggcattcct cggccttcgt      5700
gtaataccgg ccattgatcg accagcccag gtcctggcaa agctcgtaga acgtgaaggt      5760
gatcggctcg ccgataggggg tgcgcttcgc gtactccaac acctgctgcc acaccagttc      5820
gtcatcgtcg gcccgcagct cgacgccggt gtaggtgatc ttcacgtcct tgttgacgtg      5880
gaaaatgacc ttgttttgca gcgcctcgcg cgggattttc ttgttgcgcg tggtgaacag      5940
ggcagagcgg gccgtgtcgt ttggcatcgc tcgcatcgtg tccggccacg gcgcaatatc      6000
gaacaaggaa agctgcattt ccttgatctg ctgcttcgtg tgtttcagca acgcggcctg      6060
cttggcctcg ctgacctgtt ttgccaggtc ctcgccggcg gttttcgct tcttggtcgt      6120 catagttcct cgcgtgtcga tggtcatcga cttcgccaaa cctgccgcct cctgttcgag      6180
acgacgcgaa cgctccacgg cggccgatgg cgcgggcagg gcaggggag ccagttgcac      6240 gctgtcgcgc tcgatcttgg ccgtagcttg ctggaccatc gagccgacgg actggaaggt      6300
ttcgcggggc gcacgcatga cggtgcggct tgcgatggtt tcggcatcct cggcggaaaa      6360
ccccgcgtcg atcagttctt gcctgtatgc cttccggtca acgtccgat tcattcaccc      6420 tccttgcggg attgccccga ctcacgccgg ggcaatgtgc ccttattcct gatttgacccc      6480 gcctggtgcc ttggtgtcca gataatccac cttatcggca atgaagtcgg tcccgtagac      6540
cgtctggccg tccttctcgt acttggtatt ccgaatcttg ccctgcacga ataccagctc      6600
```

| | |
|---|---|
| cgcgaagtcg ctcttcttga tggagcgcat ggggacgtgc ttggcaatca cgcgcacccc | 6660 |
| ccggccgttt tagcggctaa aaaagtcatg gctctgccct cgggcggacc acgcccatca | 6720 |
| tgaccttgcc aagctcgtcc tgcttctctt cgatcttcgc cagcagggcg aggatcgtgg | 6780 |
| catcaccgaa ccgcgccgtg cgcggtcgt cggtgagcca gagtttcagc aggccgccca | 6840 |
| ggcggcccag gtcgccattg atgcgggcca gctcgcggac gtgctcatag tccacgacgc | 6900 |
| ccgtgatttt gtagccctgg ccgacggcca gcaggtaggc ctacaggctc atgcggccg | 6960 |
| ccgccgcctt ttcctcaatc gctcttcgtt cgtctggaag gcagtacacc ttgataggtg | 7020 |
| ggctgcccttt cctggttggc ttggtttcat cagccatccg cttgccctca tctgttacgc | 7080 |
| cggcggtagc cggccagcct cgcagagcag gattcccgtt gagcaccgcc aggtgcgaat | 7140 |
| aagggacagt gaagaaggaa cacccgctcg cgggtgggcc tacttcacct atcctgcccg | 7200 |
| gctgacgccg ttggatacac caaggaaagt ctacacgaac cctttggcaa aatcctgtat | 7260 |
| atcgtgcgaa aaaggatgga tataccgaaa aaatcgctat aatgaccccg aagcagggtt | 7320 |
| atgcagcgga aaagatccgt c | 7341 |

<210> SEQ ID NO 81
<211> LENGTH: 10705
<212> TYPE: DNA
<213> ORGANISM: Artificial Sequence
<220> FEATURE:
<223> OTHER INFORMATION: pMZT3

<400> SEQUENCE: 81

| | |
|---|---|
| tcaccctgtc gggcaatgcc gaggcattct ggcagcagcg ccccctggcc tgtagtggat | 60 |
| tacgtgccgg tctgttccat cctaccaccg gctattcact gccgctggcg gttgccgtgg | 120 |
| ccgaccgcct gagcgcactt gatgtcttta cgtcggcctc aattcaccag gctattaggc | 180 |
| attttgcccg cgagcgctgg cagcagcagc gcttttttccg catgctgaat cgcatgctgt | 240 |
| ttttagccgg accgccgat tcacgctggc gggttatgca gcgttttat ggtttacctg | 300 |
| aagatttaat tgcccgtttt tatgcgggaa aactcacgct gaccgatcgg ctacgtattc | 360 |
| tgagcggcaa gccgcctgtt ccggtattag cagcattgca agccattatg acgactcatc | 420 |
| gttaagagac agaacgaagt gtgaccagaa cgcagaagcg gtctgataaa acagaatttg | 480 |
| cctggcggca gtagcgcggt ggtcccacct gaccccatgc cgaactcaga agtgaaacgc | 540 |
| cgtagcgccg atggtagtgt ggggtctccc catgcgagag tagggaactg ccaggcatca | 600 |
| aataaaacga aaggctcagt cgaaagactg ggcctttcgt tttatctgtt gtttgtcggt | 660 |
| gaacgctctc ctgagtagga caaatcttgt aggtggacca gttggtgatt ttgaactttt | 720 |
| gctttgccac ggaacggtct gcgttgtcgg gaagatgcgt gatctgatcc ttcaactcag | 780 |
| caaaagttcg atttattcaa caaagccgcc gtcccgtcaa gtcagcgtaa tgctctgcca | 840 |
| gtgttacaac caattaacca attctgatta gaaaaactca tcgagcatca aatgaaactg | 900 |
| caatttattc atatcaggat tatcaatacc atatttttga aaaagccgtt tctgtaatga | 960 |
| aggagaaaac tcaccgaggc agttccatag gatggcaaga tcctggtatc ggtctgcgat | 1020 |
| tccgactcgt ccaacatcaa tacaacctat taatttcccc tcgtcaaaaa taaggttatc | 1080 |
| aagtgagaaa tcaccatgag tgacgactga atccggtgag aatggcaaaa gcttatgcat | 1140 |
| ttctttccag acttgttcaa caggccagcc attacgctcg tcatcaaaat cactcgcatc | 1200 |
| aaccaaaccg ttattcattc gtgattgcgc ctgagcgaga cgaaatacgc gatcgctgtt | 1260 |
| aaaaggacaa ttacaaacag gaatcgaatg caaccggcgc aggaacactg ccagcgcatc | 1320 |

```
aacaatattt tcacctgaat caggatattc ttctaatacc tggaatgctg ttttcccggg      1380
gatcgcagtg gtgagtaacc atgcatcatc aggagtacgg ataaaatgct tgatggtcgg      1440
aagaggcata aattccgtca gccagtttag tctgaccatc tcatctgtaa catcattggc      1500
aacgctacct ttgccatgtt tcagaaacaa ctctggcgca tcgggcttcc catacaatcg      1560
atagattgtc gcacctgatt gcccgacatt atcgcgagcc catttatacc catataaatc      1620
agcatccatg ttggaattta atcgcggcct cgagcaagac gtttcccgtt gaatatggct      1680
cataacaccc cttgtattac tgtttatgta agcagacagt tttattgttc atgatgatat      1740 attttatct tgtgcaatgt aacatcagag attttgagac acaacgtggc tttccccccc      1800
ccccctgcag gtccgacacg gggatggatg gcgttcccga tcatggtcct gcttgcttcg      1860
ggtggcatcg gaatgccggc gctgcaagca atgttgtcca ggcaggtgga tgaggaacgt      1920
caggggcagc tgcaaggctc actggcggcg ctcaccagcc tgacctcgat cgtcggaccc      1980
ctcctcttca cggcgatcta tgcggcttct ataacaacgt ggaacgggtg gcatggatt      2040 gcaggcgctg ccctctactt gctctgcctg ccggcgctgc gtcgcgggct ttggagcggc      2100
gcagggcaac gagccgatcg ctgatcgtgg aaacgatagg cctatgccat gcgggtcaag      2160
gcgacttccg gcaagctata cgcgccctag aattgtcaat tttaatcctc tgtttatcgg      2220
cagttcgtag agcgcgccgt gcgtcccgag cgatactgag cgaagcaagt gcgtcgagca      2280
gtgcccgctt gttcctgaaa tgccagtaaa gcgctggctg ctgaaccccc agccggaact      2340
gaccccacaa ggccctagcg tttgcaatgc accaggtcat cattgaccca ggcgtgttcc      2400
accaggccgc tgcctcgcaa ctcttcgcag gcttcgccga cctgctcgcg ccacttcttc      2460
acgcgggtgg aatccgatcc gcacatgagg cggaaggttt ccagcttgag cgggtacggc      2520
tcccggtgcg agctgaaata gtcgaacatc cgtcgggccg tcggcgacag cttgcggtac      2580
ttctcccata tgaatttcgt gtagtggtcg ccagcaaaca gcacgacgat ttcctcgtcg      2640
atcaggacct ggcaacggga cgttttcttg ccacggtcca ggacgcggaa gcggtgcagc      2700
agcgacaccg attccaggtg cccaacgcgg tcggacgtga agcccatcgc cgtcgcctgt      2760
aggcgcgaca ggcattcctc ggccttcgtg taataccggc cattgatcga ccagcccagg      2820
tcctggcaaa gctcgtagaa cgtgaaggtg atcggctcgc cgatagggt gcgcttcgcg      2880 tactccaaca cctgctgcca caccagttcg tcatcgtcgg cccgcagctc gacgccggtg      2940
taggtgatct tcacgtcctt gttgacgtgg aaaatgacct tgttttgcag cgcctcgcgc      3000
gggattttct tgttgcgcgt ggtgaacagg gcagagcggg ccgtgtcgtt tggcatcgct      3060
cgcatcgtgt ccggccacgg cgcaatatcg aacaaggaaa gctgcatttc cttgatctgc      3120
tgcttcgtgt gtttcagcaa cgcggcctgc ttggcctcgc tgacctgttt tgccaggtcc      3180
tcgccggcgg tttttcgctt cttggtcgtc atagttcctc gcgtgtcgat ggtcatcgac      3240
ttcgccaaac ctgccgcctc ctgttcgaga cgacgcgaac gctccacggc ggccgatggc      3300
gcgggcaggg caggggagc cagttgcacg ctgtcgcgct cgatcttggc cgtagcttgc      3360
tggaccatcg agccgacgga ctggaaggtt tcgcggggcg cacgcatgac ggtgcggctt      3420
gcgatggttt cggcatcctc ggcggaaaac cccgcgtcga tcagttcttg cctgtatgcc      3480
ttccggtcaa acgtccgatt cattcaccct ccttgcggga ttgccccgac tcacgccggg      3540
gcaatgtgcc cttattcctg atttgacccg cctggtgcct tggtgtccag ataatccacc      3600
ttatcggcaa tgaagtcggt cccgtagacc gtctggccgt ccttctcgta cttggtattc      3660
```

```
cgaatcttgc cctgcacgaa taccagctcc gcgaagtcgc tcttcttgat ggagcgcatg    3720
gggacgtgct tggcaatcac gcgcaccccc cggccgtttt agcggctaaa aaagtcatgg    3780
ctctgccctc gggcggacca cgcccatcat gaccttgcca agctcgtcct gcttctcttc    3840
gatcttcgcc agcagggcga ggatcgtggc atcaccgaac cgcgccgtgc gcgggtcgtc    3900
ggtgagccag agtttcagca ggccgcccag gcggcccagg tcgccattga tgcgggccag    3960
ctcgcggacg tgctcatagt ccacgacgcc cgtgattttg tagccctggc cgacggccag    4020
caggtaggcc tacaggctca tgccggccgc cgccgccttt cctcaatcg ctcttcgttc    4080 gtctggaagg cagtacacct tgataggtgg gctgcccttc ctggttggct tggtttcatc    4140
agccatccgc ttgccctcat ctgttacgcc ggcggtagcc ggccagcctc gcagagcagg    4200
attcccgttg agcaccgcca ggtgcgaata agggacagtg aagaaggaac acccgctcgc    4260
gggtgggcct acttcaccta tcctgcccgg ctgacgccgt tggatacacc aaggaaagtc    4320
tacacgaacc ctttggcaaa atcctgtata tcgtgcgaaa aaggatggat ataccgaaaa    4380
aatcgctata atgaccccga agcagggtta tgcagcggaa aagatccgtc gacccttccc    4440
gacgctcacc gggctggttg ccctcgccgc tgggctggcg gccgtctatg gcctgcaaa    4500 cgcgccagaa acgccgtcga agccgtgtgc gagacaccgc ggccgccggc gttgtggata    4560
cctcgcggaa aacttggccc tcactgacag atgaggggcg gacgttgaca cttgaggggc    4620
cgactcaccc ggcgcggcgt tgacagatga ggggcaggct cgatttcggc cggcgacgtg    4680
gagctggcca gcctcgcaaa tcggcgaaaa cgcctgattt tacgcgagtt ccccacagat    4740
gatgtggaca agcctgggga taagtgccct gcggtattga cacttgaggg gcgcgactac    4800
tgacagatga ggggcgcgat ccttgacact tgaggggcag agtgctgaca gatgagggc    4860 gcacctattg acatttgagg ggctgtccac aggcagaaaa tccagcattt gcaagggttt    4920
ccgcccgttt ttcggccacc gctaacctgt cttttaacct gcttttaaac caatatttat    4980
aaaccttgtt tttaaccagg gctgcgccct gtgcgcgtga ccgcgcacgc cgaaggggg     5040 tgccccccct tctcgaaccc tcccggcccg ctaacgcggg cctccatcc ccccaggggc     5100 tgcgcccctc ggccgcgaac ggcctcaccc caaaaatggc agccaagctg accacttctg    5160
cgctcggccc ttccggctgg ctggtttatt gctgataaat ctggagccgg tgagcgtggg    5220
tctcgcggta tcattgcagc actggggcca atggtaagc cctcccgtat cgtagttatc     5280
tacacgacgg ggagtcaggc aactatggat gaacgaaata gacagatcgc tgagataggt    5340
gcctcactga ttaagcattg gtaactgtca gaccaagttt actcatatat actttagatt    5400
gatttaaaac ttcattttta atttaaaagg atcaggtgaa agatcctttt tgataatctc    5460
atgaccaaaa tcccttaacg tgagttttcg ttccactgag cgtcagaccc cgtagaaaag    5520
atcaaaggat cttcttgaga tccttttttt ctgcgcgtaa tctgctgctt gcaaacaaaa    5580
aaaccaccgc taccagcggt ggtttgtttg ccggatcaag agctaccaac tcttttccg    5640 aaggtaactg gcttcagcag agcgcagata ccaaatactg tccttctagt gtagccgtag    5700
ttaggccacc acttcaagaa ctctgtagca ccgcctacat acctcgctct gctaatcctg    5760
ttaccagtgg ctgctgccag tggcgataag tcgtgtctta ccgggttgga ctcaagacga    5820
tagttaccgg ataaggcgca gcggtcgggc tgaacggggg gttcgtgcac acagcccagc    5880
ttggagcgaa cgacctacac cgaactgaga tacctacagc gtgagctatg agaaagcgcc    5940
acgcttcccg aagggagaaa ggcggacagg tatccggtaa gcggcagggt cggaacagga    6000
gagcgcacga gggagcttcc agggggaaac gcctggtatc tttatagtcc tgtcgggttt    6060
```

```
cgccacctct gacttgagcg tcgattttt tgatgctcgt caggggggcg gagcctatgg    6120
aaaaacgcca gcaacgcggc cttttttacgg ttcctggcct tttgctggcc ttttgctcac    6180
atgttctttc ctgcgttatc ccctgattct gtggataacc gtattaccgc ctttgagtga    6240
gctgataccg ctcgccgcag ccgaacgacc gagcgcagcg agtcagtgag cgaggaagcg    6300
gaagagcgcc caatacgcaa accgcctctc cccgcgcgtt ggccgattca ttaatgcagc    6360
tggcagccag cgcttcgtta atacagatgt aggtgttcca cagggtagcc agcagcatcc    6420
tgcgatgcag atccggaaca taatggtgca gggcgctgac tttatagcta gctcagccct    6480
tggtacaatg ctagcgagca accaacactt aaagaggaga aaatgtatcc gtttataagg    6540
acagcccgaa tgacggtctg cgcaaaaaaa cacgttcatc tcactcgcga tgctgcggag    6600
cagttactgg ctgatattga tcgacgcctt gatcagttat tgcccgtgga gggagaacgg    6660
gatgttgtgg gtgccgcgat gcgtgaaggt gcgctggcac cgggaaaacg tattcgcccc    6720
atgttgctgt tgctgaccgc ccgcgatctg ggttgcgctg tcagccatga cggattactg    6780
gatttggcct gtgcggtgga aatggtccac gcggcttcgc tgatccttga cgatatgccc    6840
tgcatggacg atgcgaagct gcggcgcgga cgccctacca ttcattctca ttacggagag    6900
catgtggcaa tactggcggc ggttgccttg ctgagtaaag cctttggcgt aattgccgat    6960
gcagatggcc tcacgccgct ggcaaaaaat cgggcggttt ctgaactgtc aaacgccatc    7020
ggcatgcaag gattggttca gggtcagttc aaggatctgt ctgaagggga taagccgcgc    7080
agcgctgaag ctattttgat gacgaatcac tttaaaacca gcacgctgtt ttgtgcctcc    7140
atgcagatgg cctcgattgt tgcgaatgcc tccagcgaag cgcgtgattg cctgcatcgt    7200
ttttcacttg atcttggtca ggcatttcaa ctgctggacg atttgaccga tggcatgacc    7260
gacaccggta aggatagcaa tcaggacgcc ggtaaatcga cgctggtcaa tctgttaggc    7320
cctagggcgg ttgaagaacg tctgagacaa catcttcatc ttgccagtga gcatctctct    7380
gcggcctgcc aacacgggca cgccactcaa cattttattc aggcctggtt tgacaaaaaa    7440
ctcgctgccg tcagttaaag gtctctagac aggatgtgtc acacaggaaa ccatgaaacc    7500
aactacggta attggtgcag gcttcggtgg cctggcactg gcaattcgtc tacaggctgc    7560
ggggatcccc gtcttactgc ttgaacaacg tgataaaccc ggcggtcggg cttatgtcta    7620
cgaggatcag gggtttacct ttgatgcagg cccgacggtt atcaccgatc ccagtgccat    7680
tgaagaactg tttgcactgg caggaaaaca gttaaaagag tatgtcgaac tgctgccggt    7740
tacgccgttt taccgcctgt gttgggagtc agggaaggtc tttaattacg ataacgatca    7800
aacccggctc gaagcgcaga ttcagcagtt taatcccgc gatgtcgaag ttatcgtca    7860 gtttctggac tattcacgcg cggtgtttaa agaaggctat ctgaagctcg gtactgtccc    7920
ttttttatcg ttcagagaca tgcttcgcgc cgcacctcaa ctggcgaaac tgcaggcatg    7980
gagaagcgtt tacagtaagg ttgccagtta catcgaagat gaacatctgc gccaggcgtt    8040
ttctttccac tcgctgttgg tgggcggcaa tcccttcgcc acctcatcca tttatacgtt    8100
gatacacgcg ctggagcgtg agtggggcgt ctggtttccg cgtggcggca ccggcgcatt    8160
agttcagggg atgataaagc tgtttcagga tctgggtggt gaagtcgtgt taaacgccag    8220
agtcagccat atggaaacga caggaaacaa gattgaagcc gtgcatttag aggacggtcg    8280
caggttcctg acgcaagccg tcgcgtcaaa tgcagatgtg gttcatacct atcgcgacct    8340
gttaagccag caccctgccg cggttaagca gtccaacaaa ctgcagacta gcgtatgag    8400
```

-continued

```
taactctctg tttgtgctct attttggttt gaatcaccat catgatcagc tcgcgcatca    8460
cacggtttgt ttcggcccgc gttaccgcga actgattgac gagatttta atcatgatgg    8520
cctcgcagaa gacttctcac tttatctgca cgcgccctgt gtcacggatt cgtcactggc    8580
gcctgaaggt tgcggcagtt actatgtgtt ggcgccggtg ccgcatttag gcaccgcgaa    8640
cctcgactgg acggttgagg ggccaaaact acgcgaccgt attttttgagt accttgagca    8700
gcattacatg cctggcttac ggagtcagct ggtcacgcac cagatgttta cgccgtttga    8760
ttttcgcgac cagcttaatg cctatcaggg ctcagccttt tctgtggagc ccgttcttac    8820
ccagagcgcc tggtttcggc cgcataaccg cgataaaacc attactaatc tctacctggt    8880
cggcgcaggc acgcatcccg gcgcaggcat tcctggcgtc atcggctcgg caaaagcgac    8940
agcaggtttg atgctggagg atctgattta agtgatcgtt gagtggtgaa cttaaagagg    9000
agaaaatgaa taatccgtcg ttactcaatc atgcggtcga aacgatggca gttggctcga    9060
aaagttttgc gacagcctca aagttatttg atgcaaaaac ccggcgcagc gtactgatgc    9120
tctacgcctg gtgccgccat tgtgacgatg ttattgacga ccagacgctg ggcttccagg    9180
cccggcagcc tgccttacaa acgcccgaac aacgtctgat gcaacttgag atgaaaacgc    9240
gccaggccta tgcaggatcg cagatgcacg aaccggcgtt tgcggctttt caggaagtgg    9300
ctatggctca tgatatcgcc ccggcttacg cgtttgatca tctggaaggc ttcgccatgg    9360
atgtacgcga agcgcaatac agccaactgg acgatacgct gcgctattgc tatcacgttg    9420
caggcgttgt cggcttgatg atggcgcaaa tcatgggcgt acgggataac gccacgctgg    9480
accgcgcctg tgaccttggg ctggcatttc agttgaccaa tattgctcgc gatattgtgg    9540
acgatgcgca tgcgggccgc tgttatctgc cggcaagctg gctggagcat gaaggtctga    9600
acaaagagaa ttatgcggca cctgaaaacc gtcaggcgct gagccgtatc gcccgtcgtt    9660
tggtgcagga agcagaacct tactatttgt ctgccacagc gggcctggct gggttgcccc    9720
tgcgttcggc ctgggcaatc gctacggcga agcaggttta ccggaaaata ggtgtcaaag    9780
ttgaacaggc cggtcagcaa gcctgggatc agcggcagtc aacgaccacg cccgaaaaat    9840
taacgctgct gctggccgcc tctggtcagg cccttacttc ccggatgcgg gctcatcctc    9900
cccgccctgc gcatctctgg cagcgcccgc tctaatcacg tagcaagctg acagtttaaa    9960
gaggagaaaa tgggagcggc tatgcaaccg cattatgatc tgattctcgt gggggctgga   10020
ctcgcgaatg gccttatcgc cctgcgtctt cagcagcagc aacctgatat gcgtattttg   10080
cttatcgacg ccgcacccca ggcgggcggg aatcatacgt ggtcatttca ccacgatgat   10140
ttgactgaga gccaacatcg ttggatagct tcgctggtgg ttcatcactg gcccgactat   10200
caggtacgct ttcccacacg ccgtcgtaag ctgaacagcg gctacttctg tattacttct   10260
cagcgtttcg ctgaggtttt acagcgacag tttggcccgc acttgtggat ggataccgcg   10320
gtcgcagagt taatgcgga atctgttcgg ttgaaaaagg gtcaggttat cggtgcccgc   10380
gcggtgattg acgggcgggg ttatgcggca aactcagcac tgagcgtggg cttccaggcg   10440
tttattggcc aggaatggcg attgagccac ccgcatggtt tatcgtctcc cattatcatg   10500
gatgccacgg tcgatcagca aaatggttat cgcttcgtgt acagcctgcc gctctcgccg   10560
accagattgt taattgaaga cacgcactat atcgataatg cgacattaga tcctgaacgc   10620
gcgcggcaaa atatttgcga ctatgccgcg caacagggtt ggcagcttca gacattgctg   10680
cgtgaagaac agggcgcctt accca                                          10705
```

```
<210> SEQ ID NO 82
<211> LENGTH: 1773
<212> TYPE: DNA
<213> ORGANISM: Methylosinus trichosporum

<400> SEQUENCE: 82
atggccagaa aaatgaccgg agcggaaatg gtcgtcgaag ccctgaagga tcagggcgtc      60
gagattatct tcggctatcc cggcggcgcc gtgcttccga tctatgacgc gctcttccac     120
caggagaagg tgcagcacat tctcgtgcgc acgagcagg gcgccgccca tgcggccgag     180
ggctatgcgc gctcctccgg caaggtcggc gtgctgctgg tcacctccgg accggcgcc     240 accaacacca tcaccggcct caccgatgcg ctgatggact ccattcccgt ggtctgcatc     300
accggccagg tgccgacgca tctcatcggc tcggacgcct tcaagagtg cgatacggtc     360 ggcatcaccc gtcactgcac caagcataat tatctggtga gagcgtcga cgatctgccg     420 cgcattctgc acgaggcctt ctatgtcgcc tcgagcgggc ggccgggccc tgtggtcatc     480
gacatcccca aggatgtgca attgccagc ggaacctata ccggcccgcg caacgtccat     540
cacaagacct atcagcccaa gctcgagggc gacacggagt ctatccgccg cgccgtgaag     600
atgatggccg ccgccaagcg gccgatcttc tacaccggcg gcggcgtcat caattccggt     660
cccgcggcct cgacgctgct gcgcgagctg gtgtcgctga ccggctttcc gatcacctcg     720
accttgatgg gcctcggcgc ctatccgggc tccggcccca ttggctcgg catgctcggc     780 atgcacggca ccttcgaggc caataatgcg atgcatgatt gcgatctgat gatcgccgtc     840
ggcgcgcgtt tcgacgatcg catcaccgga cggctcgacg ccttctcgcc cggctcgaag     900
aagatccaca tcgatatcga tcgctcctcg atcaataaga atgtgaagat cgatctgccg     960
atcgtcggcg actgcggcca tgtgctggag agtctggtgc gcgtctggcg ctccgaggcg    1020
atgcacgccg agaagcagcc gctcgacggc tggtggaaga cgatcgacca ttggcgcgag    1080
cgcaagtcgc tcgccttccg caattcggac aaggtgatca agccgcaata cgccgtgcag    1140
cggctctatg cgctcaccaa ggatcgcgat ccctacatca cgacggaagt cggccagcat    1200
cagatgtggg ccgcgcagca ttatcattc gacgagccca atcgctggat gacttccggc    1260
gggctcggca ccatgggcta tggtctgccg gcggcgatcg gcgcgcagct cgcgcatccg    1320
aaatcgctgg tcgtcgacat cgccggcgag gcctcgatcc tgatgaacat tcaggagatg    1380
tcgacggcga tccaatatcg gctgccggtg aaggtgttca tcctcaacaa tgaatatatg    1440
ggcatggtgc gccagtggca ggagctgctg cacggcgggc gctactcgca ctcctattcg    1500
gaggcgctgc ccgatttcgt gaagctcgcc gaagccttcg ggggcaaggg catccgctgc    1560
tcggacccgg cggagctcga tagcgcgatt ctcgagatga tcgactatga cgggccggtg    1620
atcttcgatt gtctcgtcga gaaaaacgag aattgcttcc cgatgatccc gtcgggcaag    1680
gcgcataacg acatgctgct cgccgatctc ggcgacgacg ccggcgtcga gctcggctcg    1740
atcatcgacg agaagggcaa gatgctggtg tga                                 1773

<210> SEQ ID NO 83
<211> LENGTH: 1056
<212> TYPE: DNA
<213> ORGANISM: Methylosinus trichosporum

<400> SEQUENCE: 83
atgtccacca agcctatgc cgttgcgtcc gccgaggcgc tcttcggccc gctcgcgatc      60
gagcgccgcg cgctcgggcc cgaggatgta gagatcgaca tcctctattg cggcgtctgc     120
```

| | |
|---|---|
| cattccgatc tgcacacggc gcgcagtgaa tggccgggca cgcgctaccc atgcgtcccg | 180 |
| ggccacgaga ttgtcggccg cgtcaccgct gtcggcgcga aggtgacgaa attttcggtc | 240 |
| ggcgatctcg ccgccgtcgg ctgcatggtc gacagctgcc ggcgatgctt gtcctgcgac | 300 |
| gacgggctcg aacaatattg cgagcacggt ttcaccgcca cctataacgg cccgatctac | 360 |
| ggctcgggcg agaacacctt tggcggctat tcggagaaaa tcgtcgtcga cgcgcatttc | 420 |
| gtgctggcga tccaccattc tgagacgcag cttgccggag tcgcgccgct gctctgcgcc | 480 |
| ggcatcacca cttggtcgcc gctcaagcat tggggtgtcg gcccgggaaa atcggtcggc | 540 |
| atcgtcggca tcggcgggct cggccatatg ggggtcaagc tcgcccatgc gctcggcgcc | 600 |
| catgtcgtcg ccttcaccac ctcgccgtca agcgcgacg cggccctcgc gctcggcgcc | 660 |
| gacgaggtcg tcgtctccac agatcctgcc gctatggcgg cgcgggcggg aagcctcgac | 720 |
| ttcattctcg atacggtcgc cgtcgccat gacctcgacg cttatgtgaa tctgttgaag | 780 |
| cgcgatggcg ctctggtgct cgtcggcgtg ccggcgacgc cgcatccctc gccatcggcg | 840 |
| ggcgggttga tcttcaagcg gcgccaggtc gccggctcgc tgatcggcgg cgtaaaggag | 900 |
| acgcaggaga tgctcgactt ctgcgccgag cgcggcattg tcgcggacat agagacgatc | 960 |
| gccatgcagc agatcgagac cgcctatgcg cgcatgctga agaatgatgt gaaataccgc | 1020 |
| ttcgtcatcg acatggcgac gctgaaggcg gcgtga | 1056 |

<210> SEQ ID NO 84
<211> LENGTH: 1029
<212> TYPE: DNA
<213> ORGANISM: Methylococcus capsulatus

<400> SEQUENCE: 84

| | |
|---|---|
| atgaaagctt gggtgatcga ccgaatcggc ccgctggact cgtcgcgaac tctgctacgc | 60 |
| gccaccgacc tcccggtgcc ggagcccggc cctggcgaaa tcctgctgca ggtggcggtt | 120 |
| tgcggcgtct gccacaccga aatcgacgag atcgagggcc gcaccgcgcc gccgcgcctg | 180 |
| ccggtcgtgc ccggacacca gcggtcggt cggatcgcgg ctctcggctc cggcgtggcg | 240 |
| gaattcgctt tgggcgaccg cgtcggcgtg gcctggatcc tttctgcctg cggagaatgc | 300 |
| gaattctgcc ggtcgggacg ggagaacctc tgtttcgcat tctgtgccac cgggcgcgat | 360 |
| gtcgacggcg gctacgccca gtacatgacc gtcccggcgg cctttgcttt ccgcattccg | 420 |
| gagggattca ccgatgccga agcggcgccg cttctgtgcg ccggcgccat cggttaccgt | 480 |
| tcgctcaatc tcagcgggct gaaaaacggc cagccgctgg ggctcaccgg gttcggggct | 540 |
| tccgcccatc tggtgctgat gatggcccgg taccggtttc ccgattcgga agtctatgtc | 600 |
| tttgcgcgtc atcccgagga gcgcgcgttc gcgctgcagc tgggcgcggt ctgggccggc | 660 |
| gacaccgcgg acattgctcc cgcccgctg gccgccatca tcgacacgac gccggcgtgg | 720 |
| aagccggtgg tcgcagcgct cgccaacctc gctcccggtg gccggctggt cgttaatgcg | 780 |
| atccgcaagg cgccggacga tcgcgcctgt ctcgccgaac tcgactatgc ccggcacttg | 840 |
| tggatggaac gggaaatcaa gtcggtcgcc aacgtggcgc gcagtgacgt ggccgggttc | 900 |
| ctggcgctgg cggcggaaat gggcatccgt cccgagacgg aggagtaccc gttcgaggat | 960 |
| gccgaccggg cgctgctcga cctcaagcaa cgccggattc gcggggcgaa ggtgttgcgg | 1020 |
| gtgacttga | 1029 |

<210> SEQ ID NO 85
<211> LENGTH: 1068

```
<212> TYPE: DNA
<213> ORGANISM: Methylococcus capsulatus

<400> SEQUENCE: 85
atgcctacag ccaaagccta tgccgctttt tccgcagact cggcgctggc gccgttcgtc      60
ctgcagcggc gcgacccact gccccaggac atccgcatcg aatcctgta ctgcggtgtc      120 tgccattccg acctgcacca ggcacgcaat gagtggaatg cgaccacata tccttgtgtg    180
ccaggccatg agatcgtcgg caaggtcctt gaagtcggcc gcagcgtgac gaagttcaag    240
cccggcgaca cggtcgcggt gggctgcatg gtggattcct gccggacctg cccgaactgc    300
gtggacgccc tggaacagca ctgcgagcac ggccccgtct tcacctacaa cagccccgat    360
ccgcacggcg gcggcatgac cttcggtggc tatgccgaga gcatcgtggt cgacgaggcc    420
ttcgtgctgc ggataccgga cggactggac ctcgcggccg ccgccccgct gttgtgcgcc    480
gggattacca cctattcgcc cctgcggcac tggaaagtgg gggcgggtca gcgggtcggg    540
gtcgtcggtc tgggtggact gggacacatg gcgctcaagt tcgcgcatac cttcggcgcc    600
gaaacggtgc tgttcacgac gacgccggac aaggcggagg atgcccgtcg gctgggagcg    660
gacgaggtcg tcgtgtcgag ggatcccgag gccatggcgc ggcaggccgg ccggttcgat    720
ttcatcctcg acaccgtctc ggcgcccat gacatcgatg cctatctgaa cctgctgagg    780
cgggacggca cgctgaccct ggtcggcgta cctccgcaag gggtacaggt catgcccttc    840
agcctgatcg gcgggcgccg cgactggct ggttcattga tcggcggcat ccgggaaacc    900
caggagatgc tggatttctg cggcgaacac ggcatcgtct gcgacatcga gctgattccg    960
atccaaggaa tcaacgacgc cttcgagcgc atgctcaaaa gcgacgtgaa ataccgtttc   1020
gtgatcgaca tggcgacgct gaacggggag tcgtccggag gcgatga                1068

<210> SEQ ID NO 86
<211> LENGTH: 1647
<212> TYPE: DNA
<213> ORGANISM: Lactococcus lactis

<400> SEQUENCE: 86
atgtacaccg tgggcgacta tctgctggac cggctgcatg aactgggcat cgaggaaatc     60
ttcggcgtcc ccggcgacta taacctgcag ttcctggacc agatcatcag ccgcaaggac    120
atgaagtggg tgggcaacgc caacgagctg aacgcctcgt acatggcgga cggctatgcc    180
cggaccaaga aggccgcggc cttcctgacc accttcggcg tcggcgaact gagcgccgtg    240
aacggcctgg cgggctcgta cgccgagaac ctgccggtcg tggaaatcgt cggctccccc    300
accagcaagg tgcagaacga gggcaagttc gtccaccata ccctggccga cggcgacttc    360
aagcacttca tgaagatgca tgaaccggtg accgcggccc gcaccctgct gaccgccgag    420
aacgcgaccg tcgaaatcga ccgcgtgctg agcgcgctgc tgaaggagcg gaagccggtc    480
tatatcaacc tgcccgtcga cgtggcggcc gcgaaggccg agaagccgtc cctgcccctg    540
aagaaggaaa cccccacctc gaacacctcc gaccaggaga tcctgaacaa gatccaggaa    600
agcctgaaga acgccaagaa gccgatcgtg atcaccggcc acgagatcat ctcgttcggc    660
ctggaaaaca ccgtcacca gttcatctcc aagaccaagc tgccgatcac cacccctgaac    720 ttcggcaaga gctcggtgga cgagaccctg ccctcgttcc tgggcatcta caacggcaag    780
ctgtccgaac cgaacctgaa ggagttcgtg gaaagcgcgg acttcatcct gatgctgggc    840
gtcaagctga ccgactccag caccggcgcc ttcacccacc atctgaacga aacaagatg    900
```

| | |
|---|---:|
| atctcgctga acatcgacga gggcaagatc ttcaacgaat ccatccagaa cttcgacttc | 960 |
| gaaagcctga tctcgtccct gctggacctg tccggcatcg agtacaaggg caagtatatc | 1020 |
| gacaagaagc aggaagactt cgtcccgagc aacgcgctgc tgtcgcagga ccgcctgtgg | 1080 |
| caggccgtgg agaacctgac ccagagcaac gagaccatcg tcgcggaaca gggcaccctcg | 1140 |
| ttcttcggcg ccagctcgat cttcctgaag ccgaagtcgc acttcatcgg ccagcccctg | 1200 |
| tggggctcca tcggctacac cttccccgcc gcgctgggct cgcagatcgc ggacaaggaa | 1260 |
| tcccggcatc tgctgttcat cggcgacggc agcctgcagc tgaccgtgca ggagctgggc | 1320 |
| ctggccatcc gcgaaaagat caacccgatc tgcttcatca tcaacaacga cggctatacc | 1380 |
| gtcgagcggg aaatccacgg cccgaaccag tcgtacaacg acatccccat gtggaactat | 1440 |
| tccaagctgc cggagagctt cggcgccacc gaggaacgcg tcgtgtccaa gatcgtccgg | 1500 |
| accgagaacg agttcgtcag cgtgatgaag gaagcccagc cggaccccaa ccggatgtac | 1560 |
| tggatcgagc tggtgctggc gaaggaagac gccccgaagg tcctgaagaa gatgggcaag | 1620 |
| ctgttcgccg aacagaacaa gagctga | 1647 |

<210> SEQ ID NO 87
<211> LENGTH: 1692
<212> TYPE: DNA
<213> ORGANISM: Saccharomyces cerevisiae

<400> SEQUENCE: 87

| | |
|---|---:|
| atgtcggaaa tcaccctggg caagtacctg ttcgagcggc tgaagcaggt caacgtcaac | 60 |
| accatcttcg gcctgcccgg cgacttcaac ctgagcctgc tggacaagat ctacgaggtc | 120 |
| gacggcctgc gctgggccgg caacgcgaac gaactgaacg ccgcgtacgc cgcggacggc | 180 |
| tatgcccgga tcaagggcct gtcggtcctg gtgaccacct tcggcgtggg cgagctgtcg | 240 |
| gccctgaacg gcatcgccgg ctcctacgcg gaaacgtcg gcgtgctgca tgtcgtgggc | 300 |
| gtcccgagca tctcggccca ggcgaagcag ctgctgctgc accataccct gggcaacggc | 360 |
| gacttcaccg tgttccaccg catgtccgcc aacatcagcg agaccacctc gatgatcacc | 420 |
| gacatcgcca ccgcgccgag cgaaatcgac cgcctgatcc ggaccacctt catcacccag | 480 |
| cggccgtcgt acctgggcct gccgccaac ctggtcgacc tgaaggtgcc gggcagcctg | 540 |
| ctggagaagc ccatcgacct gtcgctgaag ccgaacgacc ccgaggccga aaaggaagtc | 600 |
| atcgacaccg tgctggaact gatccagaac agcaagaacc cggtcatcct gtccgacgcc | 660 |
| tgcgcgagcc gccacaacgt gaagaaggag acccagaagc tgatcgacct gacccagttc | 720 |
| ccggccttcg tcaccccct gggcaagggc tccatcgacg agcagcatcc gcggtacggc | 780 |
| ggcgtctatg tgggcaccct gagcaagcag gacgtcaagc aggccgtgga aagcgcggac | 840 |
| ctgatcctgt cggtgggcgc cctgctgtcc gacttcaaca ccggctcctt cagctactcg | 900 |
| tataagacca gaacgtcgt ggagttccat tcggactacg tcaaggtgaa gaacgcgacc | 960 |
| ttcctgggcg tccagatgaa gttcgccctg cagaacctgc tgaaggtgat cccggacgtc | 1020 |
| gtgaagggct ataagtccgt cccggtgccc accaagaccc ccgccaacaa gggcgtcccg | 1080 |
| gcgtcgaccc ccctgaagca ggaatggctg tggaacgagc tgtccaagtt cctgcaggaa | 1140 |
| ggcgacgtga tcatctcgga ccggcacc tccgcgttcg gcatcaacca gaccatcttc | 1200 |
| ccgaaggacg cctacggcat cagccaggtc ctgtggggct cgatcggctt caccaccggc | 1260 |
| gccaccctgg gcgccgcgtt cgccgcggag gaaatcgacc cgaacaagcg cgtcatcctg | 1320 |
| ttcatcggcg acggctccct gcagctgacc gtgcaggaaa tcagcaccat gatccggtgg | 1380 |

```
ggcctgaagc cctacctgtt cgtgctgaac aacgacggct ataccatcga gaagctgatc    1440
cacggcccgc atgcggaata caacgagatc cagacctggg accacctggc cctgctgccc    1500
gccttcggcg cgaagaagta tgaaaaccat aagatcgcca ccaccggcga gtgggacgcg    1560
ctgaccaccg actccgagtt ccagaagaac agcgtcatcc gcctgatcga gctgaagctg    1620
ccggtgttcg acgccccga aagcctgatc aagcaggcgc agctgaccgc cgcgaccaac     1680
gccaagcagt ga                                                        1692
```

<210> SEQ ID NO 88
<211> LENGTH: 1908
<212> TYPE: DNA
<213> ORGANISM: Saccharomyces cerevisiae

<400> SEQUENCE: 88

```
atggcccccg tcaccatcga gaagttcgtc aaccaggaag agcggcatct ggtgtccaac      60
cggagcgcga ccatcccgtt cggcgagtac atcttcaagc gcctgctgag catcgacacc    120
aagtcggtgt tcggcgtgcc gggcgacttc aacctgagcc tgctggagta cctgtatagc    180
ccctcggtcg aatcggccgg cctgcgctgg gtgggcacct gcaacgaact gaacgccgcg    240
tacgccgcgg acggctactc ccggtatagc aacaagatcg gctgcctgat caccacctat    300
ggcgtcggcg aactgtcggc gctgaacggc atcgcgggct ccttcgccga gaacgtgaag    360
gtcctgcaca tcgtgggcgt cgccaagtcg atcgactccc gcagctcgaa cttctcggac    420
cggaacctgc accatctggt cccgcagctg catgactcca acttcaaggg ccccaaccac    480
aaggtgtacc atgacatggt gaaggaccgc gtcgcgtgct ccgtggccta tctggaggac    540
atcgaaaccg cctgcgacca ggtggacaac gtcatccggg acatctacaa gtatagcaag    600
ccgggttaca tcttcgtccc cgcggacttc gccgacatgt ccgtgacctg cgacaacctg    660
gtgaacgtcc cgcgcatcag ccagcaggac tgcatcgtgt acccctccga aaaccagctg    720
agcgacatca tcaacaagat cacctcgtgg atctactcca gcaagacccc ggccatcctg    780
ggcgacgtcc tgaccgaccg gtatggcgtg agcaacttcc tgaacaagct gatctgcaag    840
accggcatct ggaacttctc gaccgtcatg ggcaagtcgg tgatcgacga atccaacccg    900
acctacatgg ccagtataa cggcaaggaa ggcctgaagc aggtctacga gcacttcgaa    960
ctgtgcgacc tggtcctgca tttcggcgtg gacatcaacg agatcaacaa cggccactac   1020
accttcacct ataagccgaa cgcgaagatc atccagttcc atcccaacta catccgcctg   1080
gtggacaccc ggcagggcaa cgaacagatg ttcaagggca tcaacttcgc cccgatcctg   1140
aaggagctgt ataagcgcat cgacgtcagc aagctgtcgc tgcagtacga cagcaacgtg   1200
acccagtata ccaacgagac catgcggctg aagaccccca ccaacggcca gtcgtccatc   1260
atcacccagg tccacctgca gaagaccatg ccgaagttcc tgaacccggg cgacgtcgtg   1320
gtctgcgaga ccggctcctt ccagttcagc gtgcgcgact cgcgttccc gagccagctg    1380 aagtacatct cgcagggctt cttcctgtcc atcggcatgg ccctgcccgc cgcgctgggc   1440
gtcggcatcg cgatgcagga ccactcgaac gcccatatca acggcggcaa cgtgaaggaa   1500
gactacaagc gcggctgat cctgttcgaa ggcgacggcg ccgcgcagat gaccatccag    1560
gagctgtcca ccatcctgaa gtgcaacatc ccgctggaag tcatcatctg gaacaacaac   1620
ggctacacca tcgagcgcgc catcatgggc cccaccccga gctataacga cgtgatgtcg   1680
tggaagtgga ccaagctgtt cgaagcgttc ggcgacttcg acggcaagta caccaactcc   1740
```

| | |
|---|---|
| accctgatcc agtgcccgag caagctggcc ctgaagctgg aggaactgaa gaactcgaac | 1800 |
| aagcgctccg gcatcgagct gctggaagtc aagctgggcg agctggactt ccccgaacag | 1860 |
| ctgaagtgca tggtggaggc cgcggccctg aagcggaaca agaagtga | 1908 |

<210> SEQ ID NO 89
<211> LENGTH: 1047
<212> TYPE: DNA
<213> ORGANISM: Saccharomyces cerevisiae

<400> SEQUENCE: 89

| | |
|---|---|
| atgagcatcc ccgagaccca gaaggccatc atcttctacg agagcaacgg caagctggaa | 60 |
| cataaggaca tcccggtgcc caagcccaag ccgaacgaac tgctgatcaa cgtgaagtac | 120 |
| agcggcgtct gccacaccga cctgcacgcg tggcatggcg actggccgct gcccaccaag | 180 |
| ctgcccctgg tgggcggcca tgaaggcgcc ggcgtcgtgg tcggcatggg cgagaacgtc | 240 |
| aagggctgga agatcggcga ctacgcgggc atcaagtggc tgaacggcag ctgcatggcc | 300 |
| tgcgagtatt gcgaactggg caacgaatcg aactgcccgc acgcggacct gtccggctac | 360 |
| acccatgacg gcagcttcca ggagtatgcc accgcggacg ccgtgcaggc cgcgcacatc | 420 |
| ccgcagggca ccgacctggc ggaggtggcc cccatcctgt gcgccggcat caccgtctac | 480 |
| aaggcgctga gagcgccaa cctgcgcgcg ggccattggg ccgcgatctc gggcgccgcc | 540 |
| ggtggcctgg gctccctggc cgtgcagtac gcgaaggcga tgggctaccg cgtcctgggc | 600 |
| atcgacggcg gtccgggcaa ggaagagctg ttcacctccc tgggcggcga agtgttcatc | 660 |
| gacttcacca aggagaagga catcgtcagc gccgtggtca aggcgaccaa cggcggcgcc | 720 |
| cacggcatca tcaacgtgtc ggtctccgaa gccgcgatcg aggcgtcgac ccgctactgc | 780 |
| cgggccaacg gcaccgtggt cctggtgggc ctgcccgcgg cgccaagtg cagctcggac | 840 |
| gtcttcaacc atgtggtcaa gagcatctcg atcgtgggct cgtatgtcgg caaccgcgcc | 900 |
| gacacccgcg aggccctgga cttcttcgcc cgtggcctgg tcaagtcccc gatcaaggtg | 960 |
| gtcggcctgt ccagcctgcc cgagatctac gaaaagatgg agaagggcca gatcgccggc | 1020 |
| cgctatgtgg tcgacacctc caagtga | 1047 |

<210> SEQ ID NO 90
<211> LENGTH: 1692
<212> TYPE: DNA
<213> ORGANISM: Saccharomyces cerevisiae

<400> SEQUENCE: 90

| | |
|---|---|
| atgagcgaga tcaccctggg caagtacctg ttcgagcggc tgaagcaggt caacgtcaac | 60 |
| accgtcttcg gcctgcccgg cgacttcaac ctgagcctgc tggacaagat ctacgaggtc | 120 |
| gaaggcatgc gctgggcggg caacgccaac gagctgaacg ccgcgtacgc cgcggacggc | 180 |
| tatgcccgga tcaagggcat gtcgtgcatc atcaccacct tcggcgtggg cgagctgtcc | 240 |
| gccctgaacg gcatcgcggg cagctacgcc gaacacgtcg gcgtgctgca tgtcgtgggc | 300 |
| gtcccgagca tctcggccca ggcgaagcag ctgctgctgc accatacccct gggcaacggc | 360 |
| gacttcaccg tgttccaccg catgtccgcg aacatcagcg agaccaccgc catgatcacc | 420 |
| gacatcgcca ccgcgccggc cgaaatcgac cgctgcatcc ggaccaccta cgtcacccag | 480 |
| cggcccgtgt atcgggcct gccggccaac ctggtcgacc tgaacgtgcc cgcgaagctg | 540 |
| ctgcagaccc cgatcgacat gtcgctgaag cccaacgacg ccgagtccga aaaggaagtc | 600 |
| atcgacacca tcctggcgct ggtcaaggac gccaagaacc cggtgatcct ggcggacgcc | 660 |

```
tgctgctccc gccacgacgt caaggccgag accaagaagc tgatcgacct gacccagttc    720
cccgccttcg tgaccccgat gggcaagggc tccatcgacg aacagcatcc gcggtacggc    780
ggcgtctatg tgggcaccct gagcaagccc gaagtcaagg aagccgtgga aagcgccgac    840
ctgatcctgt cggtcggcgc cctgctgtcc gacttcaaca ccggctcctt cagctactcg    900
tataagacca agaacatcgt ggagttccac agcgaccaca tgaagatccg caacgccacc    960
ttccccggcg tccagatgaa gttcgtgctg cagaagctgc tgaccaccat cgccgacgcc    1020
gcgaagggct acaagccggt cgcggtgccc gcccggaccc cggcgaacgc cgcggtcccc    1080
gcctcgaccc cgctgaagca ggaatggatg tggaaccagc tgggcaactt cctgcaggaa    1140
ggcgacgtcg tgatcgcgga aaccggcacc tccgccttcg gcatcaacca gaccaccttc    1200
ccgaacaaca cctacggcat cagccaggtg ctgtggggct cgatcggctt caccaccggc    1260
gccaccctgg gcgccgcgtt cgccgcggag gaaatcgacc gaagaagcg cgtcatcctg    1320 ttcatcggcg acggcagcct gcagctgacc gtgcaggaaa tctcgaccat gatccggtgg    1380
ggcctgaagc cctacctgtt cgtcctgaac aacgacggct ataccatcga gaagctgatc    1440
cacgccccga aggcccagta caacgaaatc cagggctggg accatctgtc gctgctgccc    1500
accttcggcg ccaaggacta tgagacccat cgcgtggcga ccaccggcga atgggacaag    1560
ctgacccagg acaagtcgtt caacgacaac tccaagatcc ggatgatcga gatcatgctg    1620
cccgtcttcg acgcgccgca gaacctggtg aacaggcca agctgaccgc cgcgaccaac    1680
gcgaagcagt ga                                                       1692

<210> SEQ ID NO 91
<211> LENGTH: 3147
<212> TYPE: DNA
<213> ORGANISM: Saccharomyces cerevisiae

<400> SEQUENCE: 91
atgaagtcgg aatacaccat cggccgctat ctgctggacc gcctgagcga gctgggcatc      60
cgccacatct tcggcgtccc cggcgactac aacctgtcgt tcctggacta catcatggag     120
tataagggca tcgactgggt cggcaactgc aacgaactga cgccggcta cgccgcggac      180 ggctatgccc gcatcaacgg catcggcgcg atcctgacca ccttcggcgt cggcgagctg     240
tccgccatca cgccatcgc gggcgcctac gcggaacagg tgccggtcgt gaagatcacc      300
ggcatcccca ccgccaaggt ccgcgacaac ggcctgtatg tgcaccatac cctgggcgac     360
ggccgcttcg accacttctt cgagatgttc cggaagtca ccgtggccga ggcgctgctg      420
agcgaggaaa acgccgcgca ggaaatcgac cgcgtgctga tctcgtgctg gcgccagaag     480
cggccggtcc tgatcaacct gcccatcgac gtgtacgaca gccgatcaa caagccgctg      540 aagcccctgc tggactatac catcagctcg aacaaggaag ccgcgtgcga gttcgtcacc     600
gagatcgtgc cgatcatcaa ccgcgccaag aagcccgtca tcctggcgga ctacggcgtg     660
taccggtatc aggtccagca cgtgctgaag aacctggcgg agaagaccgg cttcccggtc     720
gccaccctgt cgatgggcaa gggcgtgttc aacgaagccc atccgcagtt catcggcgtc     780
tacaacggcg acgtgtccag ccctatctg cgccagcggg tcgacgaggc cgactgcatc      840
atctcggtcg gcgtgaagct gaccgactcc accaccggcg gcttctccca cggcttcagc     900
aagcgcaacg tgatccatat cgaccgttc tccatcaagg ccaagggcaa gaagtacgcg      960
cccatcacca tgaaggacgc cctgaccgaa ctgacctcga agatcgagca ccggaacttc    1020
```

```
gaagacctgg acatcaagcc gtacaagtcc gacaaccaga agtatttcgc gaaggagaag    1080
cccatcaccc agaagcgctt cttcgaacgg atcgcccatt tcatcaagga aaggacgtc     1140 ctgctggcgg aacagggcac ctgcttcttc ggcgccagca ccatccagct gccgaaggac    1200
gcgaccttca tcggccagcc cctgtggggc tccatcggct acaccctgcc ggccctgctg    1260
ggcagccagc tggcggacca gaagcgtcgc aacatcctgc tgatcggcga cggcgccttc    1320
cagatgaccg cgcaggagat ctcgaccatg ctgcgcctgc agatcaagcc gatcatcttc    1380
ctgatcaaca cgacggcta caccatcgag cgcgccatcc acggcgggga acaggtgtac     1440
aacaacatcc agatgtggcg gtatcataac gtcccgaagg tgctgggccc caaggaatgc    1500
agcctgacct tcaaggtcca gtcggagacc gaactggaga aggccctgct ggtcgccgac    1560
aaggactgcg agcacctgat cttcatcgaa gtcgtgatgg accgctacga caagccggag    1620
cccctggaac gcctgtccaa gcggttcgcc aaccagaaca acggctatgc gcggatcaac    1680
ggcatcggcg ccattttaac caccttcggc gtgggcgagc tgagcgcgat caacgcgatc    1740
gccggcgcct acgcggagca ggtgccggtg gtcaaaatta ccggcatccc caccgcgaag    1800
gtgcgggaca acggcctgta cgtccatcac accctgggcg acggccggtt cgaccatttc    1860
ttcgaaatgt tccgggaggt gaccgtcgcc gaggcgctgc tgtcggaaga gaacgcggcc    1920
caggagatcg accgcgtcct gatcagctgc tggcggcaga agcgccccgt gctgatcaac    1980
ctgccgatcg acgtctatga caagcccatc aacaagcccc tgaagccgct gctggactac    2040
accatctcgt ccaacaagga agccgcctgc gagttcgtca ccgaaatcgt cccccatcatc   2100 aaccgcgcga agaagccggt gatcctggcc gactatggcg tctatcggta tcaggtgcag    2160
catgtcctga agaacctggc cgaaaagacc ggcttccccg tggccaccct gagcatgggc    2220
aagggcgtct tcaacgaggc gcaccccag ttcatcggcg tgtataacgg cgacgtgagc     2280
tcgccgtacc tgcggcagcg cgtggacgaa gccgactgca tcatcagcgt cggcgtcaag    2340
ctgaccgact cgaccaccgg cggcttctcg cacggcttct cgaagcggaa cgtcatccac    2400
atcgacccgt tctcgatcaa ggcgaagggc aagaagtatg ccccgatcac catgaaggac    2460
gcgctgaccg aactgaccag caagatcgaa catcgcaact tcgaggacct ggacatcaag    2520
ccctacaagt cggacaacca gaagtacttc gccaaggaaa agccgattac tcagaagcgc    2580
ttcttcgagc gcatcgcgca cttcatcaag gaaaaggacg tcctgctggc cgagcaaggc    2640
acctgcttct tcggtgcgtc gaccatccag ctgcccaagg acgccacctt catcggccag    2700
ccgctgtggg gctcgatcgg ctataccctg cccgcgctgc tgggctccca gctggccgat    2760
caaaaacgtc gcaatatttt actgatcggc gacggcgcgt tccagatgac cgcccaggag    2820
atcagcacca tgctgcggct gcagatcaag cccattatct tcctgattaa caacgacggc    2880
tataccatcg aacgggcgat ccacggccgc gagcaggtct ataataatat tcaaatgtgg    2940
cggtatcata atgtgcccaa ggtcctgggc ccgaaggaat gctcgctgac cttcaaggtg    3000
cagagcgaaa ccgagctgga aaaggccctg ctggtcgccg ataaggactg cgaacatctg    3060
atcttcatcg aggtggtcat ggaccggtat gacaagcccg aaccctgga acggctgagc     3120 aagcgcttcg cgaaccagaa caactga                                        3147
```

<210> SEQ ID NO 92
<211> LENGTH: 35
<212> TYPE: DNA
<213> ORGANISM: Artificial Sequence
<220> FEATURE:
<223> OTHER INFORMATION: JPS00082

```
<400> SEQUENCE: 92
tgcaaggtac actgtcagaa cgcagaagcg gtctg                              35

<210> SEQ ID NO 93
<211> LENGTH: 28
<212> TYPE: DNA
<213> ORGANISM: Artificial Sequence
<220> FEATURE:
<223> OTHER INFORMATION: JPS00031

<400> SEQUENCE: 93
ggtttattcc tccttattta atcgatac                                     28

<210> SEQ ID NO 94
<211> LENGTH: 34
<212> TYPE: DNA
<213> ORGANISM: Artificial Sequence
<220> FEATURE:
<223> OTHER INFORMATION: JPS00032

<400> SEQUENCE: 94
aaggaggaat aaaccatggg cacggttgag cctg                              34

<210> SEQ ID NO 95
<211> LENGTH: 33
<212> TYPE: DNA
<213> ORGANISM: Artificial Sequence
<220> FEATURE:
<223> OTHER INFORMATION: GMV257

<400> SEQUENCE: 95
cacatcctgt ctagatcagc cctcgccctt gac                               33

<210> SEQ ID NO 96
<211> LENGTH: 58
<212> TYPE: DNA
<213> ORGANISM: Artificial Sequence
<220> FEATURE:
<223> OTHER INFORMATION: JPS00118)

<400> SEQUENCE: 96
tctagacagg atgtgtcaca caggaaacca tgtcttatcc tgagaaattt gaaggtat    58

<210> SEQ ID NO 97
<211> LENGTH: 41
<212> TYPE: DNA
<213> ORGANISM: Artificial Sequence
<220> FEATURE:
<223> OTHER INFORMATION: JPS00119

<400> SEQUENCE: 97
acagtgtacc ttgcactagt ctgaaaattc tttgtcgtag c                      41

<210> SEQ ID NO 98
<211> LENGTH: 70
<212> TYPE: DNA
<213> ORGANISM: Artificial Sequence
<220> FEATURE:
<223> OTHER INFORMATION: ESG00087

<400> SEQUENCE: 98
gtgttggttg ctcgctagca ttgtaccaag ggctgagcta gctataaagt cagcgccctg  60
caccattatg                                                         70
```

<210> SEQ ID NO 99
<211> LENGTH: 46
<212> TYPE: DNA
<213> ORGANISM: Artificial Sequence
<220> FEATURE:
<223> OTHER INFORMATION: GMV251

<400> SEQUENCE: 99
gagcaaccaa cacttaaaga ggagaaaatg ggcacggttg agcctg                    46

<210> SEQ ID NO 100
<211> LENGTH: 149
<212> TYPE: DNA
<213> ORGANISM: Artificial Sequence
<220> FEATURE:
<223> OTHER INFORMATION: IDT gBlock synthesized rnpB

<400> SEQUENCE: 100
gctagcacta gtgatcacgt gcttaagccg gcttatcggt cagtttcacc tgatttacgt    60
aaaaacccgc ttcggcgggt ttttgctttt ggaggggcag aaagatgaat gactgtccac   120
gacgctatac ccaaaagaaa accggtacc                                      149

<210> SEQ ID NO 101
<211> LENGTH: 35
<212> TYPE: DNA
<213> ORGANISM: Artificial Sequence
<220> FEATURE:
<223> OTHER INFORMATION: JPS00161

<400> SEQUENCE: 101
gcctgataca gattattgta ggtggaccag ttggt                               35

<210> SEQ ID NO 102
<211> LENGTH: 34
<212> TYPE: DNA
<213> ORGANISM: Artificial Sequence
<220> FEATURE:
<223> OTHER INFORMATION: JPS00162

<400> SEQUENCE: 102
ggtttattcc tccttgattt gtcctactca ggag                                34

<210> SEQ ID NO 103
<211> LENGTH: 34
<212> TYPE: DNA
<213> ORGANISM: Artificial Sequence
<220> FEATURE:
<223> OTHER INFORMATION: JPS00163

<400> SEQUENCE: 103
aaggaggaat aaaccgctag cactagtgat cacg                                34

<210> SEQ ID NO 104
<211> LENGTH: 34
<212> TYPE: DNA
<213> ORGANISM: Artificial Sequence
<220> FEATURE:
<223> OTHER INFORMATION: JPS00164

<400> SEQUENCE: 104
taatctgtat caggcggtac cggttttctt ttgg                                34

<210> SEQ ID NO 105
<211> LENGTH: 34

```
<212> TYPE: DNA
<213> ORGANISM: Artificial Sequence
<220> FEATURE:
<223> OTHER INFORMATION: JPS00172

<400> SEQUENCE: 105
atcagactaa gccttgtgct taagccggct tatc                                34

<210> SEQ ID NO 106
<211> LENGTH: 51
<212> TYPE: DNA
<213> ORGANISM: Artificial Sequence
<220> FEATURE:
<223> OTHER INFORMATION: JPS00173

<400> SEQUENCE: 106
aaggaggaat aaaccgctag cactagtgat cacttgacgg ctagctcagt c             51

<210> SEQ ID NO 107
<211> LENGTH: 33
<212> TYPE: DNA
<213> ORGANISM: Artificial Sequence
<220> FEATURE:
<223> OTHER INFORMATION: JPS00174

<400> SEQUENCE: 107
tgaacaggtc tgacttcagt gctgcgccga ggc                                 33

<210> SEQ ID NO 108
<211> LENGTH: 51
<212> TYPE: DNA
<213> ORGANISM: Artificial Sequence
<220> FEATURE:
<223> OTHER INFORMATION: JPS00176

<400> SEQUENCE: 108
agtcagacct gttcattaaa gaggagaaaa tgcagattta ctacgacaaa g             51

<210> SEQ ID NO 109
<211> LENGTH: 34
<212> TYPE: DNA
<213> ORGANISM: Artificial Sequence
<220> FEATURE:
<223> OTHER INFORMATION: JPS00177

<400> SEQUENCE: 109
aagtgttggt tgctctcagt tcttgctcgt gtcc                                34

<210> SEQ ID NO 110
<211> LENGTH: 45
<212> TYPE: DNA
<213> ORGANISM: Artificial Sequence
<220> FEATURE:
<223> OTHER INFORMATION: JPS00157

<400> SEQUENCE: 110
gagcaaccaa cacttaaaga ggagaaaatg accgacaagc acccc                    45

<210> SEQ ID NO 111
<211> LENGTH: 33
<212> TYPE: DNA
<213> ORGANISM: Artificial Sequence
<220> FEATURE:
<223> OTHER INFORMATION: JPS00178

<400> SEQUENCE: 111
```

```
aaggcttagt ctgattcaga ggccgtcgtc ggt                                     33
```

<210> SEQ ID NO 112
<211> LENGTH: 430
<212> TYPE: DNA
<213> ORGANISM: Artificial Sequence
<220> FEATURE:
<223> OTHER INFORMATION: IDT gBlock synthesized Me-AM1 PmxaF

<400> SEQUENCE: 112

```
atggtgcagg gcgcttcccg cttggtcggg ccgcttcgcg agggcccgtt gacgacaacg        60
gtgcgatggg tcccggcccc ggtcaagacg atgccaatac gttgcgacac tacgccttgg      120
cactttttaga attgccttat cgtcctgata agaaatgtcc gaccagctaa agacatcgcg    180
tccaatcaaa gcctagaaaa tataggcgaa gggacgctaa taagtctttc ataagaccgc      240
gcaaatctaa aaatatcctt agattcacga tgcggcactt cggatgactt ccgagcgagc      300
ctggaacctc agaaaaacgt ctgagagata ccgcgaggcc gaaaggcgag gcggttcagc      360
gaggagacgc aggatgagca ggtttgtgac atcagtctcg gccttggcgg ctagcgagca      420
accaacactt                                                              430
```

<210> SEQ ID NO 113
<211> LENGTH: 34
<212> TYPE: DNA
<213> ORGANISM: Artificial Sequence
<220> FEATURE:
<223> OTHER INFORMATION: JPS00169

<400> SEQUENCE: 113

```
agcgccctgc accattatgt tccggatctg catc                                    34
```

<210> SEQ ID NO 114
<211> LENGTH: 46
<212> TYPE: DNA
<213> ORGANISM: Artificial Sequence
<220> FEATURE:
<223> OTHER INFORMATION: GMV00251

<400> SEQUENCE: 114

```
gagcaaccaa cacttaaaga ggagaaaatg ggcacggttg agcctg                       46
```

<210> SEQ ID NO 115
<211> LENGTH: 32
<212> TYPE: DNA
<213> ORGANISM: Artificial Sequence
<220> FEATURE:
<223> OTHER INFORMATION: (PS00170

<400> SEQUENCE: 115

```
atggtgcagg gcgcttcccg cttggtcggg cc                                      32
```

<210> SEQ ID NO 116
<211> LENGTH: 19
<212> TYPE: DNA
<213> ORGANISM: Artificial Sequence
<220> FEATURE:
<223> OTHER INFORMATION: JPS00171

<400> SEQUENCE: 116

```
aagtgttggt tgctcgcta                                                     19
```

<210> SEQ ID NO 117
<211> LENGTH: 68

```
<212> TYPE: DNA
<213> ORGANISM: Artificial Sequence
<220> FEATURE:
<223> OTHER INFORMATION: JPS00153

<400> SEQUENCE: 117
accactcaac gatcagctag cactgtacct aggactgagc tagccgtcaa gtcagcgccc     60
tgcaccat                                                              68

<210> SEQ ID NO 118
<211> LENGTH: 48
<212> TYPE: DNA
<213> ORGANISM: Artificial Sequence
<220> FEATURE:
<223> OTHER INFORMATION: JPS00151

<400> SEQUENCE: 118
tgatcgttga gtggtttaaa gaggagaaaa tgcgtgaaac gatacctc                  48

<210> SEQ ID NO 119
<211> LENGTH: 33
<212> TYPE: DNA
<213> ORGANISM: Artificial Sequence
<220> FEATURE:
<223> OTHER INFORMATION: JPS00154

<400> SEQUENCE: 119
aagtgttggt tgctctcagt gctgcgccga ggc                                  33

<210> SEQ ID NO 120
<211> LENGTH: 33
<212> TYPE: DNA
<213> ORGANISM: Artificial Sequence
<220> FEATURE:
<223> OTHER INFORMATION: JPS00183

<400> SEQUENCE: 120
tgagctagct ataaagtgat cactagtgct agc                                  33

<210> SEQ ID NO 121
<211> LENGTH: 55
<212> TYPE: DNA
<213> ORGANISM: Artificial Sequence
<220> FEATURE:
<223> OTHER INFORMATION: JPS00185

<400> SEQUENCE: 121
ttatagctag ctcagcccctt ggtacaatgc tagctgatcg ttgagtggtt taaag         55

<210> SEQ ID NO 122
<211> LENGTH: 35
<212> TYPE: DNA
<213> ORGANISM: Artificial Sequence
<220> FEATURE:
<223> OTHER INFORMATION: J23100

<400> SEQUENCE: 122
ttgacggcta gctcagtcct aggtacagtg ctagc                                35

<210> SEQ ID NO 123
<211> LENGTH: 35
<212> TYPE: DNA
<213> ORGANISM: Artificial Sequence
<220> FEATURE:
<223> OTHER INFORMATION: J23100 hybrid
```

<400> SEQUENCE: 123
ttgacggcta gctcagccct tggtacaatg ctagc      35

<210> SEQ ID NO 124
<211> LENGTH: 35
<212> TYPE: DNA
<213> ORGANISM: Artificial Sequence
<220> FEATURE:
<223> OTHER INFORMATION: J23115

<400> SEQUENCE: 124
tttatagcta gctcagccct tggtacaatg ctagc      35

<210> SEQ ID NO 125
<211> LENGTH: 22
<212> TYPE: DNA
<213> ORGANISM: Artificial Sequence
<220> FEATURE:
<223> OTHER INFORMATION: GMV00233

<400> SEQUENCE: 125
tgccagctgc attaatgaat cg      22

<210> SEQ ID NO 126
<211> LENGTH: 45
<212> TYPE: DNA
<213> ORGANISM: Artificial Sequence
<220> FEATURE:
<223> OTHER INFORMATION: GMV00235

<400> SEQUENCE: 126
ttaatgcagc tggcagccag cgcttcgtta atacagatgt aggtg      45

<210> SEQ ID NO 127
<211> LENGTH: 52
<212> TYPE: DNA
<213> ORGANISM: Artificial Sequence
<220> FEATURE:
<223> OTHER INFORMATION: GMV00433

<400> SEQUENCE: 127
gatcgttgag tggtgaactt aaagaggaga aaatgggcac ggttgagcct gg      52

<210> SEQ ID NO 128
<211> LENGTH: 19
<212> TYPE: DNA
<213> ORGANISM: Artificial Sequence
<220> FEATURE:
<223> OTHER INFORMATION: GMV00434

<400> SEQUENCE: 128
tgcattcgat tcctgtttg      19

<210> SEQ ID NO 129
<211> LENGTH: 19
<212> TYPE: DNA
<213> ORGANISM: Artificial Sequence
<220> FEATURE:
<223> OTHER INFORMATION: GMV00435

<400> SEQUENCE: 129
caggaatcga atgcaaccg      19

<210> SEQ ID NO 130
<211> LENGTH: 49

<212> TYPE: DNA
<213> ORGANISM: Artificial Sequence
<220> FEATURE:
<223> OTHER INFORMATION: GMV00436

<400> SEQUENCE: 130
gagcaaccaa cactcacaca ggaaaccatg catattacat acgatctgc         49

<210> SEQ ID NO 131
<211> LENGTH: 39
<212> TYPE: DNA
<213> ORGANISM: Artificial Sequence
<220> FEATURE:
<223> OTHER INFORMATION: GMV00437

<400> SEQUENCE: 131
gttcaccact caacgatctt aagcgtcaac gaaaccggt                    39

<210> SEQ ID NO 132
<211> LENGTH: 69
<212> TYPE: DNA
<213> ORGANISM: Artificial Sequence
<220> FEATURE:
<223> OTHER INFORMATION: GMV00438

<400> SEQUENCE: 132
tgaacaggtc tgactgctag cattgtacca agggctgagc tagctataaa gatttgtcct    60
actcaggag                                                             69

<210> SEQ ID NO 133
<211> LENGTH: 53
<212> TYPE: DNA
<213> ORGANISM: Artificial Sequence
<220> FEATURE:
<223> OTHER INFORMATION: GMV00439

<400> SEQUENCE: 133
agtcagacct gttcattaaa gaggagaaaa tgagcggaaa acccttttac gac        53

<210> SEQ ID NO 134
<211> LENGTH: 42
<212> TYPE: DNA
<213> ORGANISM: Artificial Sequence
<220> FEATURE:
<223> OTHER INFORMATION: GMV00440

<400> SEQUENCE: 134
aaggcttagt ctgattcaga cggcgcgcaa ggcggcgacg at                   42

<210> SEQ ID NO 135
<211> LENGTH: 49
<212> TYPE: DNA
<213> ORGANISM: Artificial Sequence
<220> FEATURE:
<223> OTHER INFORMATION: GMV00441

<400> SEQUENCE: 135
atcagactaa gcctttcaca caggaaacca tgcacgacag actgatcat           49

<210> SEQ ID NO 136
<211> LENGTH: 35
<212> TYPE: DNA
<213> ORGANISM: Artificial Sequence
<220> FEATURE:
<223> OTHER INFORMATION: GMV00442

<400> SEQUENCE: 136

```
ggtttattcc tcctttcaca catccccgac ttgcg                               35
```

<210> SEQ ID NO 137
<211> LENGTH: 49
<212> TYPE: DNA
<213> ORGANISM: Artificial Sequence
<220> FEATURE:
<223> OTHER INFORMATION: ESG00084

<400> SEQUENCE: 137

```
gagacagaac gaagtgtgac cagaacgcag aagcggtctg ataaaacag                49
```

<210> SEQ ID NO 138
<211> LENGTH: 70
<212> TYPE: DNA
<213> ORGANISM: Artificial Sequence
<220> FEATURE:
<223> OTHER INFORMATION: ESG00088

<400> SEQUENCE: 138

```
gtgttggttg ctcgctagca ctgtacctag gactgagcta gccgtcaagt cagcgccctg    60
caccattatg                                                           70
```

<210> SEQ ID NO 139
<211> LENGTH: 10705
<212> TYPE: DNA
<213> ORGANISM: Artificial Sequence
<220> FEATURE:
<223> OTHER INFORMATION: pMZT37

<400> SEQUENCE: 139

```
tcaccctgtc gggcaatgcc gaggcattct ggcagcagcg ccccctggcc tgtagtggat    60
tacgtgccgg tctgttccat cctaccaccg gctattcact gccgctggcg gttgccgtgg   120
ccgaccgcct gagcgcactt gatgtcttta cgtcggcctc aattcaccag gctattaggc   180
attttgcccg cgagcgctgg cagcagcagc gcttttttccg catgctgaat cgcatgctgt   240
ttttagccgg acccgccgat tcacgctggc gggttatgca gcgttttat ggtttacctg    300 aagatttaat tgcccgtttt tatgcgggaa aactcacgct gaccgatcgg ctacgtattc   360
tgagcggcaa gccgcctgtt ccggtattag cagcattgca agccattatg acgactcatc   420
gttaagagac agaacgaagt gtgaccagaa cgcagaagcg gtctgataaa acagaatttg   480
cctggcggca gtagcgcggt ggtcccacct gaccccatgc cgaactcaga agtgaaacgc   540
cgtagcgccg atggtagtgt ggggtctccc catgcgagag tagggaactg ccaggcatca   600
aataaaacga aaggctcagt cgaaagactg gcctttcgt tttatctgtt gtttgtcggt    660
gaacgctctc ctgagtagga caaatcttgt aggtggacca gttggtgatt ttgaactttt   720
gctttgccac ggaacggtct gcgttgtcgg aagatgcgt gatctgatcc ttcaactcag    780
caaaagttcg atttattcaa caaagccgcc gtcccgtcaa gtcagcgtaa tgctctgcca   840
gtgttacaac caattaacca attctgatta gaaaaactca tcgagcatca aatgaaactg   900
caatttattc atatcaggat tatcaatacc atatttttga aaaagccgtt tctgtaatga   960
aggagaaaac tcaccgaggc agttccatag gatggcaaga tcctggtatc ggtctgcgat  1020
tccgactcgt ccaacatcaa tacaacctat taatttcccc tcgtcaaaaa taaggttatc  1080
aagtgagaaa tcaccatgag tgacgactga atccggtgag aatggcaaaa gcttatgcat  1140
ttctttccag acttgttcaa caggccagcc attacgctcg tcatcaaaat cactcgcatc  1200
```

```
aaccaaaccg ttattcattc gtgattgcgc ctgagcgaga cgaaatacgc gatcgctgtt    1260
aaaaggacaa ttacaaacag gaatcgaatg caaccggcgc aggaacactg ccagcgcatc    1320
aacaatattt tcacctgaat caggatattc ttctaatacc tggaatgctg ttttcccggg    1380
gatcgcagtg gtgagtaacc atgcatcatc aggagtacgg ataaaatgct tgatggtcgg    1440
aagaggcata aattccgtca gccagtttag tctgaccatc tcatctgtaa catcattggc    1500
aacgctacct ttgccatgtt tcagaaacaa ctctggcgca tcgggcttcc catacaatcg    1560
atagattgtc gcacctgatt gcccgacatt atcgcgagcc catttatacc catataaatc    1620
agcatccatg ttggaattta atcgcggcct cgagcaagac gtttcccgtt gaatatggct    1680
cataacaccc cttgtattac tgtttatgta agcagacagt tttattgttc atgatgatat    1740
attttttatct tgtgcaatgt aacatcagag atttttgagac acaacgtggc tttcccccccc   1800
cccctgcag gtccgacacg gggatggatg gcgttcccga tcatggtcct gcttgcttcg    1860
ggtggcatcg gaatgccggc gctgcaagca atgttgtcca ggcaggtgga tgaggaacgt    1920
caggggcagc tgcaaggctc actggcggcg ctcaccagcc tgacctcgat cgtcggaccc    1980
ctcctcttca cggcgatcta tgcggcttct ataacaacgt ggaacgggtg gcatggatt     2040
gcaggcgctg ccctctactt gctctgcctg ccggcgctgc gtcgcgggct ttggagcggc    2100
gcagggcaac gagccgatcg ctgatcgtgg aaacgatagg cctatgccat gcgggtcaag    2160
gcgacttccg gcaagctata cgcgccctag aattgtcaat tttaatcctc tgtttatcgg    2220
cagttcgtag agcgcgccgt gcgtcccgag cgatactgag cgaagcaagt gcgtcgagca    2280
gtgcccgctt gttcctgaaa tgccagtaaa gcgctggctg ctgaaccccc agccggaact    2340
gaccccacaa ggccctagcg tttgcaatgc accaggtcat cattgaccca ggcgtgttcc    2400
accaggccgc tgcctcgcaa ctcttcgcag gcttcgccga cctgctcgcg ccacttcttc    2460
acgcgggtgg aatccgatcc gcacatgagg cggaaggttt ccagcttgag cgggtacggc    2520
tcccggtgcg agctgaaata gtcgaacatc cgtcgggccg tcggcgacag cttgcggtac    2580
ttctcccata tgaatttcgt gtagtggtcg ccagcaaaca gcacgacgat ttcctcgtcg    2640
atcaggacct ggcaacggga cgttttcttg ccacggtcca ggacgcggaa gcggtgcagc    2700
agcgacaccg attccaggtg cccaacgcgg tcggacgtga agcccatcgc cgtcgcctgt    2760
aggcgcgaca ggcattcctc ggccttcgtg taataccggc cattgatcga ccagcccagg    2820
tcctggcaaa gctcgtagaa cgtgaaggtg atcggctcgc cgatagggt gcgcttcgcg     2880
tactccaaca cctgctgcca caccagttcg tcatcgtcgg cccgcagctc gacgccggtg    2940
taggtgatct tcacgtcctt gttgacgtgg aaaatgacct tgttttgcag cgcctcgcgc    3000
gggattttct tgttgcgcgt ggtgaacagg gcagagcggg ccgtgtcgtt tggcatcgct    3060
cgcatcgtgt ccggccacgg cgcaatatcg aacaaggaaa gctgcatttc cttgatctgc    3120
tgcttcgtgt gtttcagcaa cgcggcctgc ttggcctcgc tgacctgttt tgccaggtcc    3180
tcgccggcgg ttttttcgctt cttggtcgtc atagttcctc gcgtgtcgat ggtcatcgac    3240
ttcgccaaac ctgccgcctc ctgttcgaga cgacgcgaac gctccacggc ggccgatggc    3300
gcgggcaggg caggggagc cagttgcacg ctgtcgcgct cgatcttggc cgtagcttgc     3360
tggaccatcg agccgacgga ctggaaggtt tcgcggggcg cacgcatgac ggtgcggctt    3420
gcgatggttt cggcatcctc ggcggaaaac cccgcgtcga tcagttcttg cctgtatgcc    3480
ttccggtcaa acgtccgatt cattcaccct ccttgcggga ttgccccgac tcacgccggg    3540
```

```
gcaatgtgcc cttattcctg atttgacccg cctggtgcct tggtgtccag ataatccacc    3600
ttatcggcaa tgaagtcggt cccgtagacc gtctggccgt ccttctcgta cttggtattc    3660
cgaatcttgc cctgcacgaa taccagctcc gcgaagtcgc tcttcttgat ggagcgcatg    3720
gggacgtgct tggcaatcac gcgcaccccc ggccgttttt agcggctaaa aaagtcatgg    3780
ctctgccctc gggcggacca cgcccatcat gaccttgcca agctcgtcct gcttctcttc    3840
gatcttcgcc agcagggcga ggatcgtggc atcaccgaac cgcgccgtgc gcgggtcgtc    3900
ggtgagccag agtttcagca ggccgcccag gcggcccagg tcgccattga tgcgggccag    3960
ctcgcggacg tgctcatagt ccacgacgcc cgtgattttg tagccctggc cgacggccag    4020
caggtaggcc tacaggctca tgccggccgc cgccgccttt cctcaatcg ctcttcgttc    4080
gtctggaagg cagtacacct tgataggtgg gctgcccttc ctggttggct tggtttcatc    4140
agccatccgc ttgccctcat ctgttacgcc ggcggtagcc ggccagcctc gcagagcagg    4200
attcccgttg agcaccgcca ggtgcgaata agggacagtg aagaaggaac acccgctcgc    4260
gggtgggcct acttcaccta tcctgcccgg ctgacgccgt tggatacacc aaggaaagtc    4320
tacacgaacc ctttggcaaa atcctgtata tcgtgcgaaa aaggatggat ataccgaaaa    4380
aatcgctata atgaccccga agcagggtta tgcagcggaa aagatccgtc gacccttttcc    4440
gacgctcacc gggctggttg ccctcgccgc tgggctggcg ccgtctatg gccctgcaaa    4500
cgcgccagaa acgcgtcga agccgtgtgc gagacaccgc ggccgccggc gttgtggata    4560
cctcgcggaa aacttggccc tcactgacag atgaggggcg gacgttgaca cttgaggggc    4620
cgactcaccc ggcgcggcgt tgacagatga ggggcaggct cgatttcggc cggcgacgtg    4680
gagctggcca gcctcgcaaa tcggcgaaaa cgcctgattt tacgcgagtt tcccacagat    4740
gatgtgacaa gcctgggga taagtgccct gcggtattga cacttgaggg gcgcgactac    4800
tgacagatga ggggcgcgat ccttgacact tgaggggcag agtgctgaca gatgaggggc    4860
gcacctattg acatttgagg ggctgtccac aggcagaaaa tccagcattt gcaagggttt    4920
ccgcccgttt ttcggccacc gctaacctgt cttttaacct gcttttaaac caatatttat    4980
aaaccttgtt tttaaccagg ctgcgcccct gtgcgcgtga ccgcgcacgc cgaaggggg    5040
tgcccccct tctcgaaccc tcccggcccg ctaacgcggg cctcccatcc cccagggc    5100
tgcgcccctc ggccgcgaac ggcctcaccc caaaaatggc agccaagctg accacttctg    5160
cgctcggccc ttccggctgg ctggtttatt gctgataaat ctggagccgg tgagcgtggg    5220
tctcgcggta tcattgcagc actggggcca gatggtaagc cctcccgtat cgtagttatc    5280
tacacgacgg ggagtcaggc aactatggat gaacgaaata gacagatcgc tgagataggt    5340
gcctcactga ttaagcattg gtaactgtca gaccaagttt actcatatat actttagatt    5400
gatttaaaac ttcattttta atttaaaagg atctaggtga agatccttt tgataatctc    5460
atgaccaaaa tcccttaacg tgagttttcg ttccactgag cgtcagaccc cgtagaaaag    5520
atcaaaggat cttcttgaga tcctttttt ctgcgcgtaa tctgctgctt gcaaacaaaa    5580
aaaccaccgc taccagcggt ggtttgtttg ccggatcaag agctaccaac tctttttccg    5640
aaggtaactg gcttcagcag agcgcagata ccaaatactg tccttctagt gtagccgtag    5700
ttaggccacc acttcaagaa ctctgtagca ccgcctacat acctcgctct gctaatcctg    5760
ttaccagtgg ctgctgccag tggcgataag tcgtgtctta ccgggttgga ctcaagacga    5820
tagttaccgg ataggcgca gcggtcgggc tgaacggggg gttcgtgcac acagcccagc    5880
ttggagcgaa cgacctacac cgaactgaga tacctacagc gtgagctatg agaaagcgcc    5940
```

-continued

```
acgcttcccg aagggagaaa ggcggacagg tatccggtaa gcggcagggt cggaacagga    6000
gagcgcacga gggagcttcc aggggggaaac gcctggtatc tttatagtcc tgtcgggttt    6060
cgccacctct gacttgagcg tcgattttg tgatgctcgt caggggggcg gagcctatgg    6120
aaaaacgcca gcaacgcggc ctttttacgg ttcctggcct tttgctggcc ttttgctcac    6180
atgttctttc ctgcgttatc ccctgattct gtggataacc gtattaccgc ctttgagtga    6240
gctgataccg ctcgccgcag ccgaacgacc gagcgcagcg agtcagtgag cgaggaagcg    6300
gaagagcgcc caatacgcaa accgcctctc cccgcgcgtt ggccgattca ttaatgcagc    6360
tggcagccag cgcttcgtta atacagatgt aggtgttcca cagggtagcc agcagcatcc    6420
tgcgatgcag atccggaaca taatggtgca gggcgctgac ttgacggcta gctcagtcct    6480
aggtacagtg ctagcgagca accaacactt aaagaggaga aaatgtatcc gtttataagg    6540
acagcccgaa tgacggtctg cgcaaaaaaa cacgttcatc tcactcgcga tgctgcggag    6600
cagttactgg ctgatattga tcgacgcctt gatcagttat tgcccgtgga gggagaacgg    6660
gatgttgtgg gtgccgcgat gcgtgaaggt gcgctggcac cgggaaaacg tattcgcccc    6720
atgttgctgt tgctgaccgc ccgcgatctg ggttgcgctg tcagccatga cggattactg    6780
gatttggcct gtgcggtgga aatggtccac gcggcttcgc tgatccttga cgatatgccc    6840
tgcatggacg atgcgaagct gcggcgcgga cgccctacca ttcattctca ttacggagag    6900
catgtggcaa tactggcggc ggttgccttg ctgagtaaag cctttggcgt aattgccgat    6960
gcagatggcc tcacgccgct ggcaaaaaat cgggcggttt ctgaactgtc aaacgccatc    7020
ggcatgcaag gattggttca gggtcagttc aaggatctgt ctgaaggga taagccgcgc    7080
agcgctgaag ctattttgat gacgaatcac tttaaaacca gcacgctgtt ttgtgcctcc    7140
atgcagatgg cctcgattgt tgcgaatgcc tccagcgaag cgcgtgattg cctgcatcgt    7200
ttttcacttg atcttggtca ggcatttcaa ctgctggacg atttgaccga tggcatgacc    7260
gacaccggta aggatagcaa tcaggacgcc ggtaaatcga cgctggtcaa tctgttaggc    7320
cctagggcgg ttgaagaacg tctgagacaa catcttcatc ttgccagtga gcatctctct    7380
gcggcctgcc aacacgggca cgccactcaa catttattc aggcctggtt tgacaaaaaa    7440
ctcgctgccg tcagttaaag gtctctagac aggatgtgtc acacaggaaa ccatgaaacc    7500
aactacggta attggtgcag gcttcggtgg cctggcactg gcaattcgtc tacaggctgc    7560
ggggatcccc gtcttactgc ttgaacaacg tgataaaccc ggcggtcggg cttatgtcta    7620
cgaggatcag gggtttacct tgatgcagg cccgacggtt atcaccgatc ccagtgccat    7680
tgaagaactg tttgcactgg caggaaaaca gttaaaagag tatgtcgaac tgctgccggt    7740
tacgccgttt taccgcctgt gttgggagtc agggaaggtc tttaattacg ataacgatca    7800
aacccggctc gaagcgcaga ttcagcagtt taatccccgc gatgtcgaag ttatcgtca    7860
gtttctggac tattcacgcg cggtgtttaa agaaggctat ctgaagctcg gtactgtccc    7920
tttttatcg ttcagagaca tgcttcgcgc cgcacctcaa ctggcgaaac tgcaggcatg    7980
gagaagcgtt tacagtaagg ttgccagtta catcgaagat gaacatctgc gccaggcgtt    8040
ttctttccac tcgctgttgg tgggcggcaa tcccttcgcc acctcatcca tttatacgtt    8100
gatacacgcg ctggagcgtg agtgggcgt ctggtttccg cgtggcggca ccggcgcatt    8160
agttcagggg atgataaagc tgtttcagga tctgggtggt gaagtcgtgt taacgccag    8220
agtcagccat atggaaacga caggaaacaa gattgaagcc gtgcatttag aggacggtcg    8280
```

```
caggttcctg acgcaagccg tcgcgtcaaa tgcagatgtg gttcatacct atcgcgacct    8340
gttaagccag caccctgccg cggttaagca gtccaacaaa ctgcagacta agcgtatgag    8400
taactctctg tttgtgctct attttggttt gaatcaccat catgatcagc tcgcgcatca    8460
cacggtttgt ttcggcccgc gttaccgcga actgattgac gagatttta atcatgatgg     8520
cctcgcagaa gacttctcac tttatctgca cgcgccctgt gtcacggatt cgtcactggc    8580
gcctgaaggt tgcggcagtt actatgtgtt ggcgccggtg ccgcatttag gcaccgcgaa    8640
cctcgactgg acggttgagg ggccaaaact acgcgaccgt atttttgagt accttgagca    8700
gcattacatg cctggcttac ggagtcagct ggtcacgcac cagatgttta cgccgtttga    8760
ttttcgcgac cagcttaatg cctatcaggg ctcagccttt tctgtggagc ccgttcttac    8820
ccagagcgcc tggtttcggc cgcataaccg cgataaaacc attactaatc tctacctggt    8880
cggcgcaggc acgcatcccg cgcaggcat tcctggcgtc atcggctcgg caaaagcgac      8940
agcaggtttg atgctggagg atctgattta agtgatcgtt gagtggtgaa cttaaagagg    9000
agaaaatgaa taatccgtcg ttactcaatc atgcggtcga aacgatggca gttggctcga    9060
aaagttttgc gacagcctca aagttatttg atgcaaaaac ccggcgcagc gtactgatgc    9120
tctacgcctg gtgccgccat tgtgacgatg ttattgacga ccagacgctg gcttccagg     9180
cccggcagcc tgccttacaa acgcccgaac aacgtctgat gcaacttgag atgaaaacgc    9240
gccaggccta tgcaggatcg cagatgcacg aaccggcgtt tgcggctttt caggaagtgg    9300
ctatggctca tgatatcgcc ccggcttacg cgtttgatca tctggaaggc ttcgccatgg    9360
atgtacgcga agcgcaatac agccaactgg acgatacgct gcgctattgc tatcacgttg    9420
caggcgttgt cggcttgatg atggcgcaaa tcatgggcgt acgggataac gccacgctgg    9480
accgcgcctg tgaccttggg ctggcatttc agttgaccaa tattgctcgc gatattgtgg    9540
acgatgcgca tgcgggccgc tgttatctgc cggcaagctg gctggagcat gaaggtctga    9600
acaaagagaa ttatgcggca cctgaaaacc gtcaggcgct gagccgtatc gcccgtcgtt    9660
tggtgcagga agcagaacct tactatttgt ctgccacagc gggcctggct gggttgcccc    9720
tgcgttcggc ctgggcaatc gctacggcga agcaggttta ccggaaaata ggtgtcaaag    9780
ttgaacaggc cggtcagcaa gcctgggatc agcggcagtc aacgaccacg cccgaaaaat    9840
taacgctgct gctggccgcc tctggtcagg cccttacttc ccggatgcgg gctcatcctc    9900
cccgccctgc gcatctctgg cagcgcccgc tctaatcacg tagcaagctg acagtttaaa    9960
gaggagaaaa tgggagcggc tatgcaaccg cattatgatc tgattctcgt gggggctgga    10020
ctcgcgaatg gccttatcgc cctgcgtctt cagcagcagc aacctgatat gcgtattttg    10080
cttatcgacg ccgcacccca ggcgggcggg aatcatacgt ggtcatttca ccacgatgat    10140
ttgactgaga gccaacatcg ttggatagct tcgctggtgg ttcatcactg gcccgactat    10200
caggtacgct ttcccacacg ccgtcgtaag ctgaacagcg gctacttctg tattacttct    10260
cagcgtttcg ctgaggtttt acagcgacag tttggcccgc acttgtggat ggataccgcg    10320
gtcgcagagg ttaatgcgga atctgttcgg ttgaaaaagg gtcaggttat cggtgcccgc    10380
gcggtgattg acgggcgggg ttatgcggca aactcagcac tgagcgtggg cttccaggcg    10440
tttattggcc aggaatggcg attgagccac ccgcatggtt tatcgtctcc cattatcatg    10500
gatgccacgg tcgatcagca aaatggttat cgcttcgtgt acagcctgcc gctctcgccg    10560
accagattgt taattgaaga cacgcactat atcgataatg cgacattaga tcctgaacgc    10620
gcgcggcaaa atatttgcga ctatgccgcg caacagggt ggcagcttca gacattgctg    10680
```

```
cgtgaagaac agggcgcctt accca                                          10705

<210> SEQ ID NO 140
<211> LENGTH: 411
<212> TYPE: DNA
<213> ORGANISM: Artificial Sequence
<220> FEATURE:
<223> OTHER INFORMATION: MaFAR-g1

<400> SEQUENCE: 140
gagcaaccaa cacttaaaga ggagaaaatg gcgacccagc agcagcagaa cggcgcctcg     60
gcgagcggcg tcctggaaca gttgcgcggg aagcatgtcc tgataaccgg taccaccggt    120
ttccttggca aggtagtcct ggaaaagctg atccgcacag tcccggacat cggcggcatc    180
cacctcctga tccggggcaa caagaggcat ccggccgccc gtgaacggtt cttgaacgag    240
atcgccagca gttcggtctt cgagcgtctg cgccacgacg acaacgaggc cttcgaaacc    300
ttcctggaag aaagggtgca ctgtataacc ggagaggtca ccgagagtcg tttcggcctt    360
accccggagc gcttccgcgc gctggcgggt caggtggacg ccttcatcaa t              411

<210> SEQ ID NO 141
<211> LENGTH: 465
<212> TYPE: DNA
<213> ORGANISM: Artificial Sequence
<220> FEATURE:
<223> OTHER INFORMATION: MaFAR-g2

<400> SEQUENCE: 141
gacgccttca tcaattcggc cgcctccgtc aacttccgcg aggaactgga caaggcgctg     60
aagatcaata cgctgtgcct ggagaatgtc gcggcccttg ctgaactcaa cagtgcgatg    120
gcggtcatcc aggtttcgac ctgctacgtt aacggcaaga atagcgggca gatcaccgaa    180
tcggtcatca gcccgcgggg ggagtccatc ccgcgtagca ccgatgggta ctatgaaatc    240
gaagaattgg tgcacctgct gcaggacaaa atcagcgatg tgaaggcccg atactccggg    300
aaggttctgg aaaaaaaatt ggtggaccta ggcatccggg aagccaataa ctacgggtgg    360
agcgatacat ataccttcac caagtggctg gcgaacagcc tcctcatgaa ggccctgagc    420
ggcagatcgc tgaccatcgt gcggccgtcg atcatcgagt cggca                     465

<210> SEQ ID NO 142
<211> LENGTH: 374
<212> TYPE: DNA
<213> ORGANISM: Artificial Sequence
<220> FEATURE:
<223> OTHER INFORMATION: MaFAR-g3

<400> SEQUENCE: 142
atcatcgagt cggcattgga agagcccagc ccggggtgga ttgaaggcgt caaggtcgcc     60
gatgccatca tactggccta cgcgagggag aaggtatcgc tctttcctgg caagcggagc    120
ggcatcatcg acgtcatccc agtggatctg gtggccaatt cgatcattct gtccctggcg    180
gaggcgctct ccggttcggg ccagcggcgt atctatcagt gctgcagcgg cggctcgaac    240
cccatctccc tcgggaagtt catcgactat ctgatggcgg aggcgaagac caactacgcg    300
gcctacgatc agctgttcta ccgccgcccc accaagccgt tcgtggccgt caaccgcaaa    360
ctcttcgacg tcgt                                                      374

<210> SEQ ID NO 143
```

```
<211> LENGTH: 376
<212> TYPE: DNA
<213> ORGANISM: Artificial Sequence
<220> FEATURE:
<223> OTHER INFORMATION: MaFAR-g4

<400> SEQUENCE: 143
actcttcgac gtcgtcgtgg gcggcatgcg ggtcccgctc tcgatcgcgg gcaaagccat      60
gcgcctggcg ggacaaaacc gcgaactgaa ggtcctgaag aatctggata cgacccggtc     120
cctggccacc attttcgggt tctacaccgc tccggactac atctttcgca atgacagcct     180
gatggccctg gcctcgcgca tgggcgagct ggaccgcgtg ttgttccccg ttgacgcccg     240
tcagatcgac tggcagctgt atctgtgcaa aatccacctc ggcgggctga atcggtacgc     300
gctcaaggaa cgtaagctgt actcgctccg ggccgccgac actcgcaaga aggcagcctg     360
agagacagaa cgaagt                                                     376

<210> SEQ ID NO 144
<211> LENGTH: 47
<212> TYPE: DNA
<213> ORGANISM: Artificial Sequence
<220> FEATURE:
<223> OTHER INFORMATION: GMV410

<400> SEQUENCE: 144
gagcaaccaa cacttaaaga ggagaaaatg cgcccctgc acccat                      47

<210> SEQ ID NO 145
<211> LENGTH: 47
<212> TYPE: DNA
<213> ORGANISM: Artificial Sequence
<220> FEATURE:
<223> OTHER INFORMATION: GMV411

<400> SEQUENCE: 145
gagcaaccaa cacttaaaga ggagaaaatg cgcctgctga ccgccgt                    47

<210> SEQ ID NO 146
<211> LENGTH: 47
<212> TYPE: DNA
<213> ORGANISM: Artificial Sequence
<220> FEATURE:
<223> OTHER INFORMATION: GMV412

<400> SEQUENCE: 146
gagcaaccaa cacttaaaga ggagaaaatg tccgtgatgt ccccgac                    47

<210> SEQ ID NO 147
<211> LENGTH: 47
<212> TYPE: DNA
<213> ORGANISM: Artificial Sequence
<220> FEATURE:
<223> OTHER INFORMATION: GMV413

<400> SEQUENCE: 147
gagcaaccaa cacttaaaga ggagaaaatg ccggtcaccg actccat                    47

<210> SEQ ID NO 148
<211> LENGTH: 47
<212> TYPE: DNA
<213> ORGANISM: Artificial Sequence
<220> FEATURE:
<223> OTHER INFORMATION: GMV414

<400> SEQUENCE: 148
```

```
gagcaaccaa cacttaaaga ggagaaaatg gccccgaccg actccct            47
```

<210> SEQ ID NO 149
<211> LENGTH: 47
<212> TYPE: DNA
<213> ORGANISM: Artificial Sequence
<220> FEATURE:
<223> OTHER INFORMATION: GMV415

<400> SEQUENCE: 149

```
gagcaaccaa cacttaaaga ggagaaaatg cccctgccga tgtcccc            47
```

<210> SEQ ID NO 150
<211> LENGTH: 35
<212> TYPE: DNA
<213> ORGANISM: Artificial Sequence
<220> FEATURE:
<223> OTHER INFORMATION: GMV416

<400> SEQUENCE: 150

```
acttcgttct gtctctcagt tggcggtctt gatgt                         35
```

<210> SEQ ID NO 151
<211> LENGTH: 35
<212> TYPE: DNA
<213> ORGANISM: Artificial Sequence
<220> FEATURE:
<223> OTHER INFORMATION: ACTTCGTTCTGTCTCTCACGGGGCCAGCTTCTTCA

<400> SEQUENCE: 151

```
acttcgttct gtctctcacg gggccagctt cttca                         35
```

<210> SEQ ID NO 152
<211> LENGTH: 35
<212> TYPE: DNA
<213> ORGANISM: Artificial Sequence
<220> FEATURE:
<223> OTHER INFORMATION: GMV418

<400> SEQUENCE: 152

```
acttcgttct gtctctcagg tgccgctcgc ggcca                         35
```

<210> SEQ ID NO 153
<211> LENGTH: 35
<212> TYPE: DNA
<213> ORGANISM: Artificial Sequence
<220> FEATURE:
<223> OTHER INFORMATION: GMV419

<400> SEQUENCE: 153

```
acttcgttct gtctctcaca gcagggccgc ttcca                         35
```

<210> SEQ ID NO 154
<211> LENGTH: 35
<212> TYPE: DNA
<213> ORGANISM: Artificial Sequence
<220> FEATURE:
<223> OTHER INFORMATION: GMV420

<400> SEQUENCE: 154

```
acttcgttct gtctctcaca ggccgaccgc ggttt                         35
```

<210> SEQ ID NO 155
<211> LENGTH: 35
<212> TYPE: DNA

```
<213> ORGANISM: Artificial Sequence
<220> FEATURE:
<223> OTHER INFORMATION: GMV421

<400> SEQUENCE: 155
acttcgttct gtctctcaga tgcccaccgc gcgtt                              35

<210> SEQ ID NO 156
<211> LENGTH: 1149
<212> TYPE: DNA
<213> ORGANISM: Saccharomyces cerevisiae

<400> SEQUENCE: 156
atgcgggcgc tggcgtattt caagaagggc gacatccatt tcaccaacga catccccgg     60 ccggagatcc agaccgacga cgaagtgatc atcgacgtct cctggtgcgg catctgcggc   120
agcgacctgc acgagtacct ggacggcccc atcttcatgc cgaaggacgg cgaatgccac   180
aagctgagca cgccgcgct gccctggcg atgggccatg agatgtcggg catcgtctcc    240
aaagtgggcc cgaaggtgac caaggtcaaa gtgggcgacc acgtcgtggt cgacgccgcg   300
agctcgtgcg ccgacctgca ctgctggccc cattccaagt tctataacag caagccgtgc   360
gacgcctgcc agcgcggctc ggagaacctg tgcacccatg cgggcttcgt cggcctgggc   420
gtgatcagcg gcggcttcgc cgaacaggtg gtcgtgtcgc agcaccatat catcccggtc   480
cccaaggaga tcccctgga cgtcgccgcc ctggtcgagc gctgtcggt cacctggcac    540 gccgtgaaga tctccggctt caagaagggc tccagcgccc tggtcctggg cgcgggcccc   600
atcggcctgt gcaccatcct ggtgctgaag ggcatgggcg cgtcgaagat cgtcgtgtcc   660
gagatcgccg aacgtcgcat cgagatggcg aagaagctgg gcgtcgaagt gttcaacccg   720
agcaagcacg gccataagtc gatcgagatc ctgcggggcc tgaccaagtc ccacgacggc   780
ttcgactaca gctatgactg ctcgggcatc caggtcacct tcgaaaccag cctgaaggcc   840
ctgaccttca gggcaccgc caccaacatc gcggtctggg gcccgaagcc cgtgccgttc    900
cagccgatgg acgtcacccct gcaggagaag gtgatgaccg gctcgatcgg ctacgtcgtg   960
gaagacttcg aggaagtcgt gcgcgccatc cataacggcg acatcgcgat ggaggactgc  1020
aagcagctga tcaccggcaa gcagcggatc gaggacggct gggaaaaggg cttccaggag  1080
ctgatggacc acaaggaatc caacgtgaag atcctgctga ccccgaacaa ccacggcgaa  1140
atgaagtga                                                         1149

<210> SEQ ID NO 157
<211> LENGTH: 382
<212> TYPE: PRT
<213> ORGANISM: Saccharomyces cerevisiae

<400> SEQUENCE: 157

Met Arg Ala Leu Ala Tyr Phe Lys Lys Gly Asp Ile His Phe Thr Asn
1               5                   10                  15

Asp Ile Pro Arg Pro Glu Ile Gln Thr Asp Asp Glu Val Ile Ile Asp
                20                  25                  30

Val Ser Trp Cys Gly Ile Cys Gly Ser Asp Leu His Glu Tyr Leu Asp
            35                  40                  45

Gly Pro Ile Phe Met Pro Lys Asp Gly Glu Cys His Lys Leu Ser Asn
        50                  55                  60

Ala Ala Leu Pro Leu Ala Met Gly His Glu Met Ser Gly Ile Val Ser
65                  70                  75                  80
```

```
Lys Val Gly Pro Lys Val Thr Lys Val Lys Val Gly Asp His Val Val
             85                  90                  95

Val Asp Ala Ala Ser Ser Cys Ala Asp Leu His Cys Trp Pro His Ser
        100                 105                 110

Lys Phe Tyr Asn Ser Lys Pro Cys Asp Ala Cys Gln Arg Gly Ser Glu
            115                 120                 125

Asn Leu Cys Thr His Ala Gly Phe Val Gly Leu Gly Val Ile Ser Gly
        130                 135                 140

Gly Phe Ala Glu Gln Val Val Ser Gln His His Ile Ile Pro Val
145                 150                 155                 160

Pro Lys Glu Ile Pro Leu Asp Val Ala Ala Leu Val Glu Pro Leu Ser
                165                 170                 175

Val Thr Trp His Ala Val Lys Ile Ser Gly Phe Lys Lys Gly Ser Ser
            180                 185                 190

Ala Leu Val Leu Gly Ala Gly Pro Ile Gly Leu Cys Thr Ile Leu Val
        195                 200                 205

Leu Lys Gly Met Gly Ala Ser Lys Ile Val Val Ser Glu Ile Ala Glu
        210                 215                 220

Arg Arg Ile Glu Met Ala Lys Lys Leu Gly Val Glu Val Phe Asn Pro
225                 230                 235                 240

Ser Lys His Gly His Lys Ser Ile Glu Ile Leu Arg Gly Leu Thr Lys
            245                 250                 255

Ser His Asp Gly Phe Asp Tyr Ser Tyr Asp Cys Ser Gly Ile Gln Val
            260                 265                 270

Thr Phe Glu Thr Ser Leu Lys Ala Leu Thr Phe Lys Gly Thr Ala Thr
            275                 280                 285

Asn Ile Ala Val Trp Gly Pro Lys Pro Val Pro Phe Gln Pro Met Asp
            290                 295                 300

Val Thr Leu Gln Glu Lys Val Met Thr Gly Ser Ile Gly Tyr Val Val
305                 310                 315                 320

Glu Asp Phe Glu Glu Val Val Arg Ala Ile His Asn Gly Asp Ile Ala
                325                 330                 335

Met Glu Asp Cys Lys Gln Leu Ile Thr Gly Lys Gln Arg Ile Glu Asp
            340                 345                 350

Gly Trp Glu Lys Gly Phe Gln Glu Leu Met Asp His Lys Glu Ser Asn
            355                 360                 365

Val Lys Ile Leu Leu Thr Pro Asn Asn His Gly Glu Met Lys
            370                 375                 380

<210> SEQ ID NO 158
<211> LENGTH: 47
<212> TYPE: DNA
<213> ORGANISM: Artificial Sequence
<220> FEATURE:
<223> OTHER INFORMATION: GMV00268

<400> SEQUENCE: 158
gagcaaccaa cacttaaaga ggagaaaatg cgggcgctgg cgtattt                47

<210> SEQ ID NO 159
<211> LENGTH: 35
<212> TYPE: DNA
<213> ORGANISM: Artificial Sequence
<220> FEATURE:
<223> OTHER INFORMATION: GMV00271

<400> SEQUENCE: 159
```

```
acttcgttct gtctctcact tcatttcgcc gtggt                              35
```

<210> SEQ ID NO 160
<211> LENGTH: 990
<212> TYPE: DNA
<213> ORGANISM: Escherichia coli

<400> SEQUENCE: 160

```
atgcatatta catacgatct gccggttgct attgatgaca ttattgaagc gaaacaacga    60
ctggctgggc gaatttataa acaggcatg cctcgctcca actatttttag tgaacgttgc   120
aaaggtgaaa tattcctgaa gtttgaaaat atgcagcgta cgggttcatt taaaattcgt   180
ggcgcattta ataaattaag ttcactgacc gatgcggaaa aacgcaaagg cgtggtggcc   240
tgttctgcgg gcaaccatgc gcaaggggtt tccctctcct gcgcgatgct gggtatcgac   300
ggtaaagtgg tgatgccaaa aggtgcgcca aaatccaaag tagcggcaac gtgcgactac   360
tccgcagaag tcgttctgca tggtgataac ttcaacgaca ctatcgctaa agtgagcgaa   420
attgtcgaaa tggaaggccg tatttttatc ccaccttacg atgatccgaa agtgattgct   480
ggccagggaa cgattggtct ggaaattatg aagatctct atgatgtcga taacgtgatt   540
gtgccaattg gtggtggcgg tttaattgct ggtattgcgg tggcaattaa atctattaac   600
ccgaccattc gtgttattgg cgtacagtct gaaaacgttc acggcatggc ggcttctttc   660
cactccgag aaataaccac gcaccgaact accggcaccc tggcggatgg ttgtgatgtc   720
tcccgcccgg gtaatttaac ttacgaaatc gttcgtgaat tagtcgatga catcgtgctg   780
gtcagcgaag acgaaatcag aaacagtatg attgccttaa ttcagcgcaa taaagtcgtc   840
accgaaggcg caggcgctct ggcatgtgct gcattattaa gcggtaaatt agaccaatat   900
attcaaaaca gaaaaaccgt cagtattatt tccggcggca atatcgatct ttctcgcgtc   960
tctcaaatca ccggtttcgt tgacgcttaa                                   990
```

<210> SEQ ID NO 161
<211> LENGTH: 329
<212> TYPE: PRT
<213> ORGANISM: Escherichia coli

<400> SEQUENCE: 161

```
Met His Ile Thr Tyr Asp Leu Pro Val Ala Ile Asp Asp Ile Ile Glu
1               5                   10                  15

Ala Lys Gln Arg Leu Ala Gly Arg Ile Tyr Lys Thr Gly Met Pro Arg
            20                  25                  30

Ser Asn Tyr Phe Ser Glu Arg Cys Lys Gly Glu Ile Phe Leu Lys Phe
        35                  40                  45

Glu Asn Met Gln Arg Thr Gly Ser Phe Lys Ile Arg Gly Ala Phe Asn
    50                  55                  60

Lys Leu Ser Ser Leu Thr Asp Ala Glu Lys Arg Lys Gly Val Val Ala
65                  70                  75                  80

Cys Ser Ala Gly Asn His Ala Gln Gly Val Ser Leu Ser Cys Ala Met
                85                  90                  95

Leu Gly Ile Asp Gly Lys Val Val Met Pro Lys Gly Ala Pro Lys Ser
            100                 105                 110

Lys Val Ala Ala Thr Cys Asp Tyr Ser Ala Glu Val Val Leu His Gly
        115                 120                 125

Asp Asn Phe Asn Asp Thr Ile Ala Lys Val Ser Glu Ile Val Glu Met
    130                 135                 140
```

```
Glu Gly Arg Ile Phe Ile Pro Pro Tyr Asp Asp Pro Lys Val Ile Ala
145                 150                 155                 160

Gly Gln Gly Thr Ile Gly Leu Glu Ile Met Glu Asp Leu Tyr Asp Val
                165                 170                 175

Asp Asn Val Ile Val Pro Ile Gly Gly Gly Leu Ile Ala Gly Ile
            180                 185                 190

Ala Val Ala Ile Lys Ser Ile Asn Pro Thr Ile Arg Val Ile Gly Val
        195                 200                 205

Gln Ser Glu Asn Val His Gly Met Ala Ala Ser Phe His Ser Gly Glu
    210                 215                 220

Ile Thr Thr His Arg Thr Thr Gly Thr Leu Ala Asp Gly Cys Asp Val
225                 230                 235                 240

Ser Arg Pro Gly Asn Leu Thr Tyr Glu Ile Val Arg Glu Leu Val Asp
                245                 250                 255

Asp Ile Val Leu Val Ser Glu Asp Glu Ile Arg Asn Ser Met Ile Ala
            260                 265                 270

Leu Ile Gln Arg Asn Lys Val Val Thr Glu Gly Ala Gly Ala Leu Ala
        275                 280                 285

Cys Ala Ala Leu Leu Ser Gly Lys Leu Asp Gln Tyr Ile Gln Asn Arg
    290                 295                 300

Lys Thr Val Ser Ile Ile Ser Gly Gly Asn Ile Asp Leu Ser Arg Val
305                 310                 315                 320

Ser Gln Ile Thr Gly Phe Val Asp Ala
                325

<210> SEQ ID NO 162
<211> LENGTH: 590
<212> TYPE: PRT
<213> ORGANISM: Methylosinus trichosporium

<400> SEQUENCE: 162

Met Ala Arg Lys Met Thr Gly Ala Glu Met Val Val Glu Ala Leu Lys
1               5                   10                  15

Asp Gln Gly Val Glu Ile Ile Phe Gly Tyr Pro Gly Gly Ala Val Leu
            20                  25                  30

Pro Ile Tyr Asp Ala Leu Phe His Gln Glu Lys Val Gln His Ile Leu
        35                  40                  45

Val Arg His Glu Gln Gly Ala Ala His Ala Ala Glu Gly Tyr Ala Arg
    50                  55                  60

Ser Ser Gly Lys Val Gly Val Leu Leu Val Thr Ser Gly Pro Gly Ala
65                  70                  75                  80

Thr Asn Thr Ile Thr Gly Leu Thr Asp Ala Leu Met Asp Ser Ile Pro
                85                  90                  95

Val Val Cys Ile Thr Gly Gln Val Pro Thr His Leu Ile Gly Ser Asp
            100                 105                 110

Ala Phe Gln Glu Cys Asp Thr Val Gly Ile Thr Arg His Cys Thr Lys
        115                 120                 125

His Asn Tyr Leu Val Lys Ser Val Asp Asp Leu Pro Arg Ile Leu His
    130                 135                 140

Glu Ala Phe Tyr Val Ala Ser Ser Gly Arg Pro Gly Pro Val Val Ile
145                 150                 155                 160

Asp Ile Pro Lys Asp Val Gln Phe Ala Ser Gly Thr Tyr Thr Gly Pro
                165                 170                 175

Arg Asn Val His His Lys Thr Tyr Gln Pro Lys Leu Glu Gly Asp Thr
            180                 185                 190
```

Glu Ser Ile Arg Arg Ala Val Lys Met Met Ala Ala Lys Arg Pro
    195                 200                 205

Ile Phe Tyr Thr Gly Gly Val Ile Asn Ser Gly Pro Ala Ala Ser
    210                 215                 220

Thr Leu Arg Glu Leu Val Ser Leu Thr Gly Phe Pro Ile Thr Ser
225                 230                 235                 240

Thr Leu Met Gly Leu Gly Ala Tyr Pro Gly Ser Gly Pro Asn Trp Leu
                    245                 250                 255

Gly Met Leu Gly Met His Gly Thr Phe Glu Ala Asn Asn Ala Met His
                260                 265                 270

Asp Cys Asp Leu Met Ile Ala Val Gly Ala Arg Phe Asp Asp Arg Ile
            275                 280                 285

Thr Gly Arg Leu Asp Ala Phe Ser Pro Gly Ser Lys Lys Ile His Ile
    290                 295                 300

Asp Ile Asp Arg Ser Ser Ile Asn Lys Asn Val Lys Ile Asp Leu Pro
305                 310                 315                 320

Ile Val Gly Asp Cys Gly His Val Leu Glu Ser Leu Val Arg Val Trp
                325                 330                 335

Arg Ser Glu Ala Met His Ala Glu Lys Gln Pro Leu Asp Gly Trp Trp
                340                 345                 350

Lys Thr Ile Asp His Trp Arg Glu Arg Lys Ser Leu Ala Phe Arg Asn
            355                 360                 365

Ser Asp Lys Val Ile Lys Pro Gln Tyr Ala Val Gln Arg Leu Tyr Ala
    370                 375                 380

Leu Thr Lys Asp Arg Asp Pro Tyr Ile Thr Thr Glu Val Gly Gln His
385                 390                 395                 400

Gln Met Trp Ala Ala Gln His Tyr His Phe Asp Glu Pro Asn Arg Trp
                405                 410                 415

Met Thr Ser Gly Gly Leu Gly Thr Met Gly Tyr Gly Leu Pro Ala Ala
                420                 425                 430

Ile Gly Ala Gln Leu Ala His Pro Lys Ser Leu Val Val Asp Ile Ala
            435                 440                 445

Gly Glu Ala Ser Ile Leu Met Asn Ile Gln Glu Met Ser Thr Ala Ile
    450                 455                 460

Gln Tyr Arg Leu Pro Val Lys Val Phe Ile Leu Asn Asn Glu Tyr Met
465                 470                 475                 480

Gly Met Val Arg Gln Trp Gln Glu Leu Leu His Gly Arg Tyr Ser
                485                 490                 495

His Ser Tyr Ser Glu Ala Leu Pro Asp Phe Val Lys Leu Ala Glu Ala
            500                 505                 510

Phe Gly Gly Lys Gly Ile Arg Cys Ser Asp Pro Ala Glu Leu Asp Ser
    515                 520                 525

Ala Ile Leu Glu Met Ile Asp Tyr Asp Gly Pro Val Ile Phe Asp Cys
530                 535                 540

Leu Val Glu Lys Asn Glu Asn Cys Phe Pro Met Ile Pro Ser Gly Lys
545                 550                 555                 560

Ala His Asn Asp Met Leu Leu Ala Asp Leu Gly Asp Asp Ala Gly Val
                565                 570                 575

Glu Leu Gly Ser Ile Ile Asp Glu Lys Gly Lys Met Leu Val
            580                 585                 590

<210> SEQ ID NO 163
<211> LENGTH: 351

<212> TYPE: PRT
<213> ORGANISM: Methylosinus trichosporium

<400> SEQUENCE: 163

```
Met Ser Thr Lys Ala Tyr Ala Val Ala Ser Ala Glu Ala Leu Phe Gly
1               5                   10                  15

Pro Leu Ala Ile Glu Arg Arg Ala Leu Gly Pro Glu Asp Val Glu Ile
            20                  25                  30

Asp Ile Leu Tyr Cys Gly Val Cys His Ser Asp Leu His Thr Ala Arg
        35                  40                  45

Ser Glu Trp Pro Gly Thr Arg Tyr Pro Cys Val Pro Gly His Glu Ile
    50                  55                  60

Val Gly Arg Val Thr Ala Val Gly Ala Lys Val Thr Lys Phe Ser Val
65                  70                  75                  80

Gly Asp Leu Ala Ala Val Gly Cys Met Val Asp Ser Cys Arg Arg Cys
                85                  90                  95

Leu Ser Cys Asp Asp Gly Leu Glu Gln Tyr Cys Glu His Gly Phe Thr
            100                 105                 110

Ala Thr Tyr Asn Gly Pro Ile Tyr Gly Ser Gly Glu Asn Thr Phe Gly
        115                 120                 125

Gly Tyr Ser Glu Lys Ile Val Val Asp Ala His Phe Val Leu Ala Ile
    130                 135                 140

His His Ser Glu Thr Gln Leu Ala Gly Val Ala Pro Leu Leu Cys Ala
145                 150                 155                 160

Gly Ile Thr Thr Trp Ser Pro Leu Lys His Trp Gly Val Gly Pro Gly
                165                 170                 175

Lys Ser Val Gly Ile Val Gly Ile Gly Gly Leu Gly His Met Gly Val
            180                 185                 190

Lys Leu Ala His Ala Leu Gly Ala His Val Val Ala Phe Thr Thr Ser
        195                 200                 205

Pro Ser Lys Arg Asp Ala Ala Leu Ala Leu Gly Ala Asp Glu Val Val
    210                 215                 220

Val Ser Thr Asp Pro Ala Ala Met Ala Ala Arg Ala Gly Ser Leu Asp
225                 230                 235                 240

Phe Ile Leu Asp Thr Val Ala Val Ala His Asp Leu Asp Ala Tyr Val
                245                 250                 255

Asn Leu Leu Lys Arg Asp Gly Ala Leu Val Leu Val Gly Val Pro Ala
            260                 265                 270

Thr Pro His Pro Ser Pro Ser Ala Gly Gly Leu Ile Phe Lys Arg Arg
        275                 280                 285

Gln Val Ala Gly Ser Leu Ile Gly Gly Val Lys Glu Thr Gln Glu Met
    290                 295                 300

Leu Asp Phe Cys Ala Glu Arg Gly Ile Val Ala Asp Ile Glu Thr Ile
305                 310                 315                 320

Ala Met Gln Gln Ile Glu Thr Ala Tyr Ala Arg Met Leu Lys Asn Asp
                325                 330                 335

Val Lys Tyr Arg Phe Val Ile Asp Met Ala Thr Leu Lys Ala Ala
            340                 345                 350
```

<210> SEQ ID NO 164
<211> LENGTH: 342
<212> TYPE: PRT
<213> ORGANISM: Methylococcus capsulatus

<400> SEQUENCE: 164

Met Lys Ala Trp Val Ile Asp Arg Ile Gly Pro Leu Asp Ser Ser Arg
1               5                   10                  15

Thr Leu Leu Arg Ala Thr Asp Leu Pro Val Pro Glu Pro Gly Pro Gly
            20                  25                  30

Glu Ile Leu Leu Gln Val Ala Val Cys Gly Val Cys His Thr Glu Ile
            35                  40                  45

Asp Glu Ile Glu Gly Arg Thr Ala Pro Pro Arg Leu Pro Val Val Pro
50                  55                  60

Gly His Gln Ala Val Gly Arg Ile Ala Ala Leu Gly Ser Gly Val Ala
65                  70                  75                  80

Glu Phe Ala Leu Gly Asp Arg Val Gly Val Ala Trp Ile Phe Ser Ala
            85                  90                  95

Cys Gly Glu Cys Glu Phe Cys Arg Ser Gly Arg Glu Asn Leu Cys Phe
            100                 105                 110

Ala Phe Cys Ala Thr Gly Arg Asp Val Asp Gly Gly Tyr Ala Gln Tyr
            115                 120                 125

Met Thr Val Pro Ala Ala Phe Ala Phe Arg Ile Pro Glu Gly Phe Thr
            130                 135                 140

Asp Ala Glu Ala Ala Pro Leu Leu Cys Ala Gly Ala Ile Gly Tyr Arg
145                 150                 155                 160

Ser Leu Asn Leu Ser Gly Leu Lys Asn Gly Gln Pro Leu Gly Leu Thr
            165                 170                 175

Gly Phe Gly Ala Ser Ala His Leu Val Leu Met Met Ala Arg Tyr Arg
            180                 185                 190

Phe Pro Asp Ser Glu Val Tyr Val Phe Ala Arg His Pro Glu Glu Arg
            195                 200                 205

Ala Phe Ala Leu Gln Leu Gly Ala Val Trp Ala Gly Asp Thr Ala Asp
            210                 215                 220

Ile Ala Pro Ala Pro Leu Ala Ala Ile Ile Asp Thr Thr Pro Ala Trp
225                 230                 235                 240

Lys Pro Val Val Ala Leu Ala Asn Leu Ala Pro Gly Gly Arg Leu
            245                 250                 255

Val Val Asn Ala Ile Arg Lys Ala Pro Asp Asp Arg Ala Cys Leu Ala
            260                 265                 270

Glu Leu Asp Tyr Ala Arg His Leu Trp Met Glu Arg Glu Ile Lys Ser
            275                 280                 285

Val Ala Asn Val Ala Arg Ser Asp Val Ala Gly Phe Leu Ala Leu Ala
            290                 295                 300

Ala Glu Met Gly Ile Arg Pro Glu Thr Glu Tyr Pro Phe Glu Asp
305                 310                 315                 320

Ala Asp Arg Ala Leu Leu Asp Leu Lys Gln Arg Arg Ile Arg Gly Ala
            325                 330                 335

Lys Val Leu Arg Val Thr
            340

<210> SEQ ID NO 165
<211> LENGTH: 355
<212> TYPE: PRT
<213> ORGANISM: Methylococcus capsulatus

<400> SEQUENCE: 165

Met Pro Thr Ala Lys Ala Tyr Ala Ala Phe Ser Ala Asp Ser Ala Leu
1               5                   10                  15

Ala Pro Phe Val Leu Gln Arg Arg Asp Pro Leu Pro Gln Asp Ile Arg
            20                  25                  30

```
Ile Gly Ile Leu Tyr Cys Gly Val Cys His Ser Asp Leu His Gln Ala
        35                  40                  45
Arg Asn Glu Trp Asn Ala Thr Thr Tyr Pro Cys Val Pro Gly His Glu
 50                  55                  60
Ile Val Gly Lys Val Leu Glu Val Gly Arg Ser Val Thr Lys Phe Lys
 65                  70                  75                  80
Pro Gly Asp Thr Val Ala Val Gly Cys Met Val Asp Ser Cys Arg Thr
                    85                  90                  95
Cys Pro Asn Cys Val Asp Ala Leu Glu Gln His Cys Glu His Gly Pro
                100                 105                 110
Val Phe Thr Tyr Asn Ser Pro Asp Pro His Gly Gly Met Thr Phe
                115                 120                 125
Gly Gly Tyr Ala Glu Ser Ile Val Val Asp Glu Ala Phe Val Leu Arg
            130                 135                 140
Ile Pro Asp Gly Leu Asp Leu Ala Ala Ala Pro Leu Leu Cys Ala
145                 150                 155                 160
Gly Ile Thr Thr Tyr Ser Pro Leu Arg His Trp Lys Val Gly Ala Gly
                        165                 170                 175
Gln Arg Val Gly Val Val Gly Leu Gly Gly Leu Gly His Met Ala Leu
                180                 185                 190
Lys Phe Ala His Thr Phe Gly Ala Glu Thr Val Leu Phe Thr Thr Thr
                195                 200                 205
Pro Asp Lys Ala Glu Asp Ala Arg Arg Leu Gly Ala Asp Glu Val Val
            210                 215                 220
Val Ser Arg Asp Pro Glu Ala Met Ala Arg Gln Ala Gly Arg Phe Asp
225                 230                 235                 240
Phe Ile Leu Asp Thr Val Ser Ala Pro His Asp Ile Asp Ala Tyr Leu
                    245                 250                 255
Asn Leu Leu Arg Arg Asp Gly Thr Leu Thr Leu Val Gly Val Pro Pro
                260                 265                 270
Gln Gly Val Gln Val Met Pro Phe Ser Leu Ile Gly Gly Arg Arg Arg
            275                 280                 285
Leu Ala Gly Ser Leu Ile Gly Gly Ile Arg Glu Thr Gln Glu Met Leu
            290                 295                 300
Asp Phe Cys Gly Glu His Gly Ile Val Cys Asp Ile Glu Leu Ile Pro
305                 310                 315                 320
Ile Gln Gly Ile Asn Asp Ala Phe Glu Arg Met Leu Lys Ser Asp Val
                    325                 330                 335
Lys Tyr Arg Phe Val Ile Asp Met Ala Thr Leu Asn Gly Glu Ser Ser
                340                 345                 350
Gly Gly Arg
        355

<210> SEQ ID NO 166
<211> LENGTH: 548
<212> TYPE: PRT
<213> ORGANISM: Lactococcus lactis

<400> SEQUENCE: 166

Met Tyr Thr Val Gly Asp Tyr Leu Leu Asp Arg Leu His Glu Leu Gly
 1               5                  10                  15
Ile Glu Glu Ile Phe Gly Val Pro Gly Asp Tyr Asn Leu Gln Phe Leu
                20                  25                  30
Asp Gln Ile Ile Ser Arg Lys Asp Met Lys Trp Val Gly Asn Ala Asn
```

```
                35                  40                  45
Glu Leu Asn Ala Ser Tyr Met Ala Asp Gly Tyr Ala Arg Thr Lys Lys
 50                  55                  60

Ala Ala Ala Phe Leu Thr Thr Phe Gly Val Gly Glu Leu Ser Ala Val
 65                  70                  75                  80

Asn Gly Leu Ala Gly Ser Tyr Ala Glu Asn Leu Pro Val Val Glu Ile
                 85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
                115                 120                 125

Pro Val Thr Ala Ala Arg Thr Leu Leu Thr Ala Glu Asn Ala Thr Val
130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Pro Thr Ser Asn Thr Ser Asp Gln
                180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Asn Thr
210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Thr Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asn Glu Asn Lys Met Ile Ser Leu Asn
290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Gly Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445

Pro Ile Cys Phe Ile Ile Asn Asn Asp Gly Tyr Thr Val Glu Arg Glu
450                 455                 460
```

```
Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Val Leu Ala Lys
        515                 520                 525

Glu Asp Ala Pro Lys Val Leu Lys Lys Met Gly Lys Leu Phe Ala Glu
    530                 535                 540

Gln Asn Lys Ser
545

<210> SEQ ID NO 167
<211> LENGTH: 563
<212> TYPE: PRT
<213> ORGANISM: Saccharomyces cerevisiae

<400> SEQUENCE: 167

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
```

```
                275                 280                 285
Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Lys Gly Tyr Lys Ser Val Pro Val Pro Thr Lys
                340                 345                 350

Thr Pro Ala Asn Lys Gly Val Pro Ala Ser Thr Pro Leu Lys Gln Glu
                355                 360                 365

Trp Leu Trp Asn Glu Leu Ser Lys Phe Leu Gln Glu Gly Asp Val Ile
                370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Asn Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
                450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
                500                 505                 510

Ala Thr Thr Gly Glu Trp Asp Ala Leu Thr Thr Asp Ser Glu Phe Gln
                515                 520                 525

Lys Asn Ser Val Ile Arg Leu Ile Glu Leu Lys Leu Pro Val Phe Asp
                530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 168
<211> LENGTH: 635
<212> TYPE: PRT
<213> ORGANISM: Saccharomyces cerevisiae

<400> SEQUENCE: 168

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
                20                  25                  30

Lys Arg Leu Leu Ser Ile Asp Thr Lys Ser Val Phe Gly Val Pro Gly
            35                  40                  45

Asp Phe Asn Leu Ser Leu Leu Glu Tyr Leu Tyr Ser Pro Ser Val Glu
            50                  55                  60

Ser Ala Gly Leu Arg Trp Val Gly Thr Cys Asn Glu Leu Asn Ala Ala
65              70                  75                  80

Tyr Ala Ala Asp Gly Tyr Ser Arg Tyr Ser Asn Lys Ile Gly Cys Leu
```

```
                85                  90                  95
Ile Thr Thr Tyr Gly Val Gly Glu Leu Ser Ala Leu Asn Gly Ile Ala
            100                 105                 110
Gly Ser Phe Ala Glu Asn Val Lys Val Leu His Ile Val Gly Val Ala
            115                 120                 125
Lys Ser Ile Asp Ser Arg Ser Ser Asn Phe Ser Asp Arg Asn Leu His
            130                 135                 140
His Leu Val Pro Gln Leu His Asp Ser Asn Phe Lys Gly Pro Asn His
145                 150                 155                 160
Lys Val Tyr His Asp Met Val Lys Asp Arg Val Ala Cys Ser Val Ala
                165                 170                 175
Tyr Leu Glu Asp Ile Glu Thr Ala Cys Asp Gln Val Asp Asn Val Ile
                180                 185                 190
Arg Asp Ile Tyr Lys Tyr Ser Lys Pro Gly Tyr Ile Phe Val Pro Ala
                195                 200                 205
Asp Phe Ala Asp Met Ser Val Thr Cys Asp Asn Leu Val Asn Val Pro
            210                 215                 220
Arg Ile Ser Gln Gln Asp Cys Ile Val Tyr Pro Ser Glu Asn Gln Leu
225                 230                 235                 240
Ser Asp Ile Ile Asn Lys Ile Thr Ser Trp Ile Tyr Ser Ser Lys Thr
                245                 250                 255
Pro Ala Ile Leu Gly Asp Val Leu Thr Asp Arg Tyr Gly Val Ser Asn
            260                 265                 270
Phe Leu Asn Lys Leu Ile Cys Lys Thr Gly Ile Trp Asn Phe Ser Thr
            275                 280                 285
Val Met Gly Lys Ser Val Ile Asp Glu Ser Asn Pro Thr Tyr Met Gly
            290                 295                 300
Gln Tyr Asn Gly Lys Glu Gly Leu Lys Gln Val Tyr Glu His Phe Glu
305                 310                 315                 320
Leu Cys Asp Leu Val Leu His Phe Gly Val Asp Ile Asn Glu Ile Asn
                325                 330                 335
Asn Gly His Tyr Thr Phe Thr Tyr Lys Pro Asn Ala Lys Ile Ile Gln
            340                 345                 350
Phe His Pro Asn Tyr Ile Arg Leu Val Asp Thr Arg Gln Gly Asn Glu
            355                 360                 365
Gln Met Phe Lys Gly Ile Asn Phe Ala Pro Ile Leu Lys Glu Leu Tyr
            370                 375                 380
Lys Arg Ile Asp Val Ser Lys Leu Ser Leu Gln Tyr Asp Ser Asn Val
385                 390                 395                 400
Thr Gln Tyr Thr Asn Glu Thr Met Arg Leu Glu Asp Pro Thr Asn Gly
                405                 410                 415
Gln Ser Ser Ile Ile Thr Gln Val His Leu Gln Lys Thr Met Pro Lys
            420                 425                 430
Phe Leu Asn Pro Gly Asp Val Val Cys Glu Thr Gly Ser Phe Gln
            435                 440                 445
Phe Ser Val Arg Asp Phe Ala Phe Pro Ser Gln Leu Lys Tyr Ile Ser
            450                 455                 460
Gln Gly Phe Phe Leu Ser Ile Gly Met Ala Leu Pro Ala Ala Leu Gly
465                 470                 475                 480
Val Gly Ile Ala Met Gln Asp His Ser Asn Ala His Ile Asn Gly Gly
                485                 490                 495
Asn Val Lys Glu Asp Tyr Lys Pro Arg Leu Ile Leu Phe Glu Gly Asp
            500                 505                 510
```

```
Gly Ala Ala Gln Met Thr Ile Gln Glu Leu Ser Thr Ile Leu Lys Cys
            515                 520                 525

Asn Ile Pro Leu Glu Val Ile Ile Trp Asn Asn Gly Tyr Thr Ile
        530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
                565                 570                 575

Tyr Thr Asn Ser Thr Leu Ile Gln Cys Pro Ser Lys Leu Ala Leu Lys
                580                 585                 590

Leu Glu Glu Leu Lys Asn Ser Asn Lys Arg Ser Gly Ile Glu Leu Leu
            595                 600                 605

Glu Val Lys Leu Gly Glu Leu Asp Phe Pro Glu Gln Leu Lys Cys Met
            610                 615                 620

Val Glu Ala Ala Leu Lys Arg Asn Lys Lys
625                 630                 635

<210> SEQ ID NO 169
<211> LENGTH: 348
<212> TYPE: PRT
<213> ORGANISM: Saccharomyces cerevisiae

<400> SEQUENCE: 169

Met Ser Ile Pro Glu Thr Gln Lys Ala Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205

Glu Leu Phe Thr Ser Leu Gly Gly Glu Val Phe Ile Asp Phe Thr Lys
    210                 215                 220

Glu Lys Asp Ile Val Ser Ala Val Val Lys Ala Thr Asn Gly Gly Ala
225                 230                 235                 240

His Gly Ile Ile Asn Val Ser Val Ser Glu Ala Ala Ile Glu Ala Ser
```

-continued

```
                245                 250                 255
Thr Arg Tyr Cys Arg Ala Asn Gly Thr Val Val Leu Val Gly Leu Pro
            260                 265                 270

Ala Gly Ala Lys Cys Ser Ser Asp Val Phe Asn His Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
            325                 330                 335

Gln Ile Ala Gly Arg Tyr Val Val Asp Thr Ser Lys
        340                 345

<210> SEQ ID NO 170
<211> LENGTH: 563
<212> TYPE: PRT
<213> ORGANISM: Saccharomyces cerevisiae

<400> SEQUENCE: 170

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
            85                  90                  95

His Val Val Gly Val Pro Ser Ile Ser Ala Gln Ala Lys Gln Leu Leu
        100                 105                 110

Leu His His Thr Leu Gly Asn Gly Asp Phe Thr Val Phe His Arg Met
    115                 120                 125

Ser Ala Asn Ile Ser Glu Thr Thr Ala Met Ile Thr Asp Ile Ala Thr
130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
            165                 170                 175

Pro Ala Lys Leu Leu Gln Thr Pro Ile Asp Met Ser Leu Lys Pro Asn
        180                 185                 190

Asp Ala Glu Ser Glu Lys Glu Val Ile Asp Thr Ile Leu Ala Leu Val
    195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
            245                 250                 255

Pro Arg Tyr Gly Gly Val Tyr Val Gly Thr Leu Ser Lys Pro Glu Val
        260                 265                 270
```

```
Lys Glu Ala Val Glu Ser Ala Asp Leu Ile Leu Ser Val Gly Ala Leu
            275                 280                 285
Leu Ser Asp Phe Asn Thr Gly Ser Phe Ser Tyr Ser Tyr Lys Thr Lys
        290                 295                 300
Asn Ile Val Glu Phe His Ser Asp His Met Lys Ile Arg Asn Ala Thr
305                 310                 315                 320
Phe Pro Gly Val Gln Met Lys Phe Val Leu Gln Lys Leu Leu Thr Thr
                325                 330                 335
Ile Ala Asp Ala Ala Lys Gly Tyr Lys Pro Val Ala Val Pro Ala Arg
            340                 345                 350
Thr Pro Ala Asn Ala Ala Val Pro Ala Ser Thr Pro Leu Lys Gln Glu
        355                 360                 365
Trp Met Trp Asn Gln Leu Gly Asn Phe Leu Gln Glu Gly Asp Val Val
    370                 375                 380
Ile Ala Glu Thr Gly Thr Ser Ala Phe Gly Ile Asn Gln Thr Thr Phe
385                 390                 395                 400
Pro Asn Asn Thr Tyr Gly Ile Ser Gln Val Leu Trp Gly Ser Ile Gly
                405                 410                 415
Phe Thr Thr Gly Ala Thr Leu Gly Ala Ala Phe Ala Ala Glu Glu Ile
            420                 425                 430
Asp Pro Lys Lys Arg Val Ile Leu Phe Ile Gly Asp Gly Ser Leu Gln
        435                 440                 445
Leu Thr Val Gln Glu Ile Ser Thr Met Ile Arg Trp Gly Leu Lys Pro
    450                 455                 460
Tyr Leu Phe Val Leu Asn Asn Asp Gly Tyr Thr Ile Glu Lys Leu Ile
465                 470                 475                 480
His Gly Pro Lys Ala Gln Tyr Asn Glu Ile Gln Gly Trp Asp His Leu
                485                 490                 495
Ser Leu Leu Pro Thr Phe Gly Ala Lys Asp Tyr Glu Thr His Arg Val
            500                 505                 510
Ala Thr Thr Gly Glu Trp Asp Lys Leu Thr Gln Asp Lys Ser Phe Asn
        515                 520                 525
Asp Asn Ser Lys Ile Arg Met Ile Glu Ile Met Leu Pro Val Phe Asp
    530                 535                 540
Ala Pro Gln Asn Leu Val Glu Gln Ala Lys Leu Thr Ala Ala Thr Asn
545                 550                 555                 560
Ala Lys Gln

<210> SEQ ID NO 171
<211> LENGTH: 1048
<212> TYPE: PRT
<213> ORGANISM: Clostridium acetobutylicum

<400> SEQUENCE: 171

Met Lys Ser Glu Tyr Thr Ile Gly Arg Tyr Leu Leu Asp Arg Leu Ser
1               5                   10                  15
Glu Leu Gly Ile Arg His Ile Phe Gly Val Pro Gly Asp Tyr Asn Leu
            20                  25                  30
Ser Phe Leu Asp Tyr Ile Met Glu Tyr Lys Gly Ile Asp Trp Val Gly
        35                  40                  45
Asn Cys Asn Glu Leu Asn Ala Gly Tyr Ala Ala Asp Gly Tyr Ala Arg
    50                  55                  60
Ile Asn Gly Ile Gly Ala Ile Leu Thr Thr Phe Gly Val Gly Glu Leu
65                  70                  75                  80
```

```
Ser Ala Ile Asn Ala Ile Ala Gly Ala Tyr Ala Glu Gln Val Pro Val
                85                  90                  95

Val Lys Ile Thr Gly Ile Pro Thr Ala Lys Val Arg Asp Asn Gly Leu
            100                 105                 110

Tyr Val His His Thr Leu Gly Asp Gly Arg Phe Asp His Phe Phe Glu
            115                 120                 125

Met Phe Arg Glu Val Thr Val Ala Glu Ala Leu Leu Ser Glu Glu Asn
            130                 135                 140

Ala Ala Gln Glu Ile Asp Arg Val Leu Ile Ser Cys Trp Arg Gln Lys
145                 150                 155                 160

Arg Pro Val Leu Ile Asn Leu Pro Ile Asp Val Tyr Asp Lys Pro Ile
                165                 170                 175

Asn Lys Pro Leu Lys Pro Leu Leu Asp Tyr Thr Ile Ser Ser Asn Lys
            180                 185                 190

Glu Ala Ala Cys Glu Phe Val Thr Glu Ile Val Pro Ile Ile Asn Arg
            195                 200                 205

Ala Lys Lys Pro Val Ile Leu Ala Asp Tyr Gly Val Tyr Arg Tyr Gln
    210                 215                 220

Val Gln His Val Leu Lys Asn Leu Ala Glu Lys Thr Gly Phe Pro Val
225                 230                 235                 240

Ala Thr Leu Ser Met Gly Lys Gly Val Phe Asn Glu Ala His Pro Gln
                245                 250                 255

Phe Ile Gly Val Tyr Asn Gly Asp Val Ser Ser Pro Tyr Leu Arg Gln
            260                 265                 270

Arg Val Asp Glu Ala Asp Cys Ile Ile Ser Val Gly Val Lys Leu Thr
            275                 280                 285

Asp Ser Thr Thr Gly Gly Phe Ser His Gly Phe Ser Lys Arg Asn Val
    290                 295                 300

Ile His Ile Asp Pro Phe Ser Ile Lys Ala Lys Gly Lys Lys Tyr Ala
305                 310                 315                 320

Pro Ile Thr Met Lys Asp Ala Leu Thr Glu Leu Thr Ser Lys Ile Glu
                325                 330                 335

His Arg Asn Phe Glu Asp Leu Asp Ile Lys Pro Tyr Lys Ser Asp Asn
            340                 345                 350

Gln Lys Tyr Phe Ala Lys Glu Lys Pro Ile Thr Gln Lys Arg Phe Phe
            355                 360                 365

Glu Arg Ile Ala His Phe Ile Lys Glu Lys Asp Val Leu Leu Ala Glu
            370                 375                 380

Gln Gly Thr Cys Phe Phe Gly Ala Ser Thr Ile Gln Leu Pro Lys Asp
385                 390                 395                 400

Ala Thr Phe Ile Gly Gln Pro Leu Trp Gly Ser Ile Gly Tyr Thr Leu
                405                 410                 415

Pro Ala Leu Leu Gly Ser Gln Leu Ala Asp Gln Lys Arg Arg Asn Ile
            420                 425                 430

Leu Leu Ile Gly Asp Gly Ala Phe Gln Met Thr Ala Gln Glu Ile Ser
            435                 440                 445

Thr Met Leu Arg Leu Gln Ile Lys Pro Ile Ile Phe Leu Ile Asn Asn
    450                 455                 460

Asp Gly Tyr Thr Ile Glu Arg Ala Ile His Gly Arg Glu Gln Val Tyr
465                 470                 475                 480

Asn Asn Ile Gln Met Trp Arg Tyr His Asn Val Pro Lys Val Leu Gly
                485                 490                 495

Pro Lys Glu Cys Ser Leu Thr Phe Lys Val Gln Ser Glu Thr Glu Leu
```

```
              500                 505                 510
Glu Lys Ala Leu Leu Val Ala Asp Lys Asp Cys Glu His Leu Ile Phe
            515                 520                 525
Ile Glu Val Val Met Asp Arg Tyr Asp Lys Pro Glu Pro Leu Glu Arg
        530                 535                 540
Leu Ser Lys Arg Phe Ala Asn Gln Asn Asn Gly Tyr Ala Arg Ile Asn
545                 550                 555                 560
Gly Ile Gly Ala Ile Leu Thr Thr Phe Gly Val Gly Glu Leu Ser Ala
                565                 570                 575
Ile Asn Ala Ile Ala Gly Ala Tyr Ala Glu Gln Val Pro Val Val Lys
            580                 585                 590
Ile Thr Gly Ile Pro Thr Ala Lys Val Arg Asp Asn Gly Leu Tyr Val
        595                 600                 605
His His Thr Leu Gly Asp Gly Arg Phe Asp His Phe Phe Glu Met Phe
    610                 615                 620
Arg Glu Val Thr Val Ala Glu Ala Leu Leu Ser Glu Glu Asn Ala Ala
625                 630                 635                 640
Gln Glu Ile Asp Arg Val Leu Ile Ser Cys Trp Arg Gln Lys Arg Pro
                645                 650                 655
Val Leu Ile Asn Leu Pro Ile Asp Val Tyr Asp Lys Pro Ile Asn Lys
            660                 665                 670
Pro Leu Lys Pro Leu Leu Asp Tyr Thr Ile Ser Ser Asn Lys Glu Ala
        675                 680                 685
Ala Cys Glu Phe Val Thr Glu Ile Val Pro Ile Ile Asn Arg Ala Lys
    690                 695                 700
Lys Pro Val Ile Leu Ala Asp Tyr Gly Val Tyr Arg Tyr Gln Val Gln
705                 710                 715                 720
His Val Leu Lys Asn Leu Ala Glu Lys Thr Gly Phe Pro Val Ala Thr
                725                 730                 735
Leu Ser Met Gly Lys Gly Val Phe Asn Glu Ala His Pro Gln Phe Ile
            740                 745                 750
Gly Val Tyr Asn Gly Asp Val Ser Ser Pro Tyr Leu Arg Gln Arg Val
        755                 760                 765
Asp Glu Ala Asp Cys Ile Ile Ser Val Gly Val Lys Leu Thr Asp Ser
    770                 775                 780
Thr Thr Gly Gly Phe Ser His Gly Phe Ser Lys Arg Asn Val Ile His
785                 790                 795                 800
Ile Asp Pro Phe Ser Ile Lys Ala Lys Gly Lys Lys Tyr Ala Pro Ile
                805                 810                 815
Thr Met Lys Asp Ala Leu Thr Glu Leu Thr Ser Lys Ile Glu His Arg
            820                 825                 830
Asn Phe Glu Asp Leu Asp Ile Lys Pro Tyr Lys Ser Asp Asn Gln Lys
        835                 840                 845
Tyr Phe Ala Lys Glu Lys Pro Ile Thr Gln Lys Arg Phe Phe Glu Arg
    850                 855                 860
Ile Ala His Phe Ile Lys Glu Lys Asp Val Leu Leu Ala Glu Gln Gly
865                 870                 875                 880
Thr Cys Phe Phe Gly Ala Ser Thr Ile Gln Leu Pro Lys Asp Ala Thr
                885                 890                 895
Phe Ile Gly Gln Pro Leu Trp Gly Ser Ile Gly Tyr Thr Leu Pro Ala
            900                 905                 910
Leu Leu Gly Ser Gln Leu Ala Asp Gln Lys Arg Arg Asn Ile Leu Leu
        915                 920                 925
```

Ile Gly Asp Gly Ala Phe Gln Met Thr Ala Gln Glu Ile Ser Thr Met
            930                 935                 940

Leu Arg Leu Gln Ile Lys Pro Ile Ile Phe Leu Ile Asn Asn Asp Gly
945                 950                 955                 960

Tyr Thr Ile Glu Arg Ala Ile His Gly Arg Glu Gln Val Tyr Asn Asn
                965                 970                 975

Ile Gln Met Trp Arg Tyr His Asn Val Pro Lys Val Leu Gly Pro Lys
            980                 985                 990

Glu Cys Ser Leu Thr Phe Lys Val Gln Ser Glu Thr Glu Leu Glu Lys
        995                 1000                1005

Ala Leu Leu Val Ala Asp Lys Asp Cys Glu His Leu Ile Phe Ile
    1010                1015                1020

Glu Val Val Met Asp Arg Tyr Asp Lys Pro Glu Pro Leu Glu Arg
    1025                1030                1035

Leu Ser Lys Arg Phe Ala Asn Gln Asn Asn
    1040                1045

<210> SEQ ID NO 172
<211> LENGTH: 645
<212> TYPE: DNA
<213> ORGANISM: Methylococcus capsulatus

<400> SEQUENCE: 172
atggcaagac cattgattca gctcgccctg gacacgctgg acatcccgca gaccctgaag      60
ctcgcaagcc tcaccgcgcc ctatgtcgat atcttcgaaa tcggcacccc cagcatcaag     120
cacaacggca tcgccctggt gaaggagttc aaaaaacgct cccccaacaa gctgctcctg     180
gtcgacctca aaaccatgga cgccggtgaa tacgaagcca ccccttctt cgccgccggc      240 gccgacatca ccaccgtcct cggcgtcgca ggactggcca ccatcaaggg cgtcatcaac     300
gccgccaaca agcacaacgc cgaggtccag gtcgacctga tcaacgtccc cgacaaggcc     360
gcctgcgccc gtgagtccgc caaggccggc gcccagatcg tcggcatcca caccggcctc     420
gacgcccagg ccgccggcca gacccccttc gccgacctcc aggccatcgc caagctcggc     480
ctccccgtcc gcatctccgt cgccggcggc atcaaggcct ccaccgccca acaggtcgtc     540
aaaaccggtg ccaacatcat cgtcgtcgga gccgccatct acggcgccgc ctcccccgcc     600
gatgccgcgc gcgaaatcta cgaacaggtc gtcgccgctt ccgcc                     645

<210> SEQ ID NO 173
<211> LENGTH: 215
<212> TYPE: PRT
<213> ORGANISM: Methylococcus capsulatus

<400> SEQUENCE: 173

Met Ala Arg Pro Leu Ile Gln Leu Ala Leu Asp Thr Leu Asp Ile Pro
1               5                   10                  15

Gln Thr Leu Lys Leu Ala Ser Leu Thr Ala Pro Tyr Val Asp Ile Phe
            20                  25                  30

Glu Ile Gly Thr Pro Ser Ile Lys His Asn Gly Ile Ala Leu Val Lys
        35                  40                  45

Glu Phe Lys Lys Arg Phe Pro Asn Lys Leu Leu Val Asp Leu Lys
    50                  55                  60

Thr Met Asp Ala Gly Glu Tyr Glu Ala Thr Pro Phe Phe Ala Ala Gly
65                  70                  75                  80

Ala Asp Ile Thr Thr Val Leu Gly Val Ala Gly Leu Ala Thr Ile Lys

```
                   85                  90                  95
Gly Val Ile Asn Ala Ala Asn Lys His Asn Ala Glu Val Gln Val Asp
               100                 105                 110
Leu Ile Asn Val Pro Asp Lys Ala Ala Cys Ala Arg Glu Ser Ala Lys
               115                 120                 125
Ala Gly Ala Gln Ile Val Gly Ile His Thr Gly Leu Asp Ala Gln Ala
               130                 135                 140
Ala Gly Gln Thr Pro Phe Ala Asp Leu Gln Ala Ile Ala Lys Leu Gly
145                 150                 155                 160
Leu Pro Val Arg Ile Ser Val Ala Gly Gly Ile Lys Ala Ser Thr Ala
               165                 170                 175
Gln Gln Val Val Lys Thr Gly Ala Asn Ile Ile Val Val Gly Ala Ala
               180                 185                 190
Ile Tyr Gly Ala Ala Ser Pro Ala Asp Ala Ala Arg Glu Ile Tyr Glu
               195                 200                 205
Gln Val Val Ala Ala Ser Ala
               210                 215

<210> SEQ ID NO 174
<211> LENGTH: 531
<212> TYPE: DNA
<213> ORGANISM: Methylococcus capsulatus

<400> SEQUENCE: 174
atgcatcaga aactgatcat agacaaaatc tccggcatcc tcgccgccac cgatgccggc     60
tatgatgcaa aactgactgc catgctcgac caggcctccc gcatcttcgt cgcgggggcc    120
ggccggtcgg gcctggtcgc caagttcttc gccatgcgcc tcatgcacgg cggctatgac    180
gtcttcgtcg tcggcgaaat cgtcacccc agcatccgca aggcgactt gctgatcgtg    240
atctccggct ccggtgaaac cgaaaccatg ctcgccttca ccaaaaaagc caaggagcag    300
ggcgcctcca tcgccctcat ctccaccgc gacagctcct ccctcggcga cctcgccgac    360
tccgtcttcc gcatcggctc ccagagctc ttcggaaaag tcgtcggcat gcccatgggc    420
accgtcttcg agctctccac cctcctcttc ctcgaggcca ccatctctca catcatccac    480
gagaaaggca tccccgaaga gaaatgaga actcgtcacg ccaacctgga a              531

<210> SEQ ID NO 175
<211> LENGTH: 177
<212> TYPE: PRT
<213> ORGANISM: Methylococcus capsulatus

<400> SEQUENCE: 175

Met His Gln Lys Leu Ile Ile Asp Lys Ile Ser Gly Ile Leu Ala Ala
1               5                  10                  15
Thr Asp Ala Gly Tyr Asp Ala Lys Leu Thr Ala Met Leu Asp Gln Ala
                20                  25                  30
Ser Arg Ile Phe Val Ala Gly Ala Gly Arg Ser Gly Leu Val Ala Lys
                35                  40                  45
Phe Phe Ala Met Arg Leu Met His Gly Gly Tyr Asp Val Phe Val Val
                50                  55                  60
Gly Glu Ile Val Thr Pro Ser Ile Arg Lys Gly Asp Leu Leu Ile Val
65                  70                  75                  80
Ile Ser Gly Ser Gly Glu Thr Glu Thr Met Leu Ala Phe Thr Lys Lys
                85                  90                  95
Ala Lys Glu Gln Gly Ala Ser Ile Ala Leu Ile Ser Thr Arg Asp Ser
```

-continued

```
                    100                 105                 110
Ser Ser Leu Gly Asp Leu Ala Asp Ser Val Phe Arg Ile Gly Ser Pro
        115                 120                 125

Glu Leu Phe Gly Lys Val Val Gly Met Pro Met Gly Thr Val Phe Glu
        130                 135                 140

Leu Ser Thr Leu Leu Phe Leu Glu Ala Thr Ile Ser His Ile Ile His
145                 150                 155                 160

Glu Lys Gly Ile Pro Glu Glu Glu Met Arg Thr Arg His Ala Asn Leu
                165                 170                 175

Glu
```